(12) United States Patent
Winters et al.

(10) Patent No.: US 11,560,422 B2
(45) Date of Patent: *Jan. 24, 2023

(54) SULFONAMIDE-CONTAINING LINKAGE SYSTEMS FOR DRUG CONJUGATES

(71) Applicant: ZYMEWORKS INC., Vancouver (CA)

(72) Inventors: Geoffrey C. Winters, Vancouver (CA); Alexander L. Mandel, Vancouver (CA); Elyse Marie Josée Bourque, L'Etang-du-Nord (CA); James R. Rich, Vancouver (CA); Tom Han Hsiao Hsieh, Vancouver (CA)

(73) Assignee: ZYMEWORKS INC.

( * ) Notice: Subject to any disclaimer, the term of this patent is extended or adjusted under 35 U.S.C. 154(b) by 373 days.

This patent is subject to a terminal disclaimer.

(21) Appl. No.: 15/108,247

(22) PCT Filed: Dec. 29, 2014

(86) PCT No.: PCT/CA2014/000920
§ 371 (c)(1),
(2) Date: Jun. 24, 2016

(87) PCT Pub. No.: WO2015/095953
PCT Pub. Date: Jul. 2, 2015

(65) Prior Publication Data
US 2017/0029490 A1    Feb. 2, 2017

Related U.S. Application Data

(60) Provisional application No. 61/921,242, filed on Dec. 27, 2013, provisional application No. 62/051,899, filed on Sep. 17, 2014.

(51) Int. Cl.
*C07K 16/18*    (2006.01)
*A61K 47/68*    (2017.01)
*C07K 5/06*    (2006.01)

(52) U.S. Cl.
CPC .......... *C07K 16/18* (2013.01); *A61K 47/6817* (2017.08); *A61K 47/6851* (2017.08);
(Continued)

(58) Field of Classification Search
None
See application file for complete search history.

(56) References Cited

U.S. PATENT DOCUMENTS 5,349,066 A    9/1994 Kaneko et al.
5,502,032 A    3/1996 Haupt et al.
(Continued)

FOREIGN PATENT DOCUMENTS

CN    101039701 A    9/2007
EP    2620433 A1    7/2013
(Continued)

OTHER PUBLICATIONS

U.S. Appl. No. 14/213,504, entitled, "Cytotoxic and Anti-Mitotic Compounds, and Methods of Using the Same," filed on Mar. 14, 2014, of Zymeworks Inc. (Issued as U.S. Pat. No. 9,522,876 on Dec. 20, 2016).

(Continued)

*Primary Examiner* — Karl J Puttlitz
(74) *Attorney, Agent, or Firm* — Squire Patton Boggs (US) LLP

(57) ABSTRACT

Sulfonamide-containing linkage systems for release of payload compounds from an attached targeting moiety in drug conjugates. The conjugates have the formula of [(P)-(L)]m-(T), wherein (P) is a payload compound, (L) is a linker, (T) is a targeting moiety and m is an integer from 1- to 10. Also provided are pharmaceutical compositions comprising such conjugates and there use in treating cancer.

38 Claims, 17 Drawing Sheets

(52) U.S. Cl.
CPC ............ *A61K 47/6889* (2017.08); *C07K 5/06* (2013.01); *C07K 2319/00* (2013.01)

(56) References Cited

U.S. PATENT DOCUMENTS

| | | | |
|---|---|---|---|
| 5,635,483 | A | 6/1997 | Pettit et al. |
| 5,663,149 | A | 9/1997 | Pettit et al. |
| 5,780,588 | A | 7/1998 | Pettit et al. |
| 6,124,431 | A | 9/2000 | Sakakibara et al. |
| 6,153,590 | A | 11/2000 | Anderson et al. |
| 6,214,345 | B1 | 4/2001 | Firestone et al. |
| 6,323,315 | B1 | 11/2001 | Pettit et al. |
| 6,569,834 | B1 | 5/2003 | Pettit et al. |
| 6,870,028 | B1 | 3/2005 | Andersen et al. |
| 6,884,869 | B2 | 4/2005 | Senter et al. |
| 7,064,211 | B2 | 6/2006 | Kowalczyk et al. |
| 7,078,562 | B2 | 7/2006 | Furukawa et al. |
| 7,078,572 | B2 | 7/2006 | Kendall |
| 7,192,972 | B2 | 3/2007 | Kowalczyk et al. |
| 7,211,696 | B2 | 5/2007 | Werbovetz |
| 7,390,910 | B2 | 6/2008 | Zask et al. |
| 7,410,951 | B2 | 8/2008 | Andersen et al. |
| 7,528,152 | B2 | 5/2009 | Kowalczyk et al. |
| 7,553,969 | B1 | 6/2009 | Matsuoka et al. |
| 7,579,323 | B1 | 8/2009 | Andersen et al. |
| 7,585,976 | B2 | 9/2009 | Campagna et al. |
| 7,626,023 | B2 | 12/2009 | Zask et al. |
| 7,659,241 | B2 | 2/2010 | Senter et al. |
| 7,772,397 | B2 | 8/2010 | Andersen et al. |
| 7,851,437 | B2 | 12/2010 | Senter et al. |
| 7,994,135 | B2 * | 8/2011 | Doronina ............... C07K 16/32 514/19.3 |
| 8,097,648 | B2 | 1/2012 | Littlefield et al. |
| 8,129,407 | B2 | 3/2012 | Kowalczyk et al. |
| 8,394,922 | B2 | 3/2013 | Cheng et al. |
| 8,609,105 | B2 | 12/2013 | Senter et al. |
| 8,633,224 | B2 | 1/2014 | Kowalczyk et al. |
| 8,992,932 | B2 | 3/2015 | Lerchen et al. |
| 9,522,876 | B2 * | 12/2016 | Winters ............... C07C 311/51 |
| 9,801,951 | B2 | 10/2017 | Miao et al. |
| 9,879,086 | B2 | 1/2018 | Winters et al. |
| 2004/0121965 | A1 | 6/2004 | Greenberger et al. |
| 2005/0171014 | A1 | 8/2005 | Tarasova et al. |
| 2005/0180972 | A1 * | 8/2005 | Wahl ............... A61K 47/6851 424/144.1 |
| 2006/0106082 | A1 | 5/2006 | Del Soldato et al. |
| 2007/0026478 | A1 | 2/2007 | Greenberger et al. |
| 2008/0108820 | A1 | 5/2008 | Campagna et al. |
| 2008/0300192 | A1 | 12/2008 | Doronina et al. |
| 2008/0305044 | A1 | 12/2008 | McDonagh et al. |
| 2009/0155289 | A1 | 6/2009 | Roberts et al. |
| 2009/0264487 | A1 | 10/2009 | Anderson et al. |
| 2011/0020343 | A1 | 1/2011 | Senter et al. |
| 2011/0027274 | A1 | 2/2011 | Cheng et al. |
| 2011/0293704 | A1 | 12/2011 | Holst et al. |
| 2012/0041196 | A1 | 2/2012 | Raffaella et al. |
| 2013/0095123 | A1 | 4/2013 | Lerchen et al. |
| 2013/0129753 | A1 | 5/2013 | Doroski et al. |
| 2013/0190248 | A1 | 7/2013 | Mendelsohn et al. |
| 2013/0231320 | A1 | 9/2013 | Kawaminami et al. |
| 2015/0105540 | A1 | 4/2015 | Miao et al. |
| 2015/0141646 | A1 | 5/2015 | Miao et al. |
| 2015/0250896 | A1 | 9/2015 | Zhao |
| 2015/0284416 | A1 | 10/2015 | Zhao |
| 2016/0038606 | A1 | 2/2016 | Winters et al. |
| 2016/0311853 | A1 | 10/2016 | Geirstanger et al. |
| 2017/0029490 | A1 | 2/2017 | Winters et al. |
| 2017/0246310 | A1 | 8/2017 | Rich et al. |
| 2017/0247408 | A1 | 8/2017 | Winters et al. |
| 2018/0117163 | A9 | 5/2018 | Rich et al. |

FOREIGN PATENT DOCUMENTS

| | | |
|---|---|---|
| WO | WO 1996/14856 | 5/1996 |
| WO | WO 1996/14856 A1 | 5/1996 |
| WO | WO 1996/33211 A1 | 10/1996 |
| WO | WO 1999/32509 A2 | 7/1999 |
| WO | WO 2000/044770 A1 | 8/2000 |
| WO | WO 2001/18032 A2 | 3/2001 |
| WO | WO 2003/072754 A2 | 9/2003 |
| WO | WO 2003/082268 A2 | 10/2003 |
| WO | WO 2004/010957 A2 | 2/2004 |
| WO | WO 2004/026293 A2 | 4/2004 |
| WO | WO 2004/026814 A2 | 4/2004 |
| WO | WO-2004026293 A2 * | 4/2004 ........... A61K 31/191 |
| WO | WO 2005/026169 A1 | 3/2005 |
| WO | WO 2005021558 A2 | 3/2005 |
| WO | WO 2005/030794 A2 | 4/2005 |
| WO | WO 2005/039492 A2 | 5/2005 |
| WO | WO 2005/082023 A2 | 9/2005 |
| WO | WO 2006/027711 A2 | 3/2006 |
| WO | WO-2006027711 A2 * | 3/2006 ............. A61K 47/60 |
| WO | WO 2006/039652 A2 | 4/2006 |
| WO | WO 2006/065533 A2 | 6/2006 |
| WO | WO 2006/067446 A1 | 6/2006 |
| WO | WO 2006/132670 A2 | 12/2006 |
| WO | WO 2007/008603 A1 | 1/2007 |
| WO | WO 2007/008848 A2 | 1/2007 |
| WO | WO 2009/047264 A2 | 4/2009 |
| WO | WO 2009/059309 A2 | 5/2009 |
| WO | WO 2009/095447 A1 | 8/2009 |
| WO | WO 2009/117531 A1 | 9/2009 |
| WO | WO 2010/033207 A1 | 3/2010 |
| WO | WO 2010/115981 A1 | 10/2010 |
| WO | WO 2011/025541 A1 | 3/2011 |
| WO | WO 2011/154359 A1 | 12/2011 |
| WO | WO 2012/059882 A2 | 5/2012 |
| WO | WO 2012/113847 A1 | 8/2012 |
| WO | WO 2012/123957 A1 | 9/2012 |
| WO | WO 2012/135440 A1 | 10/2012 |
| WO | WO 2013/068874 A1 | 5/2013 |
| WO | WO 2013/071035 A1 | 5/2013 |
| WO | WO 2013/173391 A1 | 11/2013 |
| WO | WO 2013/173392 A1 | 11/2013 |
| WO | WO 2013/173393 A1 | 11/2013 |
| WO | WO 2013/185117 A1 | 12/2013 |
| WO | WO 2013/192360 A1 | 12/2013 |
| WO | WO 2014/004376 A2 | 1/2014 |
| WO | WO 2014/074658 A1 | 5/2014 |
| WO | WO 2014/080251 A1 | 5/2014 |
| WO | WO 2014/100762 A1 | 6/2014 |
| WO | WO 2014/144871 A1 | 9/2014 |
| WO | WO 2015/095301 A2 | 6/2015 |
| WO | WO 2015/095952 A1 | 7/2015 |
| WO | WO 2015/095953 A1 | 7/2015 |
| WO | WO 2016/123412 A1 | 8/2016 |

OTHER PUBLICATIONS

U.S. Appl. No. 14/776,654, entitled, "Cytotoxic and Anti-Mitotic Compounds, and Methods of Using the Same," filed on Sep. 14, 2015, of Zymeworks Inc. (Published as 2016-0038606 on Feb. 11, 2016).

U.S. Appl. No. 14/857,733, entitled, "Cytotoxic and Anti-Mitotic Compounds, and Methods of Using the Same," filed on Sep. 17, 2015, of Zymeworks Inc. (Issued as U.S. Pat. No. 9,879,086 on Jan. 30, 2018).

U.S. Appl. No. 15/108,258, entitled, "VAR2CSA-Drug Conjugates," filed on Jun. 24, 2016, of Zymeworks Inc. (Published as 2017-0246310 on Aug. 31, 2017).

U.S. Appl. No. 15/512,030, entitled, "Cytotoxic and Anti-Mitotic Compounds, and Methods of Using the Same," filed on Mar. 16, 2017, of Zymeworks Inc. (Published as 2017-0247408 on Aug. 31, 2017).

U.S. Appl. No. 15/872,642, entitled, "Ytotoxic and Anti-Mitotic Compounds, and Methods of Using the Same," filed on Jan. 16, 2018, of Zymeworks Inc. (Published as 2018-0208667 on Jul. 26, 2018).

Alexander-Bryant et al., "Bioengineering Strategies for Designing Targeted Cancer Therapies," Adv Cancer Res, vol. 118, pp. 1-59 (2013).

(56) References Cited

OTHER PUBLICATIONS

Alley et al., "Contribution of Linker Stability to the Activities of Anticancer Immunoconjugates," Bioconjugate Chem., vol. 19, pp. 759-765 (2008).
Badescu et al, "Bridging Disulfides for Stable and Defined Antibody Drug Conjugates," Bioconjugate Chem., vol. 25 (6), pp. 1124-1136 (2014).
Bai et al., "Interactions of the Sponge-Derived Antimitotic Tripeptide Hemiasterlin with Tubulin: Comparison with Dolastatin 10 and Cyrpotphycin 1," Biochemistry, vol. 38, pp. 14302-14310 (1999).
Baldwin, A. D. And Kiick, K. L., "Tunable Degradation of Maleimide-Thiol Adducts in Reducing Environments," Bioconjugate Chem., Vo. 22, pp. 1946-1953 (2011).
Beaulieu, P.L. et al., "Allosteric N-acetamide-indole-6-carboxylic acid thumb pocket 1 inhibitors of hepatitis C virus NS5B polymerase—Acylsulfonamides and acylsulfamides as carboxylic acid replacements," Can J. Chem., vol. 91, pp. 66-81 (2013).
Bongo et al., "Efficient approach for profiling photoaffinity labeled peptides with a cleavable biotinyl photoprobe," Bioorganic & Medicinal Chemistry Letters, vol. 20, pp. 1834-1836 (2010).
Burke et al., "Design, Synthesis and Biological Evaluation of Antibody-Drug Conjugates Comprised of Potent Camptothecin Analogues," Bioconjugate Chem., vol. 20, pp. 1242-1250 (2009).
Burke et al., "Novel immunoconjugates comprised of streptonigrin and 17-amino-geldanamycin attached via dipeptide-p-aminobenzyl-amine linker system," Biorg. Med. Chem. Lett., vol. 19, pp. 2650-2653 (2009).
Cancer-prevention, http://www.mcancer.org/cancer-prevention, downloaded Nov. 10, 2017.
Cancer-Prevention, http://www.cancerresearchuk.org/about-cancer/causes-of-cancer-be-prevented, downloaded Jan. 8, 2018.
CAS RN 1350253-85-8, STN Entry Date: Dec. 7, 2011.
Chakraborty et al., "Nucleation of β-Hairpin Structures with Cis Amide Bonds in E-Vinylogous Proline-Containing Peptides," J. Org. Chem., vol. 68, pp. 6459-6462 (2003).
Chan et al., "Mitosis-targeted anti-cancer therapies: where they stand," Cell Death and Disease, vol. 3, pp. 1-11 (2012).
Chen, J. et al., "The Bcl-2/Bcl-XL/Bcl-w Inhibitor, Navitoclax, Enhances the Activity of Chemotherapeutic Agents In Vitro and In Vivo," Mol Cancer Ther, 10(12), pp. 2340-2349, (2011).
Cheng-Bin Yim et al., "Spacer Effects on in vivo Properties of DOTA-Conjugated Dimeric [Tyr3]Octreotate Peptides Synthesized by a "Cul-Click" and "Sulfo-Click" Ligation Method," Chembiochem, vol. 12, No. 5, pp. 750-760 (2011).
Choi, K.Y., "Protease-Activated Drug Development," Theranostics, 2(2), pp. 156-178, (2012).
Coleman et al., "Cytotoxic Peptides from the Marine Sponge *Cymbastella* sp.," Tetrahedron vol. 51, No. 39, pp. 10653-10662 (1995).
Doronina et al., "Development of potent monoclonal antibody auristatin conjugates for cancer therapy," Nature Biotechnology, vol. 21, No. 7, pp. 778-784 (2003).
Doronina et al., "Enhanced Activity of Monomethylauristatin F through Monoclonal Antibody Delivery: Effects of Linker Technology on Efficacy and Toxicity," Bioconjugate Chem., vol. 17, pp. 114-124 (2006).
Doronina et al., "Novel Peptide Linkers for Highly Potent Antibody—Auristatin Conjugate," Bioconjugate Chem., vol. 19, pp. 1960-1963 (2008).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem., vol. 13, pp. 855-869 (2002).
"Expert Scientific Group on Phase One Clinical Trails Final Report" Nov. 30, 2006, pp. C1, C35-C38.
Fennell et al., "Effects of the antimitotic natural product dolastatin 10, and related peptides, on the human malarial parasite Plasmodium falciparum," Antimicrob. Chemother., vol. 51, pp. 833-841 (2003).
Francisco et al., "cAC10-vcMMAE, and anti-CD30-monomethyl auristatin E conjugate with potent and selective antitumor activity," Blood, vol. 102, No. 4, pp. 1458-1465 (2003).
Gajula et al., "A Synthetic Dolastatin 10 Analgoue Supresses Mictrotubule Dynamics, Inhibits Cell Proliferation, and Induces Apoptotic Cell Death," J. Med. Chem, vol. 56, pp. 2235-2245 (2013).
Govindaraju et al., "Supporting Information Surface Immobilization of Biomolecules by Click Sulfonamide Reaction," Supplemental Material (ESI) for Chemical Communications, The Royal Society of Chemistry (2008) Downloaded from: (http://www.rsc.org/suppdata/cc/b8/b80674c/b806764c.pdf).
Grison, C. et al., "Stereoselective synthesis of vinylogous peptides," Tetrahedron, 57, pp. 4903-4923 (2001).
Grison et al., "Structural Investigation of "cis" and "trans" Vinylogous Peptides: cis-Vinylog Turn in Folded cis-Vinylogous Peptides, an Excelletn Mimic of the Natural β-Turn," J. Org. Chem. vol. 70, pp. 10753-10764 (2005).
Gura, T.,"Cancer Models: Systems for Identifiying New Drugs are Often Faulty," Science 7, vol. 278, No. 5340, pp. 1041-1042 (2007).
Haba, K., "Single-Triggered Trimeric Prodrugs," Angew. Chem. Int. Ed., vol. 44, pp. 716-720 (2005).
Hadaschik, B.A. et al., "Intravesical Chemotherapy of High-Grade Bladder Cancer with HTI-286, a Synthetic Analogue of the Marine Sponge Product Hemiasterlin," Clin Cancer Res., vol. 14, pp. 1510-1518 (2008).
Hamada et al., caplus an 2008:324765.
Huang, S. et al., "Synthesis and evaluation of N-acyl sulfonamides as potential prodrugs of cyclin-dependent kinase inhibitor JNJ-7706621," Bioorganic & Medicinal Chemistry Letters, vol. 16, pp. 3639-3641 (2006).
Ishikawa et al, "Preparation of endothelin antagonistic peptide derivatives," caplus an Eur. Pat. Appl., p. 121, 1992:256053.
Jeffrey et al., "Design, Synthesis, and in Vitro Evaluation of Dipeptide-Based Antibody Minor Groove Binder Conjugates," J. Med. Chem., vol. 48, pp. 1344-1358 (2005).
Jeffrey et al., "Dipeptide-based highly potent doxorubicin antibody conjugates," Biorg. Med. Chem. Lett. vol. 16, pp. 358-362 (2006).
Jeffrey et al., "Expanded Utility of the β-Glucuronide Linker: ADCs That Deliver Phenolic Cytotoxic Agents," ACS Med. Chem. lett., vol. 1, pp. 277-280 (2010).
Jiang, Y. et al., "Discovery of Danoprevir (ITMN-191/R7227), a Highly Selective and Potent Inhibitor of Hepatitis C Virus (HCV) NS3/4A Protease," J. Med. Chem., vol. 57, pp. 1753-1769 (2014).
Johansson, A. et al., "Acyl Sulfonamides as Potent Protease Inhibitors of the Hepatitis C Virus Full-Length NS3 (Protease-Helicase/NTPase): A Comparative Study of Different C-Terminals," Bioorganic & Medicinal Chemistry, 11, pp. 2551-2568 (2003).
Kamb, A., "What's wrong with our cancer models?," Nature Reviews Drug Discovery 4, vol. 4, pp. 161-165 (2005).
Koniev, O. et al, "Selective Irreversible Chemical Tagging of Cysteine with 3-Arylpropiolonitriles," Bioconjugate Chem., vol. 25 (2), pp. 202-206 (2014).
Kuznetsov et al., "Tubulin-based antimitotic mechanism of E7974, a novel analogue of the marine sponge natural product hemiasterlin," Mol Cancer Ther, 8(10), pp. 2852-2860 (2009).
Leaf, C., "Why are We Losing the War on Cancer (and How to Win It)," Health Administrator vol. XVII, No. 1, pp. 172-183 (2005).
Lesma, et al., "Hemiasterlin Analogues Incorporating an Aromatic, and Heterocyclic Type C-terminus: Design, Synthesis and Biological Evaluation," Mol Divers.,18(2), pp. 357-373 (2004).
Li et al., "Immunotoxins and Cancer Therapy," Cellular & Molecular Immunology, vol. 6, No. 2, pp. 106-112 (2005).
Loganzo et al., "HTI-286 , a Synthetic Analogue of the Tripeptide Hemiasterlin, Is a Potent Antimicrotubule Agent that Circumvents P-Glycoprotein-mediated Resistance in Vitro and in Vivo," Cancer Res, 63, pp. 1838-1845 (2003).
Luo et al., "Principle of Cancer Therapy: Oncogen and Non-oncogene Addiction," Cell vol. 136, pp. 823-837 (2009).
Mader, M.M. et al., "Acyl sulfonamide anti-proliferatives. Part 2: Activity of heterocyclic sulfonamide derivatives," Bioorganic & Medicinal Chemistry Letters, 15, pp. 617-620 (2005).

(56) References Cited

OTHER PUBLICATIONS

Marzo et al., "Antimitotic drugs in cancer chemotherapy: Promises and pitfalls," Biochemical Pharmacology, Vo. 86, pp. 703-710 (2013).
Merkx et al., "Resin-bound sulfonyl-azides: Efficient loading and activation strategy for the preparation of the N-acyl sulfonamide linker," J. Org. Chem., vol. 72, pp. 4574-4577 (2007).
Melnyk, O. et al, "Phenylthiocarbamate or N-Carbothiophenyl Group Chemistry in Peptide Synthesis and Bioconjugation," Bioconjugate Chem., vol. 25, pp. 629-639 (2014).
Mitra, A. and Sept D., "Localization of the Antimitotic Peptide and Depsipeptide Binding Site on B-tubulin," Biochemistry, 43, pp. 13955-13962 (2004).
Miyazawa, T. et al, "Effect of copper(II) chloride on suppression of racemization in peptide synthesis by the carbodiimide method," Int. J. Peptide Protein Res., vol. 39, pp. 237-244 (1992).
Neidle, S., "Failure Modes in Clinical Development," Cancer Drug Design and Discovery, ed. (Elsevier/Academic Press) pp. 427-431 (2008).
Niu et al., "Absolute configurations of tubulin inhibitors taltobulin (HTI-286) and HTI-042 characterized by X-ray diffraction analysis and NMR studies," Bioorganic & Medicinal Chmistry Letters, 20, pp. 1535-1538 (2010).
Olsen et al., caplus an 2010:213501.
Otani et al., "TZT-1027, an antimicrotubule agent, attacks tumor vasculature and induces tumor cell death," Jpn. J. Cancer Res., vol. 91, pp. 837-844 (2000).
Papisov et al., "Semisynthetic Hydrophilic Polyals," Biomacromolecules,vol. 6, pp. 2659-2670 (2005).
Pettit et al., "Antineoplastic agents 337. Synthesis of dolastatin 10 structural modifications," Anti-Cancer Drug Des., vol. 10, pp. 529-544 (1995).
Pettit et al., "Specific activities of dolastatin 10 and peptide derivatives against *Cryptococcus neoformans*," Antimicrob. Agents Chemother., vol. 42, pp. 2961-2965 (1998).
Pettit et al., "Antineoplastic agents 365. Dolastatin 10 SAR probes," Anti-Cancer Drug Des., vol. 13, pp. 243-277 (1998).
Pettit et al., "Antineoplastic agents. 592. Highly effective cancer cell growth inhibitory structural modifications of dolastatin 10," J. Nat. Prod., vol. 74, pp. 962-968 (2011).
Ratain et al., "Phase I and pharmacological study of HTI-286, a novel antimicrotubule agent: correlation of neutropenia with time above a threshold serum concentration," Proc. Am. Soc. Clin. Oncol., vol. 22, p. 129 (2003).
Ravi M. et al., "Structure-Based Identification of the Binding Site for the Hemiasterlin Analogue HTI-286 on Tubulin," Biochemistry, 44, pp. 15871-15879 (2005).
Rich, J.R., et al., CAPLUS AN 2015:1087487.
Rocha-Lima et al., "A Phase 1 Trial of E7974 Administrated on Day 1 of a 21 Day Cycle in Patients with Advanced Solid Tumors," Cancer, pp. 4262-4270, Sep. 1, 2012.
Scola, P.M. et al., "The Discovery of Asunaprevir (BMS-650032), an Orally Efficacious NS3 Protease Inhibitor for the Treatment of Hepatitis C Virus Infection," J. Med. Chem., 57, pp. 1730-1752 (2014).
Schumacher, F.F. et al, "In Situ Maleimide Bridging of Disulfides and a New Approach to Protein Pegylation," Bioconjugate Chem., vol. 22, pp. 132-136 (2011).
Shabat et al., "In vivo activity in a catalytic antibody-prodrug system: Antibody catalyzed etoposide prodrug activation for selective chemotherapy," PNAS, vol. 98, No. 13, pp. 7528-7533 (2001).
Shannon et al., "Investigating the Proteome Reactivity and Selectivity of Aryl Halides," J. Am. Chem. Soc., vol. 136, pp. 3330-3333 (2014).
Shnyder et al., "Auristatin PYE, a novel synthetic derivative of dolastatin 10, is highly effective in human colon tumour models," Int. J. Oncol., vol. 31, pp. 353-360 (2007).
Steiner, M. et al., "Spacer length shapes drug release and therapeutic efficacy of traceless disulfide-linked ADCs targeting the tumor neovasculature," Chem. Sci., vol. 4, pp. 297-302 (2013).
Winters, G., et al., CAPLUS AN 2015:1087672.
Sutherland, M.S.K., et al., "Lysosomal Trafficking and Cysteine Protease Metabolism Confer Target-specific Cytotoxicity by Peptide-linked Anti-CD30-Auristatin Conjugates," Journal of Biological Chemistry, Vo. 281, No. 15, pp. 10540-10547 (2006).
Talpir et al., "Hemiasterlin and Geodiamolide TA; Two New Cytotoxic Peptides from the Marine Sponge Hemiasterella Minor (Kirkpatrick)," Tetrahedron Letters, vol. 35, No. 25, pp. 4453-4456 (1994).
Temming et al., "Improved Efficacy of αvβ3-Targeted Albumin Conjugates by Conjugation of a Novel Auristatin Derivative," Molecular Pharmaceutics, vol. 4, No. 5, pp. 686-694 (2007).
Thomssen et al., "Prognostic value of the cysteine proteases cathepsins B and cathepsin L in human breast cancer," Clinical Cancer Research, vol. 1, pp. 741-746 (1995).
Toki et al., "Protease-Mediated Fragmentation of p-Aminobenzyl Ethers: A New Strategy for the Activation of Anticancer Prodrugs," J. Org. Chem., vol. 67, pp. 1866-1872 (2002).
Toure, B.C. et al., "The Role of the Acidity of N-Heteroaryl Sulfonamides as Inhibitors of Bcl-2 Family Protein-Protein Interactions," ACS Med. Chem. Lett., vol. 4, pp. 186-190 (2013).
Uehling, D.E. et al., "Synthesis and Evaluation of Potent and Selective β3 Adrenergic Receptor Agonists Containing Acylsulfonamide, Sulfonylsulfonamide, and Sulfonylurea Carboxylic Acid Isosteres," J. Med. Chem., vol. 45, pp. 567-583 (2002).
Vedejs, et al., "A Total Synthesis of (-)-Hemiasterlin Using N-Bts Methodology," J. Org. Chem., vol. 66, pp. 7355-7364 (2001).
Walker et al., "Monoclonal antibody mediated intracellular targeting of tallysomycin S10b," Bioorganic & Medicinal Chemistry Letters, vol. 14, pp. 4323-4327 (2004).
Werboretz et al., "Selective Antimicrotubule Activity of N1-Phenyl-3-5-dinitro- 4,N-4-di-n-propylsulfanilamide (GB-II-5) against Kinetoplastid Parasites," Mol. Pharmacol., vol. 64, pp. 1325-1333 (2003).
Wilkinson et al., "Synthesis of MUC1 glycopeptide thioesters and ligation via direct aminolysis," Biopolymers, vol. 96(2), pp. 137-146 (2011).
Woyke et al., "In vitro activities and postantifungal effects of the potent dolastatin 10 derivative Auristatin PHE," Antimicrob. Agents Chemother., vol. 45, pp. 3580-3584 (2001).
Yamashita et al., "Synthesis and Activity of Novel Analogs of Hemiasterlin as Inhibitors of Tubulin Polymerization: Modification of the A Segment," Bioorganic and Medicinal Chemistry Letters, vol. 14, pp. 5317-5322 (2004).
Yan, S. et al., "Thiazolone-acylsulfonamides as novel HCV NS5B polymerase allosteric inhibitors: convergence of structure-based drug design and X-ray crystallographic study," Bioorganic & Medicinal Chemistry Letters, vol. 17, pp. 1991-1995 (2007).
Yurkovestkiy et al., "Synthesis of a Macromolecular Camptothecin Conjugate with Dual Phase Drug Release," Mol Pharm., vol. 1:5, pp. 375-382 (2004).
Zask et al., "D-piece Modifications of the Hemiasterlin Analog HTI-286 Produce Potent Tubulin Inhibitors," Bioorganic & Medicinal Chemistry Letters, vol. 14, pp. 4353-4358 (2004).
Zask et al., "Synthesis and Biological Activity of Analogues of the Antimicrotubule Agent N,β,β-Trimethyl-l-phenylalanyl-N1-[(1S,2E)-3-carboxy-1-isopropylbut-2-enyl]-N1,3-dimethyl-l-valinamide (HTI-286)," J. Med. Chem., vol. 47, pp. 4774-4786 (2004).
Chen, X. et al., "Fusion protein linkers: property, design and funtionality,", Adv Drug Deliv Rev., vol. 65(10), pp. 1357-1369 (2013).
Matsuoka et al., caplus an 2000:535162 (WO2000044770)—Chugai.
Neiman et al., "Synthesis and Antimitotic/Cytotoxic Activity of Hemiasterlin Analogues," J. Nat. Prod. vol. 66, pp. 183-199 (2003).
Final Office Action dated May 18, 2016 in U.S. Appl. No. 14/213,504.
Notice of Allowance dated Aug. 23, 2016 in U.S. Appl. No. 14/213,504.
Restriction Requirement dated Aug. 29, 2016 in U.S. Appl. No. 14/776,654.
Non-final Office Action dated Nov. 16, 2016 in U.S. Appl. No. 14/776,654.
Final Office Action dated May 9, 2017 in U.S. Appl. No. 14/776,654.
Advisory Action dated Jul. 14, 2017 in U.S. Appl. No. 14/776,654.

(56) References Cited

OTHER PUBLICATIONS

Non-final Office Action dated Sep. 15, 2017 in U.S. Appl. No. 14/776,654.
Notice of Allowance dated Feb. 5, 2018 in U.S. Appl. No. 14/776,654.
Restriction Requirement dated Aug. 30, 2016 in U.S. Appl. No. 14/857,733.
Non-final Office Action dated Nov. 14, 2016 in U.S. Appl. No. 14/857,733.
Non-final Office Action dated Jun. 6, 2017 in U.S. Appl. No. 14/857,733.
Notice of Allowance dated Sep. 14, 2017 in U.S. Appl. No. 14/857,733.
Restriction Requirement dated Oct. 5, 2017 in U.S. Appl. No. 15/108,258.
Restriction Requirement dated Sep. 11, 2017 in U.S. Appl. No. 15/512,030.
Non-final Office Action dated Jan. 19, 2018 in U.S. Appl. No. 15/512,030.
Final Office Action dated Jun. 8, 2018 in U.S. Appl. No. 15/512,030.
Restriction Requirement dated May 16, 2018 in U.S. Appl. No. 15/872,642.
Non-final Office Action dated Sep. 13, 2018 in U.S. Appl. No. 15/872,642.
Ducry, L. and Stump, B., "Antibody-Drug Conjugates: Linking cytotoxic payloads to Monoclonal Antibodies," Bioconjugate Chem, vol. 21, pp. 5-13 (2010).
Milton et al., "Mapping the bound conformation and protein interations of microtubule destabilizing peptides by STD-NMR spectroscopy," Bioorganic & medicinal Chemistry Letters, Pergamon, Amsterdam, NL, vol. 16, No. 16 (2006).
Zubovych et al., "A missense mutation in Caenorhabditits elegans prohibitin 2 confers an atypical mltidrug resistance," PNAS, vol. 102, No. 42, pp. 15523-15528 (2006).
Non-final Office Action dated May 18, 2018 in U.S. Appl. No. 15/108,258.
Non-final Office Action dated Mar. 19, 2019 in U.S. Appl. No. 15/108,258.
Non-final Office Action dated Oct. 2, 2015 in U.S. Appl. No. 14/213,504.
Non-final Office Action dated Nov. 27, 2018 in U.S. Appl. No. 15/512,030.
Notice of Allowance dated May 16, 2019 in U.S. Appl. No. 15/512,030.
Notice of Allowance dated Apr. 4, 2019 in U.S. Appl. No. 15/872,642.
Dosio et al., "Immunotoxins and Anticancer Drug Conjugates Assemblies: The role of the linkage between components", Toxins, vol. 3(7), pp. 848-883 (2011).
Restriction Requirement dated Jul. 8, 2020 in U.S. Appl. No. 16/523,942.
Non-final Office Action dated Jan. 21, 2021 in U.S. Appl. No. 16/523,942.
Restriction Requirement dated Dec. 18, 2019 in U.S. Appl. No. 16/273,045.
Office Action dated Jun. 24, 2020 in U.S. Appl. No. 16/273,045.
Office Action dated Feb. 25, 2021 in U.S. Appl. No. 16/273,045.
Notice of Allowance dated Dec. 12, 2019 in U.S. Appl. No. 15/108,258.
U.S. Appl. No. 16/273,045, entitled: "Cytotoxic and Antimitotic Compounds, and Methods of Using the Same", filed Feb. 11, 2019; Published as US20190269785, on Sep. 5, 2019.
U.S. Appl. No. 16/523,942, entitled: "Cytotoxic and Antimitotic Compounds, and Methods of Using the Same", filed Aug. 9, 2019; Published as US20190345254, on Nov. 14, 2019.
Final Office Action dated Jul. 20, 2021 in U.S. Appl. No. 16/523,942.
Non-final Office Action dated Mar. 2, 2022 in U.S. Appl. No. 16/523,942.

\* cited by examiner

Body weights of NSG mice inoculated with NCI-N87 tumour cells and treated on Day 22 with a single IV injection of either vehicle, T-DM1, T-I, or T-K at 12mg/kg, n=10.

Tumour volumes of NSG mice inoculated with NCI-N87 tumour cells and treated on Day 22 with a single IV injection of either vehicle, T-DM1, T-I, or T-K at 12mg/kg, n=10.

Survival of NSG mice inoculated with NCI-N87 tumour cells and treated on Day 22 with a single IV injection of either vehicle, T-DM1, T-I, or T-K at 12mg/kg, n=10.

Body weights of study mice. Body weight, represented as percent change of baseline (Day 27), for NSG mice inoculated with NCI-N87 cells (with matrigel) and treated on Day 27 with a single IV injection of vehicle, Trastuzumab (T), T-DM1, T-E at 1, 3, 7 or 12mg/kg. Data separated by dose (mg/kg). Data is shown as averages (+/ SEM) n=6 (Veh and T), n=7 (T-DM1 3mg/kg), and n=8 for all other groups.

Tumour volumes of study mice following a single dose of ADC, Trastuzumab or vehicle.

Days to tumour recurrence (2-fold increase in volume compared to treatment day) of NCI N87 tumour volumes (with matrigel) in NSG mice treated on Day 27 with a single IV injection of vehicle, Trastuzumab (T), T-DM1, or T-E at 1, 3, 7 or 12mg/kg. Data are shown as averages (+/ SEM) n=6 (Veh and T), n=7 (T-DM1 3mg/kg), and n=8. *** P<0.001

SULFONAMIDE-CONTAINING LINKAGE SYSTEMS FOR DRUG CONJUGATES

CROSS REFERENCE TO RELATED APPLICATIONS

This application claims the benefit under 35 U.S.C. § 119(e) of U.S. Provisional Patent Application No. 61/921,242, filed Dec. 27, 2013, and U.S. Provisional Patent Application No. 62/051,899, filed Sep. 17, 2014, which applications are incorporated herein by reference in their entireties.

BACKGROUND

Field

The invention relates to linkage systems for release of payload from an attached targeting moiety, and methods of using the same.

Description of the Related Art

Delivery scaffolds find many uses in the biological, chemical, and medical fields. For example, the delivery of drugs and other agents to target cells or tissues for the treatment of cancer and other diseases has been the focus of considerable research for many years. Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., chemotherapeutic (anti-cancer)) that can be administered. Although oral administration of drugs is considered to be a convenient and economical mode of administration, it shares the same concerns of non-specific toxicity to non-target cells once the drug has been absorbed into the systemic circulation. Further complications involve problems with oral bioavailability and residence of drug in the gastrointestinal tract leading to additional exposure of the gastrointestinal tract to the drug and hence risk of gastrointestinal tract toxicities.

Accordingly, a major goal has been to develop methods for specifically targeting agents to cells and tissues. The benefits of such treatment include avoiding the general physiological effects of inappropriate delivery of such agents to other cells and tissues. The use of antibody-drug conjugates for the targeted delivery of cytotoxic or anti-mitotic agents (e.g., drugs to kill or inhibit tumor cells in the treatment of cancer) can allow targeted delivery of the drug moiety to tumors and accumulation in tumor cells and the tumor environment. In contrast, systemic administration of unconjugated drug agents may result in unacceptable levels of toxicity to normal cells as well as the tumor cells sought to be eliminated.

The linkage of drugs to antibodies or other targeting moieties to form conjugates that are capable of releasing free drug involves consideration of a variety of factors, including the identity and location of the chemical group for conjugation of the drug, the mechanism of drug release (e.g., via a cleavable bond), the structural elements providing for drug release (e.g., an enzyme recognition sequence and a cleavable bond), and any structural modifications resulting from drug release. What is required is a means for conjugation and specific drug release that does not compromise drug activity. In some instances, the installation of a chemical handle in a drug of interest may be desirable for effective conjugations and drug delivery.

In the medical field, there is a need for drug conjugates that can release potent anti-mitotic and cytotoxic compounds selectively at desired target locations. The present disclosure fulfills these needs and provides further related advantages.

BRIEF SUMMARY

In brief, the present disclosure is directed to compositions comprising a payload compound linked to a targeting moiety in a conjugate, and related methods of manufacture and use thereof. In one embodiment, the invention provides conjugates that are enzymatically cleavable and capable of releasing payload compound from targeting moiety upon enzymatic cleavage. In one embodiment, the targeting moiety is an antibody. In one embodiment, the payload compound is a biologically active compound. In one embodiment, the payload compound is a cytotoxic or cytostatic drug. In one embodiment, the payload is a labeling moiety.

Accordingly, in one embodiment, the invention provides compositions having the following structure:

wherein (P) is a payload compound, (L) is a linker, (T) is a targeting moiety, and m is an integer from 1 to 10. In certain embodiments, m is 1.

In one embodiment, (P) is linked to (T) through (L) as depicted in the following structure:

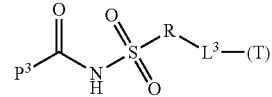

wherein:

R is selected from the group consisting of optionally substituted alkyl, optionally substituted alkylamino, optionally substituted cycloalkyl, optionally substituted aryl, optionally substituted heterocyclyl, optionally substituted heteroaryl, —$COR^{27}$—, —$CSR^{27}$—, —$OR^{27}$—, and —$NHR^{27}$— wherein each $R^{27}$ is, independently, optionally substituted alkyl, optionally substituted alkylamino, optionally substituted cycloalkyl, optionally substituted aryl, optionally substituted heterocyclyl, and optionally substituted heteroaryl, $P^3$ is (P) or a portion of (P), $L^3$ is (L) or a portion of (L), and (T) is a targeting moiety.

In a preferred embodiment, R is selected from the group consisting of optionally substituted alkyl, optionally substituted alkylamino, optionally substituted cycloalkyl, optionally substituted aryl, optionally substituted heterocyclyl and optionally substituted heteroaryl.

As disclosed herein, in one embodiment of the invention, N-acyl sulfonamide-containing conjugates may be synthesized such that an N-acyl sulfonamide moiety is covalently linked to a chemical group, (R), which comprises a nitrogen atom that forms a peptide bond (the junction peptide bond (JPB)) with the carbonyl group of an amino acid that forms part of the linker (L). In one embodiment, the JPB is enzymatically cleavable. Moieties similar to N-acyl sulfonamides, such as N-acyl sulfamamides (owing to the nature of (R)), may also be used.

Accordingly, in some embodiments, a compound of formula (I) is provided wherein (P) is linked to (T) through (L) as depicted in the following structure:

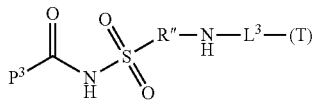

(XXVI)

wherein -L³-(T) has the following structure:

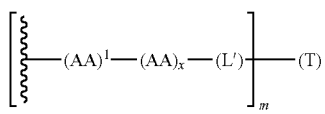

(III)

wherein P³ is the remaining portion of payload compound (P) and the —NH— group bonded to R" forms a peptide bond referred to herein as the junction peptide bond (JPB) with (AA)¹ in formula (III), wherein R" is selected from the group consisting of optionally substituted alkyl, optionally substituted alkylamino, optionally substituted cycloalkyl, optionally substituted aryl, optionally substituted heterocyclyl, optionally substituted heteroaryl, —COR²⁷—, —CSR²⁷—, —OR²⁷—, and —NHR²⁷—, wherein each R²⁷ is, independently, optionally substituted alkyl, optionally substituted alkylamino, optionally substituted cycloalkyl, optionally substituted aryl, optionally substituted heterocyclyl, and optionally substituted heteroaryl, wherein each AA is independently an amino acid, wherein x is an integer from 0 to 25, wherein (L') is the remaining portion (if any) of linker (L), wherein (T) is the targeting moiety. In one embodiment, (AA)¹-(AA)ₓ taken together comprises an amino acid sequence capable of facilitating enyzmatic cleavage of the JPB.

In one embodiment, a plurality of payload moieteies (P) are attached to a single linker moiety (L).

In some embodiments, —R"—NH— in formula (XXVI) is selected from the group consisting of:

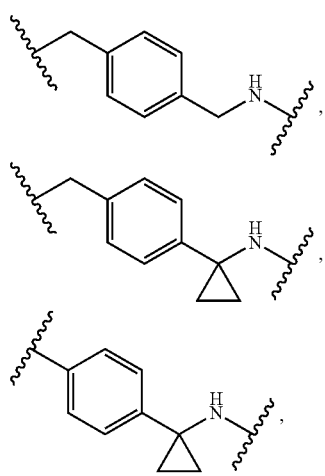

In some embodiments, —R"—NH— in formula (XXVI) is selected from the group consisting of:

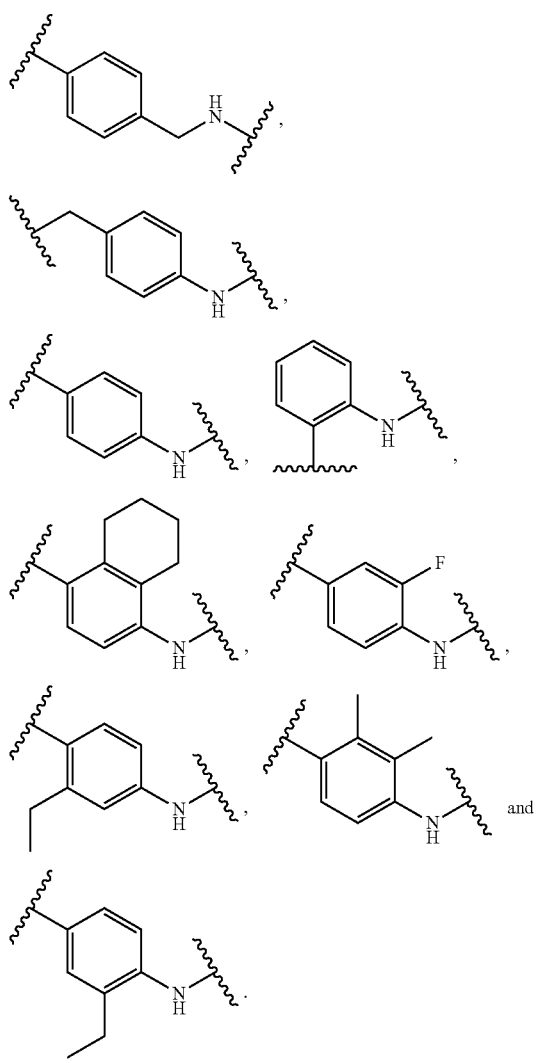

-continued

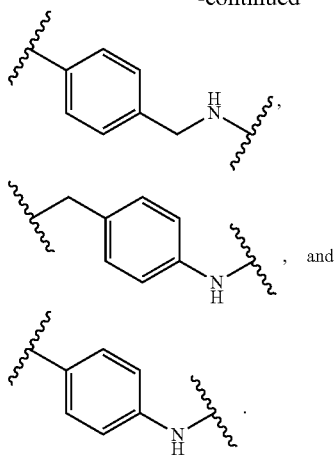

In one embodiment, cleavage of a compound of formula (I) results in a compound of formula (IV):

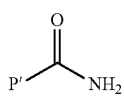

(IV)

wherein P' corresponds to P³ in formula (XXVI).

In one embodiment, cleavage of a compound of formula (I) results in a compound of formula (XIX)

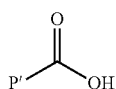

(XIX)

wherein P' corresponds to P³ in formula (XXVI).

In one embodiment, cleavage of the JPB results in a compound of formula (V):

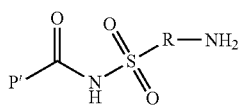

(V)

wherein P' corresponds to P³ in formula (XXVI).

In one embodiment, the invention provides a method of making a composition having structure (I). Compositions having structure (I) can be produced using a wide range of synthetic routes and a wide range of reactants. For example, the N-acyl sulfonamide moiety and the R group of formula (XXVI) may be present in the same reactant or different reactants. The N-acyl sulfonamide moiety may be present on a single reactant or may be formed by two reactants in a conjugation reaction step. The JPB may be intact within a reactant or may be formed by two reactants in a conjugation reaction step. The JPB may be intact within a single reactant that also contains the amino acid sequence facilitating enzymatic cleavage of the JPB, or the amino acid sequence facilitating enzymatic cleavage may be formed and brought together with the JPB by multiple reactants in a conjugation reaction step. It will be appreciated that in combination with the group "R", compounds of formulas (I), (II) (III), (XXI), and (XXVI) may be similar to N-acyl sulfonamides (e.g., sulfamamides).

In another embodiment, a pharmaceutical composition is provided comprising a composition having structure (I), or a stereoisomer, pharmaceutically acceptable salt or prodrug thereof, and a pharmaceutically acceptable carrier, diluent or excipient.

In another embodiment, a method of using a composition having structure (I) in therapy is provided. In particular, the present disclosure provides a method of treating cancer in a mammal comprising administering to a mammal in need thereof an effective amount of a composition having structure (I) or a pharmaceutical composition comprising a composition having structure (I) and a pharmaceutically acceptable carrier diluent or excipient.

In another embodiment, the present disclosure provides a method of inhibiting tumor growth in a mammal comprising administering to a mammal in need thereof an effective amount of a composition having structure (I) or a pharmaceutical composition comprising a composition having structure (I) and a pharmaceutically acceptable carrier, diluent or excipient.

In another embodiment, the present disclosure provides a method of killing cancer cells in vitro using a composition having structure (I). In another embodiment, the present disclosure provides a method of killing cancer cells in vivo in a mammal, comprising administering to a mammal in need thereof an effective amount of a composition having structure (I) or a pharmaceutical composition comprising a composition having structure (I) and a pharmaceutically acceptable carrier, diluent or excipient.

These and other aspects of the disclosure will be apparent upon reference to the following detailed description.

DETAILED DESCRIPTION

Figure 1:
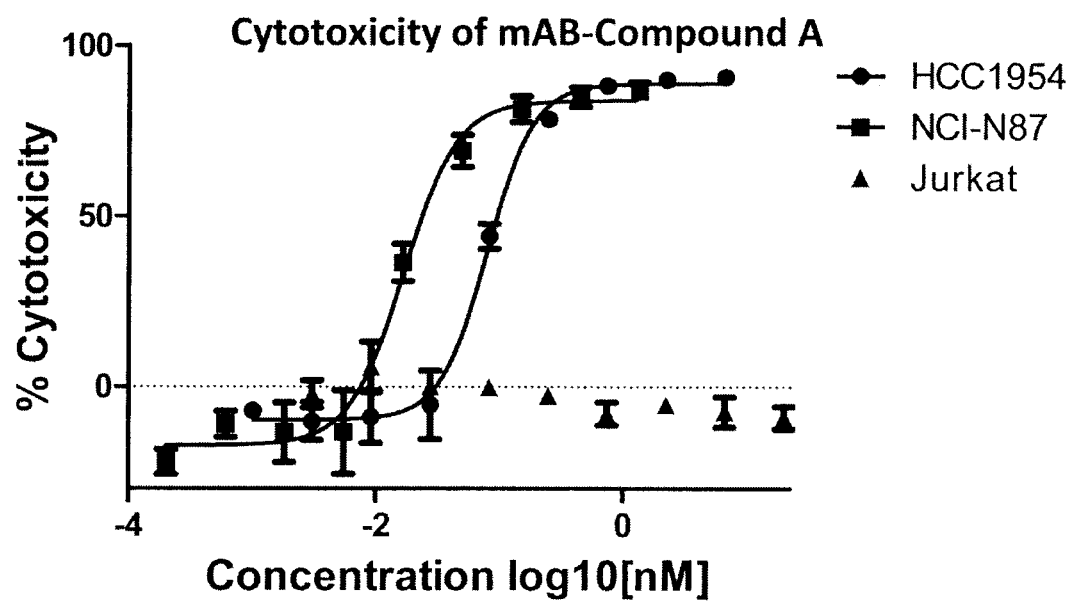
FIG. 1 shows a cytotoxicity data plot for Compound A on three cell lines (HCC1954, NCI-N87, and Jurkat).
Figure 2:
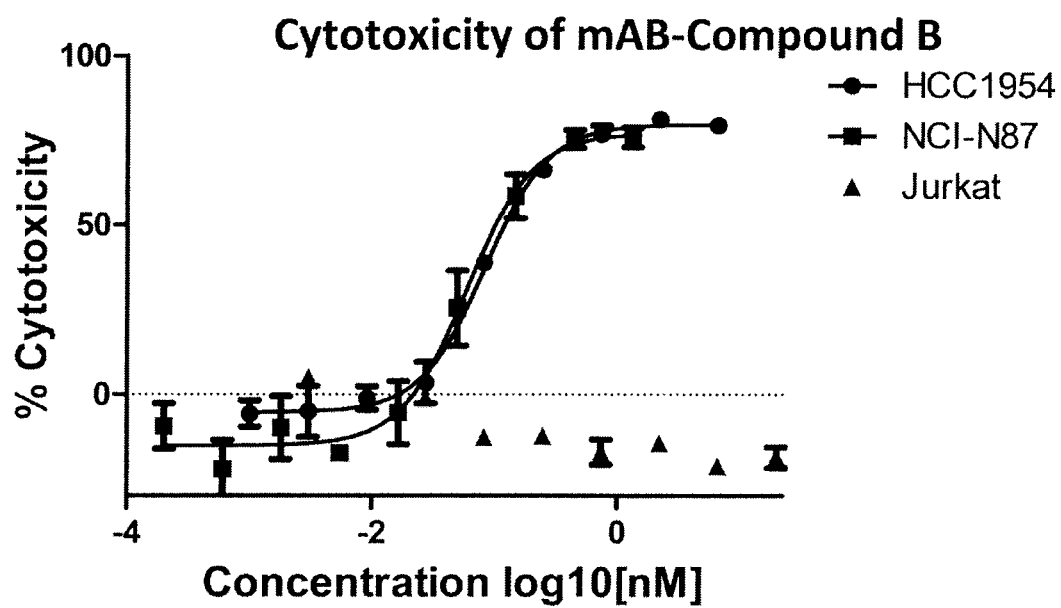
FIG. 2 shows a cytotoxicity data plot for Compound B on three cell lines (HCC1954, NCI-N87, and Jurkat).
Figure 3:
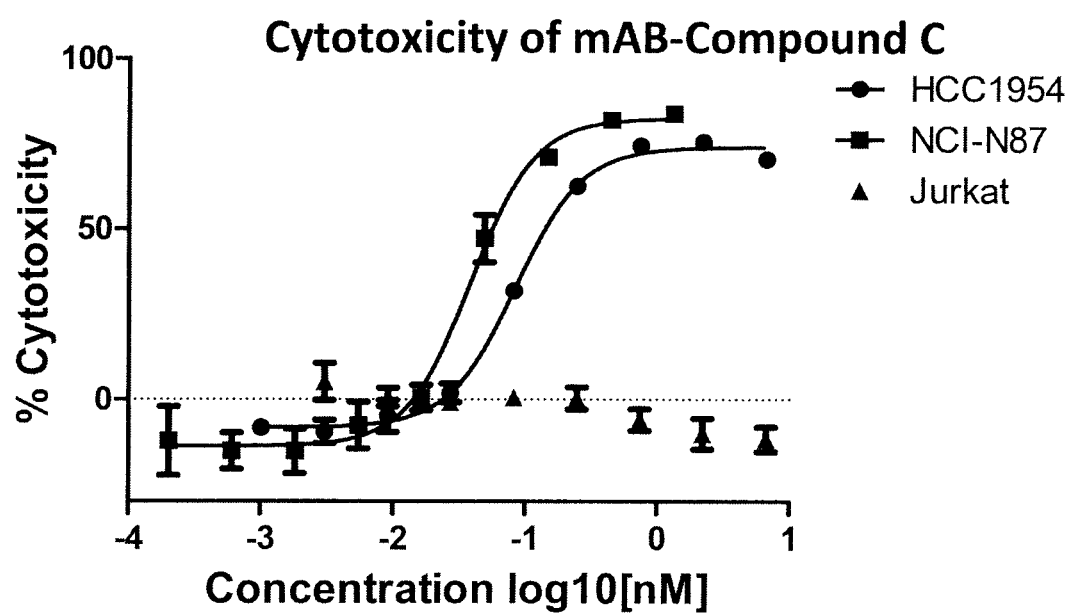
FIG. 3 shows a cytotoxicity data plot for Compound C on three cell lines (HCC1954, NCI-N87, and Jurkat).
Figure 4:
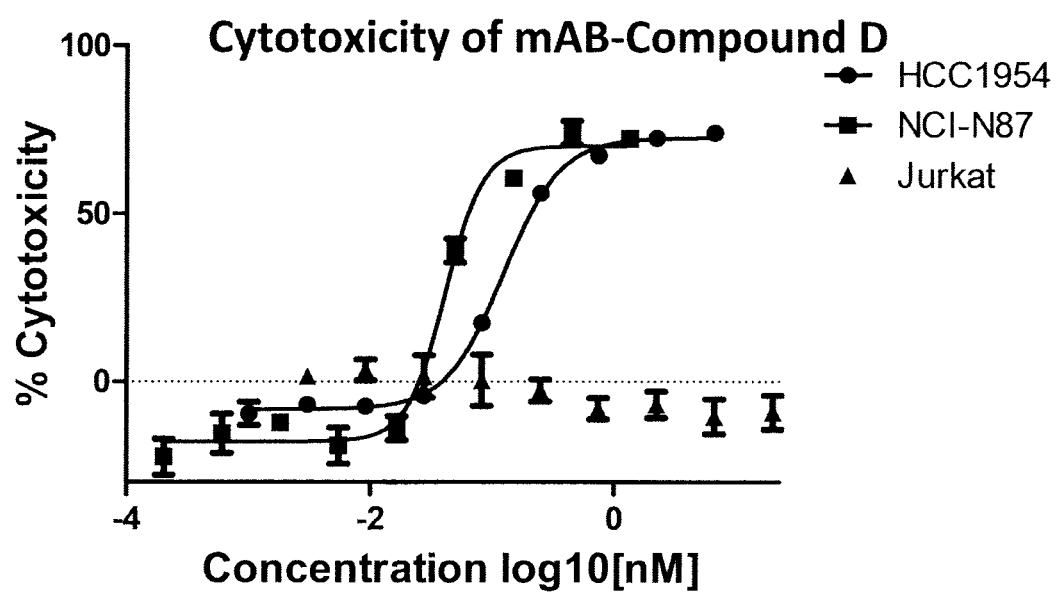
FIG. 4 shows a cytotoxicity data plot for Compound D on three cell lines (HCC1954, NCI-N87, and Jurkat).
Figure 5:
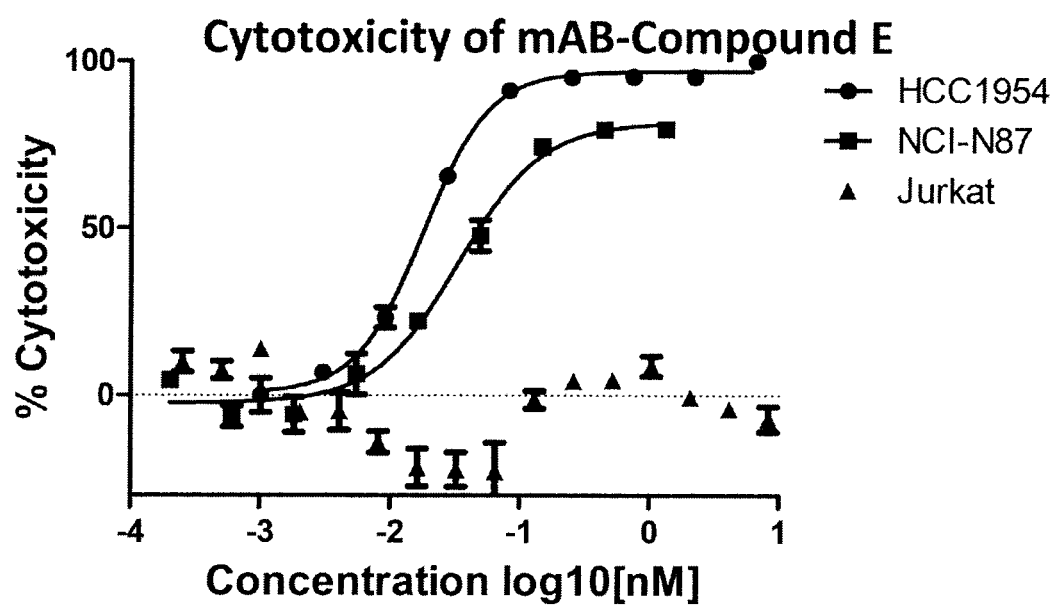
FIG. 5 shows a cytotoxicity data plot for Compound E on three cell lines (HCC1954, NCI-N87, and Jurkat).
Figure 6:
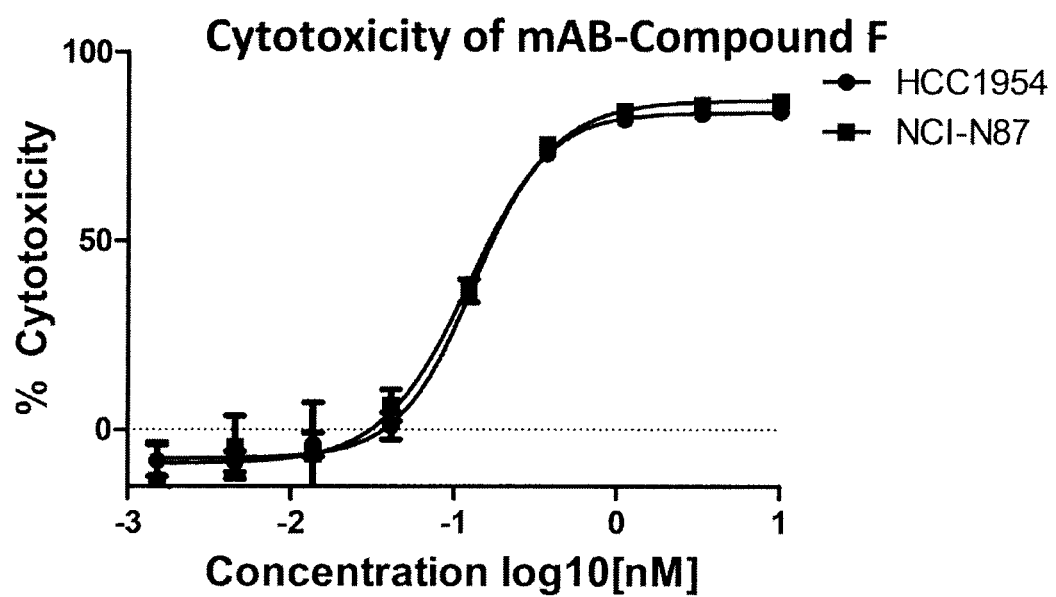
FIG. 6 shows a cytotoxicity data plot for Compound F on two cell lines (HCC1954 and NCI-N87).
Figure 7:
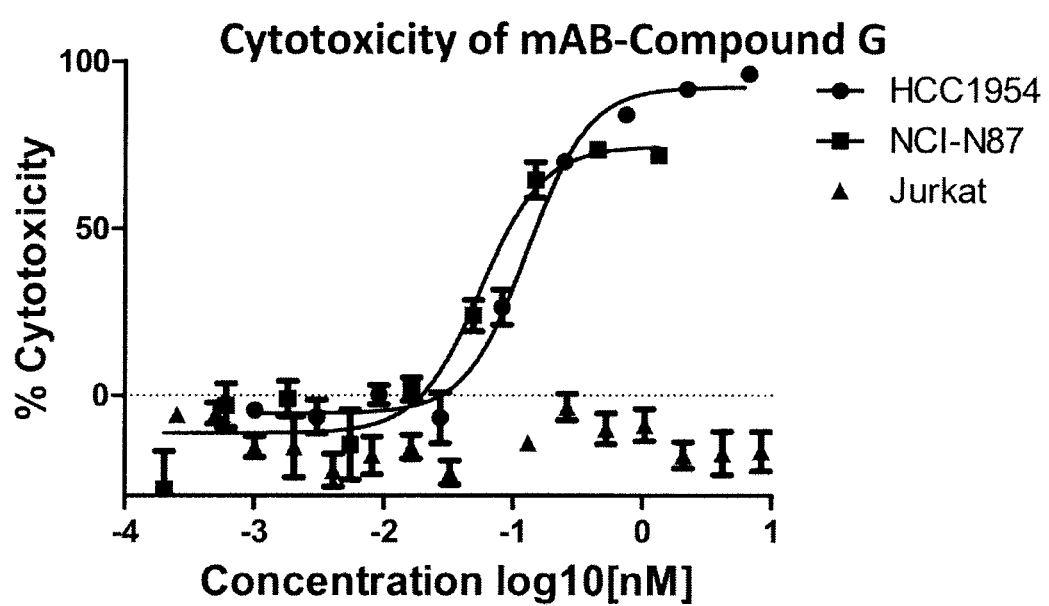
FIG. 7 shows a cytotoxicity data plot for Compound G on three cell lines (HCC1954, NCI-N87, and Jurkat).
Figure 8:
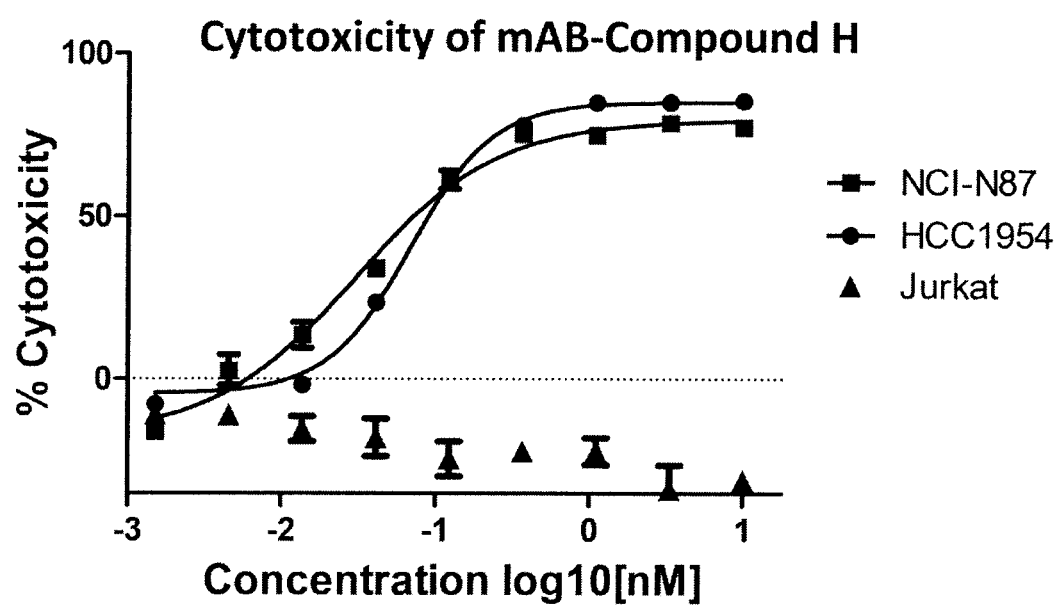
FIG. 8 shows a cytotoxicity data plot for Compound H on three cell lines (HCC1954, NCI-N87, and Jurkat).
Figure 9:
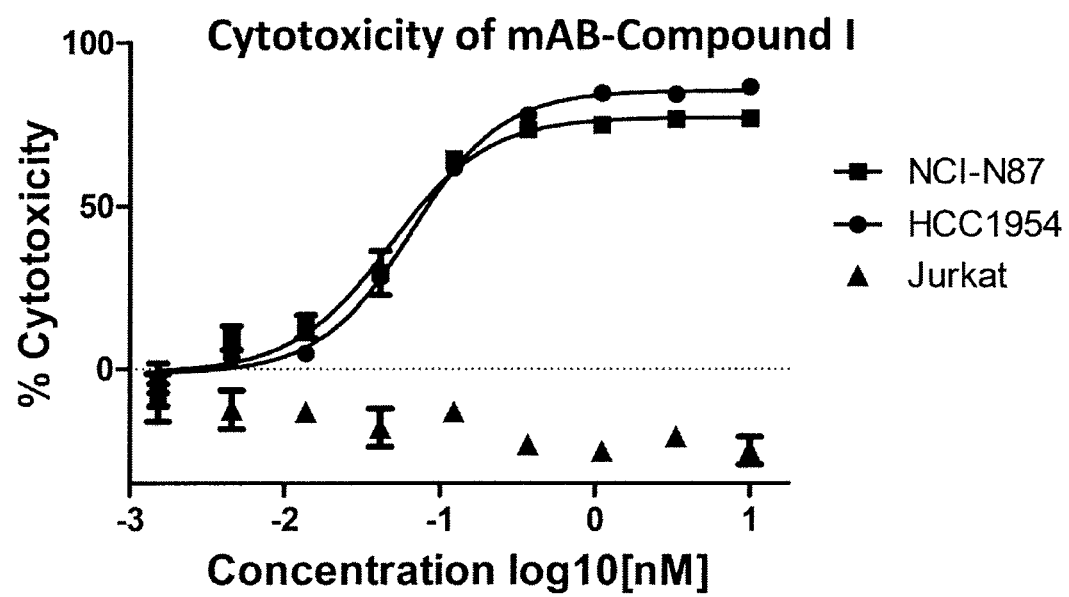
FIG. 9 shows a cytotoxicity data plot for Compound I on three cell lines (HCC1954, NCI-N87, and Jurkat).
Figure 10:
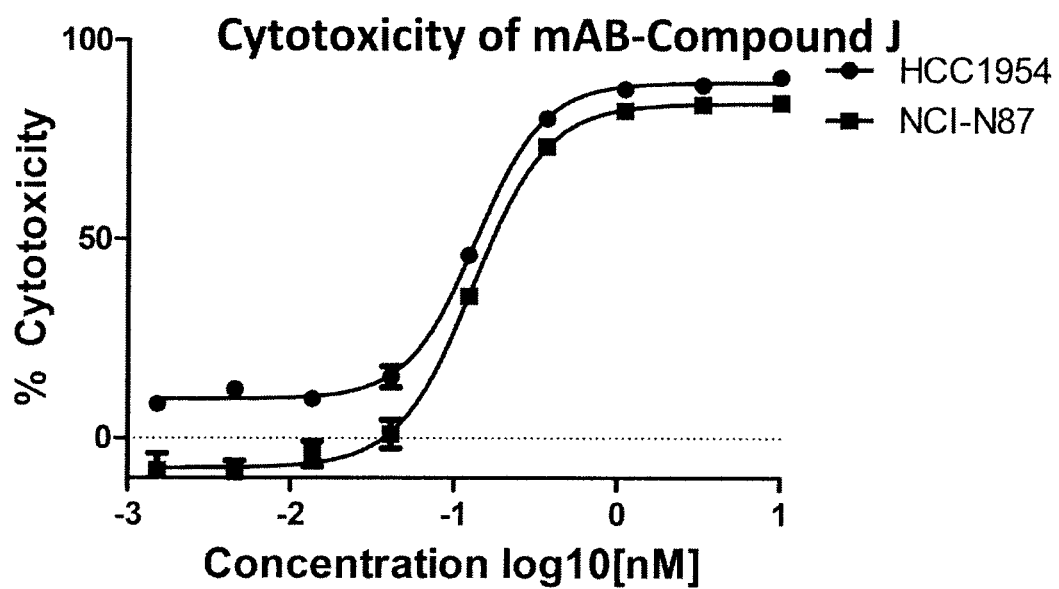
FIG. 10 shows a cytotoxicity data plot for Compound J on two cell lines (HCC1954 and NCI-N87).
Figure 11:
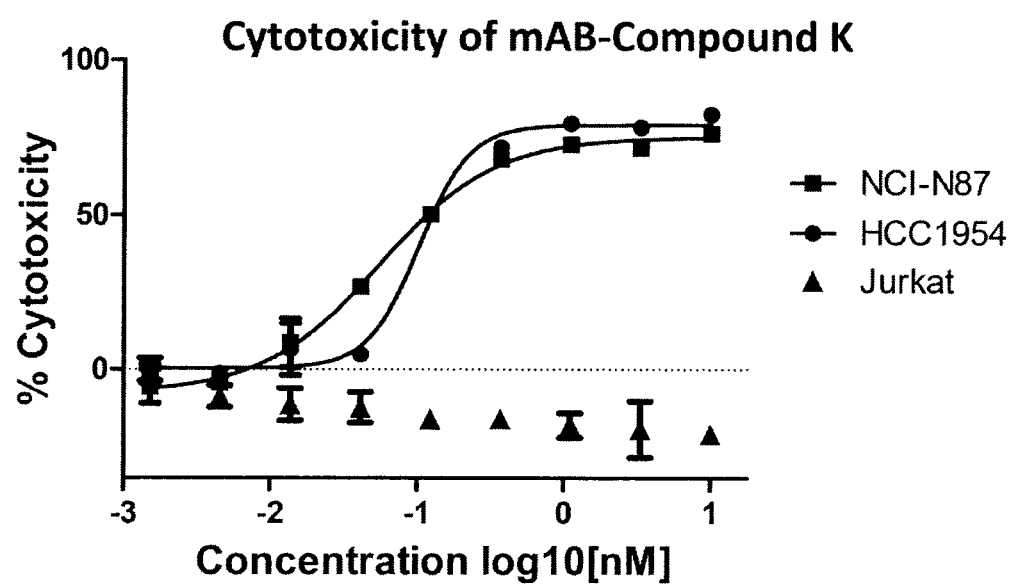
FIG. 11 shows a cytotoxicity data plot for Compound K on three cell lines [HCC1954 (human breast cancer), NCI-N87 (human gastric cancer), and Jurkat (human T cell leukemia)].

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless stated otherwise, the following terms and phrases as used herein are intended to have the following meanings. When trade names are used herein, applicants intend to independently include the trade name product formulation, the generic drug, and the active pharmaceutical ingredient(s) of the trade name product.

The term "antibody" herein is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity. The term "antibody" refers to a full-length immunoglobulin molecule or a functionally active portion of a full-length immunoglobulin molecule, i.e., a molecule that contains an antigen binding site that immunospecifically binds an antigen of a target of interest or part thereof. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect the immunoglobulin is of human, murine, or rabbit origin. In another aspect, the antibodies are polyclonal, monoclonal, multi-specific (e.g., bispecific), human, humanized or chimeric antibodies, linear antibodies, single chain antibodies, diabodies, maxibodies, minibodies, Fv, Fab fragments, F(ab') fragments, F(ab')2 fragments, fragments produced by a Fab expression library, anti-idiotypic (anti-Id) antibodies, CDR's, and epitope-binding fragments of any of the above which immunospecifically bind to a target antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies (see, e.g., U.S. Pat. No. 4,816,567; and Morrison et al., 1984, Proc. Natl. Acad. Sci. USA 81:6851-6855). Monoclonal antibodies also include humanized antibodies may contain a completely human constant region and a CDRs from a nonhuman source.

An "intact" antibody is one which comprises an antigen-binding variable region as well as a light chain constant domain (CL) and heavy chain constant domains, $C_{H1}$, $C_{H2}$ and $C_{H3}$. The constant domains may be native sequence constant domains (e.g., human native sequence constant domains) or amino acid sequence variant thereof.

An intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity (CDC; Fc receptor binding; antibody-dependent cell-mediated cytotoxicity (ADCC); phagocytosis; down regulation of cell surface receptors (e.g., B cell receptor; BCR), etc. In some embodiments, the antibody lacks effector function.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; maxibodies; minibodies; and multispecific antibodies formed from antibody fragment(s).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful in targeting a cell expressing the antigen.

A "native sequence" polypeptide is one which has the same amino acid sequence as a polypeptide derived from nature. Such native sequence polypeptides can be isolated from nature or can be produced by recombinant or synthetic means. Thus, a native sequence polypeptide can have the amino acid sequence of naturally-occurring human polypeptide, murine polypeptide, or polypeptide from any other mammalian species.

The term "amino acid" or "residue" as used herein includes any one of the twenty naturally occurring amino acids, the D-form of any one of the naturally-occurring amino acids, non-naturally occurring amino acids, and derivatives, analogs, and mimetics thereof. Any amino acid, including naturally occurring amino acids, may be purchased commercially or synthesized by methods known in the art. Examples of non-naturally-occurring amino acids include citrulline ("Cit"), norleucine ("Nle"), norvaline ("Nva"), β-Alanine, L- or D-naphthalanine, ornithine ("Orn"), homoarginine (homoArg) and others well known in the peptide art, including those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Common amino acids may be referred to by their full name, standard single-letter notation, or standard three-letter notation for example: A, Ala, alanine; C, Cys, cysteine; D, Asp, aspartic; E, Glu, glutamic acid; F, Phe, phenylalanine; G, Gly, glycine; H, His, histidine; I, Ile isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; Y, Tyr, tyrosine. Any and all of the amino acids in the compositions herein can be naturally occurring, synthetic, and derivatives or mimetics thereof. When the amino acid residues contain one or more chiral centers, any of the D, L, meso, threo or erythro (as appropriate) racemates or mixtures thereof, fall within the scope of this invention. The terms "intracellularly cleaved" and "intracellular cleavage" refer to a process or reaction inside a cell on a composition of the invention. In one embodiment, the junction peptide bond (JPB) linking the payload (P) to the linker (L) is broken, liberating payload (P) from targeting moiety (T) inside the cell. As disclosed herein, in one embodiment, the liberated payload (P) may be a compound having a structure selected from formula (IV) and formula (V) and formula (XIX). Other linkers known in the art may also be used in the invention. Linkers may be, for example, enzymatically cleavable or chemically cleavable, or non-cleavable. In one embodiment, a payload may be liberated through the degradation or proteolysis of (T) and/or (L).

The terms "extracellularly cleaved" and "extracellular cleavage" refer to a process or reaction outside a cell on a composition of the invention. In one embodiment, the junction peptide bond (JPB) linking the payload (P) to the linker (L) is broken, liberating payload (P) from targeting moiety (T) outside a cell. As disclosed herein, in one embodiment, the liberated payload (P) is a compound having a structure selected from formula (IV), (V) and (XIX). Accordingly, in one embodiment, the invention provides compositions having the following structure:

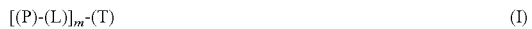

wherein (P) is a payload compound, (L) is absent or a linker, (T) is a targeting moiety, and m is an integer between from 1 to 10. In certain embodiments, m is 1.

In one embodiment, (P) is linked to (T) through (L) as depicted in the following structure:

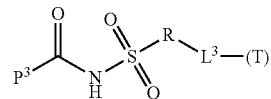

wherein:

R is selected from the group consisting of optionally substituted alkyl, optionally substituted alkylamino, optionally substituted cycloalkyl, optionally substituted aryl, optionally substituted heterocyclyl, optionally substituted heteroaryl, —COR$^{27}$—, —CSR$^{27}$—, —OR$^{27}$—, and —NHR$^{27}$—, wherein each R$^{27}$ is, independently, optionally substituted alkyl, optionally substituted alkylamino, optionally substituted cycloalkyl, optionally substituted aryl, optionally substituted heterocyclyl, and optionally substituted heteroaryl;

P$^3$ is (P) or a portion of (P);

L$^3$ is (L) or a portion of (L); and (T) is a targeting moiety.

In one embodiment, (P)-(L) has the following structure (II):

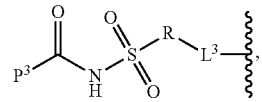

wherein:

R is selected from the group consisting of optionally substituted alkyl, optionally substituted alkylamino, optionally substituted cycloalkyl, optionally substituted aryl, optionally substituted heterocyclyl, optionally substituted heteroaryl, —COR$^{27}$—, —CSR$^{27}$—, —OR$^{27}$—, and —NHR$^{27}$—, wherein each R$^{27}$ is, independently, optionally substituted alkyl, optionally substituted alkylamino, optionally substituted cycloalkyl, optionally substituted aryl, optionally substituted heterocyclyl, and optionally substituted heteroaryl, or R is absent, (P) is P$^3$ and any portion of N-acyl sulfonamide-R bound to P$^3$ after cleavage; and (L) is L$^3$ and any portion of N-acyl sulfonamide-R bound to L$^3$ after cleavage.

In a preferred embodiment, R is selected from the group consisting of optionally substituted alkyl, optionally substituted alkylamino, optionally substituted cycloalkyl, optionally substituted aryl, optionally substituted heterocyclyl and optionally substituted heteroaryl, or R is absent.

In some embodiments, R is present and (L) is present and (L) and (P) are linked by a peptide bond.

In some embodiments, (L) and $L^3$ are absent and (P) is bonded to (T) and has the structure of Formula (XXXI):

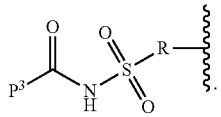
(XXXI)

A wide variety of compounds find use as (P) in the invention. Of particular interest include, antibiotics, diagnostic agents (e.g. detectable labels), anti-inflammatory agents, anti-viral agents, cytotoxic agents, and anti-cancer drugs.

Also provided are compounds of formula (I) that are enzymatically cleavable and capable of releasing payload compound (P) from targeting moiety (T) upon enzymatic cleavage. In some embodiments, the payload compound is a biologically active compound. In some embodiments, the payload compound is a cytotoxic or cytostatic drug.

As disclosed herein, N-acyl sulfonamide-containing cleavable conjugates may be synthesized such that an N-acyl sulfonamide moiety is covalently linked to a chemical group, (R), which is covalently bonded to a nitrogen atom that forms an enzymatically cleavable peptide bond (the junction peptide bond (JPB)) with the carbonyl group of an amino acid that forms part of the amino acid sequence facilitating enzymatic cleavage of the JPB. Moieties similar to N-acyl sulfonamides, such as N-acyl sulfamamides, may also be used.

In one embodiment, the invention provides compounds of Formula I:

[(P)-(L)]$_m$-(T)  (I)

wherein (P) is a biologically active compound having the following structure (XXX):

(XXX)

In one embodiment, the invention provides compounds of Formula I:

[(P)-(L)]$_m$-(T)  (I)

wherein (P) is a biologically active compound, (L) is a linker, (T) is a targeting moiety, and m is an integer from 1 to 10, wherein (P) has the following structure XX:

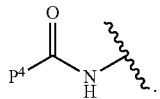
(XX)

and wherein (L)-(T) has the following structure (III):

(III)

wherein $P^4$ is the remaining portion of payload compound (P) and the —NH— group bonded to R in formula (II) forms a peptide bond referred to herein as the junction peptide bond (JPB) with (AA)$^1$ in formula (III), wherein the JPB is enzymatically cleavable, wherein R is selected from the group consisting of optionally substituted alkyl, optionally substituted alkylamino, optionally substituted cycloalkyl, optionally substituted aryl, optionally substituted heterocyclyl, optionally substituted heteroaryl, —COR$^{27}$—, —CSR$^{27}$—, —OR$^{27}$—, and —NHR$^{27}$—, wherein each R$^{27}$ is, independently, optionally substituted alkyl, optionally substituted alkylamino, optionally substituted cycloalkyl, optionally substituted aryl, optionally substituted heterocyclyl, and optionally substituted heteroaryl, wherein each AA is independently an amino acid, wherein x is an integer from 0 to 25, wherein (L') is the remaining portion (if any) of linker (L), wherein (T) is the targeting moiety, and wherein (AA)$^1$-(AA)$_x$ taken together comprises an amino acid sequence capable of facilitating enyzmatic cleavage of the JPB.

In certain embodiments, m is 1.

In some embodiments, R is selected from the group consisting of optionally substituted alkyl, optionally substituted alkylamino, optionally substituted cycloalkyl, optionally substituted aryl, optionally substituted heterocyclyl, and optionally substituted heteroaryl.

In one embodiment, —R—NH— of formula XX is selected from:

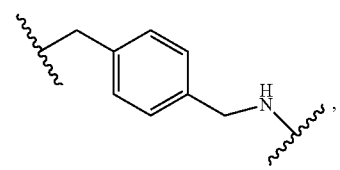

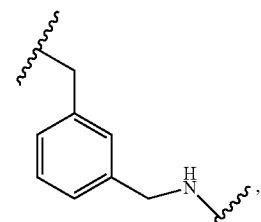

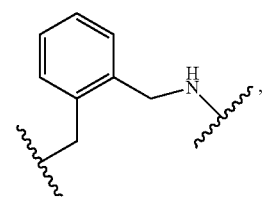

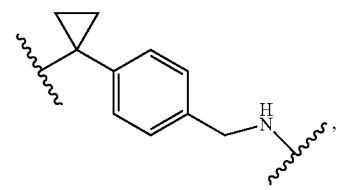

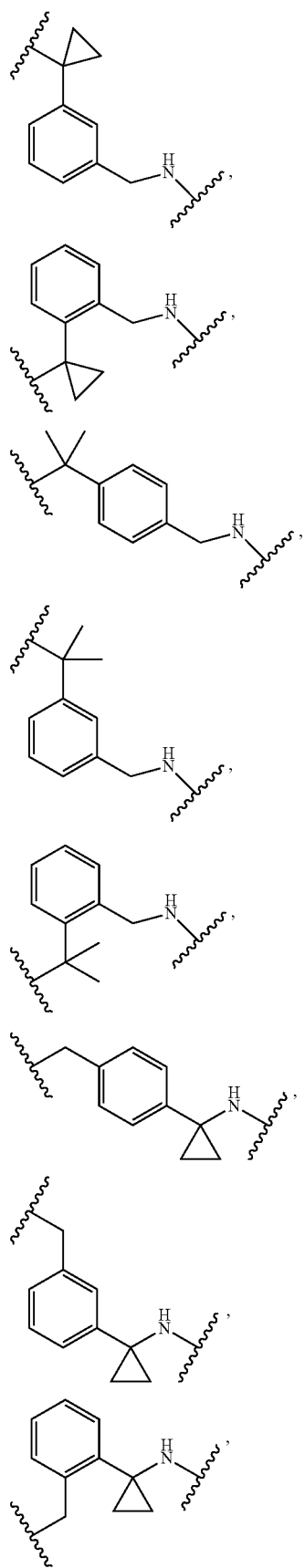
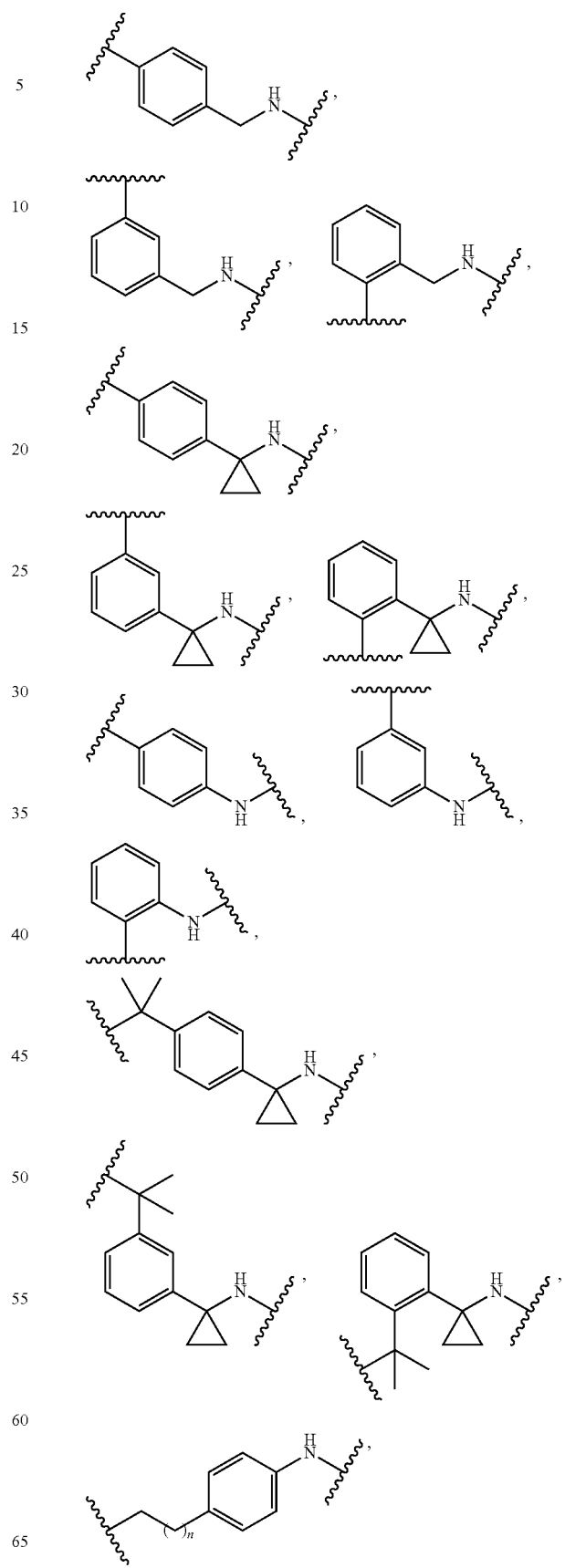

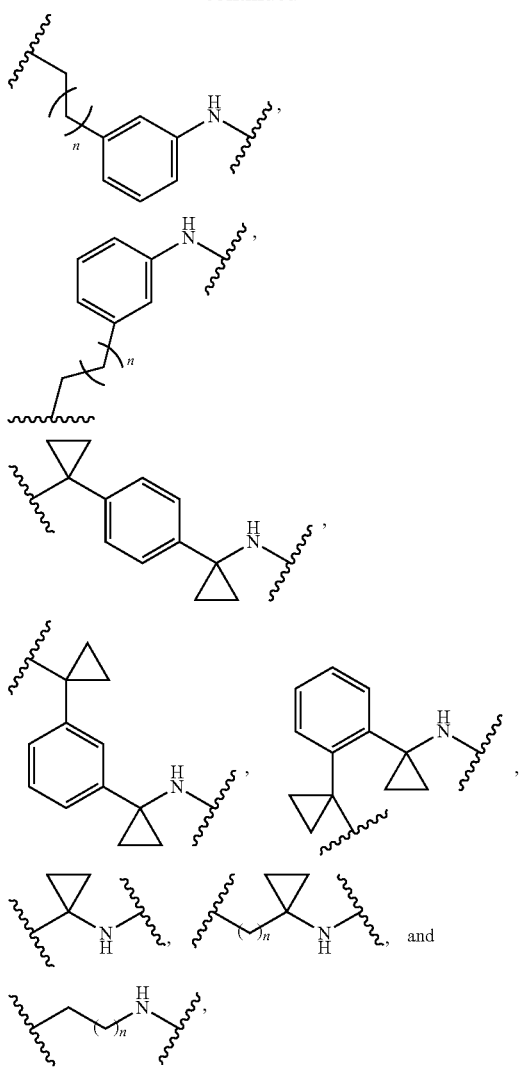
wherein each n is independently an integer from 0-10.
In a preferred embodiment, —R—NH— of formula XX is selected from:
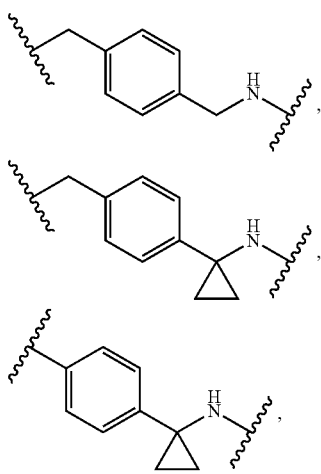
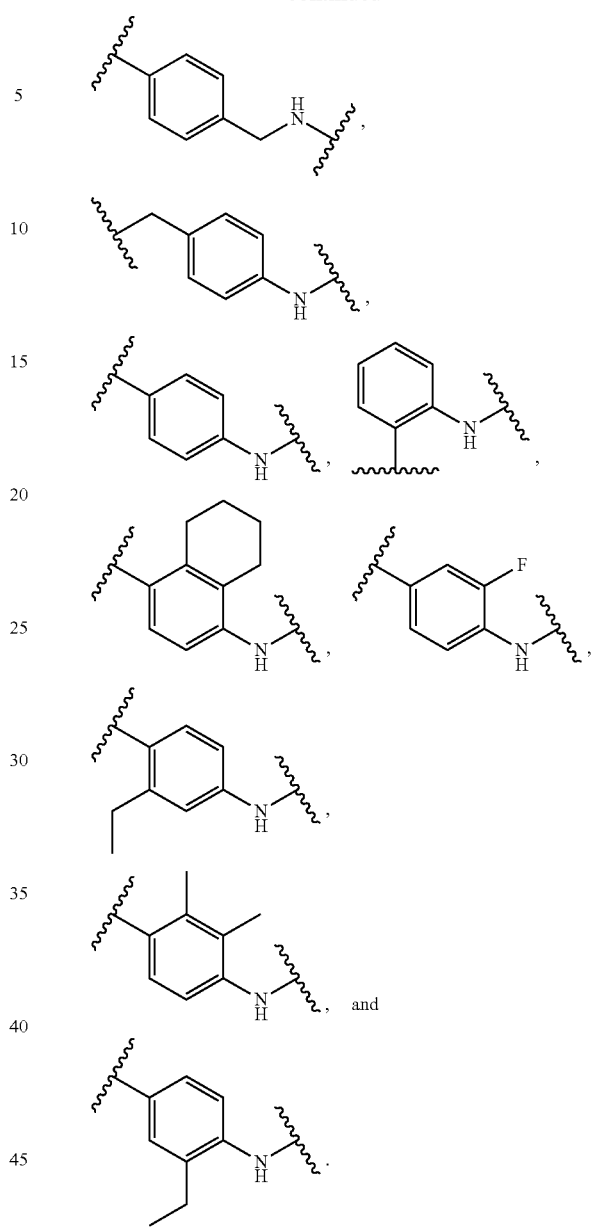
In a preferred embodiment, —R—NH— of formula XX is selected from:
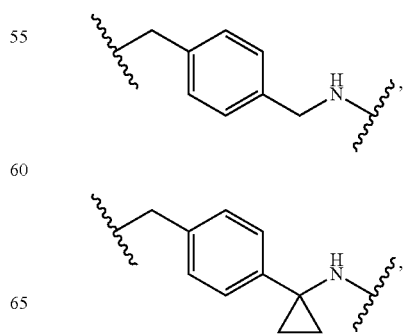

-continued

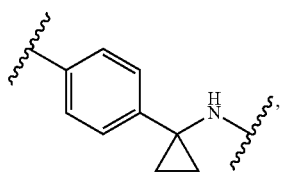

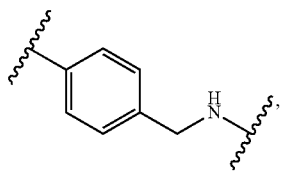

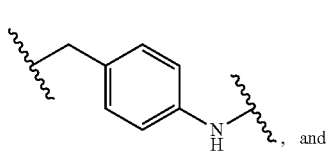, and

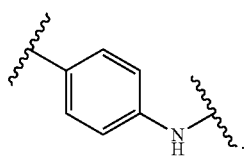.

In one embodiment, cleavage results in a compound of formula (IV):

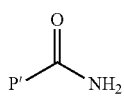

(IV)

wherein P' corresponds to P⁴ in formula XX.

In one embodiment, cleavage results in a compound of formula (XIX):

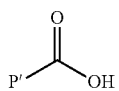

(XIX)

wherein P' corresponds to P⁴ in formula XX.

In one embodiment, cleavage of the JPB results in a compound of formula (V):

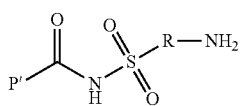

(V)

wherein P' corresponds to P⁴ in formula XX.

In one embodiment of the invention, P has the following structure (VI)

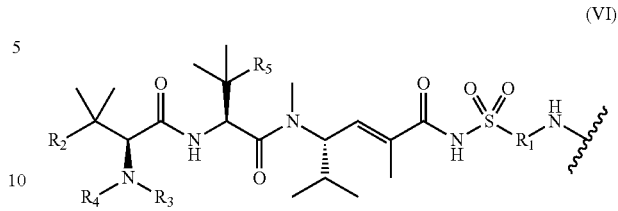

(VI)

or a stereoisomer, prodrug or pharmaceutically acceptable salt thereof, and (L)-(T) has the following structure (III):

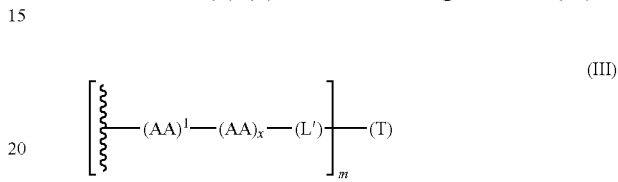

(III)

wherein:
m is an integer from 1 to 10;
$R_1$ is selected from the group consisting of optionally substituted alkyl, optionally substituted alkylamino, optionally substituted cycloalkyl, optionally substituted aryl, optionally substituted heterocyclyl and optionally substituted heteroaryl, —$COR_{24}$—, —$CSR_{24}$—, —$OR_{24}$—, and —$NHR_{24}$—, wherein each $R_{24}$ is, independently, optionally substituted alkyl, optionally substituted alkylamino, optionally substituted cycloalkyl, optionally substituted aryl, optionally substituted heterocyclyl and optionally substituted heteroaryl;
$R_2$ is selected from the group consisting of optionally substituted alkyl, optionally substituted alkylamino, optionally substituted cycloalkyl, optionally substituted aryl, optionally substituted heterocyclyl and optionally substituted heteroaryl;
$R_3$ is selected from the group consisting of H and $C_{1-6}$ alkyl;
$R_4$ is selected from the group consisting of H and $C_{1-6}$ alkyl; and
$R_5$ is selected from the group consisting of $C_{1-6}$ alkyl and —SH, and
wherein the —NH— group bonded to $R_1$ in formula (VI) forms the junction peptide bond (JPB) with $(AA)^1$ in formula (III), wherein the JPB is enzymatically cleavable, wherein each AA is independently an amino acid, wherein x is an integer from 0 to 25, wherein (L') is the remaining portion (if any) of linker (L), wherein (T) is the targeting moiety, and wherein $(AA)^1$-$(AA)_x$ taken together comprises an amino acid sequence capable of facilitating enyzmatic cleavage of the (JPB).

In a preferred embodiment, $R_3$ is H;
In a preferred embodiment, $R_4$ is methyl.
In a preferred embodiment, m is 1.
In one embodiment, $R_1$ is selected from the group consisting of optionally substituted alkyl, optionally substituted alkylamino, optionally substituted cycloalkyl, optionally substituted aryl, optionally substituted heterocyclyl and optionally substituted heteroaryl.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —$OR_{28}$, —$O_2CR_{28}$, —SH, —$SR_{28}$, —$SOCR_{28}$, —$NH_2$, —N$_3$, —NHR$_{28}$, —N(R$_{28}$)$_2$, —NHCOR$_{28}$, —NR$_{28}$COR$_{28}$, —I, —Br, —Cl, —F, —CN, —CO$_2$H, —CO$_2$R$_{28}$, —CHO, —COR$_{28}$, —CONH$_2$, —CONHR$_{28}$, —CON(R$_{28}$)$_2$, —COSH, —COSR$_{28}$, —NO$_2$, —SO$_3$H, —SOR$_{28}$ or —SO$_2$R$_{28}$, wherein each R$_{28}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, R2 is selected from one of the following structures (A), (B), (C), (D):

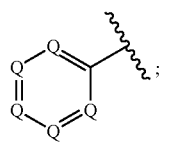 (A)

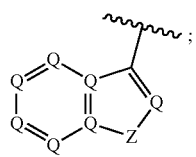 (B)

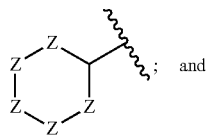 (C)

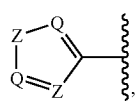 (D)

wherein:
each Q is independently selected from CR$_{29}$ or N;
each Z is independently selected from C(R$_{29}$)$_2$, NR$_{29}$, S, or O;
each R$_{29}$ is, independently, selected from the group consisting of H, —OH, —R$_{28}$, —OR$_{28}$, —O$_2$CR$_{28}$, —SH, —SR$_{28}$, —SOCR$_{28}$, —NH$_2$, —N$_3$, —NHR$_{28}$, —N(R$_{28}$)$_2$, —NHCOR$_{28}$, —NR$_{28}$COR$_{28}$, —R$_{28}$NH$_2$, —I, —Br, —Cl, —F, —CN, —CO$_2$H, —CO$_2$R$_{28}$, —CHO, —COR$_{28}$, —CONH$_2$, —CONHR$_{28}$, —CON(R$_{28}$)$_2$, —COSH, —COSR$_{28}$, —NO$_2$, —SO$_3$H, —SOR$_{28}$ or —SO$_2$R$_{28}$, wherein each R$_{28}$ is, independently, alkyl optionally substituted with halogen, —OH or —SH.

In another further embodiment, R$_2$ is selected from the group consisting of:

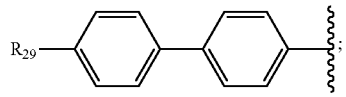

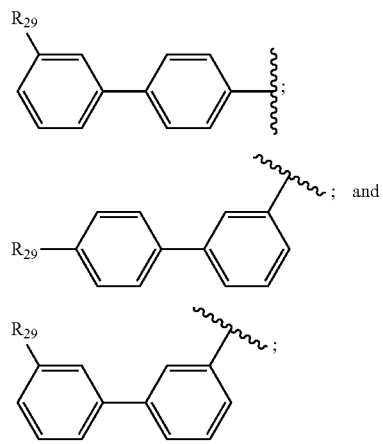

wherein each R$_{29}$ is, independently, selected from the group consisting of H, —OH, —R$_{28}$, —OR$_{28}$, —O$_2$CR$_{28}$, —SH, —SR$_{28}$, —SOCR$_{28}$, —NH$_2$, —N$_3$, —NHR$_{28}$, —N(R$_{28}$)$_2$, —NHCOR$_{28}$, —NR$_{28}$COR$_{28}$, —R$_{28}$NH$_2$, —I, —Br, —Cl, —F, —CN, —CO$_2$H, —CO$_2$R$_{28}$, —CHO, —COR$_{28}$, —CONH$_2$, —CONHR$_{28}$, —CON(R$_{28}$)$_2$, —COSH, —COSR$_{28}$, —NO$_2$, —SO$_3$H, —SOR$_{28}$ or —SO$_2$R$_{28}$, wherein each R$_{28}$ is, independently, alkyl optionally substituted with halogen, —OH or —SH.

In another further embodiment, R$_2$ is selected from the group consisting of:

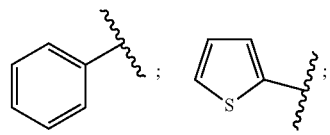

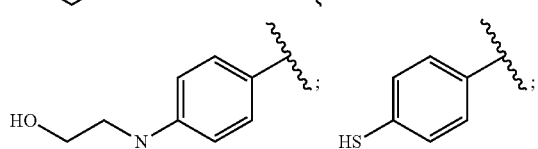

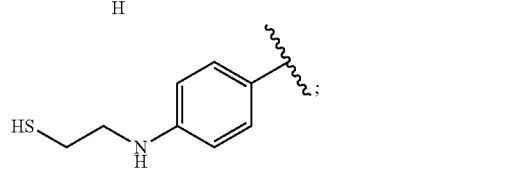

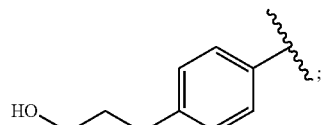

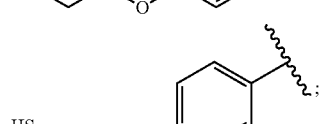

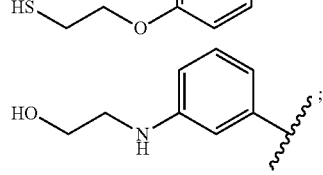

-continued

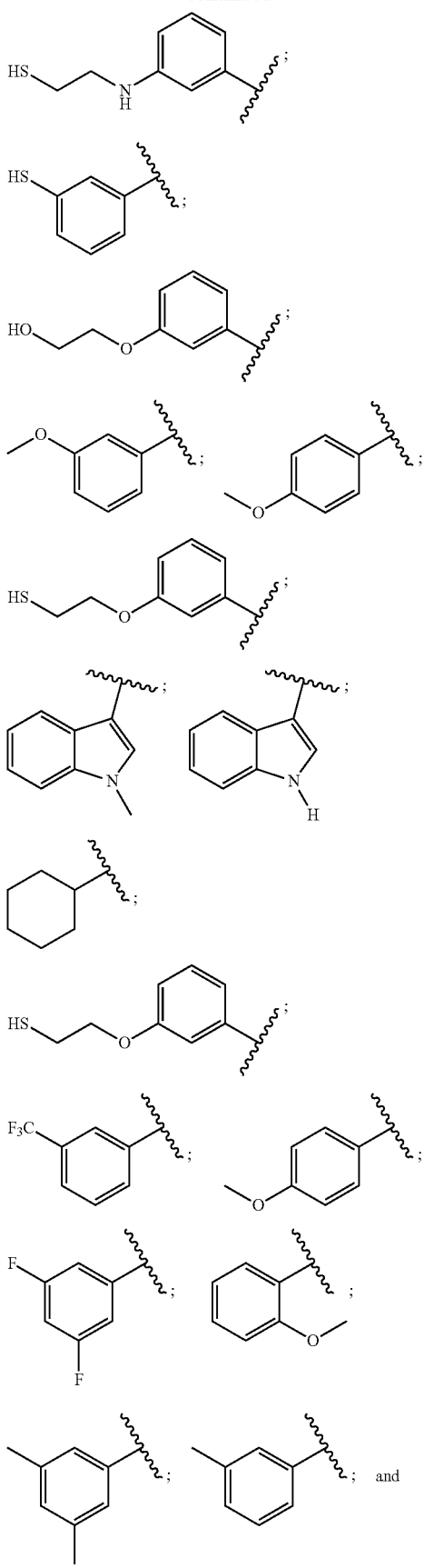

-continued

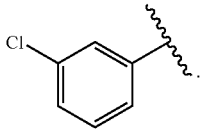

In another further embodiment, $R_2$ is:

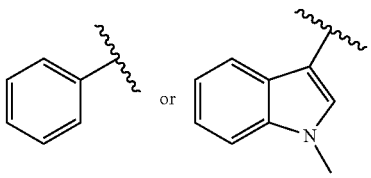

In another further embodiment, $R_3$, $R_4$ and R are each methyl.

In another further embodiment, $R_3$ is H, $R_4$ is methyl, and $R_5$ is methyl.

It is understood that any embodiment of the compounds of structure (VI), as set forth above, and any specific substituent set forth herein for a $R_1$, $R_2$, $R_3$, $R_4$, $R_5$, $R_{28}$, or $R_{29}$ group in the compounds of structure (VI), as set forth herein, may be independently combined with other embodiments and/or substituents of compounds of structure (VI) to form embodiments of the present disclosure not specifically set forth above. In addition, in the event that a list of substituents is listed for any particular $R_1$, $R_2$, $R_3$, $R_4$, $R_5$, $R_{28}$, or $R_{29}$ in a particular embodiment and/or claim, it is understood that each individual substituent may be deleted from the particular embodiment and/or claim and that the remaining list of substituents will be considered to be within the scope of the present disclosure.

In one embodiment of the invention, P has the following structure (XIV):

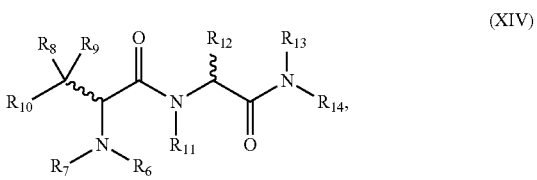

or a stereoisomer, prodrug or pharmaceutically acceptable salt thereof, and $(L^a)$-(T) has the following structure (III):

wherein:

$R_6$ and $R_7$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$; or $R_7$ and $R_{10}$ are fused and form a ring;

$R_8$ and $R_9$ are independently selected from the group consisting of: H, R', ArR'—, or $R_8$ and $R_9$ are joined to form a ring;

$R_{10}$ is selected from the group consisting of: H, R', ArR'—, and Ar; or $R_{10}$ and $R_7$ are fused and form a ring;

$R_{11}$ is selected from the group consisting of: H, R', and ArR'—;

$R_{12}$ and $R_{13}$ are independently selected from the group consisting of: H, R', and ArR'—;

$R^{14}$ is:

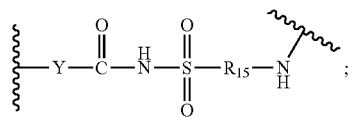

and $R_{15}$ is selected from the group consisting of optionally substituted alkyl, optionally substituted alkylamino, optionally substituted cycloalkyl, optionally substituted aryl, optionally substituted heterocyclyl and optionally substituted heteroaryl, —$COR_{24}$—, —$CSR_{24}$—, —$OR_{24}$—, and —$NHR_{24}$—, wherein each $R_{24}$ is, independently, optionally substituted alkyl, optionally substituted alkylamino, optionally substituted cycloalkyl, optionally substituted aryl, optionally substituted heterocyclyl and optionally substituted heteroaryl;

wherein R' is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —$OR_{16}$, —$O_2CR_{16}$, —SH, —$SR_{16}$, —$SOCR_{16}$, —$NH_2$, —$NHR_{16}$, —$N(R_{16})_2$, —$NHCOR_{16}$, —$NR_{16}COR_{16}$, —I, —Br, —Cl, —F, —CN, —$CO_2H$, —$CO_2R_{16}$, —CHO, —$COR_{16}$, —$CONH_2$, —$CONHR_{16}$, —$CON(R_{16})_2$, —COSH, —$COSR_{16}$, —$NO_2$, —$SO_3H$, —$SOR_{16}$, —$SO_2R_{16}$, wherein $R_{16}$ is a linear, branched or cyclic, one to ten carbon saturated or unsaturated alkyl group;

the ring formed by joining $R_8$ and $R_9$ is a three to seven member non-aromatic cyclic skeleton within the definition of R', Y is defined as a moiety selected from the group consisting of: a linear, saturated or unsaturated, one to six carbon alkyl group, optionally substituted with R', ArR'—, or X; and, X is defined as a moiety selected from the group consisting of: —OH, —OR', =O, =S, —$O_2CR'$, —SH, —SR', —SOCR', —$NH_2$, —NHR', —$N(R')_2$, —NHCOR', —NRCOR', —I, —Br, —Cl, —F, —CN, —$CO_2H$, —$CO_2R'$, —CHO, —COR', —$CONH_2$, —CONHR', —$CON(R')_2$, —COSH, —COSR', —$NO_2$, —$SO_3H$, —SOR', and —$SO_2R'$; and wherein the —NH— group bonded to $R_{15}$ in formula (XIV) forms a junction peptide bond (JPB) with $(AA)^1$ in formula (III), wherein the JPB is enzymatically cleavable, wherein each AA is independently an amino acid, wherein x is an integer from 0 to 25, wherein (L') is the remaining portion (if any) of linker (L), wherein (T) is the targeting moiety, and wherein $(AA)^1$-$(AA)_x$ taken together comprises an amino acid sequence capable of facilitating enyzmatic cleavage of the (JPB).

In one embodiment, Ar is an aromatic ring selected from the group consisting of: phenyl, naphthyl, anthracyl, pyrrolyl.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$ wherein each $R_{28}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, $R_{10}$ is selected from one of the following structures (A), (B), (C), (D):

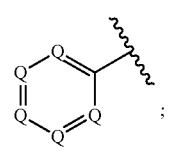

(A)

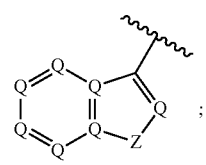

(B)

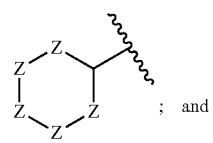

(C) ; and

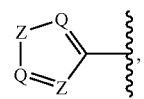

(D)

wherein:
each Q is independently selected from $CR_{29}$ or N;
each Z is independently selected from $C(R_{29})_2$, $NR_{29}$, S, or O;
each $R_{29}$ is, independently, selected from the group consisting of H, —OH, —$R_{28}$, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —$R_{28}NH_2$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, $R_{10}$ is selected from the group consisting of:

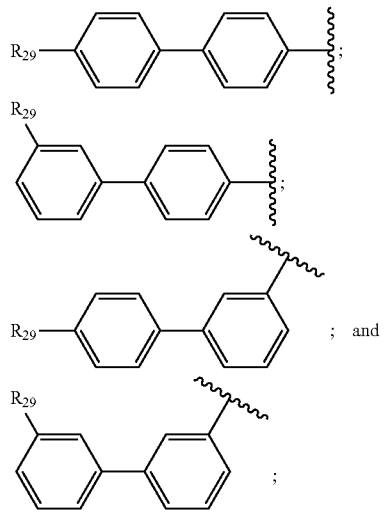

; and wherein each $R_{29}$ is, independently, selected from the group consisting of H, —OH, —$R_{28}$, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —$R_{28}NH_2$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, $R_{10}$ is selected from the group consisting of:

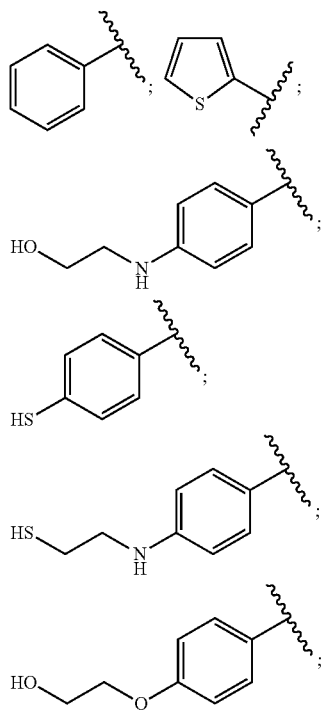

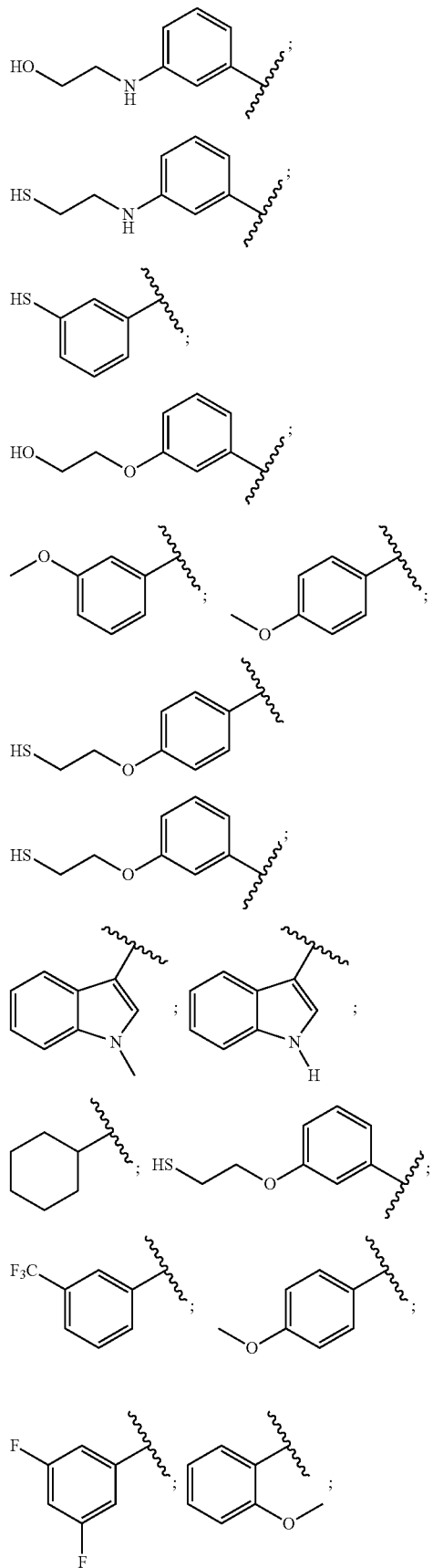

-continued

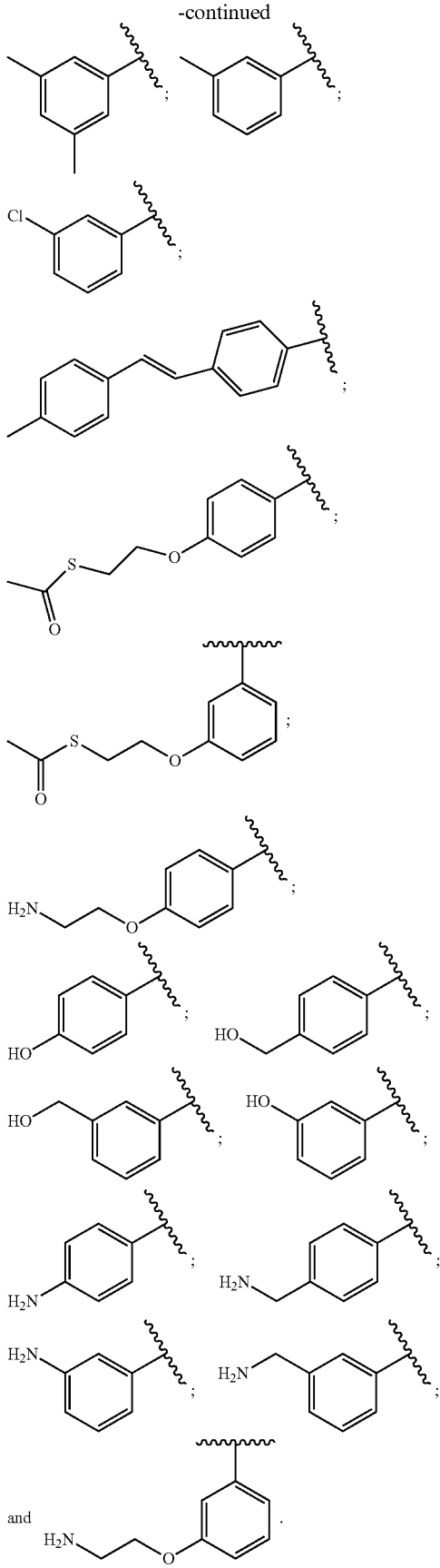

In another further embodiment, R$_{10}$ is:

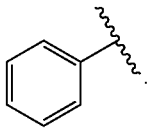 [SMILES: *c1ccccc1]

In another further embodiment, 1% and R$_7$ are each methyl.

In another further embodiment, 1% is H and R$_7$ is methyl.

In one embodiment, R$_{12}$ is branched C4 alkyl.

It is understood that any embodiment of the compounds of structure (XIV), as set forth h, and any specific substituent set forth herein for a R$_6$, R$_7$, R$_8$, R$_9$, R$_{10}$, R$_{11}$, R$_{12}$, R$_{13}$, R$_{14}$, R$_{15}$, R$_{16}$, R$_{28}$, or R$_{29}$ group in the compounds of structure (XIV), as set forth above, may be independently combined with other embodiments and/or substituents of compounds of structure (XIV) to form embodiments of the present disclosure not specifically set forth above. In addition, in the event that a list of substituents is listed for any particular R$_6$, R$_7$, R$_8$, R$_9$, R$_{10}$, R$_{11}$, R$_{12}$, R$_{13}$, R$_{14}$, R$_{15}$, R$_{16}$, R$_{28}$, or R$_{29}$ in a particular embodiment and/or claim, it is understood that each individual substituent may be deleted from the particular embodiment and/or claim and that the remaining list of substituents will be considered to be within the scope of the present disclosure.

In one embodiment of the invention, P has the following structure (XV):

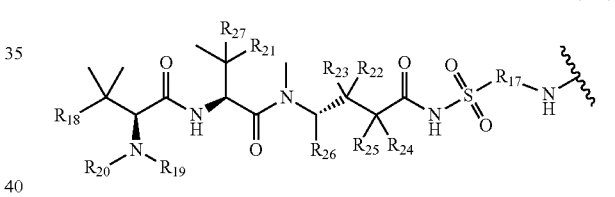

(XV)

or a stereoisomer, prodrug or pharmaceutically acceptable salt thereof; and (L)-(T) has the following structure (III):

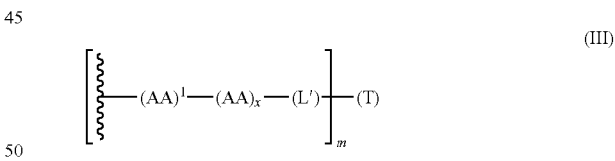

(III)

wherein:

R$_{17}$ is selected from the group consisting of optionally substituted alkyl, optionally substituted alkylamino, optionally substituted cycloalkyl, optionally substituted aryl, optionally substituted heterocyclyl and optionally substituted heteroaryl, —COR$_{24}$—, —CSR$_{24}$—, —OR$_{24}$—, and —NHR$_{24}$—, wherein each R$_{24}$ is, independently, optionally substituted alkyl, optionally substituted alkylamino, optionally substituted cycloalkyl, optionally substituted aryl, optionally substituted heterocyclyl and optionally substituted heteroaryl;

R$_{18}$ is selected from the group consisting of optionally substituted alkyl, optionally substituted alkylamino, optionally substituted cycloalkyl, optionally substituted aryl, optionally substituted heterocyclyl and optionally substituted heteroaryl;

$R_{19}$ is selected from the group consisting of H and $C_{1-6}$ alkyl;

$R_{20}$ is selected from the group consisting of H and $C_{1-6}$ alkyl;

$R_{21}$ and $R_{27}$ are independently selected from the group consisting of H, $C_{1-6}$ alkyl and —SH, with the proviso that $R_{21}$ and $R_{27}$ cannot both be H;

$R_{22}$, $R_{23}$, $R_{24}$ and $R_{25}$ are independently selected from the group consisting of H and $C_{1-6}$ alkyl, at least one of $R_{22}$ and $R_{23}$ is H; or $R_{23}$ and $R_{24}$ form a double bond, $R_{22}$ is H, and $R_{25}$ is H or $C_{1-6}$ alkyl; and $R_{26}$ is selected from the group consisting of H and $C_{1-6}$ alkyl; and wherein the —NH— group bonded to $R_{17}$ in formula (XV) forms a junction peptide bond (JPB) with $(AA)^1$ in formula (III), wherein the JPB is enzymatically cleavable, wherein each AA is independently an amino acid, wherein x is an integer from 0 to 25, wherein (L') is the remaining portion (if any) of linker (L), wherein (T) is the targeting moiety, and wherein $(AA)^1$-$(AA)_x$ taken together comprises an amino acid sequence capable of facilitating enyzmatic cleavage of the (JPB).

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —OR$_{28}$, —O$_2$CR$_{28}$, —SH, —SR$_{28}$, —SOCR$_{28}$, —NH$_2$, —N$_3$, —NHR$_{28}$, —N(R$_{28}$)$_2$, —NHCOR$_{28}$, —NR$_{28}$COR$_{28}$, —I, —Br, —Cl, —F, —CN, —CO$_2$H, —CO$_2$R$_{28}$, —CHO, —COR$_{28}$, —CONH$_2$, —CONHR$_{28}$, —CON(R$_{28}$)$_2$, —COSH, —COSR$_{28}$, —NO$_2$, —SO$_3$H, —SOR$_{28}$ or —SO$_2$R$_{28}$, wherein each R$_{28}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, $R_{18}$ is selected from one of the following structures (A), (B), (C), (D):

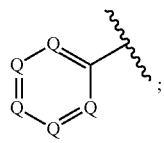

(A)

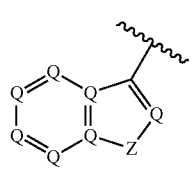

(B)

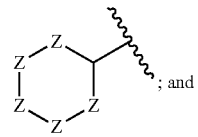

(C); and

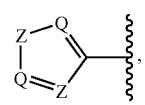

(D);

wherein:

each Q is independently CR$_{29}$ or N;

each Z is independently C(R$_{29}$)$_2$, NR$_{29}$, S, or O;

each R$_{29}$ is, independently, selected from the group consisting of H, —OH, —R$_{28}$, —OR$_{28}$, —O$_2$CR$_{28}$, —SH, —SR$_{28}$, —SOCR$_{28}$, —NH$_2$, —N$_3$, —NHR$_{28}$, —N(R$_{28}$)$_2$, —NHCOR$_{28}$, —NR$_{28}$COR$_{28}$, —R$_{28}$NH$_2$, —I, —Br, —Cl, —F, —CN, —CO$_2$H, —CO$_2$R$_{28}$, —CHO, —COR$_{28}$, —CONH$_2$, —CONHR$_{28}$, —CON(R$_{28}$)$_2$, —COSH, —COSR$_{28}$, —NO$_2$, —SO$_3$H, —SOR$_{28}$ or —SO$_2$R$_{28}$, wherein each R$_{28}$ is, independently, alkyl optionally substituted with halogen, —OH or —SH.

In another further embodiment, $R_{18}$ is selected from the group consisting of:

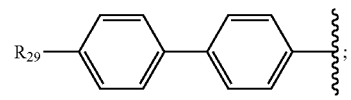

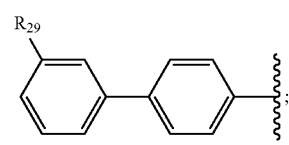

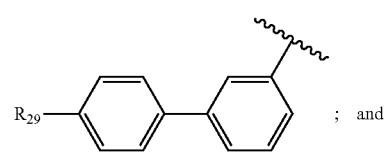; and

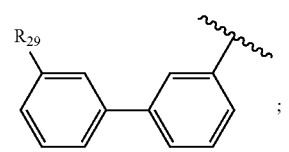;

wherein each R$_{29}$ is, independently, selected from the group consisting of H, —OH, —R$_{28}$, —OR$_{28}$, —O$_2$CR$_{28}$, —SH, —SR$_{28}$, —SOCR$_{28}$, —NH$_2$, —N$_3$, —NHR$_{28}$, —N(R$_{28}$)$_2$, —NHCOR$_{28}$, —NR$_{28}$COR$_{28}$, —R$_{28}$NH$_2$, —I, —Br, —Cl, —F, —CN, —CO$_2$H, —CO$_2$R$_{28}$, —CHO, —COR$_{28}$, —CONH$_2$, —CONHR$_{28}$, —CON(R$_{28}$)$_2$, —COSH, —COSR$_{28}$, —NO$_2$, —SO$_3$H, —SOR$_{28}$ or —SO$_2$R$_{28}$, wherein each R$_{28}$ is, independently, alkyl optionally substituted with halogen, —OH or —SH.

In another further embodiment, $R_{18}$ is selected from the group consisting of:
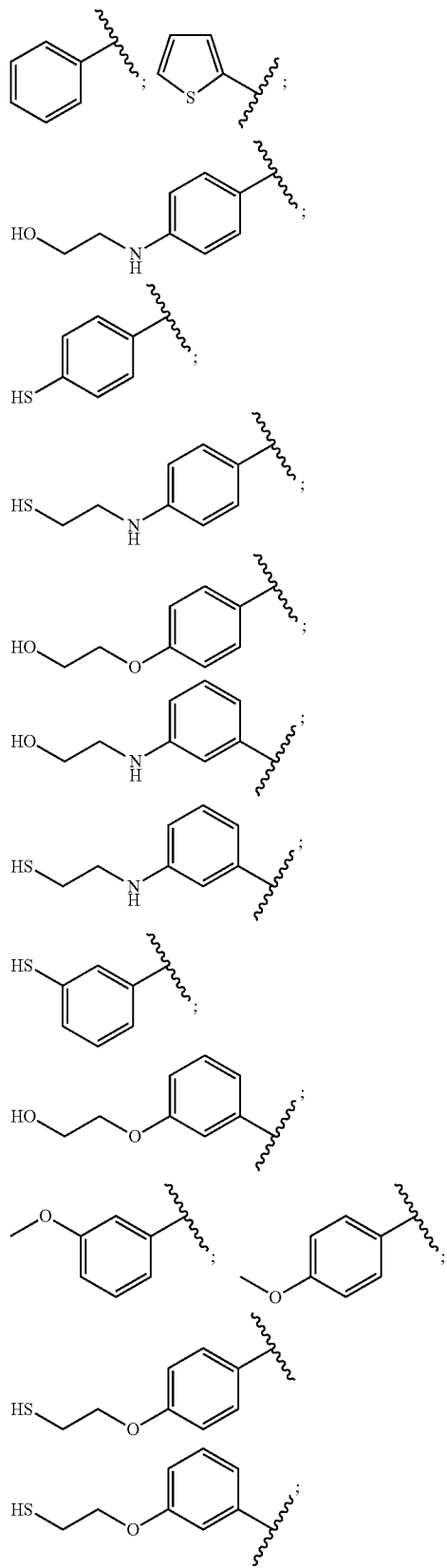
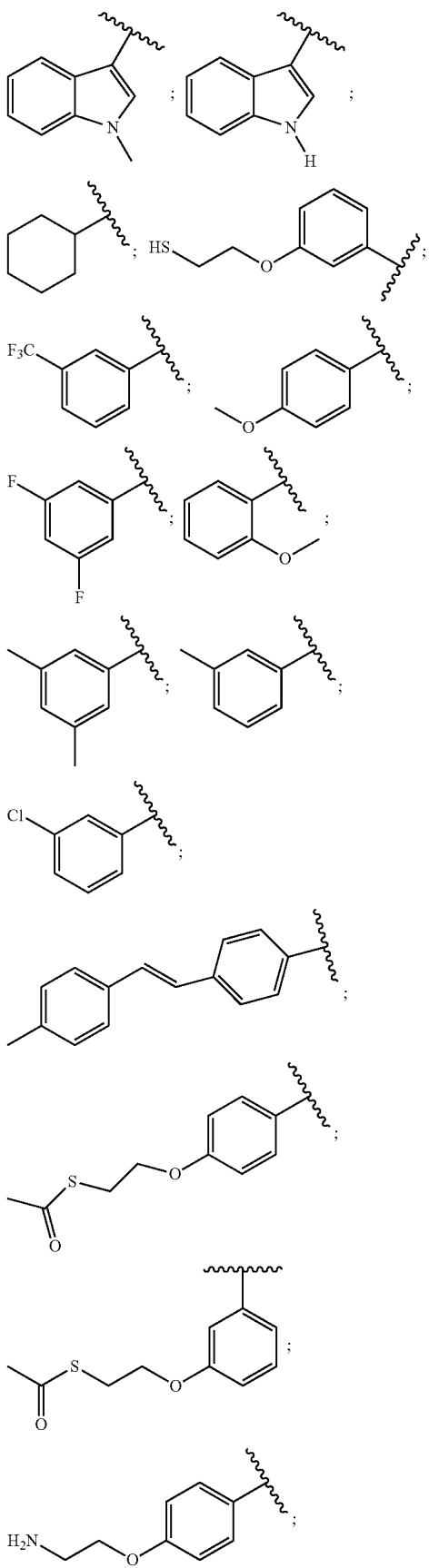

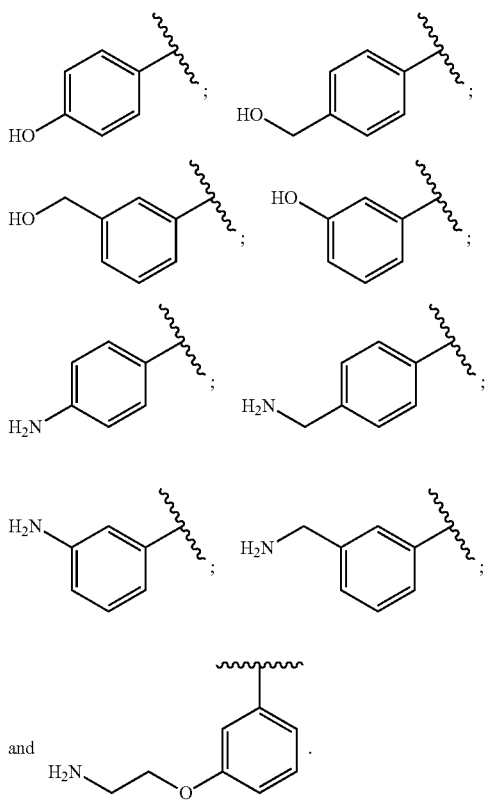

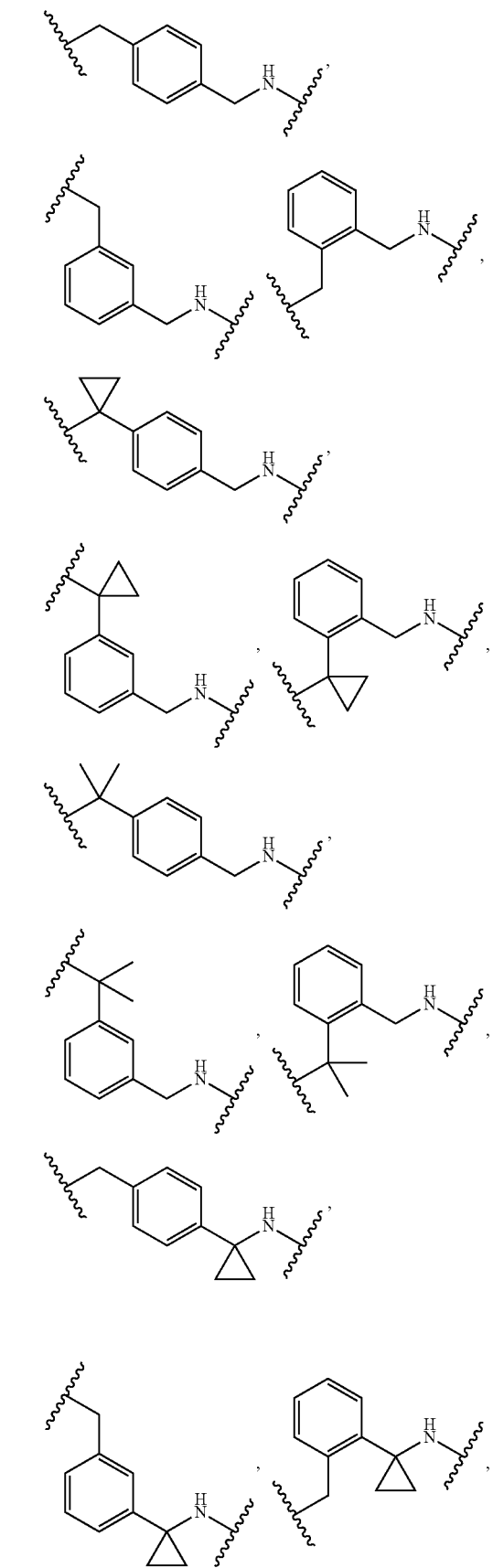

In another further embodiment, R$_{18}$ is:

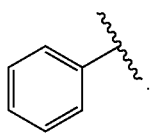

In another further embodiment, R$_{19}$, R$_{20}$, R$_{21}$, and R$_{27}$ are each methyl.

In another further embodiment, R$_{19}$ is H, R$_{20}$ is methyl, R$_{21}$ is methyl, and R$_{27}$ is methyl.

It is understood that any embodiment of the compounds of structure (XV), as set forth above, and any specific substituent set forth herein for a R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, or R$_{29}$ group in the compounds of structure (XV), as set forth above, may be independently combined with other embodiments and/or substituents of compounds of structure (XV) to form embodiments of the present disclosure not specifically set forth above. In addition, in the event that a list of substituents is listed for any particular R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, or R$_{29}$ in a particular embodiment and/or claim, it is understood that each individual substituent may be deleted from the particular embodiment and/or claim and that the remaining list of substituents will be considered to be within the scope of the present disclosure.

In one embodiment, —R$_1$—NH— in structure (VI), the —R$_{15}$—NH— in structure (XIV), or the —R$_{17}$—NH— in structure (XV) is selected from:

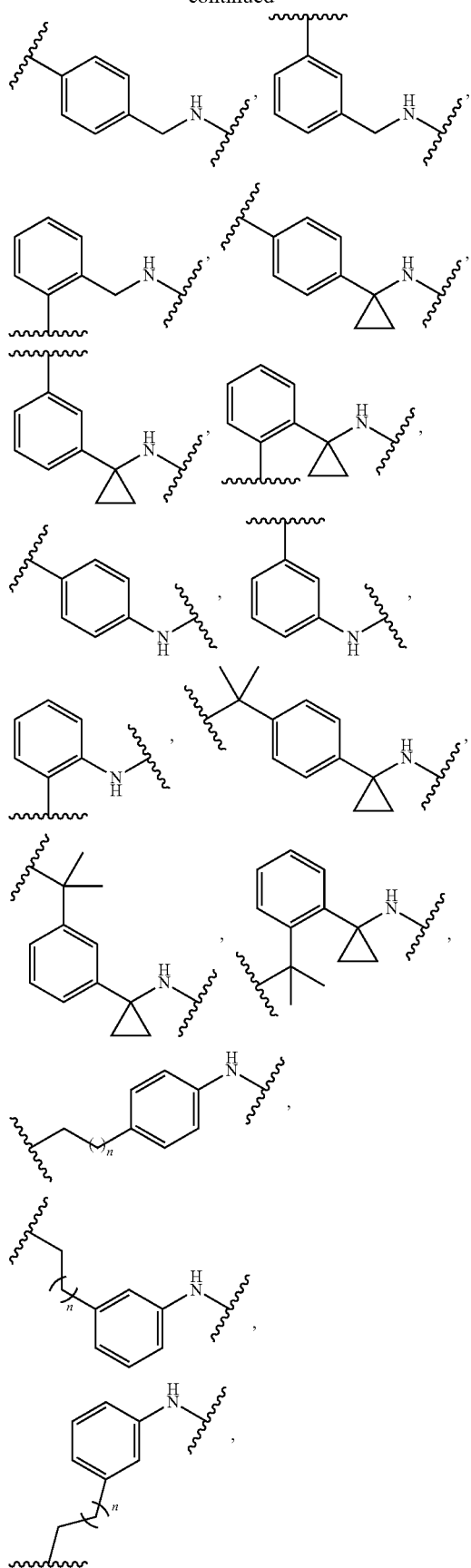
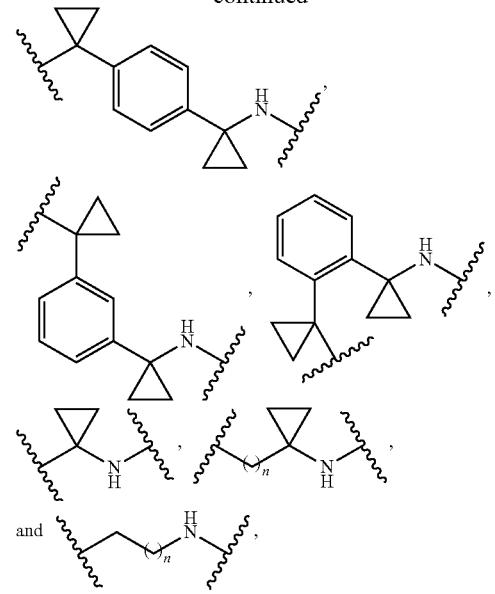
wherein each n is independently an integer from 0-10.
In a preferred embodiment, —R$_1$—NH— in structure (VI), the —R$_{15}$—NH— in structure (XIV), or the —R$_{17}$—NH— in structure (XV) is selected from:
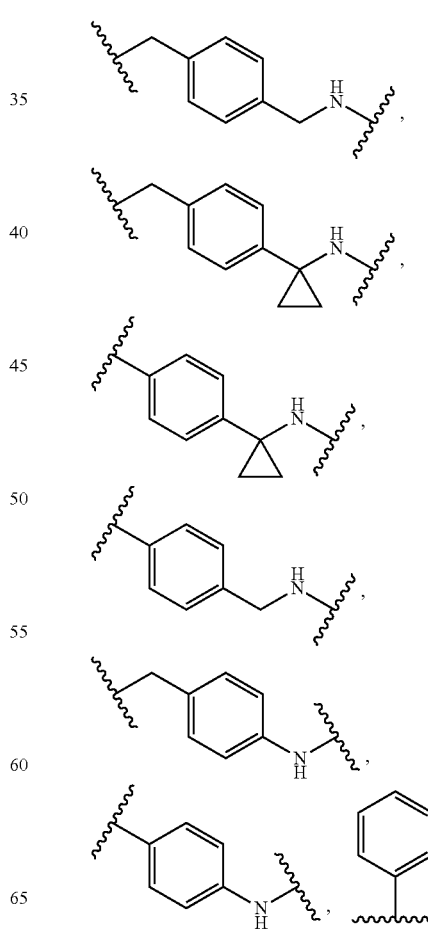

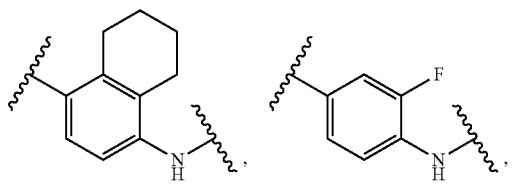 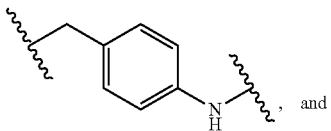

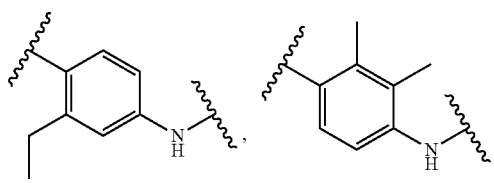 and 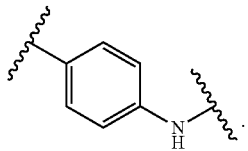

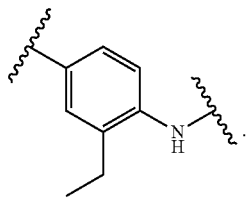

In a preferred embodiment, —R$_1$—NH— in structure (VI), the —R$_{15}$—NH— in structure (XIV), or the —R$_{17}$—NH— in structure (XV) is selected from:

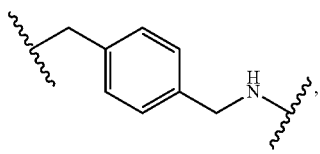

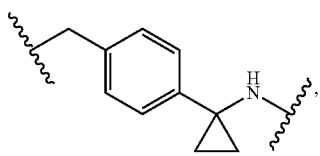

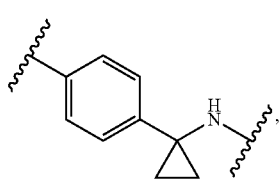

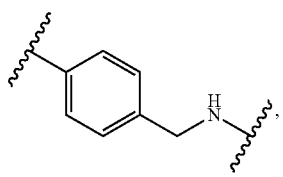

In one embodiment of the invention (P) is a compound of Formula (XI):

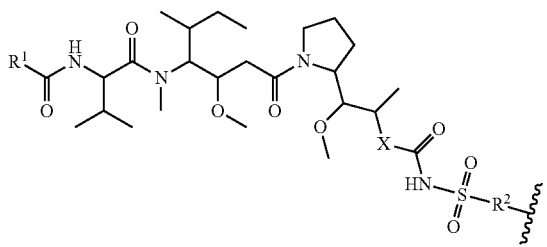

XI and pharmaceutically acceptable salts thereof, wherein:

R$^1$ is selected from: amino-C$_1$-C$_6$ alkyl, amino-aryl, amino-C$_3$-C$_7$ cycloalkyl, amino-heterocyclyl, and heterocyclyl, each optionally substituted with one or more substituents selected from aryl, aryl-C$_1$-C$_6$ alkyl, C$_1$-C$_6$ alkyl, C$_1$-C$_6$ alkylthio, carboxyl, carboxamide, C$_3$-C$_7$ cycloalkyl, C$_3$-C$_7$ cycloalkyl-C$_1$-C$_6$ alkyl, guanidino, halo, C$_1$-C$_6$ haloalkyl, heterocyclyl, heterocyclyl-C$_1$-C$_6$ alkyl, hydroxyl, and thio; or R$^1$ is R$^a$R$^b$NCH(R$^c$)—;

R$^a$ is selected from: H and C$_1$-C$_6$ alkyl;

R$^b$ is C$_1$-C$_6$ alkyl; and

R$^c$ is R$^d$—CH(CH$_3$)$_2$—; and

R$^d$ is selected from: H, aryl, C$_3$-C$_7$ cycloalkyl, and heteroaryl, each of which is optionally substituted with one or more substituents selected from: C$_1$-C$_4$ acylthio, C$_2$-C$_4$ alkenyl, C$_1$-C$_4$ alkyl, C$_1$-C$_4$ alkylamino, C$_1$-C$_4$ alkyloxy, amino, amino-C$_1$-C$_4$ alkyl, halo, C$_1$-C$_4$ haloalkyl, hydroxyl, hydroxy-C$_1$-C$_4$ alkyl, and thio, wherein C$_2$-C$_4$ alkenyl, C$_1$-C$_4$ alkylamino and C$_1$-C$_4$ alkyloxy are further optionally substituted with one substituent selected from C$_1$-C$_4$ alkylaryl, hydroxyl, and thio; or R$^b$ and R$^c$ taken together with the atoms to which they are each bonded form a heterocyclyldiyl;

R$^2$ is selected from: C$_2$-C$_6$ alkyl, aryl, aryl-C$_1$-C$_6$ alkyl, C$_4$-C$_7$ cycloalkyl, C$_3$-C$_7$ cycloalkyl-C$_1$-C$_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl; and X is —C(O)NHCH(CH$_2$R$^3$)—, or X is absent; and R$^3$ is selected from: aryl, heteroaryl, and $C_3$-$C_7$ cycloalkyl, each optionally substituted with one substituent selected from amino and hydroxyl.

Also provided are embodiments in which (P) is a compound of Formula XI, XIa, XIb, XIc, XId, XIe, XIf, XIg, XIh, XIi, XIj, or XIk, or a pharmaceutically acceptable salt thereof. (P) is covalently attached to (L), if (L) is present, or (T), if (L) is not present.

In one embodiment of the invention (P) is a compound of Formula XIa:

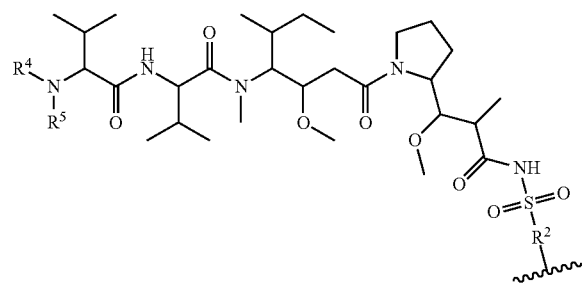

XIa and pharmaceutically acceptable salts thereof, wherein:

R$^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and R$^4$ and R$^5$ are each independently selected from: H and $C_1$-$C_6$ alkyl.

In one embodiment of the invention (P) is a compound of Formula XIa:

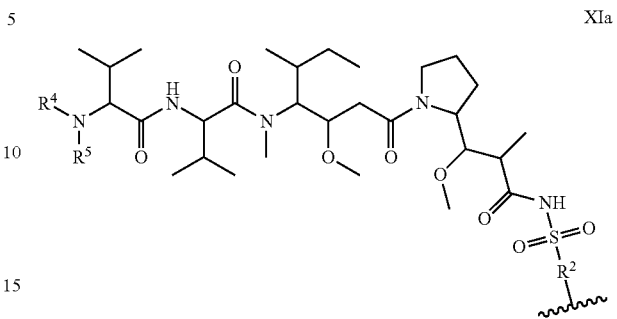

XIa and pharmaceutically acceptable salts thereof, wherein:

R$^2$ is selected from: 4-aminobenzyl, 4-(aminomethyl) benzyl, 4-(aminomethyl)phenyl, 4-aminophenyl, benzyl, 3-mercaptopropyl, 2-mercaptoethyl, 4-(mercaptomethyl) phenyl, p-tolyl, 2,4,6-trimethylphenyl, 4-(trifluoromethoxy) phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl) benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl) phenyl; and R$^4$ and R$^5$ are each independently selected from: H and methyl.

In one embodiment of the invention (P) is a compound of Formula XIb:

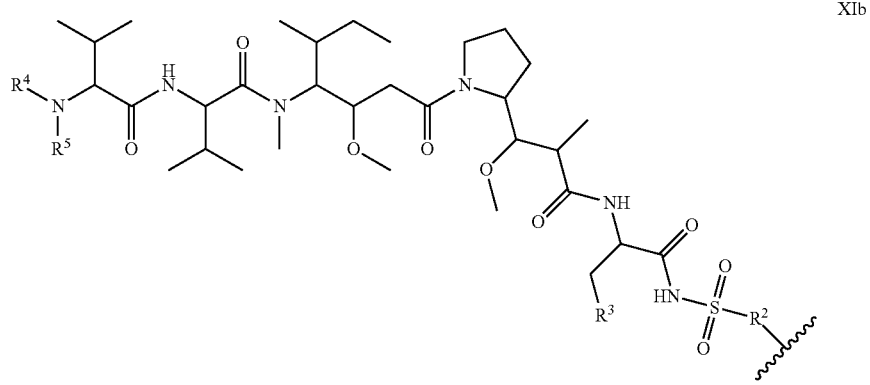

XIb and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl;

$R^3$ is selected from: aryl, heteroaryl, and $C_3$-$C_7$ cycloalkyl, each optionally substituted with one substituent selected from amino and hydroxyl; and $R^4$ and $R^5$ are each independently selected from: H and $C_1$-$C_6$ alkyl.

In one embodiment of the invention (P) is a compound of Formula XIb:

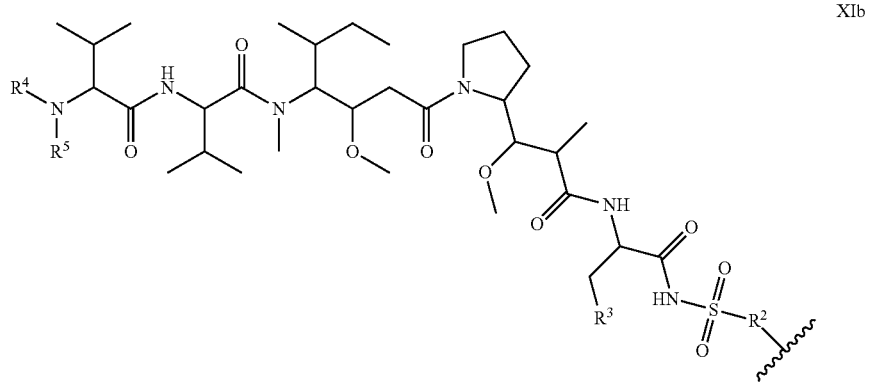

XIb and pharmaceutically acceptable salts thereof, wherein:

$R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl;

$R^3$ is selected from: 1H-indol-3-yl, 4-aminophenyl, 4-hydroxyphenyl, 5-hydroxypyridin-2-yl, cyclohexyl, and phenyl; and $R^4$ and $R^5$ are each independently selected from: H and methyl.

In one embodiment of the invention (P) is a compound of Formula XIc:

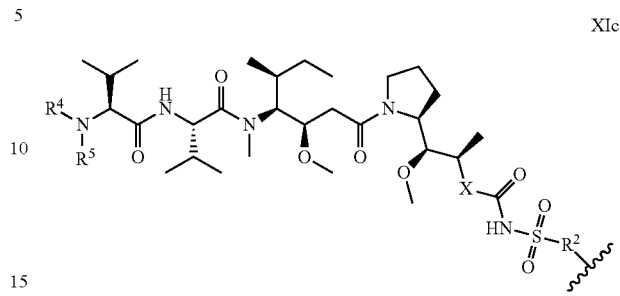

XIc and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl;

X is —C(O)NHCH($CH_2R^3$)—, or X is absent; and $R^3$ is selected from: aryl, heteroaryl, and $C_3$-$C_7$ cycloalkyl, each optionally substituted with one substituent selected from amino and hydroxyl; and $R^4$ and $R^5$ are each independently selected from: H and $C_1$-$C_6$ alkyl.

In one embodiment of the invention (P) is a compound of Formula XIc:

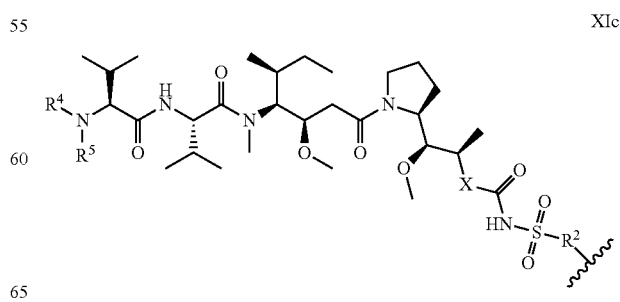

XIc or a pharmaceutically acceptable salt thereof, wherein:

R² is selected from: 4-aminobenzyl, 4-(aminomethyl)benzyl, 4-(aminomethyl)phenyl; 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and X is —C(O)NHCH(CH₂R³)—, or X is absent; and R³ is selected from: 1H-indol-3-yl, 4-aminophenyl, 4-hydroxyphenyl, 5-hydroxypyridin-2-yl, cyclohexyl, and phenyl; and R⁴ and R⁵ are each independently selected from: H and methyl.

In one embodiment of the invention (P) is a compound of Formula XId:

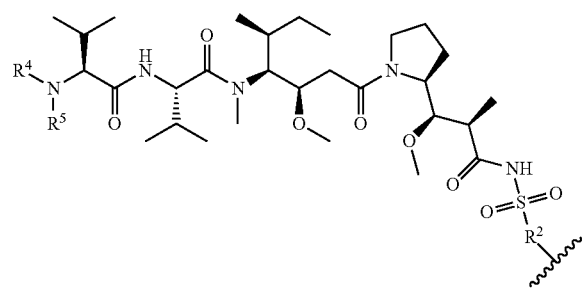

and pharmaceutically acceptable salts thereof, wherein:

R² is selected from: C₂-C₆ alkyl, aryl, aryl-C₁-C₆ alkyl, C₄-C₇ cycloalkyl, C₃-C₇ cycloalkyl-C₁-C₆ alkyl, heteroaryl, heteroaryl-C₁-C₆ alkyl, and heterocyclyl, each optionally substituted with one or more substituents selected from: C₁-C₆ alkoxy, C₁-C₆ alkoxycarbonyl, C₁-C₆ alkyl, C₁-C₆ alkylamino, amino, amino-C₁-C₆ alkyl, amino-aryl, amino-C₃-C₇ cycloalkyl, aryl, carboxamide, carboxyl, cyano, C₁-C₆ haloalkyl, C₁-C₆ haloalkoxy, halo, hydroxyl, nitro, thio, and thio-C₁-C₆ alkyl; and R⁴ and R⁵ are each independently selected from: H and C₁-C₆ alkyl.

In one embodiment of the invention (P) is a compound of Formula XId:

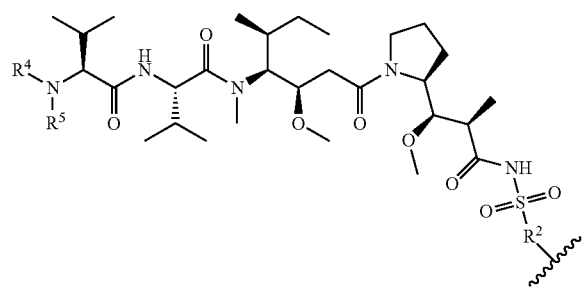

and pharmaceutically acceptable salts thereof, wherein:

R² is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and R⁴ and R⁵ are each independently selected from: H and methyl.

In one embodiment of the invention (P) is a compound of Formula XIe:

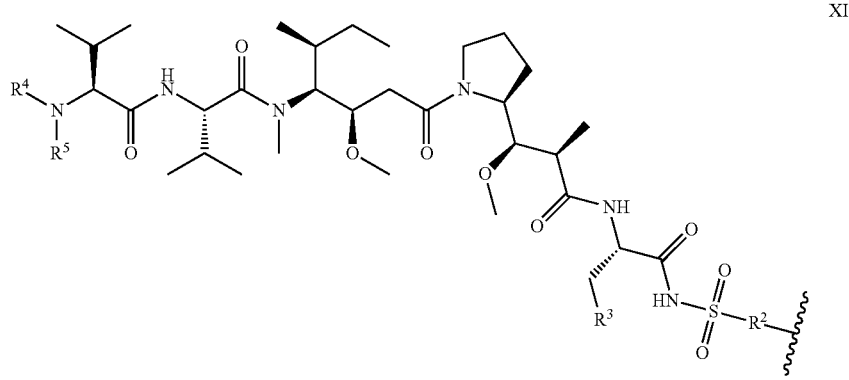

and pharmaceutically acceptable salts thereof, wherein:

R² is selected from: C₂-C₆ alkyl, aryl, aryl-C₁-C₆ alkyl, C₄-C₇ cycloalkyl, C₃-C₇ cycloalkyl-C₁-C₆ alkyl, heteroaryl, heteroaryl-C₁-C₆ alkyl, and heterocyclyl, each optionally substituted with one or more substituents selected from: C₁-C₆ alkoxy, C₁-C₆ alkoxycarbonyl, C₁-C₆ alkyl, C₁-C₆ alkylamino, amino, amino-C₁-C₆ alkyl, amino-aryl, amino-C₃-C₇ cycloalkyl, aryl, carboxamide, carboxyl, cyano, C₁-C₆ haloalkyl, C₁-C₆ haloalkoxy, halo, hydroxyl, nitro, thio, and thio-C₁-C₆ alkyl; and R³ is selected from: aryl, heteroaryl, and C₃-C₇ cycloalkyl, each optionally substituted with one substituent selected from amino and hydroxyl; and R⁴ and R⁵ are each independently selected from: H and C₁-C₆ alkyl.

In one embodiment of the invention (P) is a compound of Formula XIe:

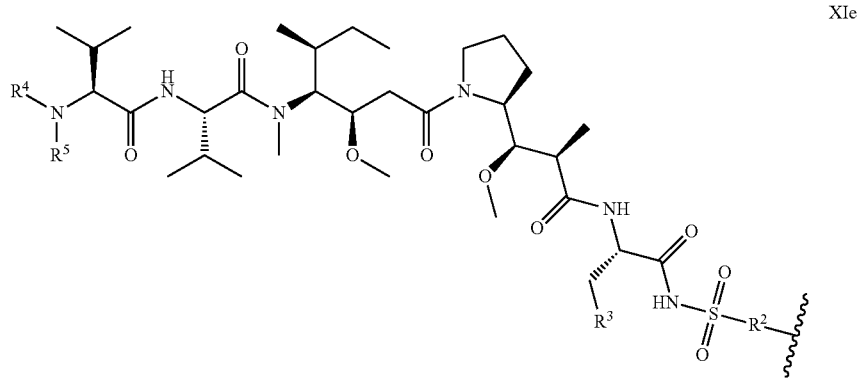

and pharmaceutically acceptable salts thereof, wherein:

R² is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and R³ is selected from: 1H-indol-3-yl, 4-aminophenyl, 4-hydroxyphenyl, 5-hydroxypyridin-2-yl, cyclohexyl, and phenyl; and R⁴ and R⁵ are each independently selected from: H and methyl.

In one embodiment of the invention (P) is a compound of Formula XIf:

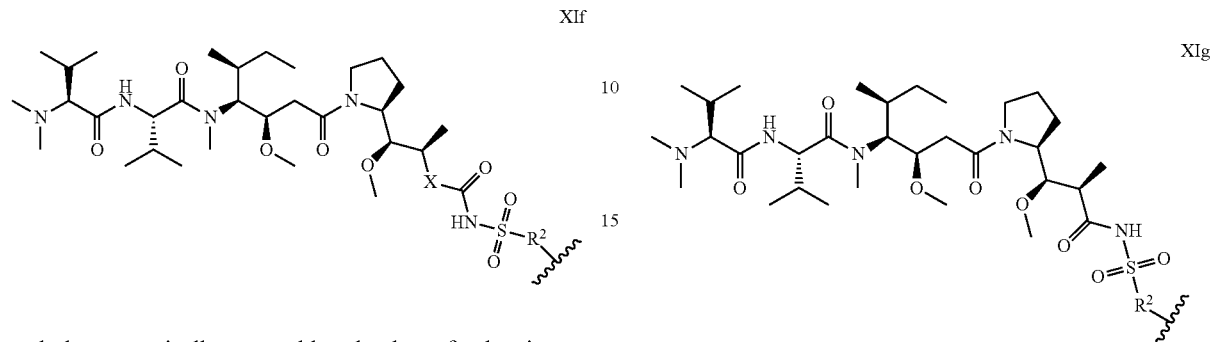

XIf and pharmaceutically acceptable salts thereof, wherein:

R² is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and X is —C(O)NHCH(CH₂R³)—, or X is absent; and R³ is selected from: aryl, heteroaryl, and $C_3$-$C_7$ cycloalkyl, each optionally substituted with one substituent selected from amino and hydroxyl.

In one embodiment of the invention (P) is a compound of Formula XIf:

XIf and pharmaceutically acceptable salts thereof, wherein:

R² is selected from: 4-aminobenzyl, 4-(aminomethyl)benzyl, 4-(aminomethyl)phenyl, 4-aminophenyl; and X is —C(O)NHCH(CH₂R³)—, or X is absent; and R³ is selected from: 1H-indol-3-yl, 4-aminophenyl, 4-hydroxyphenyl, 5-hydroxypyridin-2-yl, cyclohexyl, and phenyl.

In one embodiment of the invention (P) is a compound of Formula XIg:

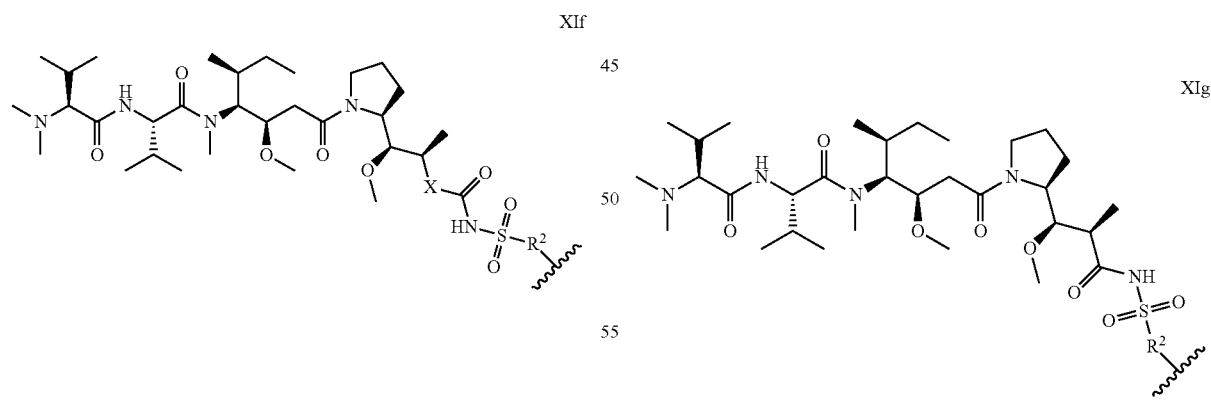

XIg and pharmaceutically acceptable salts thereof, wherein:

R² is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl.

In one embodiment of the invention (P) is a compound of Formula XIg:

XIg and pharmaceutically acceptable salts thereof, wherein:

R² is selected from: 4-aminobenzyl, 4-(aminomethyl)benzyl, 4-(aminomethyl)phenyl, 4-aminophenyl.

In one embodiment of the invention (P) is a compound of Formula XIh:

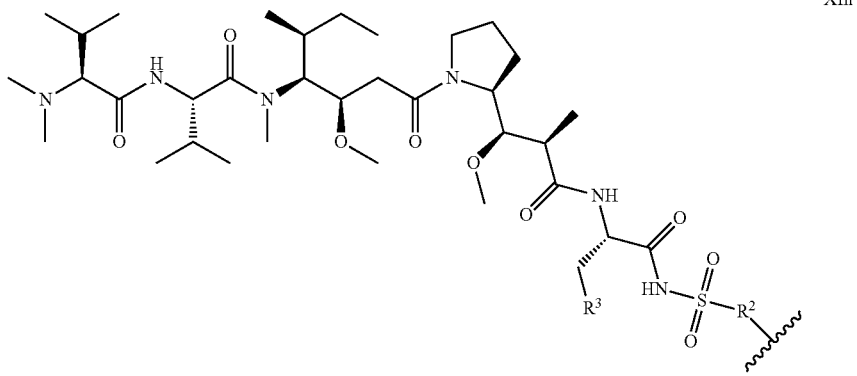

and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and $R^3$ is selected from: aryl, heteroaryl, and $C_3$-$C_7$ cycloalkyl, each optionally substituted with one substituent selected from amino and hydroxyl.

In one embodiment of the invention (P) is a compound of Formula XIh:

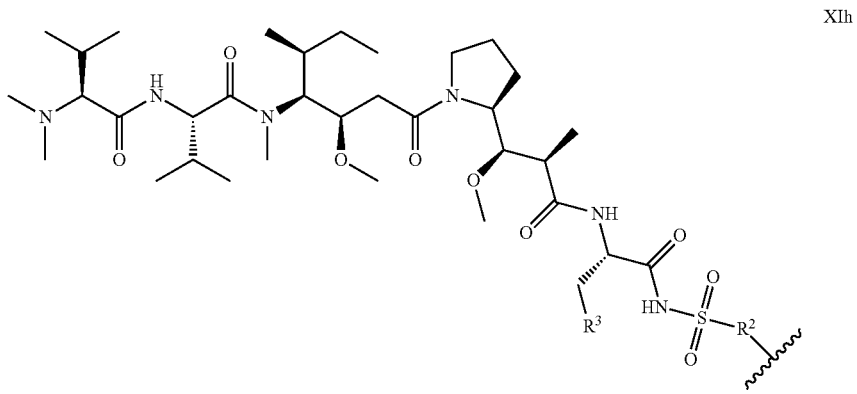

and pharmaceutically acceptable salts thereof, wherein:

$R^2$ is selected from: 4-aminobenzyl, 4-(aminomethyl)benzyl, 4-(aminomethyl)phenyl, 4-aminophenyl; and $R^3$ is selected from: 1H-indol-3-yl, 4-aminophenyl, 4-hydroxyphenyl, 5-hydroxypyridin-2-yl, cyclohexyl, and phenyl.

In one embodiment of the invention (P) is a compound of Formula XIi:

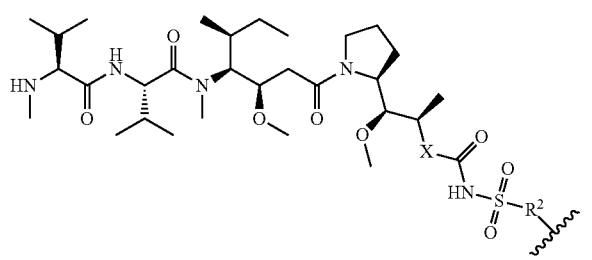

and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl;

X is —C(O)NHCH(CH$_2$R$^3$)—, or X is absent; and $R^3$ is selected from: aryl, heteroaryl, and $C_3$-$C_7$ cycloalkyl, each optionally substituted with one substituent selected from amino and hydroxyl.

In one embodiment of the invention (P) is a compound of Formula XIi:

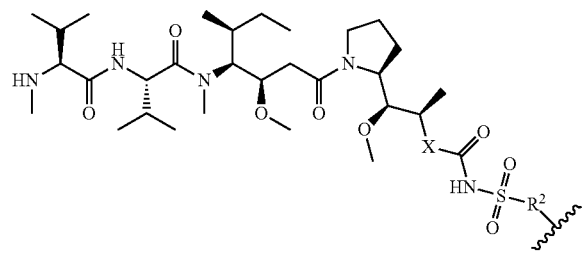

XIi and pharmaceutically acceptable salts thereof, wherein:

$R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl;

X is —C(O)NHCH($CH_2R^3$)—, or X is absent; and $R^3$ is selected from: 1H-indol-3-yl, 4-aminophenyl, 4-hydroxyphenyl, 5-hydroxypyridin-2-yl, cyclohexyl, and phenyl.

In one embodiment of the invention (P) is a compound of Formula Ij:

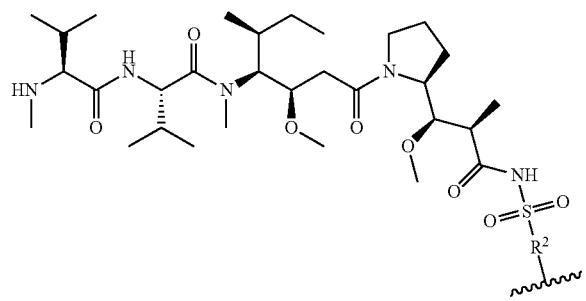

XIj and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl.

In one embodiment of the invention (P) is a compound of Formula Ij:

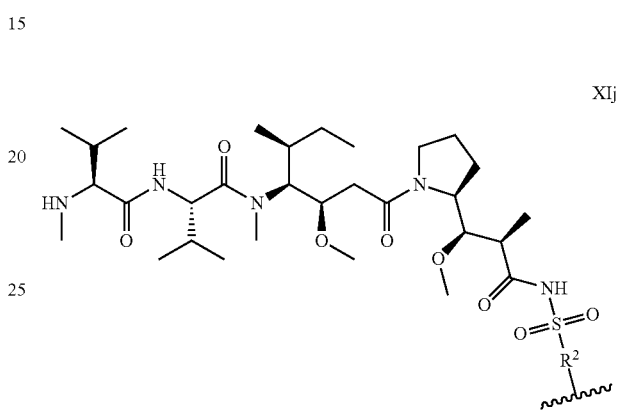

XIj or a pharmaceutically acceptable salt thereof, wherein:

$R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yi, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl.

In one embodiment of the invention (P) is a compound of Formula XIk:

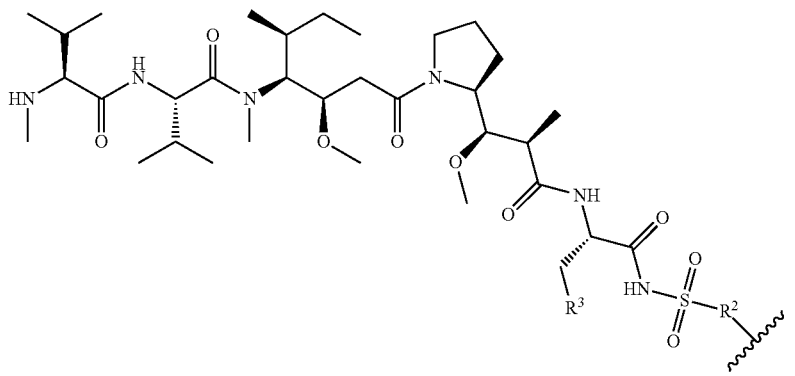

XIk and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and $R^3$ is selected from: aryl, heteroaryl, and $C_3$-$C_7$ cycloalkyl, each optionally substituted with one substituent selected from amino and hydroxyl.

In one embodiment of the invention (P) is a compound of Formula XIk:

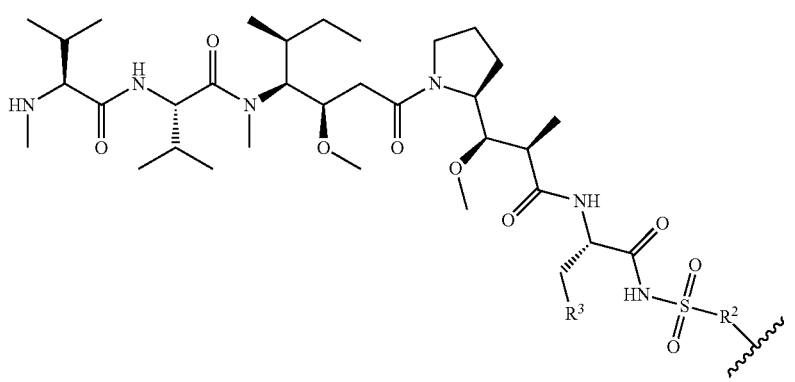

XIk and pharmaceutically acceptable salts thereof, wherein:

$R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and $R^3$ is selected from: 1H-indol-3-yl, 4-aminophenyl, 4-hydroxyphenyl, 5-hydroxypyridin-2-yl, cyclohexyl, and phenyl.

In one embodiment, (—$R^2$—) in any of Formulas XI and XIa-XIk is (—R"—NH—) wherein R" is selected from the group consisting of optionally substituted alkyl, optionally substituted alkylamino, optionally substituted cycloalkyl, optionally substituted aryl, optionally substituted heterocyclyl, optionally substituted heteroaryl, —$COR^{27}$-, —$CSR^{27}$—, —$OR^{27}$— and —$NHR^{27}$—, wherein each $R^{27}$ is, independently, optionally substituted alkyl, optionally substituted alkylamino, optionally substituted cycloalkyl, optionally substituted aryl, optionally substituted heterocyclyl, and optionally substituted heteroaryl.

In one embodiment, (—R"—NH—) is linked to -(L)-(T):

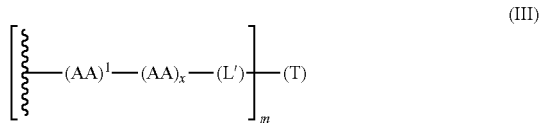
(III)

wherein the —NH— group bonded to R" forms a peptide bond referred to herein as the junction peptide bond (JPB) with (AA)$^1$ in formula (III). AA is independently an amino acid, wherein x is an integer from 0 to 25, wherein (L') is optionally the remaining portion of linker (L), and (T) is the targeting moiety. In one embodiment, (AA)$^1$-(AA)$_x$ taken together comprises an amino acid sequence that facilitates cleavage of the JPB.

In one embodiment, the targeting moiety is an antibody. Accordingly, in one embodiment, antibody-drug conjugates (ADCs) comprising a compound described herein, or a pharmaceutically acceptable salt or prodrug thereof, are provided.

In one embodiment, the invention provides a method of making a composition of Formula II.

In another embodiment, a pharmaceutical composition is provided comprising a composition of Formula II, or a pharmaceutically acceptable salt thereof, and a pharmaceutically acceptable carrier, diluent or excipient.

In another embodiment, a method of using a composition of Formula II in therapy is provided. In particular, the present disclosure provides a method of treating cancer in a mammal comprising administering to a mammal in need thereof an effective amount of a composition of Formula II or a pharmaceutical composition comprising a composition of Formula II and a pharmaceutically acceptable carrier diluent or excipient.

In another embodiment, the present disclosure provides a method of inhibiting tumor growth in a mammal comprising administering to a mammal in need thereof an effective amount of a composition of Formula II or a pharmaceutical composition comprising a composition of Formula II and a pharmaceutically acceptable carrier, diluent or excipient.

In another embodiment, the present disclosure provides a method of killing cancer cells in vitro using a composition of Formula II. In another embodiment, the present disclosure provides a method of killing cancer cells in vivo in a mammal, comprising administering to a mammal in need thereof an effective amount of a composition of Formula II or a pharmaceutical composition comprising a composition of Formula II and a pharmaceutically acceptable carrier, diluent or excipient.

In another embodiment, the present disclosure provides a method of increasing the survival time of a mammal having cancer, comprising administering to a mammal in need thereof an effective amount of a composition of Formula II or a pharmaceutical composition comprising a composition of Formula II and a pharmaceutically acceptable carrier, diluent or excipient.

In another embodiment, the present disclosure provides a use of a composition of Formula II, or a pharmaceutically acceptable salt thereof, in the manufacture of a medicament for treating cancer in a mammal.

In another embodiment, the present disclosure provides a use of a composition of Formula II, in the manufacture of a medicament for inhibiting tumor growth in a mammal.

In another embodiment, the present disclosure provides a use of a composition of Formula II, in the manufacture of a medicament for increasing survival of a mammal having cancer.

In another embodiment, the present disclosure provides a composition of Formula II or a pharmaceutical composition comprising a composition of Formula II, for use in a method of treatment of the human or animal body by therapy.

In another embodiment, the present disclosure provides a composition of Formula II or a pharmaceutical composition comprising a composition of Formula II, for use in treating cancer in a mammal.

In another embodiment, the present disclosure provides a composition of Formula II or a pharmaceutical composition comprising a composition of Formula II, for use in inhibiting tumor growth in a mammal.

In another embodiment, the present disclosure provides a composition of Formula II or a pharmaceutical composition comprising a composition of Formula II, for use in increasing survival of a mammal having cancer.

In one embodiment, cleavage of the JPB results in a compound of formula (IV) or a compound of formula (V):

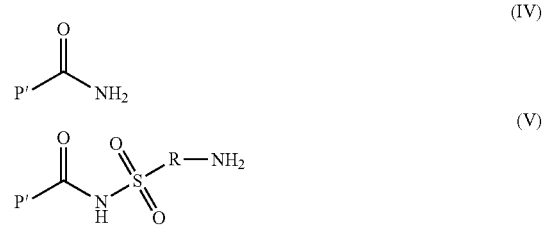

wherein P' corresponds to P' in formula (II).

"Amino" refers to the —NH$_2$ substituent.

"Cyano" refers to the —CN substituent.

"Hydroxy" or "hydroxyl" refers to the —OH substituent.

"Imino" refers to the =NH substituent.

"Nitro" refers to the —NO$_2$ substituent.

"Oxo" refers to the =O substituent.

"Thiol" refers to the —SH substituent.

"Thioxo" refers to the =S substituent.

"Alkyl" refers to a straight or branched hydrocarbon chain substituent consisting solely of carbon and hydrogen atoms, which is saturated or unsaturated (i.e., contains one or more double and/or triple bonds), having from one to twenty-five carbon atoms ($C_1$-$C_{25}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a substituent group, consisting solely of carbon and hydrogen, which is saturated or unsaturated (i.e., contains one or more double and/or triple bonds), and having from one to twenty-five carbon atoms, preferably one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the substituent group through a single or double bond. The points of attachment of the alkylene chain to the rest of the molecule and to the substituent group can be through one carbon or any two carbons within the chain. Unless stated otherwise specifically in the specification, an alkylene chain may be optionally substituted.

"Alkoxy" refers to a substituent of the formula —OR$_a$ where R$_a$ is an alkyl substituent as defined above containing one to twenty-five carbon atoms, preferably one to twelve carbon atoms. Unless stated otherwise specifically in the specification, an alkoxy group may be optionally substituted.

"Alkylamino" refers to a substituent of the formula —NHR$_a$ or —NR$_a$R$_a$ where each R$_a$ is, independently, an alkyl substituent as defined above containing one to twenty-five carbon atoms, preferably one to twelve carbon atoms. Unless stated otherwise specifically in the specification, an alkylamino group may be optionally substituted.

"Thioalkyl" refers to a substituent of the formula —SR$_a$ where R$_a$ is an alkyl substituent as defined above containing one to twenty-five carbon atoms, preferably one to twelve carbon atoms. Unless stated otherwise specifically in the specification, a thioalkyl group may be optionally substituted.

"Aryl" refers to a hydrocarbon ring system substituent comprising hydrogen, 6 to 18 carbon atoms and at least one aromatic ring. For purposes of this disclosure, the aryl substituent may be a monocyclic, bicyclic, tricyclic or tetracyclic ring system, which may include fused or bridged ring systems. Aryl substituents include, but are not limited to, aryl substituents derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl substituents that are optionally substituted.

"Aralkyl" refers to a substituent of the formula —R$_b$—R$_c$ where R$_b$ is an alkylene chain as defined above and R$_c$ is one or more aryl substituents as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon substituent consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic substituents include, for example, cyclopropyl, cyclobutyl, cyclopentyl, cyclohexyl, cycloheptyl, and cyclooctyl. Polycyclic substituents include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a substituent of the formula —R$_b$R$_d$ where R$_d$ is an alkylene chain as defined above and R$_g$ is a cycloalkyl substituent as defined above. Unless stated otherwise specifically in the specification, a cycloalkylalkyl group may be optionally substituted.

"Fused" refers to any ring structure described herein which is fused to an existing ring structure in the compounds of the disclosure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl substituent, as defined above, that is substituted by one or more halo substituents, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring substituent which consists of two to twelve carbon atoms and from one to six heteroatoms selected from the group consisting of nitrogen, oxygen and sulfur. Unless stated otherwise specifically in the specification, the heterocyclyl substituent may be a monocyclic, bicyclic, tricyclic or tetracyclic ring system, which may include fused or bridged ring systems; and the nitrogen, carbon or sulfur atoms in the heterocyclyl substituent may be optionally oxidized; the nitrogen atom may be optionally quaternized; and the heterocyclyl substituent may be partially or fully saturated. Examples of such heterocyclyl substituents include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group may be optionally substituted.

"N-heterocyclyl" refers to a heterocyclyl substituent as defined above containing at least one nitrogen and where the point of attachment of the heterocyclyl substituent to the rest of the molecule is through a nitrogen atom in the heterocyclyl substituent. Unless stated otherwise specifically in the specification, a N-heterocyclyl group may be optionally substituted.

"Heterocyclylalkyl" refers to a substituent of the formula —R$_b$R$_e$ where R$_b$ is an alkylene chain as defined above and R$_e$ is a heterocyclyl substituent as defined above, and if the heterocyclyl is a nitrogen-containing heterocyclyl, the heterocyclyl may be attached to the alkyl substituent at the nitrogen atom. Unless stated otherwise specifically in the specification, a heterocyclylalkyl group may be optionally substituted.

"Heteroaryl" refers to a 5- to 14-membered ring system substituent comprising hydrogen atoms, one to thirteen carbon atoms, one to six heteroatoms selected from the group consisting of nitrogen, oxygen and sulfur, and at least one aromatic ring. For purposes of this disclosure, the heteroaryl substituent may be a monocyclic, bicyclic, tricyclic or tetracyclic ring system, which may include fused or bridged ring systems; and the nitrogen, carbon or sulfur atoms in the heteroaryl substituent may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl substituent as defined above containing at least one nitrogen and where the point of attachment of the heteroaryl substituent to the rest of the molecule is through a nitrogen atom in the heteroaryl substituent. Unless stated otherwise specifically in the specification, an N-heteroaryl group may be optionally substituted.

"Heteroarylalkyl" refers to a substituent of the formula —$R_bR_f$ where $R_b$ is an alkylene chain as defined above and $R_f$ is a heteroaryl substituent as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as azides, amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gC(=NR_g)NR_gR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "protecting group," as used herein, refers to a labile chemical moiety which is known in the art to protect reactive groups including without limitation, hydroxyl and amino groups, against undesired reactions during synthetic procedures. Hydroxyl and amino groups which protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Groups can be selectively incorporated into compounds of the present disclosure as precursors. For example an amino group can be placed into a compound of the disclosure as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy) ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl (Teoc), 1-methyl-1-(4-biphenylyl)-ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

"Prodrug" is meant to indicate a compound that may be converted under physiological conditions or by solvolysis to a biologically active compound of the disclosure. Thus, the term "prodrug" refers to a metabolic precursor of a compound of the disclosure that is pharmaceutically acceptable. A prodrug may be inactive when administered to a subject in need thereof, but is converted in vivo to an active compound of the disclosure. Prodrugs are typically rapidly transformed in vivo to yield the parent compound of the disclosure, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol.

14, and in Bioreversible Carriers in Drug Design, Ed. Edward B. Roche, American Pharmaceutical Association and Pergamon Press, 1987.

Prodrugs of a compound of the disclosure may be prepared by modifying functional groups present in the compound of the disclosure in such a way that the modifications are cleaved, either in routine manipulation or in vivo, to the parent compound of the disclosure. Prodrugs include compounds of the disclosure wherein a hydroxy, amino or mercapto group is bonded to any group that, when the prodrug of the compound of the disclosure is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the disclosure and the like.

"Drug-antibody ratio" or "DAR" is meant to indicate the number of drug moieties conjugated to the targeting moiety, i.e., the antibody. In certain embodiments, there is the same number of payload (P) and linker (L) in [(P)-(L)] and DAR is represented by the value "m" in Formula I and can be an integer from 1 to 10. In other embodiments, the linker (L) is a multifunctional unit that links more than one payload (P) to a single targeting moiety (T).

The present disclosure also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^1$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The present disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the present disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl substituent may or may not be substituted and that the description includes both substituted aryl substituents and aryl substituents having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the disclosure. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

Non-limiting examples of disorders to be treated herein include benign and malignant tumors; leukemia and lymphoid malignancies, in particular breast, ovarian, stomach, endometrial, salivary gland, lung, kidney, colon, thyroid, pancreatic, prostate or bladder cancer; neuronal, glial, astrocytal, hypothalamic and other glandular, macrophagal, epithelial, stromal and blastocoelic disorders.

"Effective amount" or "therapeutically effective amount" refers to that amount of a compound of the disclosure which, when administered to a mammal, preferably a human, is sufficient to effect treatment, as defined below, of cancer or tumor cells in the mammal, preferably a human. The amount of a compound of the disclosure which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition.

The therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. Compounds of the present invention are preferably cytotoxic. For cancer therapy, efficacy can, for example, be measured by assessing the time to disease progression (TTP) and/or determining the response rate (RR).

An "effective amount" of drug when referred to in respect of the killing of cancer cells, refers to an amount of drug sufficient to produce the killing effect.

Solid tumors contemplated for treatment using the presently disclosed compounds include but are not limited to: sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer (e.g., gastrointestinal cancer), oral cancer, nasal cancer, throat cancer, squamous cell carcinoma (e.g., of the lung), basal cell carcinoma, adenocarcinoma (e.g., of the lung), sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, non-small cell lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. Blood-borne cancers contemplated for treatment using the presently disclosed compounds include but are not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, and multiple myeloma. Acute and chronic leukemias contemplated for treatment using the presently disclosed compounds include but are not limited to: lymphoblastic, myelogenous, lymphocytic, and myelocytic leukemias. Lymphomas contemplated for treatment using the presently disclosed compounds include but are not limited to: Hodgkin's disease, non-Hodgkin's lymphoma, multiple myeloma, Waldenstrom's macroglobulinemia, heavy chain disease, and polycythemia vera. Other cancers contemplated for treatment using the presently disclosed compounds include but are not limited to: peritoneal cancer, hepatocellular cancer, hepatoma, salivary cancer, vulval cancer, thyroid, penile cancer, anal cancer, head and neck cancer, renal cell carcinoma, acute anaplastic large cell carcinoma, and cutaneous anaplastic large cell carcinoma.

Cancers, including, but not limited to, a tumor, metastasis, or other disease or disorder characterized by uncontrolled or undesired cell growth, can be treated or prevented by administration of the presently disclosed compounds.

In other embodiments, methods for treating or preventing cancer are provided, including administering to a patient in need thereof an effective amount of a compound disclosed herein in combination with a an additional method of treatment. In one embodiment, the additional method of treatment includes treatment with a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The compound of the invention may be administered before, after, or at the same time as the chemotherapeutic agent.

In one embodiment, the additional method of treatment is radiation therapy. The compound of the invention may be administered before, after, or at the same time as the radiation.

Compounds of the invention may also be administered to a patient that has undergone or will undergo surgery as treatment for the cancer.

In a specific embodiment, the compound of the invention is administered concurrently with the chemotherapeutic agent or with radiation therapy. In another specific embodiment, the chemotherapeutic agent or radiation therapy is administered prior or subsequent to administration of compound of the invention, in one aspect at least an hour, five hours, 12 hours, a day, a week, a month, in further aspects several months (e.g., up to three months), prior or subsequent to administration of a compound of the invention.

A chemotherapeutic agent can be administered over a series of sessions. Any one or a combination of the chemotherapeutic agents listed herein or otherwise known in the art can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with a compound of the invention are provided as an alternative to chemotherapy or radiation therapy where the chemotherapy or the radiation therapy has proven or can prove too toxic, e.g., results in unacceptable or unbearable side effects, for the subject being treated. Additionally, methods of treatment of cancer with a compound of the invention are provided as an alternative to surgery where the surgery has proven or can prove unacceptable or unbearable for the subject being treated.

The compound of the invention can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a an effective dose of a compound of the invention with or without accompanying high dose radiation therapy, and the stem cell graft is infused back into the animal. In certain embodiments, the effective dose is a high dose. Supportive care is then provided while bone marrow function is restored and the animal recovers.

Methods for treating cancer further include administering to a patient in need thereof an effective amount of a compound of the invention and another therapeutic agent that is an anti-cancer agent. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, actinomycin D, dactinomycin, plicamycin, mitoxantrone, asparaginase, vinblastine, vincristine, vindesine, vinorelbine, paclitaxel, and docetaxel.

Other examples of chemotherapeutic agents include alkylating agents such as thiotepa and CYTOXAN® cyclophosphamide; alkyl sulfonates such as busulfan, treosulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; triazines such as decarbazine; nitrosureas such as carmustine, chlorozotocin, fotemustine, lomustine, nimustine, and ranimnustine; epipodophyllins, such as etoposide, teniposide, topotecan, 9-aminocamptothecin, camptothecin orcrisnatol; bisphosphonates, such as clodronate; antibiotics such as the enediyne antibiotics (e.g., calicheamicin, especially calicheamicin gammaII and calicheamicin omegaII (see, e.g., Agnew, Chem. Intl. Ed. Engl., 33:183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins (e.g., A2 and B2), cactinomycin, carabicin, caminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; photodynamic therapies, such as vertoporfin (BPD-MA), phthalocyanine, photosensitizer Pc4, and demethoxy-hypocrellin A (2BA-2-DMHA); folic acid analogues such as denopterin, pteropterin, and trimetrexate; dpurine analogs such as fludarabine, 6-mercaptopurine, thiamiprine, and thioguanine; pyrimidine analogs such as ancitabine, azacitidine, 6-azauridine, carmofur, cytarabine, cytosine arabinoside, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate and trimetrexate; anti-metabolites such as 5-fluorouracil (5-FU) and its prodrugs such as UFT, S-1 and capecitabine, floxuridine, doxifluridine and ratitrexed; and thymidylate synthase inhibitors and glycinamide ribonucleotide formyltransferase inhibitors such as raltitrexed (TOMUDEX®, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); velcade; revlimid; thalidomide; IMiD3; lovastatin; verapamil; thapsigargin; 1-methyl-4-phenylpyridinium; cell cycle inhibitors such as staurosporine; novantrone; edatrexate; daunomycin; mtoxantrone; aminopterin; xeloda; ibandronate; topoisomerase inhibitor RFS 2000; difluoromethylornithine (DMFO); vitamin D3 analogs, such as EB 1089, CB 1093 and KH 1060; retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, megastrol, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, bicalutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The compounds of the disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present disclosure includes tautomers of any said compounds.

Targeting Moiety (T)

The Targeting moiety (T) of the subject compositions includes within its scope any unit of a (T) that binds or reactively associates or complexes with a receptor, antigen or other receptive moiety associated with a given target-cell population. A targeting moiety (T) is a molecule that binds to, complexes with, or reacts with a moiety of a cell population sought to be targeted. Examples of targeting moieties include compounds capable of binding to naturally occurring molecules present on the surface of cells of interest, as well as fragments thereof and peptides derived therefrom. Such targeting moieties may or may not have biological activity alone (e.g., cytokines, which have biological activity). Examples of targeting moieties include antibodies, ligands for cell surface receptors, ligands derived from non-human cells including bacterial and pathogen derived ligands. A wide range of appropriate targeting moieties is known in the art. For example, see WO2013117705.

In one aspect, the targeting moiety (T) acts to deliver the payload compound (P), which may be a drug (D), to the particular target cell population with which the targeting moiety (T) reacts. Such targeting moieties include, but are not limited to, large molecular weight proteins such as, for example, full-length antibodies, antibody fragments, smaller molecular weight proteins, polypeptide or peptides, lectins, glycoproteins, cytokines, non-peptides, vitamins, nutrient-transport molecules (such as, but not limited to, transferrin), or any other cell binding molecule or substance, fragment thereof or peptide derived therefrom or peptide based upon the same.

A targeting moiety (T) can form a bond to a linker (L) via a heteroatom of the targeting moiety (T). Heteroatoms that may be present on a targeting moiety (T) include sulfur (in one embodiment, from a sulfhydryl group of (T)), oxygen (in one embodiment, from a hydroxyl group of (T)) and nitrogen (in one embodiment, from a primary or secondary amino group of (T)). These heteroatoms can be present on the targeting moiety (T) in its natural state, for example a naturally-occurring antibody, or can be introduced into the targeting moiety (T), e.g., via chemical modification or recombinant means.

In one embodiment, targeting moiety (T) has a sulfhydryl group bonded to linker (L) via the sulfhydryl group's sulfur atom. In another embodiment, targeting moiety (T) has one or more lysine residues that can be chemically modified to introduce one or more sulfhydryl groups. The targeting moiety (T) bonds to linker (L) via the sulfhydryl group. Reagents that can be used to modify lysines include, but are not limited to, N-succinimidyl S-acetylthioacetate (SATA) and 2-Iminothiolane hydrochloride (Traut's Reagent). In a preferred embodiment, a plurality of (L) are added to a (T).

In another embodiment, the (L) can have one or more carbohydrate groups that can be chemically modified to have one or more sulfhydryl groups. The targeting moiety (T) bonds to the linker (L) via the sulfhydryl group's sulfur atom. In yet another embodiment, (T) can have one or more carbohydrate groups that can be oxidized to provide an aldehyde (—CHO) group (see, e.g., Laguzza et al., 1989, J. Med. Chem. 32(3):548-55). The corresponding aldehyde can form a bond with a reactive site on a portion of a linker (L). Reactive sites that can react with a carbonyl group on a targeting moiety (T) include, but are not limited to, hydrazine and hydroxylamine. Other protocols for the modification of proteins for the attachment or association of linker (L) are described in Coligan et al., Current Protocols in Protein Science, vol. 2, John Wiley & Sons (2002), incorporated herein by reference.

The targeting moiety (T) can include, for example a protein, polypeptide, or peptide include, but are not limited to, transferrin, epidermal growth factors ("EGF"), bombesin, gastrin, gastrin-releasing peptide, platelet-derived growth factor, IL-2, IL-6, transforming growth factor ("TGF"), such as TGF-α or TGF-β, vaccinia growth factor ("VGF"), insulin and insulin-like growth factors I and II, lectins and apoprotein from low density lipoprotein.

The targeting moiety (T) can also include an antibody, such as polyclonal antibodies or monoclonal antibodies. The antibody can be directed to a particular antigenic determinant, including for example, a cancer cell antigen, a viral antigen, a microbial antigen, a protein, a peptide, a carbohydrate, a chemical, nucleic acid, or fragments thereof. Methods of producing polyclonal antibodies are known in the art. A monoclonal antibody (mAb) to an antigen-of-interest can be prepared by using any technique known in the art. These include, but are not limited to, the hybridoma technique originally described by Kohler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). The Selected Lymphocyte Antibody Method (SLAM) (Babcook, J. S., et al., A novel strategy for generating monoclonal antibodies from single, isolated lymphocytes producing antibodies of defined specificities. Proc Natl Acad Sci USA, 1996. 93 (15): p. 7843-8) and (McLean G R, Olsen O A, Watt I N, Rathanaswami P, Leslie K B, Babcook J S, Schrader J W. Recognition of human cytomegalovirus by human primary immunoglobulins identifies an innate foundation to an adaptive immune response; J Immunol. 2005 Apr. 15; 174(8):4768-78). Such antibodies may be of any immunoglobulin class including IgG, IgM, IgE, IgA, and IgD and any subclass thereof. The hybridoma producing the mAbs of use in this invention may be cultivated in vitro or in vivo.

The monoclonal antibody can be, for example, a human monoclonal antibody, a humanized monoclonal antibody, an antibody fragment, or a chimeric antibody (e.g., a human-mouse antibody). Human monoclonal antibodies may be made by any of numerous techniques known in the art (e.g., Teng et al., 1983, Proc. Natl. Acad. Sci. USA 80:7308-7312; Kozbor et al., 1983, Immunology Today 4:72-79; and Olsson et al., 1982, Meth. Enzymol. 92:3-16; also see, Huse et al., 1989, Science 246:1275-1281 and McLean et al. J Immunol. 2005 Apr. 15; 174(8):4768-78).

The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-539; International Publication No. WO 93/08829, Traunecker et al., 1991, EMBO J. 10:3655-3659).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_{H2}$, and $C_{H3}$ regions. It is preferred to have the first heavy-chain constant region ($C_{H1}$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

For example, the bispecific antibodies can have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details for generating bispecific antibodies see, for example, Suresh et al., 1986, Methods in Enzymology 121:210; Rodrigues et al., 1993, J. Immunology 151:6954-6961; Carter et al., 1992, Bio/Technology 10:163-167; Carter et al., 1995, J. Hematotherapy 4:463-470; Merchant et al., 1998, Nature Biotechnology 16:677-681. Using such techniques, bispecific antibodies can be prepared for use in the treatment or prevention of disease as defined herein.

Bifunctional antibodies are also described in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

The antibody also can be a functionally active fragment, derivative or analog of an antibody that immunospecifically binds to a target antigen (e.g., a cancer antigen, a viral antigen, a microbial antigen, or other antibodies bound to cells or matrix). In this regard, "functionally active" means that the fragment, derivative or analog is able to recognize the same antigen that is recognized by the antibody from which the fragment, derivative or analog is derived. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (see, e.g., Kabat et al., 1991, Sequences of Proteins of Immunological Interest, Fifth Edition, National Institute of Health, Bethesda, Md.; Kabat et al., 1980, J. Immunology 125(3):961-969).

Other useful antibodies include fragments of antibodies such as, but not limited to, F(ab')$_2$ fragments, Fab fragments, Fab', Fv fragments and heavy chain and light chain dimers of antibodies, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54).

Recombinant antibodies, such as chimeric and humanized monoclonal antibodies, comprising both human and non-human portions, which can be made using standard recombinant DNA techniques, also can be used. (See, e.g., U.S. Pat. Nos. 4,816,567; and 4,816,397.) Humanized antibodies are antibody molecules from non-human species having one or more complementarity determining regions (CDRs) from the non-human species and a framework region from a human immunoglobulin molecule. (See, e.g., U.S. Pat. No. 5,585,089.) Chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060.

Completely human antibodies can be used. Human antibodies can be prepared, for example, using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies. see, e.g., U.S. Pat. Nos. 5,625,126; 5,633,425; 5,569,825; 5,661,016; and 5,545,806.

Human antibodies that recognize a selected epitope also can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903.) Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, "The rise of monoclonal antibodies as therapeutics," in Anti-IgE and Allergic Disease, Jardieu, P. M. and Fick Jr., R. B, eds., Marcel Dekker, New York, N.Y., Chapter 20, pp. 427-469).

In other embodiments, the antibody is a fusion protein of an antibody, or a functionally active fragment thereof. For example, an antibody can be fused via a covalent bond (e.g., a peptide bond) at either the N-terminus or the C-terminus to an amino acid sequence of another protein (or portion thereof, such as at least a 10, 20 or 50 amino acid portion of the protein) that is not the antibody.

Antibodies also include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including but not limited to specific chemical cleavage, acetylation, formylation, metabolic synthesis in the presence of tunicamycin, etc. Additionally, the analog or derivative can contain one or more unnatural amino acids.

The antibodies can have modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., International Publication No. WO 97/34631, which is incorporated herein by reference in its entirety). Antibodies immunospecific for a target antigen can be obtained commercially or other source or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

Examples of antibodies available for the treatment of cancer include, but are not limited to, humanized anti HER2 monoclonal antibody, HERCEPTIN® (trastuzumab; Genentech); RITUXAN® (rituximab; Genentech) which is a chimeric anti CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized IgG1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID 10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzumab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens (exemplary cancers are indicated in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti transferrin receptor (carcinomas), p97 (melanoma), MUC1-KLH (breast cancer), CEA (colorectal), gp100 (melanoma), MART1 (melanoma), prostate specific antigen (PSA) (prostate), IL-2 receptor (T-cell leukemia and lymphomas), CD20 (non Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et al., 1993, Science 261:212-215), BR64 (Trail et al., 1997, Cancer Research 57:100-105), mAbs against the CD40 antigen, such as S2C6 mAb (Francisco et al., 2000, Cancer Res. 60:3225-3231) and chimeric and humanized variants thereof, mabs against the cD33 antigen; mabs against the EphA2 antigen; mAbs against the CD70 antigen, such as 1F6 mAb and 2F2 mAb and chimeric and humanized variants thereof, and mAbs against the CD30 antigen, such as AC10 (Bowen et al., 1993, J. Immunol. 151:5896-5906; Wahl et al., 2002, Cancer Res. 62(13):3736-42) and chimeric and humanized variants thereof. Many other internalizing antibodies that bind to tumor associated antigens can be used and have been reviewed (see, e.g., Franke et al., 2000, Cancer Biother. Radiopharm. 15:459 76; Murray, 2000, Semin. Oncol. 27:64 70; Breitling et al., Recombinant Antibodies, John Wiley, and Sons, New York, 1998).

The antibody also can be an antibody that binds to an antigen that is present on a target cell or target cell population. For example, transmembrane polypeptides and other markers can be specifically expressed on the surface of one or more particular type(s) of target cells (e.g., a cancer cell) as compared to on one or more normal (e.g., a non-cancerous cell(s)). Often, such markers are more abundantly expressed on the surface of the target cells, or exhibit greater immunogenicity, as compared to those on the surface of the normal cells. The identification of such cell surface antigen polypeptides has given rise to the ability to specifically target cells for destruction via antibody-based therapies. Thus, in some embodiments, the antibodies include, but are not limited to, antibodies against tumor-associated antigens (TAA). Such tumor-associated antigens are known in the art, and can prepared for use in generating antibodies using methods and information which are well known in the art.

See also EP2552957, WO/2012/116453, WO/2012/032080. See also Zybody™, http://www.zyngenia.com/technology.html. See also human heavy chain-only antibodies technology, http://www.crescendobiologics.com/. See also WO2010001251, yeast based human antibody yeast-based platform http://www.adimab.com/science-and-technology/technology-overview/, mAbLogix™ platform http://www.dna.com/technology, monoclonal discovery platform http://www.igenica.com/technology/, WO2009/157771, EP2560993, WO2013004842, WO2012166560.

Linker Moiety (L)

The subject compositions further include a linker moiety (L). As with the payload (P), the linker moiety (L) is characterized from the perspective of an assembled conjugate of the invention. Accordingly, the linker (L) as characterized herein does not necessarily but may correspond to a particular reactant used in the synthesis of a conjugate. The components of the linker (L) may be contributed by a number of reactants.

In one embodiment, the linker moiety (L) is a bifunctional compound which can be used to link payload (P) and targeting moiety (T) to form a conjugate compound, (T)-(L)-(P). Such conjugates allow the selective delivery of drugs to target cells (e.g., tumor cells). In certain embodiments, linker moieties include a divalent substituent such as an alkyldiyl, an aryldiyl, a heteroaryldiyl, moieties such as: —$(CR_2)_nO(CR_2)_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide. The compounds described herein can be prepared using a linker moiety having a reactive site for binding to the payload and the targeting moiety.

In some embodiments, (L) has a reactive site which has an electrophilic group that is reactive to a nucleophilic group present on (T). Useful nucleophilic groups on (T) include but are not limited to sulfhydryl, hydroxyl and amino groups. The heteroatom of the nucleophilic group of (T) is reactive to an electrophilic group on (L) and forms a covalent bond to (L). Useful electrophilic groups include, but are not limited to maleimide and haloacetamide groups. The nucleophilic group on (T) provide a convenient site for attachment to (L).

In some embodiments, (L) has a reactive site which has a nucleophilic group that is reactive to an electrophilic group present on the targeting moiety. Useful electrophilic groups on the targeting moiety include, but are not limited to, aldehyde and ketone carbonyl groups. The heteroatom of a nucleophilic group of (L) can react with an electrophilic group on the targeting moiety and form a covalent bond to the targeting moiety. Useful nucleophilic groups on (L) include, but are not limited to, hydrazide, oxime, amino, hydrazine, thiosemicarbazone, hydrazine carboxylate, and arylhydrazide. The electrophilic group on the targeting moiety provides a convenient site for attachment to (L).

Carboxylic acid functional groups and chloroformate functional groups are also useful reactive sites for (L) because they can react, for example, with an amino group of $P^1$ to form an amide linkage. Also useful as a reactive site is a carbonate functional group on (L), such as but not limited to p-nitrophenyl carbonate, which can react, for example, with an amino group of $P^1$ to form a carbamate linkage.

It will be appreciated that any linker moieties taught in the prior art, and particularly those taught for use in the context of drug delivery, may be used in the current invention. Without limiting the scope of the preceding statement, in one embodiment, (L) comprises a linker moiety disclosed in WO 2012/113847. In another embodiment, (L) comprises a linker moiety disclosed in U.S. Pat. No. 8,288,352. In another embodiment, (L) comprises a linker moiety disclosed in U.S. Pat. No. 5,028,697. In another embodiment, (L) comprises a linker moiety disclosed in U.S. Pat. No. 5,006,652. In another embodiment, (L) comprises a linker moiety disclosed in U.S. Pat. No. 5,094,849. In another embodiment, (L) comprises a linker moiety disclosed in U.S. Pat. No. 5,053,394. In another embodiment, (L) comprises a linker moiety disclosed in U.S. Pat. No. 5,122,368. In another embodiment, (L) comprises a linker moiety disclosed in U.S. Pat. No. 5,387,578. In another embodiment, (L) comprises a linker moiety disclosed in U.S. Pat. No. 5,547,667. In another embodiment, (L) comprises a linker moiety disclosed in U.S. Pat. No. 5,622,929. In another embodiment, (L) comprises a linker moiety disclosed in U.S. Pat. No. 5,708,146. In another embodiment, (L) comprises a linker moiety disclosed in U.S. Pat. No. 6,468,522. In another embodiment, (L) comprises a linker moiety disclosed in U.S. Pat. No. 6,103,236. In another embodiment, (L) comprises a linker moiety disclosed in U.S. Pat. No. 6,638,509. In another embodiment, (L) comprises a linker moiety disclosed in U.S. Pat. No. 6,214,345. In another embodiment, (L) comprises a linker moiety disclosed in U.S. Pat. No. 6,759,509. In another embodiment, (L) comprises a linker moiety disclosed in WO 2007/103288. In another embodiment, (L) comprises a linker moiety disclosed in WO 2008/083312. In another embodiment, (L) comprises a linker moiety disclosed in WO 2003/068144. In another embodiment, (L) comprises a linker moiety disclosed in WO 2004/016801. In another embodiment, (L) comprises a linker moiety disclosed in WO 2009/134976. In another embodiment, (L) comprises a linker moiety disclosed in WO 2009/134952. In another embodiment, (L) comprises a linker moiety disclosed in WO 2009/134977. In another embodiment, (L) comprises a linker moiety disclosed in WO 2002/08180. In another embodiment, (L) comprises a linker moiety disclosed in WO 2004/043493. In another embodiment, (L) comprises a linker moiety disclosed in WO 2007/018431. In another embodiment, (L) comprises a linker moiety disclosed in WO 2003/026577. In another embodiment, (L) comprises a linker moiety disclosed in WO 2005/077090. In another embodiment, (L) comprises a linker moiety disclosed in WO 2005/082023. In another embodiment, (L) comprises a linker moiety disclosed in WO 2007/011968. In another embodiment, (L) comprises a linker moiety disclosed in WO 2007/038658. In another embodiment, (L) comprises a linker moiety disclosed in WO 2007/059404. In another embodiment, (L) comprises a linker moiety disclosed in WO 2006/110476. In another embodiment, (L) comprises a linker moiety disclosed in WO 2005/112919. In another embodiment, (L) comprises a linker moiety disclosed in WO 2008/103693. In another embodiment, (L) comprises a linker moiety disclosed in U.S. Pat. No. 6,756,037. In another embodiment, (L) comprises a linker moiety disclosed in U.S. Pat. No. 7,087,229. In another embodiment, (L) comprises a linker moiety disclosed in U.S. Pat. No. 7,122,189. In another embodiment, (L) comprises a linker moiety disclosed in U.S. Pat. No. 7,332,164. In another embodiment, (L) comprises a linker moiety disclosed in U.S. Pat. No. 5,556,623. In another embodiment, (L) comprises a linker moiety disclosed in U.S. Pat. No. 5,643,573. In another embodiment, (L) comprises a linker moiety disclosed in U.S. Pat. No. 5,665,358. Linkers (L) comprising a self-immolative component may also be used. For example, see U.S. Pat. No. 6,214,345. An example of a self-immolative component is p-aminobenzylcarbamoyl (PABC). Commercially available linkers may be used in the invention. For example, the commercially available cleavable linker sulfosuccinimidyl 6-[3'(2-pyridyldithio)-propionamido]hexanoate (sulfo-LC-SPDP: Thermo Pierce Cat #21650) and Non-cleavable linker succinimidyl 4-[N-maleimidomethyl]cyclohexane-1-carboxylate (SMCC: Thermo Pierce Cat #22360) may be used, as demonstrated herein. See also, WO2012171020, WO2010138719, the range of commercially available linkers, for example, from Concortis http://www.concortis.com/home. See also Kim et al., Bioconjugate Chemistry, 21 (8): 1513-1519 August 2010. See also EP2326349. See also copper-free click chemistry linkers, Angew. Chem. Int. Ed., 2010, 49, p. 9422-9425, ChemBioChem, 2011, 12, p. 1309-1312, http://www.synaffix.com/technology/.

In some embodiments, (L) comprises: SPDP, SMCC, vcPABC, MCvcPABC, MTvc, ADvc, maleimide, NHS, biotin, streptavidin, NeutrAvidin, a glycoside, or a combination thereof.

In some embodiments, (L) comprises SPDP.
In some embodiments, (L) comprises SMCC.
In some embodiments, (L) comprises vcPABC.
In some embodiments, (L) comprises MCvcPABC.
In some embodiments, (L) comprises MTvc.
In some embodiments, (L) comprises ADvc.
In some embodiments, (L) comprises maleimide.

In some embodiments, (L) comprises NHS.
In some embodiments, (L) comprises biotin.
In some embodiments, (L) comprises streptavidin.
In some embodiments, (L) comprises NeutrAvidin.
In some embodiments, (L) comprises a glycoside.
In some embodiments, (L) is absent.

In one embodiment, the linker (L) is a bifunctional unit that links payload (P) to targeting moiety (T) to form a conjugate composition, $[(P)-(L)]_m-(T)$, that may be cleaved enzymatically at the junction peptide bond (JPB) between (P) and (L) to release (P). Such conjugates allow the selective delivery of payload (P) to target cells (e.g., tumor cells). In another embodiment, the linker (L) is a bifunctional unit that links payload (P) to targeting moiety (T) to form a conjugate composition, $[(P)-(L)]_m-(T)$, that may be cleaved enzymatically between (P) and (L) to release (P).

Certain linkers (L) are capable of binding to multiple payloads (P) and a targeting moiety (T). Thus, in certain embodiments, the linker (L) is a multifunctional unit that links more than one payload (P) to a single targeting moiety (T) to form a conjugate $[(P)-(L)]m-(T)$. In addition, it is possible that payloads (P) may be multimerized and bound to a linker (L). Accordingly, it is understood that in certain embodiments, [(P)-(L)] comprises a greater number of (P) than (L). In certain embodiments, there is the same number of payload (P) and linker (L) in [(P)-(L)]. In one embodiment of Formula I, the invention provides compositions having the structure of Formula (Ia):

$[(P)_o-(L)]_m-(T)$ (Ia)

wherein o is an integer from 1 to 1000. In one embodiment, o is an integer from 1 to 100. In another embodiment, o is an integer from 1 to 50. In another embodiment, o is an integer from 1 to 20. In another embodiment, o is an integer from 1 to 10.

In certain embodiments, the linker (L) and the targeting moiety (T) taken together have the following structure (III):

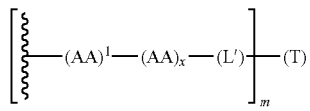

(III)

wherein the carbonyl of $(AA)^1$ forms a peptide bond referred to herein as the junction peptide bond (JPB) with the —NH— group bonded to (R) in structure (II), wherein the JPB is enzymatically cleavable, wherein each AA is independently an amino acid, wherein x is an integer from 0 to 25, wherein (L') is the remaining portion (if any) of linker (L), wherein (T) is the targeting moiety, and wherein $(AA)^1-(AA)_x$ comprises an amino acid sequence capable of facilitating enyzmatic cleavage of the JPB.

The amino acid unit $(AA)^1-(AA)_x$ comprises a recognition sequence that provides for cleavage of the junction peptide bond (JPB) to release payload (P) from the targeting moiety (T). Any sequence capable of providing for such enzymatic cleavage may be used. Such sequences include, but are not limited to, applicable sequences described in U.S. Pat. No. 6,214,345. For example, amino acid sequences known in the art to direct cleavage of a peptide bond linking a PABC self-immolative unit directly to the amino acid sequence may be used in the present invention. Additional amino acid sequences useful in the present invention can be readily determined experimentally by the artisan of reasonable skill. In certain embodiments of the invention, an amino acid unit, $(AA)^1-(AA)_x$, allows for cleavage of the (JPB) by a protease, thereby facilitating release of payload (P) from the conjugate upon exposure to such proteases. In certain embodiments of the invention, these include intracellular proteases, such as lysosomal enzymes. In yet further embodiments of the invention, these include extracellular proteases.

Exemplary amino acid units $(AA)^1-(AA)_x$ include, but are not limited to, a dipeptide, a tripeptide, a tetrapeptide, and/or a pentapeptide. Exemplary dipeptides include: Val-Cit, Ala-Phe, Phe-Lys, Val-Ala, Val-Lys(Ac), Phe-Lys(Ac), or Me-Val-Cit. It is noted that while the naming convention for peptides and proteins is to list amino acid sequence from N-terminus to C-terminus, the configuration of the JPB is such that $(AA)^1$ is the C-terminus amino acid in the $(AA)^1-(AA)_x$ amino acid sequence. Accordingly, in an embodiment where the amino acid sequence facilitating enzymatic cleavage of the JPB was valine-citrulline, $(AA)^1$ in formula (III) would be citrulline and the carbonyl group of citrulline would form JPB with the —NH— group bonded to (R) in structure (II). In some embodiments, additional amino acids are linked to valine-citrulline through the N-terminus of valine and, accordingly, "x" for $(AA)_x$ is an integer greater than one.

Exemplary tripeptides include: Gly-Val-Cit, Pro-Pro-Pro, D-Ala-Phe-Lys, (D)-Val-Leu-Lys, Gly-Gly-Arg, and Ala-Ala-Asn. For illustration and clarity, when the tripeptide is (gly-val-cit), $(AA)^1$ of formula (III) is citrulline. An amino acid unit may comprise amino acid residues that occur naturally, as well as minor amino acids and non-naturally occurring amino acid analogs, such as citrulline. D-amino acids are included for use in the invention. Amino acid units can be designed and optimized in their selectivity for enzymatic cleavage by a particular enzyme, for example, a tumor-associated protease, cathepsin B, C and D, or a plasmin protease.

Exemplary tetrapeptides include: Lys-Ser-Gly-Arg, Gly-Phe-Leu-Gly, Leu-Ser-Gly-Arg, Ala-Leu-Ala-Leu, Gly-Gly-Gly-Arg-Arg, Gly-Lys-Ala-Phe-Arg-Arg, and Homo-Gly-Arg-Ser-Arg-Gly Exemplary amino acid sequences for use in linkers of the invention include the amino acid sequences within Phe-Lys, Val-Lys, Ala-Lys, Val-Cit, Phe-Cit, Leu-Cit, Ile-Cit, Trp-Cit, Phe-Arg. These sequences have been used for release of doxorubicin. See, for example, Table 1, Dubowchik, Firestone et al. *Bioconjugate Chem.* 2002, 13, 855-869 and references contained therein. Another exemplary amino acid sequence for use in linkers of the present invention is Pro-Pro (see, for example, Gianolio et al. *Cancer Chemother Pharmacol* 2012 70, 439-449). See also Firestone et al., U.S. Pat. No. 6,214,345 for amino acid sequences useful in the present invention. See also Miao et al., WO 2013/173392 for amino acid sequences useful in the present invention, including but not limited to amino acid sequences comprising non-natural amino acids. See also Dubowchik et al., Bioorganic & Med. Chem. Letters 8:3341-3346, 1998. See also Burke et al., Bioorganic & Med. Chem. Letters 19:2650-2653, 2009. See also Jeffrey et al., Bioorganic & Med. Chem. Letters 16:358-362, 2006. The artisan of reasonable skill will appreciate that additional amino acids may be included in the linker (L) to the N-terminus side of the amino acid sequence that is factilitating enzymatic cleavage of the JPB.

In one example, the JPB is cleavable by a protease that is associated with a disease. In another example, the JPB is cleavable by a protease that is up-regulated or associated with cancers in general. In still another example, the JPB is cleavable by a protease secreted by cancer-associated cells.

In another example, the JPB is cleavable by an enzyme that is up-regulated or associated with a specific cancer.

In certain embodiments of the invention, the remaining portion of linker (L') includes a stretcher moiety (S) between the amino acid unit, $(AA)^1$-$(AA)_x$. and the Targeting moiety (T) as shown in the following structures (VII) or (VIII):

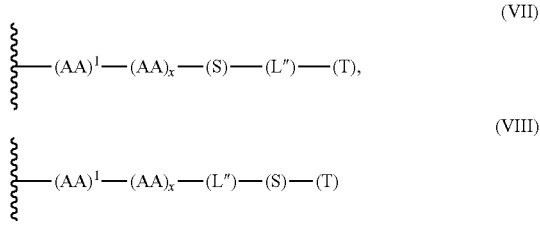

(VII)

(VIII)

wherein the carbonyl of $(AA)^1$ forms a peptide bond referred to herein as the junction peptide bond (JPB) with the —NH— group bonded to (R) in structure (II), wherein the JPB is enzymatically cleavable, wherein each AA is independently an amino acid, wherein x is an integer from 0 to 25, wherein L" is the remaining portion (if any) of linker (L'), wherein (S) is the stretcher unit, wherein (T) is the targeting moiety, and wherein $(AA)^1$-$(AA)_x$ comprises an amino acid sequence capable of facilitating enyzmatic cleavage of the JPB.

In particular embodiments of the invention, this stretcher is as described in U.S. Pat. Nos. 7,964,566 and 6,214,345.

Payload Moiety (P)

As with the linker moiety (L), the payload (P) is characterized from the perspective of an assembled conjugate of the invention. Accordingly, the payload (P) as characterized herein does not necessarily but may correspond to a particular reactant used in the synthesis of a conjugate. The components of the payload (P) may be contributed by a number of reactants.

A wide variety of compounds may be used to assemble desirable payload (P) components of a conjugate of the invention. Any compound that is functional as an amide (as in formula (IV) or as a compound containing an N-acyl sulfonamide-(R)—$NH_2$ group (as in formula (V)) could be delivered to a target cell or tissue using the present conjugate technology. Any precursor compounds that can be used (directly, or following appropriate modification) to produce amides of formula (IV) or N-acyl sulfonamide-(R)—$NH_2$ compounds of formula (V) find use in the invention. Particularly preferred are amide containing drugs, carboxylic acid containing drugs that have active amide derivatives, carboxylic acid containing drugs, and drugs having the formula (V). The route of synthesis and the particular reactants used to produce conjugates of formula (I) are not limiting. Included within the scope of biologically active compounds as payload (P) are precursors that may be activated in vivo.

In one embodiment, conjugates of formula (I) can be used to deliver biologically active compounds of formula (IV) or (V). Suitable payload compounds (P) that may be advantageously delivered by way of compositions of the invention to targeted locations include, e.g., antibiotics, diagnostic agents (e.g. detectable labels), anti-inflammatory agents, anti-viral agents, cytotoxic agents, and anti-cancer drugs. Other suitable payload (P) include diagnostic agents known in the art, including those employing one or more of a wide variety of detectable labels. The detectable label can be a reporter such as a radioactive isotope such as $^{125}I$, enzymes, fluorescent reagents or groups such as fluorescein, tetramethylrhodamine, cyanine dyes, Alexa dyes or BODIPY dyes, chemiluminescent reagents or groups, or electrochemical materials. The detectable label may also be a member of a specific binding pair as is known in the art. Other suitable detectable labels will be readily apparent to one of skill in the art.

In one embodiment, compounds of formula (IV) or (V) show cytotoxic or cytotstatic activity. The present invention provides compositions and methods for delivering biologically active compounds of formula (IV) or (V) to cells of interest.

In one embodiment, (P) is a drug compound (D). In one embodiment, (D) is a compound having the following structure (XVIII):

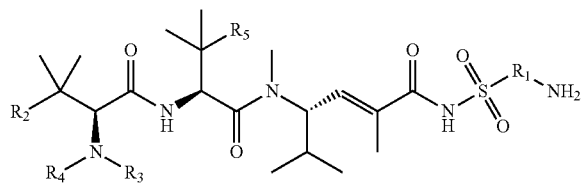

(XVIII)

or a stereoisomer, prodrug or pharmaceutically acceptable salt thereof, wherein:

$R_1$ is selected from the group consisting of optionally substituted alkyl, optionally substituted alkylamino, optionally substituted cycloalkyl, optionally substituted aryl, optionally substituted heterocyclyl, optionally substituted heteroaryl, —$COR_{24}$—, —$CSR_{24}$—, —$OR_{24}$—, and —$NHR_{24}$—, wherein each $R_{24}$ is, independently, optionally substituted alkyl, optionally substituted alkylamino, optionally substituted cycloalkyl, optionally substituted aryl, optionally substituted heterocyclyl and optionally substituted heteroaryl;

$R_2$ is selected from the group consisting of optionally substituted alkyl, optionally substituted alkylamino, optionally substituted cycloalkyl, optionally substituted aryl, optionally substituted heterocyclyl and optionally substituted heteroaryl;

$R_3$ is selected from the group consisting of H and $C_{1-6}$alkyl;

$R_4$ is selected from the group consisting of H and $C_{1-6}$ alkyl; and $R_5$ is selected from the group consisting of $C_{1-6}$ alkyl and —SH.

In one embodiment, $R_1$ is selected from the group consisting of optionally substituted alkyl, optionally substituted alkylamino, optionally substituted cycloalkyl, optionally substituted aryl, optionally substituted heterocyclyl and optionally substituted heteroaryl.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, $R_2$ is selected from one of the following structures (A), (B), (C), (D):

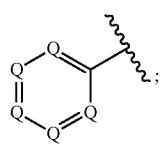 (A)

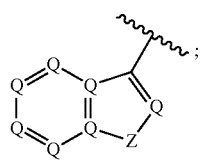 (B)

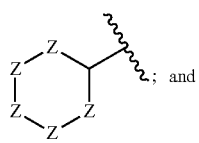 (C)

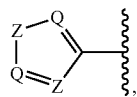 (D)

wherein:
each Q is independently $CR_{29}$ or N;
each Z is independently $C(R_{29})_2$, $NR_{29}$, S, or O;
each $R_{29}$ is, independently, selected from the group consisting of H, —OH, —$R_{28}$, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —$R_{28}NH_2$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, $R_2$ is selected from the group consisting of:

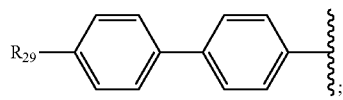

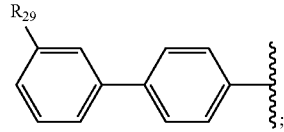

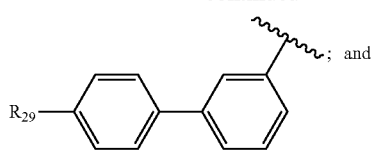

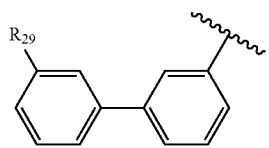

wherein each $R_{29}$ is, independently, selected from the group consisting of H, —OH, —$R_{28}$, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —$R_{28}NH_2$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, $R_2$ is selected from the group consisting of:

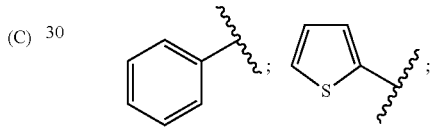

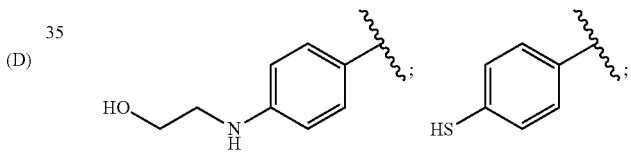

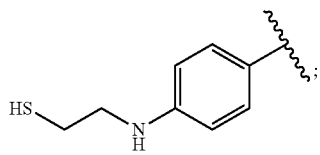

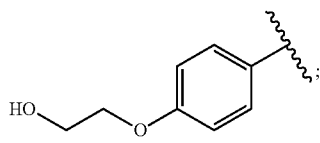

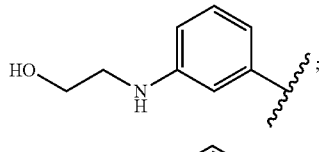

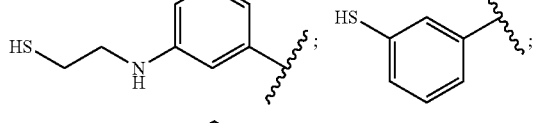

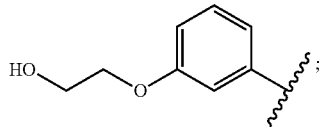

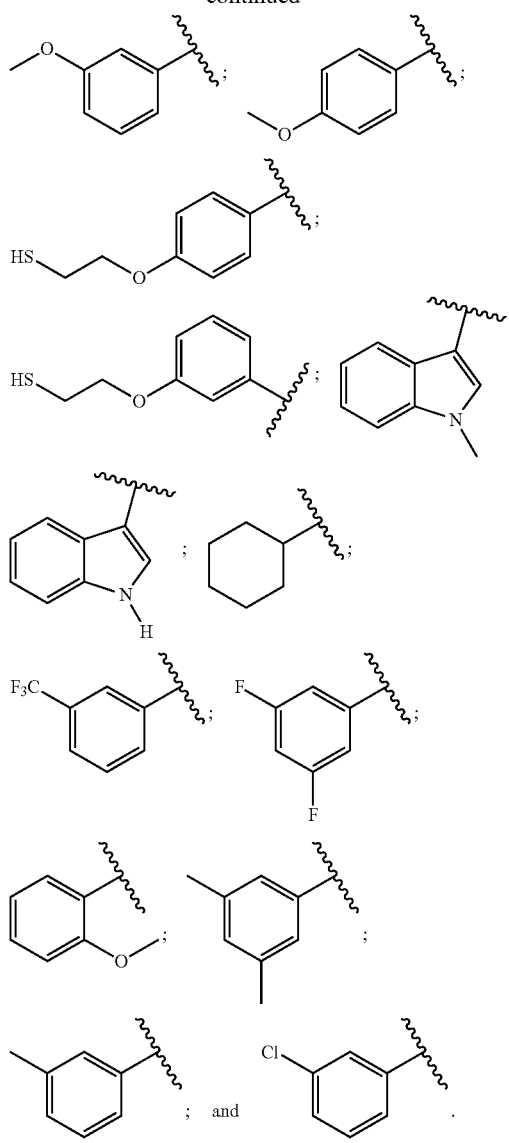

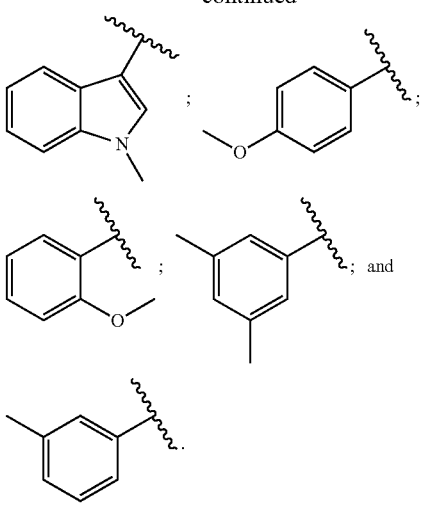

In another further embodiment, $R_3$, $R_4$ and $R_5$ are each methyl.

In another further embodiment, $R_3$ is H, $R_4$ is methyl, and $R_5$ is methyl.

It is understood that any embodiment of the compounds of structure (XVIII), as set forth above, and any specific substituent set forth herein for a $R_1$, $R_2$, $R_3$, $R_4$, $R_5$, $R_{28}$, or $R_{29}$ group in the compounds of structure (XVIII), as set forth herein, may be independently combined with other embodiments and/or substituents of compounds of structure (XVIII) to form embodiments of the present disclosure not specifically set forth above. In addition, in the event that a list of substituents is listed for any particular $R_1$, $R_2$, $R_3$, $R_4$, $R_5$, $R_{28}$, or $R_{29}$ in a particular embodiment and/or claim, it is understood that each individual substituent may be deleted from the particular embodiment and/or claim and that the remaining list of substituents will be considered to be within the scope of the present disclosure.

In another embodiment, (D) is a compound having the following structure (XVI):

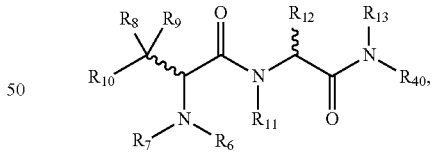

(XVI)

or a stereoisomer, prodrug or pharmaceutically acceptable salt thereof, wherein:

$R_6$ and $R_7$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO₂H, —CHO, —COSH, or —NO₂; or $R_7$ and $R_{10}$ are fused and form a ring;

$R_8$ and $R_9$ are independently selected from the group consisting of: H, R', ArR'—, or $R_8$ and $R_9$ are joined to form a ring;

In another further embodiment, $R_2$ is:

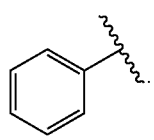

In one embodiment, $R_2$ is selected from the group consisting of:

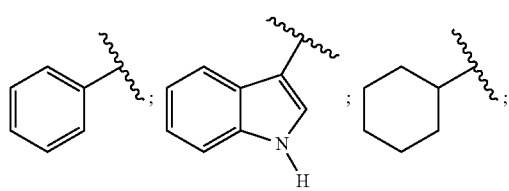

$R_{10}$ is selected from the group consisting of: H, R', ArR'—, and Ar;

or $R_{10}$ and $R_7$ are fused and form a ring;

$R_{11}$ is selected from the group consisting of: H, R', and ArR'—;

$R_{12}$ and $R_{13}$ are independently selected from the group consisting of: H, R', and ArR'—; and $R^{40}$ is:

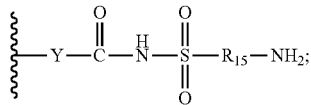

wherein:

$R_{15}$ is selected from the group consisting of optionally substituted alkyl, optionally substituted alkylamino, optionally substituted cycloalkyl, optionally substituted aryl, optionally substituted heterocyclyl and optionally substituted heteroaryl, —$COR_{24}$—, —$CSR_{24}$—, —$OR_{24}$—, and —$NHR_{24}$—, wherein each $R_{24}$ is, independently, optionally substituted alkyl, optionally substituted alkylamino, optionally substituted cycloalkyl, optionally substituted aryl, optionally substituted heterocyclyl or optionally substituted heteroaryl;

R' is defined as a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —$OR_{16}$, —$O_2CR_{16}$, —SH, —$SR_{16}$, —$SOCR_{16}$, —$NH_2$, —$NHR_{16}$, —$N(R_{16})_2$, —$NHCOR_{16}$, —$NR_{16}COR_{16}$, —I, —Br, —Cl, —F, —CN, —$CO_2H$, —$CO_2R_{16}$, —CHO, —$COR_{16}$, —$CONH_2$, —$CONHR_{16}$, —$CON(R_{16})_2$, —COSH, —$COSR_{16}$, —$NO_2$, —$SO_3H$, —$SOR_{16}$, —$SO_2R_{16}$, wherein $R_{16}$ is a linear, branched or cyclic, one to ten carbon saturated or unsaturated alkyl group;

the ring formed by joining $R_8$ and $R_9$ is a three to seven member non-aromatic cyclic skeleton within the definition of R', Y is defined as a moiety selected from the group consisting of: a linear, saturated or unsaturated, one to six carbon alkyl group, optionally substituted with R', ArR'—, or X; and X is defined as a moiety selected from the group consisting of: —OH, —OR', =O, =S, —$O_2CR'$, —SH, —SR', —SOCR', —$NH_2$, —NHR', —$N(R')_2$, —NHCOR', —NR-COR', —I, —Br, —Cl, —F, —CN, —$CO_2H$, —$CO_2R'$, —CHO, —COR', —$CONH_2$, —CONHR', —$ON(R')_2$, —COSH, —COSR', —$NO_2$, —$SO_3H$, —SOR', and —$SO_2R'$.

In one embodiment, $R_{15}$ is selected from the group consisting of optionally substituted alkyl, optionally substituted alkylamino, optionally substituted cycloalkyl, optionally substituted aryl, optionally substituted heterocyclyl and optionally substituted heteroaryl.

In one embodiment, Ar is an aromatic ring selected from the group consisting of: phenyl, naphthyl, anthracyl, pyrrolyl.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$ wherein each $R_{28}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, $R_{10}$ is selected from one of the following structures (A), (B), (C), (D):

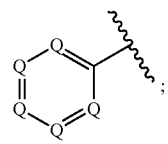

(A)

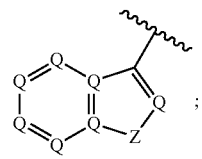

(B)

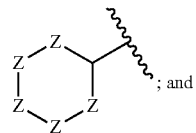

(C)

; and

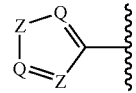

(D)

wherein:

each Q is independently $CR_{29}$ or N;

each Z is independently $C(R_{29})_2$, $NR_{29}$, S, or O;

each $R_{29}$ is, independently, selected from the group consisting of H, —OH, —$R_{28}$, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —$R_{28}NH_2$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, $R_{10}$ is selected from the group consisting of:

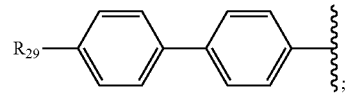

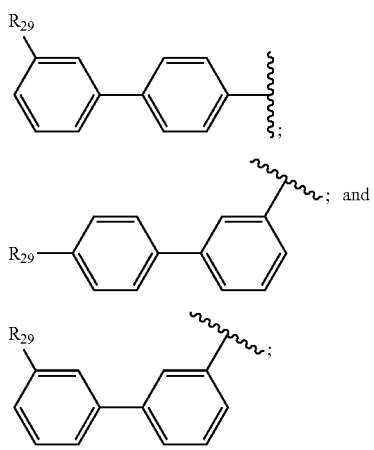

wherein each $R_{29}$ is, independently, selected from the group consisting of H, —OH, —$R_{28}$, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —$R_{28}NH_2$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, $R_{10}$ is selected from the group consisting of:

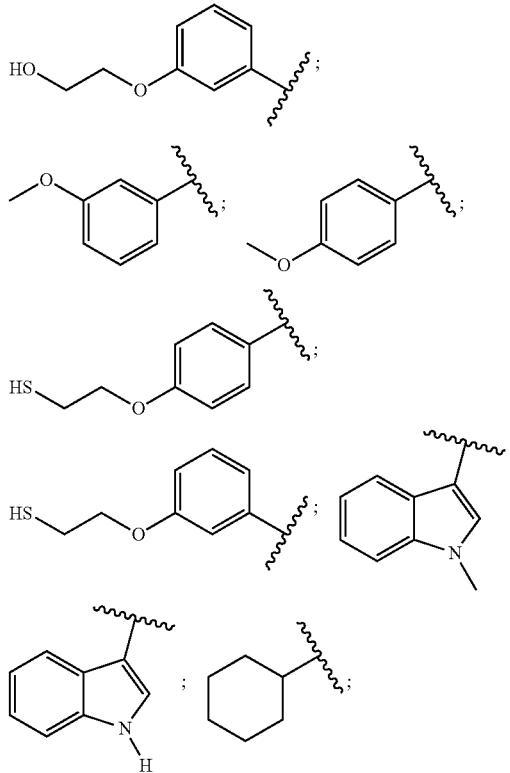

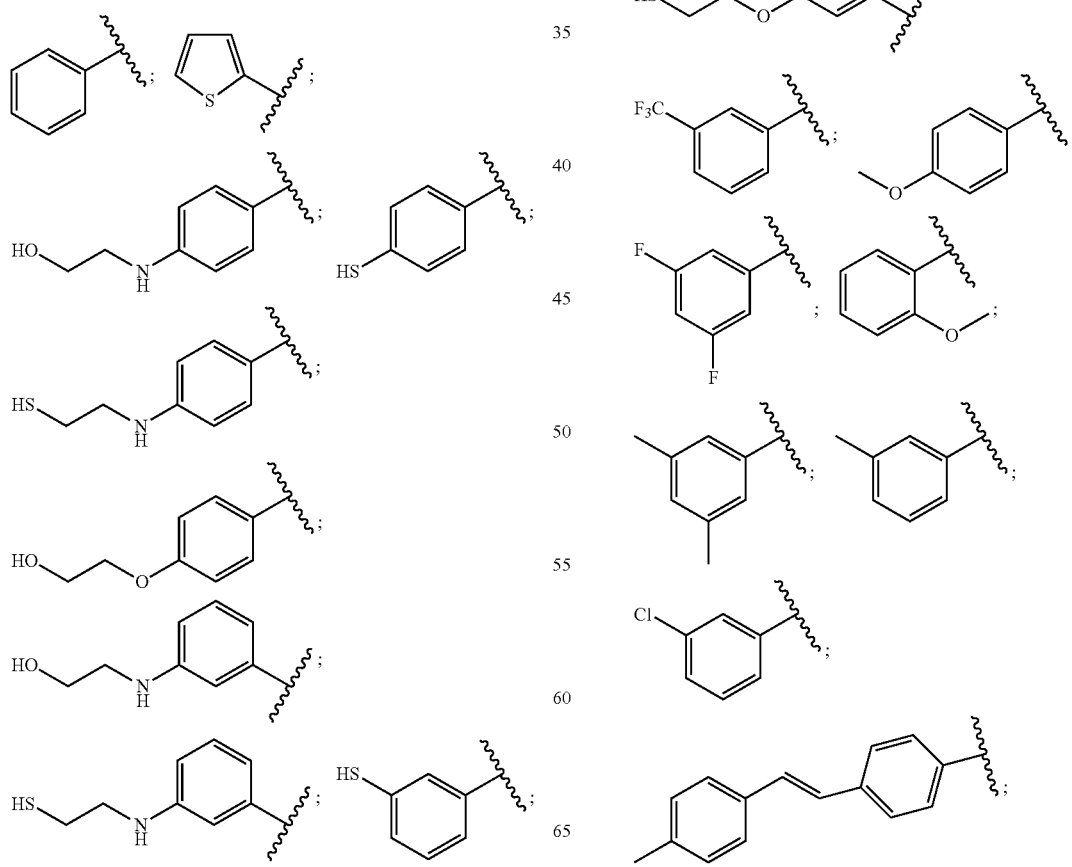

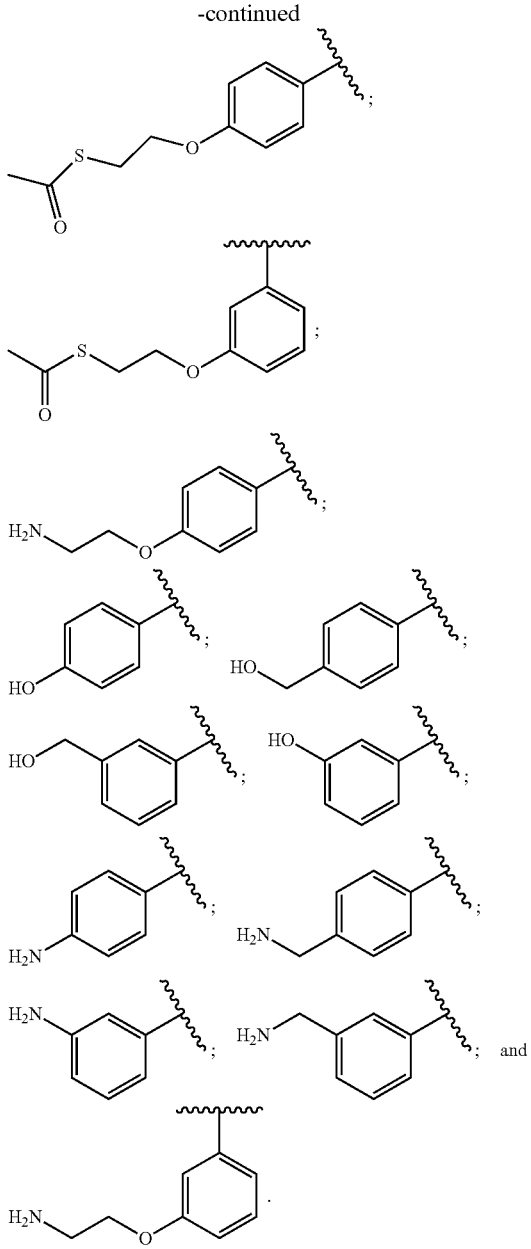

In another further embodiment, R$_{10}$ is:

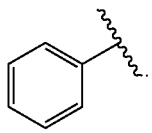 [SMILES: *c1ccccc1]

In another further embodiment, R and R$_7$ are each methyl.
In another further embodiment, R$_6$ is H and R$_7$ is methyl.
In one embodiment, R$_{12}$ is C4 branched alkyl.

It is understood that any embodiment of the compounds of structure (XVI), as set forth herein, and any specific substituent set forth herein for a R$_6$, R$_7$, R$_8$, R$_9$, R$_{10}$, R$_{11}$, R$_{12}$, R$_{13}$, R$_{14}$, R$_{15}$, R$_{16}$, R$_{28}$, or R$_{29}$ group in the compounds of structure (XVI), as set forth herein, may be independently combined with other embodiments and/or substituents of compounds of structure (XVI) to form embodiments of the present disclosure not specifically set forth above. In addition, in the event that a list of substituents is listed for any particular R$_6$, R$_7$, R$_8$, R$_9$, R$_{10}$, R$_{11}$, R$_{12}$, R$_{13}$, R$_{14}$, R$_{15}$, R$_{16}$, R$_{28}$, or R$_{29}$ in a particular embodiment and/or claim, it is understood that each individual substituent may be deleted from the particular embodiment and/or claim and that the remaining list of substituents will be considered to be within the scope of the present disclosure.

In some embodiments, (P) is a monovalent radical of a compound of Formula (XXV):

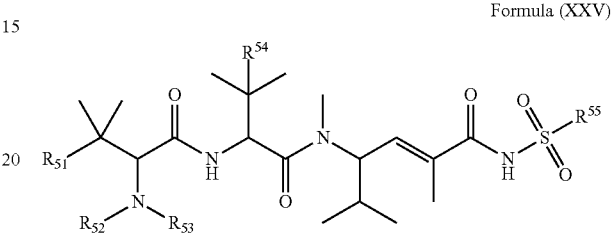

Formula (XXV)

wherein:

R$^{51}$ is selected from: aryl, C$_3$-C$_7$ cycloalkyl, and heteroaryl, each of which is optionally substituted with one or more substituents selected from: C$_1$-C$_4$ acylthio, C$_2$-C$_4$ alkenyl, C$_1$-C$_4$ alkyl, C$_1$-C$_4$ alkylamino, C$_1$-C$_4$ alkoxy, amino, amino-C$_1$-C$_4$ alkyl, halo, C$_1$-C$_4$ haloalkyl, hydroxyl, hydroxy-C$_1$-C$_4$ alkyl, and thio, wherein C$_2$-C$_4$ alkenyl, C$_1$-C$_4$ alkylamino and C$_1$-C$_4$ alkoxy are further optionally substituted with one substituent selected from C$_1$-C$_4$ alkylaryl, hydroxyl, and thio;

R$^{52}$ and R$^{53}$ are each independently selected from: H and C$_1$-C$_6$ alkyl;

R$^{54}$ is selected from the group consisting of C$_1$-C$_6$ alkyl and thio; and R$^{55}$ is selected from: C$_1$-C$_6$ alkyl, aryl, aryl-C$_1$-C$_6$ alkyl, C$_3$-C$_7$ cycloalkyl, heteroaryl, and heterocyclyl, each optionally substituted with one or more substituents selected from: C$_1$-C$_6$ alkoxy, C$_1$-C$_6$ alkoxycarbonyl, C$_1$-C$_6$ alkyl, C$_1$-C$_6$ alkylamino, amino, amino-C$_1$-C$_6$ alkyl, amino-aryl, amino-C$_3$-C$_7$ cycloalkyl, aryl, carboxamide, carboxyl, C$_3$-C$_7$ cycloalkyl, cyano, C$_1$-C$_6$ haloalkyl, C$_1$-C$_6$ haloalkoxy, halo, hydroxyl, nitro, thio, and thio-C$_1$-C$_6$ alkyl; and In some embodiments, R$^{51}$ is selected from: is selected from: H, aryl, C$_3$-C$_7$ cycloalkyl, and heteroaryl, each of which is optionally substituted with one or more substituents selected from: C$_1$-C$_4$ acylthio, C$_2$-C$_4$ alkenyl, C$_1$-C$_4$ alkyl, C$_1$-C$_4$ alkylamino, C$_1$-C$_4$ alkoxy, amino, amino-C$_1$-C$_4$ alkyl, halo, C$_1$-C$_4$ haloalkyl, hydroxyl, hydroxy-C$_1$-C$_4$ alkyl, and thio, wherein C$_2$-C$_4$ alkenyl, C$_1$-C$_4$ alkylamino and C$_1$-C$_4$ alkoxy are further optionally substituted with one substituent selected from p-tolyl, hydroxyl, and thio.

In some embodiments, R$^{51}$ is selected from: H, aryl, C$_3$-C$_7$ cycloalkyl, and heteroaryl, each of which is optionally substituted with one or more substituents selected from: (2-hydroxyethyl)amino, (2-mercaptoethyl)amino, 2-(acetylthio)ethoxy, 2-aminoethoxy, 2-hydroxyethoxy, 2-mercaptoethoxy, 3-methoxy, 4-methylstyryl, amino, aminomethyl, chloro, fluoro, hydroxyl, hydroxymethyl, methyl, thio, trifluoromethyl.

In some embodiments, R$^{51}$ is selected from: H, cyclohexyl, 1H-indol-3-yl, phenyl, and thien-2-yl each of which is optionally substituted with one or more substituents selected from: (2-hydroxyethyl)amino, (2-mercaptoethyl)

amino, 2-(acetylthio)ethoxy, 2-aminoethoxy, 2-hydroxyethoxy, 2-mercaptoethoxy, 3-methoxy, 4-methylstyryl, amino, aminomethyl, chloro, fluoro, hydroxyl, hydroxymethyl, methyl, thio, and trifluoromethyl.

In some embodiments, $R^{51}$ is selected from: H, 1H-indol-3-yl, 1-methyl-1H-indol-3-yl, 2-methoxyphenyl, 3-((2-hydroxyethyl)amino)phenyl, 3-((2-mercaptoethyl)amino)phenyl, 3-(2-(acetylthio)ethoxy)phenyl, 3-(2-hydroxyethoxy)phenyl, 3-(2-mercaptoethoxy)phenyl, 3-(4-methylstyryl)phenyl, 3-(aminomethyl)phenyl, 3-(hydroxymethyl)phenyl, 3-hydroxyphenyl, 3,5-difluorophenyl, 3,5-dimethylphenyl, 3-aminophenyl, 3-chlorophenyl, 3-mercaptophenyl, 3-methoxyphenyl, 3-trifluoromethylphenyl, 4-((2-hydroxyethyl)amino)phenyl, 4-((2-mercaptoethyl)amino)phenyl, 4-(2-(acetylthio)ethoxy)phenyl, 4-(2-aminoethoxy)phenyl, 4-(2-hydroxyethoxy)phenyl, 4-(2-mercaptoethoxy)phenyl, 4-(aminomethyl)phenyl, 4-(hydroxymethyl)phenyl, 4-aminophenyl, 4-hydroxyphenyl, 4-mercaptophenyl, 4-methoxyphenyl, cyclohexyl, thien-2-yl, m-tolyl, and phenyl.

In some embodiments, $R^{51}$ is selected from: H, 1H-indol-3-yl, 1-methyl-1H-indol-3-yl, 2-methoxyphenyl, 3-((2-hydroxyethyl)amino)phenyl, 3-((2-mercaptoethyl)amino)phenyl, 3-(2-hydroxyethoxy)phenyl, 3-(2-mercaptoethoxy)phenyl, 3,5-difluorophenyl, 3,5-dimethylphenyl, 3-chlorophenyl, 3-mercaptophenyl, 3-methoxyphenyl, 3-trifluoromethylphenyl, 4-((2-hydroxyethyl)amino)phenyl, 4-((2-mercaptoethyl)amino)phenyl, 4-4-(2-hydroxyethoxy)phenyl, 4-(2-mercaptoethoxy)phenyl, 4-mercaptophenyl, 4-methoxyphenyl, cyclohexyl, thien-2-yl, m-tolyl, and phenyl.

In some embodiments, $R^{51}$ is phenyl.
In some embodiments, $R^{52}$ is H.
In some embodiments, $R^{52}$ is methyl.
In some embodiments, $R^{53}$ is methyl.
In some embodiments, $R^{54}$ is methyl.
In some embodiments, $R^{55}$ is selected from: $C_1$-$C_6$ alkyl, aryl, aryl-$C_1$-$C_6$ alkyl, $C_3$-$C_7$ cycloalkyl, heteroaryl, and heterocyclyl, each optionally substituted with one or more substituents selected from: 1-aminocyclopropyl, 4-aminophenyl, amino, aminomethyl, bromo, tert-butyl, carboxamide, carboxyl, chloro, cyano, cyclopentyl, ethyl, fluoro, hydroxy, isopropyl, methoxy, methyl, nitro, phenyl, pyridin-3-yl, thio, thiomethyl, trifluoromethoxy, and trifluoromethyl.

In some embodiments, $R^{55}$ is selected from: 5,6,7,8-tetrahydronaphthalen-1-yl, benzyl, cyclohexyl, ethyl, hexan-2-yl, methyl, naphthalen-2-yl, piperidin-1-yl, phenyl, propyl, pyridin-3-yl, and thien-2-yl, each optionally substituted with one or more substituents selected from: 1-aminocyclopropyl, 4-aminophenyl, amino, aminomethyl, bromo, tert-butyl, carboxamide, carboxyl, chloro, cyano, cyclopentyl, ethyl, fluoro, hydroxy, isopropyl, methoxy, methyl, nitro, phenyl, pyridin-3-yl, thio, thiomethyl, trifluoromethoxy, and trifluoromethyl.

In some embodiments, $R^{55}$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, methyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, 4-aminophenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl.

In some embodiments, $R^{55}$ is selected from: aryl and aryl-$C_1$-$C_6$ alkyl, each optionally substituted with one or more substituents selected from: amino and amino-$C_1$-$C_6$ alkyl.

In some embodiments, $R^{55}$ is selected from: 4-aminobenzyl, 4-(aminomethyl)benzyl, 4-(aminomethyl)phenyl, 4-aminophenyl, and benzyl.

In some embodiments, $R^{55}$ is 4-aminobenzyl.
In some embodiments, $R^{55}$ is 4-(aminomethyl)benzyl.
In some embodiments, $R^{55}$ is 4-(aminomethyl)phenyl.
In some embodiments, $R^{55}$ is 4-aminophenyl.
In some embodiments, $R^{55}$ is benzyl.

In some embodiments P is a monovalent radical of a compound disclosed in International Application No. PCT/US14/29463 or U.S. Ser. No. 14/213,504.

In another embodiment, (D) has the following structure (XVII);

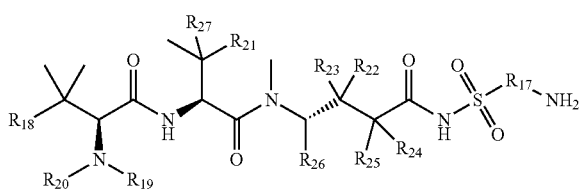

(XVII)

or a stereoisomer, prodrug or pharmaceutically acceptable salt thereof; wherein:

$R_{17}$ is selected from the group consisting of optionally substituted alkyl, optionally substituted alkylamino, optionally substituted cycloalkyl, optionally substituted aryl, optionally substituted heterocyclyl, optionally substituted heteroaryl, —$COR_{24}$—, —$CSR_{24}$—, $OR_{24}$—, and —$NHR_{24}$—, wherein each $R_{24}$ is, independently, optionally substituted alkyl, optionally substituted alkylamino, optionally substituted cycloalkyl, optionally substituted aryl, optionally substituted heterocyclyl or optionally substituted heteroaryl;

$R_{18}$ is selected from the group consisting of optionally substituted alkyl, optionally substituted alkylamino, optionally substituted cycloalkyl, optionally substituted aryl, optionally substituted heterocyclyl and optionally substituted heteroaryl;

$R_{19}$ is selected from the group consisting of H and $C_{1-6}$ alkyl;

$R_{20}$ is selected from the group consisting of H and $C_{1-6}$ alkyl;

$R_{21}$ and $R_{27}$ are independently selected from the group consisting of H, $C_{1-6}$ alkyl and —SH, with the proviso that $R_{21}$ and $R_{27}$ cannot both be H;

$R_{22}$, $R_{23}$, $R_{24}$ and $R_{25}$ are independently H and $C_{1-6}$ alkyl, at least one of $R_{22}$ and $R_{23}$ is H; or $R_{23}$ and $R_{24}$ form a double bond, $R_{22}$ is H, and $R_{25}$ is H or $C_{1-6}$ alkyl; and $R_{26}$ is selected from the group consisting of H and $C_{1-6}$ alkyl.

In one embodiment, $R_{17}$ is selected from the group consisting of optionally substituted alkyl, optionally substituted alkylamino, optionally substituted cycloalkyl, optionally substituted aryl, optionally substituted heterocyclyl, and optionally substituted heteroaryl.

In a further embodiment, each optionally substituted alkyl, optionally substituted alkylamino, optionally substituted cycloalkyl, optionally substituted aryl, optionally substituted heterocyclyl and optionally substituted heteroaryl is, independently, optionally substituted with =O, =S, —OH, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$ wherein each $R_{28}$ is, independently, alkyl optionally substituted with halogen, —OH or —SH.

In another further embodiment, each optionally substituted aryl and optionally substituted heteroaryl is, independently, selected from the group consisting of optionally substituted phenyl, optionally substituted naphthyl, optionally substituted anthracyl, optionally substituted phenanthryl, optionally substituted furyl, optionally substituted pyrrolyl, optionally substituted thiophenyl, optionally substituted benzofuryl, optionally substituted benzothiophenyl, optionally substituted quinolinyl, optionally substituted isoquinolinyl, optionally substituted imidazolyl, optionally substituted thiazolyl, optionally substituted oxazolyl, and optionally substituted pyridinyl.

In another further embodiment, $R_{18}$ is selected from one of the following structures (A), (B), (C), (D):

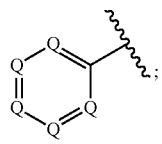

(A)

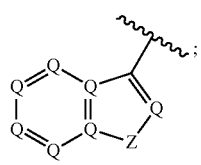

(B)

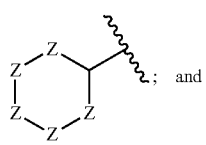

(C)

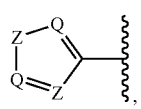

(D)

wherein:
each Q is independently $CR_{29}$ or N;
each Z is independently $C(R_{29})_2$, $NR_{29}$, S, or O;
each $R_{29}$ is, independently, selected from the group consisting of H, —OH, —$R_{28}$, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —$R_{28}NH_2$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, $R_{18}$ is selected from the group consisting of:

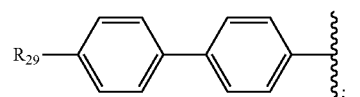

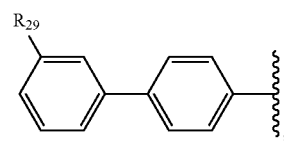

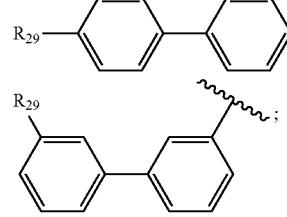

wherein each $R_{29}$ is, independently, selected from the group consisting of H, —OH, —$R_{28}$, —$OR_{28}$, —$O_2CR_{28}$, —SH, —$SR_{28}$, —$SOCR_{28}$, —$NH_2$, —$N_3$, —$NHR_{28}$, —$N(R_{28})_2$, —$NHCOR_{28}$, —$NR_{28}COR_{28}$, —$R_{28}NH_2$, —I, —Br, —Cl, —F, —CN, —$CO_2H$, —$CO_2R_{28}$, —CHO, —$COR_{28}$, —$CONH_2$, —$CONHR_{28}$, —$CON(R_{28})_2$, —COSH, —$COSR_{28}$, —$NO_2$, —$SO_3H$, —$SOR_{28}$ or —$SO_2R_{28}$, wherein each $R_{28}$ is, independently, alkyl optionally substituted with halogen, —OH or —SH.

In another further embodiment, R is selected from the group consisting of:

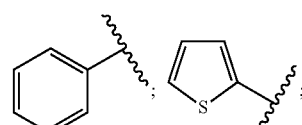
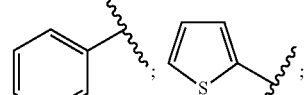

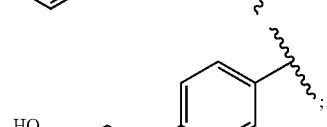
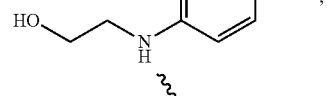

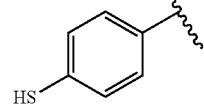

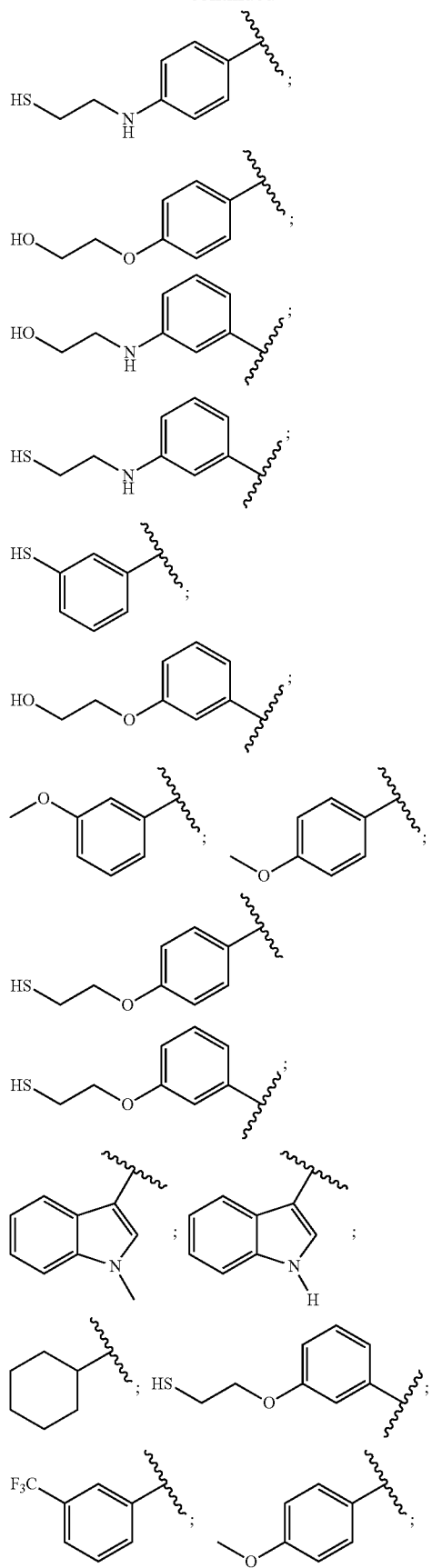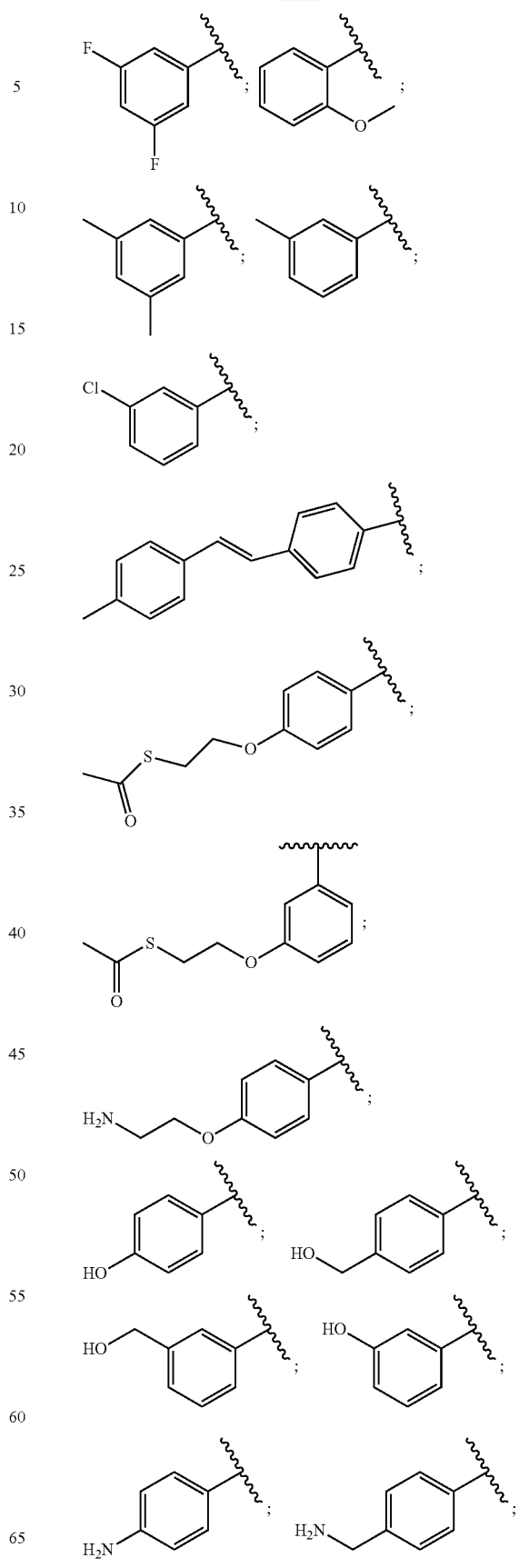

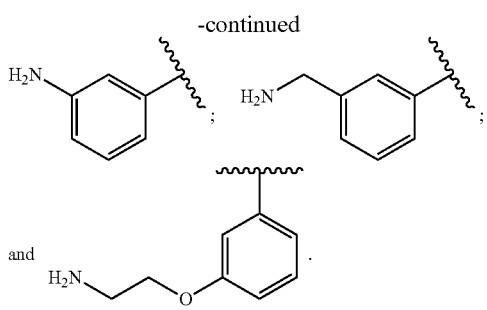

In another further embodiment, $R_{18}$ is:

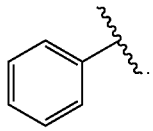

In another further embodiment, $R_{19}$, $R_{20}$, $R_{21}$, and $R_{27}$ are each methyl.

In another further embodiment, $R_{19}$ is H, $R_{20}$ is methyl, $R_{21}$ is methyl, and $R_{27}$ is methyl.

It is understood that any embodiment of the compounds of structure (XVII), as set forth herein, and any specific substituent set forth herein for a $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, or $R_{29}$ group in the compounds of structure (XVII), as set forth above, may be independently combined with other embodiments and/or substituents of compounds of structure (XVII) to form embodiments of the present disclosure not specifically set forth above. In addition, in the event that a list of substituents is listed for any particular $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, or $R_{29}$ in a particular embodiment and/or claim, it is understood that each individual substituent may be deleted from the particular embodiment and/or claim and that the remaining list of substituents will be considered to be within the scope of the present disclosure.

In some embodiments, (P) is a cytotoxic compound.

In some embodiments, (P) is a microtubule disrupting peptide toxin.

In some embodiments, (P) is hemiasterlin or an analog thereof.

In some embodiments, (P) is tubulysin or an analog thereof.

In some embodiments, (P) is auristatin or an analog thereof.

In some embodiments, (P) is a cytotoxic compound, for example, a compound disclosed in U.S. Pat. No. 7,579,323; WO 2004/026293; U.S. Pat. No. 8,129,407; US 2014/0227295; WO 2013/068874; US 2013/0095123; US 2013/0190243; WO 2014/126198; EP 2740493; WO 2014086942; WO 2013072813; WO 2012166559; WO 2012166560; WO 2012123423; WO 2011154359; WO 2006063707; WO 2003008378; WO 2002000263; US 2013/224,228; WO 2013/085925; WO 2014/009774; U.S. Pat. No. 8,476,451; U.S. 2011/0027274; or related applications or patents, or Lundquist et al., Organic Letters, (3), pp. 781-783, 2001; Domling et al., Angew. Chem. Int. Ed. 2006, 45, 7235-7239; Kaur et al., Biochem J., (2006), 396:235-242; Steinmetz et al., Angew. Chem. Int. Ed. 2004, 43, 4888-4892; Khalil et al., ChemBioChem 2006, 7, 678-683; Peltier et al., J. AM. CHEM. SOC. 2006, 128, 16018-16019.

In some embodiments, the cytotoxic compound is a polyketide from *Lithoplocamia lithistoides*. Examples of polyketides from *Lithoplocamia lithistoides* include those disclosed in Martin et al., J. Am. Chem. Soc. 2013, 135, 10164-10171. In some embodiments, the polyketide from *Lithoplocamia lithistoides* is selected from: PM050489 and PM060184.

In certain embodiments of the invention, conjugates of formula (I) are prepared by the conjugation of (T) with a (P)-(L) precursor having the following structure (XIII):

$$\text{(P)-(L)-(FG)} \tag{XIII}$$

wherein FG is a functional group that forms a covalent bond with one or more atoms of targeting moiety (T). In further embodiments of the invention FG forms a bond with a heteroatom of (T).

In particular embodiments of the invention, the FG group comprises a maleimide. As will be appreciated by the artisan of reasonable skill, additional moieties and bonding technologies may be used, including but not limited to transglutaminase sequences, 2-bromoacetamide chemistry, glycosylation chemistries, and others. See for example the linkage chemistry disclosed in WO2013173391, WO2013173392, WO2013173393, and U.S. Pat. No. 7,964,566.

For the purposes of administration, the compounds of the present disclosure may be administered as a raw chemical or may be formulated as pharmaceutical compositions. Pharmaceutical compositions of the present disclosure comprise a compound of structure (I) and a pharmaceutically acceptable carrier, diluent or excipient. The compound of structure (I) is present in the composition in an amount which is effective to treat a particular disease or condition of interest—that is, in an amount sufficient to treat cancer or tumor cell growth, and preferably with acceptable toxicity to the patient. The activity of compounds of structure (I) can be determined by one skilled in the art, for example, as described in the Examples below. Appropriate concentrations and dosages can be readily determined by one skilled in the art.

Administration of the compounds of the disclosure, or their pharmaceutically acceptable salts, in pure form or in an appropriate pharmaceutical composition, can be carried out via any of the accepted modes of administration of agents for serving similar utilities. The pharmaceutical compositions of the disclosure can be prepared by combining a compound of the disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the disclosure in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the disclosure, or a pharmaceutically acceptable salt thereof, for treatment of a disease or condition of interest in accordance with the teachings of this disclosure.

A pharmaceutical composition of the disclosure may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, pharmaceutical compositions of the present disclosure typically are either solid or liquid form, where semi-solid, semi-liquid, suspension and gel forms are included within the forms considered herein as either solid or liquid.

As a solid composition for oral administration, the pharmaceutical compositions may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

Pharmaceutical compositions of the disclosure may be in the form of a liquid, for example, an elixir, syrup, solution, emulsion or suspension. The liquid may be for oral administration or for delivery by injection, as two examples. When intended for oral administration, pharmaceutical compositions of the disclosure typically contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions of the disclosure, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Parenteral preparations can be enclosed in ampoules, disposable syringes or multiple dose vials made of glass or plastic. Physiological saline is a preferred adjuvant. An injectable pharmaceutical composition is preferably sterile.

A liquid pharmaceutical composition of the disclosure intended for either parenteral or oral administration should contain an amount of a compound of the disclosure such that a suitable dosage will be obtained.

Pharmaceutical compositions of the disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Pharmaceutical compositions of the disclosure may be intended for rectal administration, in the form, for example, of a suppository, which will melt in the rectum and release the drug. Compositions for rectal administration may contain an oleaginous base as a suitable nonirritating excipient. Such bases include, without limitation, lanolin, cocoa butter and polyethylene glycol.

Pharmaceutical compositions of the disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

Pharmaceutical compositions of the disclosure may be prepared in dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the disclosure may be delivered in single phase, bi-phasic, or tri-phasic systems in order to deliver the active ingredient (s). Delivery of the aerosol includes the necessary container, activators, valves, subcontainers, and the like, which together may form a kit. One skilled in the art, without undue experimentation may determine preferred aerosols.

The pharmaceutical compositions of the disclosure may be prepared by methodology well known in the pharmaceutical art. For example, a pharmaceutical composition intended to be administered by injection can be prepared by combining a compound of the disclosure with sterile, distilled water so as to form a solution. A surfactant may be added to facilitate the formation of a homogeneous solution or suspension. Surfactants are compounds that non-covalently interact with the compound of the disclosure so as to facilitate dissolution or homogeneous suspension of the compound in the aqueous delivery system.

The compounds of the disclosure, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the disclosure, or pharmaceutically acceptable derivatives thereof, may also be administered simultaneously with, prior to, or after administration of one or more other therapeutic agents. Such combination therapy includes administration of a single pharmaceutical dosage formulation which contains a compound of the disclosure and one or more additional active agents, as well as administration of the compound of the disclosure and each active agent in its own separate pharmaceutical dosage formulation. For example, a compound of the disclosure and the other active agent can be administered to the patient together in a single oral dosage composition such as a tablet or capsule, or each agent administered in separate oral dosage formulations. Where separate dosage formulations are used, the compounds of the disclosure and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable compounds.

It will also be appreciated by those skilled in the art that in the synthetic processes described herein the functional groups of intermediate compounds may need to be protected by suitable protecting groups. Such functional groups include hydroxy, amino, mercapto and carboxylic acid. As described above, suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like, and suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although a protected derivative of compounds of this disclosure may not possess pharmacological activity as such, they may be administered to a mammal and thereafter metabolized in the body to form compounds of the disclosure which are pharmacologically active. Such derivatives may therefore be described as "prodrugs". All prodrugs of compounds of this disclosure are included within the scope of the present disclosure.

Furthermore, compounds of the disclosure which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

The following Examples illustrate various methods of making compounds of this disclosure, i.e., compound of structures (I):

$$[(P)\text{-}(L)]_m\text{-}(T) \tag{I}$$

wherein (P) is a payload compound, (L) is a linker, (T) is a targeting moiety, and m is an integer from 1 to 10. In certain embodiments, m is 1.

It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.

General Methods for the Synthesis of P-L

SCHEME 1

Scheme 1

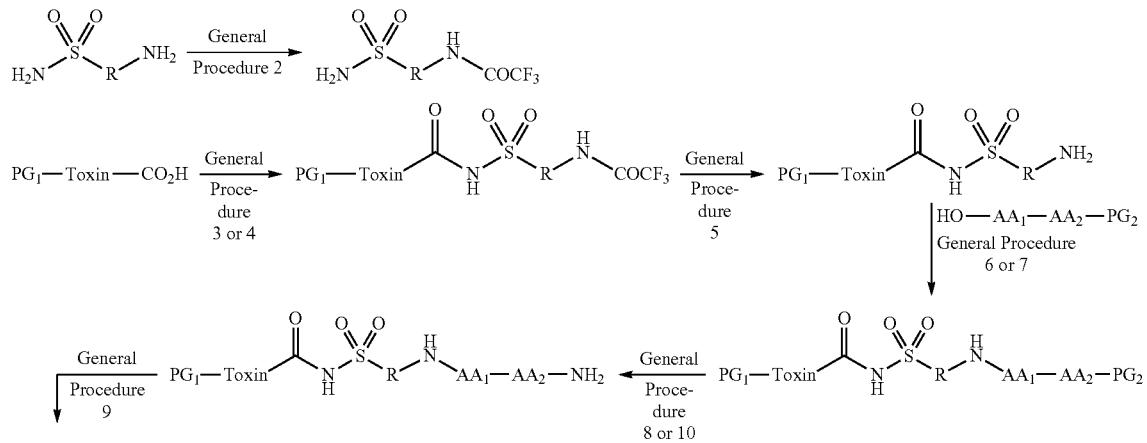

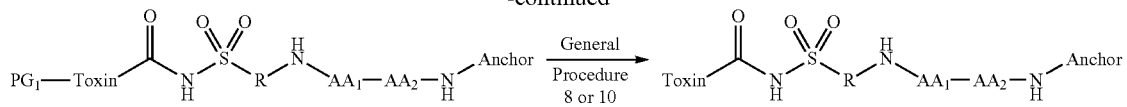

Scheme 1 illustrates a particular embodiment of a general scheme for the synthesis of a P-L complex. In further embodiments of the invention, the protecting group ($PG_1$) is removed from the Toxin (or drug) before amino acid (e.g., $AA_1$-$AA_2$) addition. In certain embodiments of the invention, the Anchor includes a functional group that can form a covalent bond with the Target. In other embodiments of the invention the Anchor comprises a Stretcher.

Scheme 2

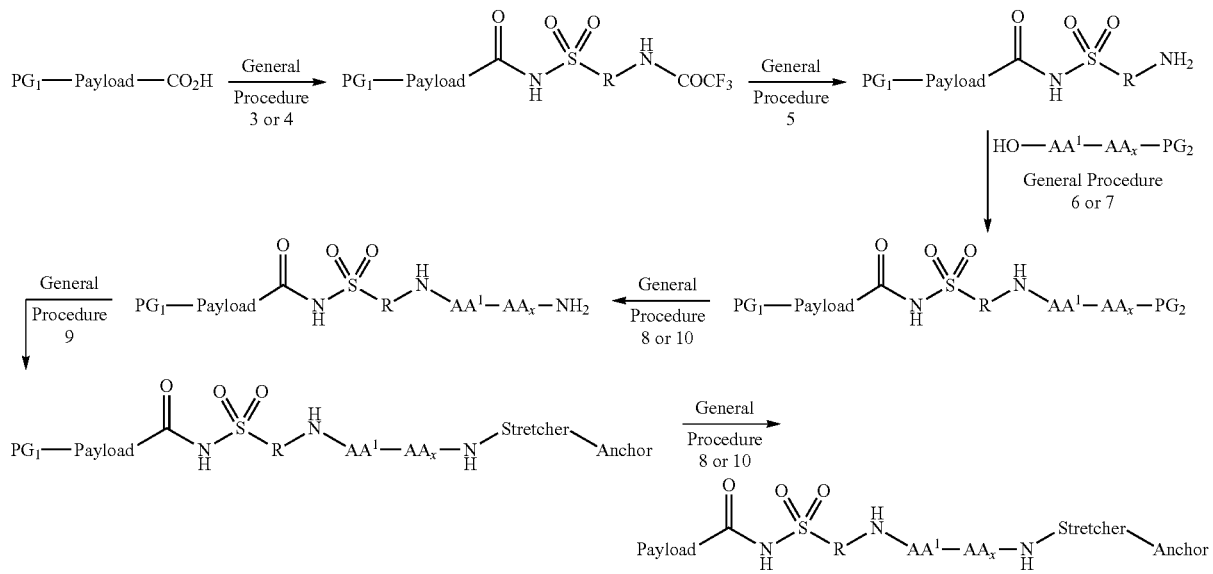

Scheme 2 illustrates a particular embodiment of a general scheme for the convergent synthesis of a P-L complex where the JPB between the payload and AA sequence is assembled prior to installation of stretcher and anchor moieties. This synthetic approach was used to generate the following compounds: Compound A, Compound B, Compound C, Compound D, Compound E, Compound F, Compound G, Compound H, Compound I, Compound J, Compound K, Compound KK, Compound N, Compound X, Compound Z, Compound AA, Compound BB, Compound CC and Compound DD.

Scheme 3

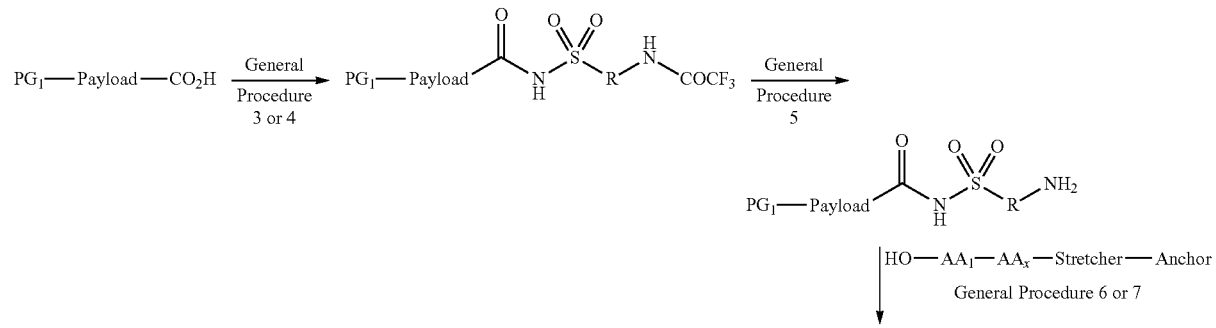

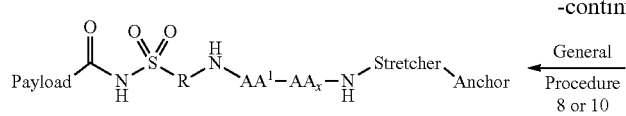 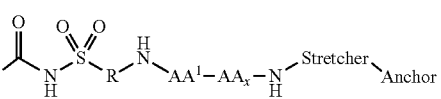

Scheme 3 illustrates a particular embodiment of a general scheme for the convergent synthesis of a P-L complex where the JPB is established between the payload and a proteolytic sequence that already contains a stretcher and anchor functionality. This synthetic approach was used to generate the following compounds: Compound L, Compound M, Compound O, Compound P, Compound Q, Compound R, Compound s, Compound T, Compound U, Compound V, and Compound W.

In certain embodiments of the invention, the general scheme comprises the procedures as discussed below. As will be understood by the reasonably skilled artisan, these procedures are illustrative of certain embodiments of the invention and could be performed with alternative solvents, reagents and protecting groups known to be suitable in the art.

EXAMPLES

General Procedure 1

4-Anilino Sulfonamide Synthesis

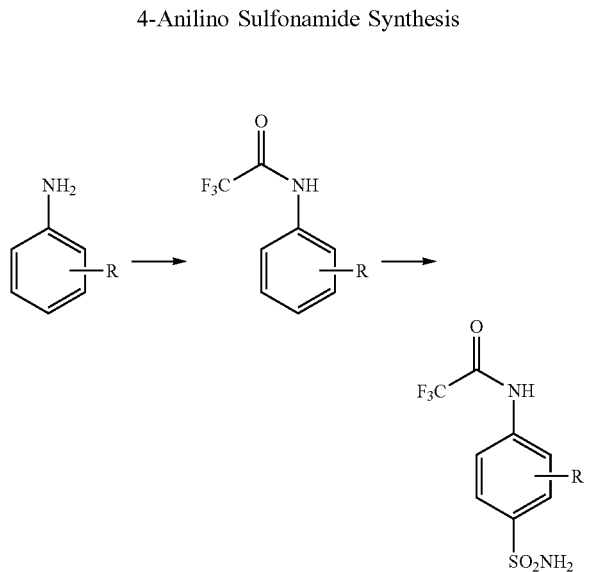

To a stirred suspension or solution of the starting aniline in CH$_2$Cl$_2$ (0.1 M) was added trifluoroacetic anhydride (1.1 equiv). The reaction was allowed to stir for ~1 h at which point it was concentrated under reduced pressure. The residue was twice dissolved in CHCl$_3$ and concentrated to give the desired trifluoroacetanilide in quantitative yield with the expected analytical results.

The trifluoroacetanilide (~8 mmol) was dissolved in CHCl$_3$ (10 mL). Chlorosulfonic acid (3 equiv) was added with stirring. The resulting solution was heated to 70° C. for 1 h, then cooled to room temperature at which time thionyl chloride (2 equiv) was added with stirring. The resulting biphasic mixture was re-heated to 70° C. for 15 minutes. The reaction mixture was then twice diluted with CHCl$_3$ and concentrated in vacuo to remove excess acids.

The resulting phenylchlorosulphonic acid was dissolved in 1,4-dioxane (~10 mL) and the resulting solution was added dropwise to a concentrated solution of aqueous ammonia (10 mL) at 0° C. with vigorous stirring. The reaction was quenched by addition of 1M citric acid and adjusted to pH=3. In most cases the sulfonamide precipitated and was filtered directly from the aqueous phase; in instances where the product did not precipitate, the reaction was diluted with ethyl acetate (~100 mL), transferred to a separatory funnel and the organic phase was washed with brine before being dried over MgSO$_4$ and concentrated to give the desired 4-trifluoroacetanilide substituted sulfonamides.

General Procedure 2

Trifluoroacetamide Installation

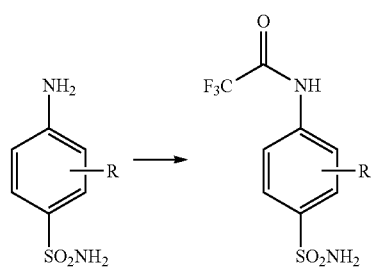

To a stirred suspension of the amine in 1,4-dioxane was added trifluoroacetic anhydride (1.1 equivalents). The reaction mixture transitioned from a suspension to a solution and back to a suspension again. The progress of the reaction was monitored by TLC and/or HPLC-MS for completion. Once the starting material was fully consumed, the reaction was diluted with hexanes or diethyl ether, filtered on a Buchner funnel and the resulting solids were dried under reduced pressure to give the pure trifluoroacetamide.

General Procedure 3

Dcc/Dmap Mediated N-Acyl Sulfonamide Formation

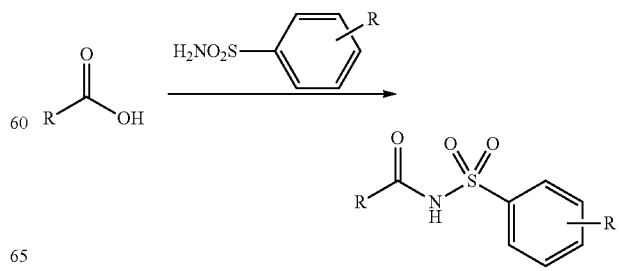

To a stirred solution of the acid in dichloromethane was added a solution of the sulfonamide (1.3 equivalents, in dichloromethane, N,N-dimethylformamide, or a mixture thereof, as necessary). Dicyclohexylcarbodiimide (1.2 equivalents) was added and subsequently N,N-dimethylaminopyridine (1.2 equivalents). Reaction course was monitored by HPLC-MS (typically 16 h) and excess by-products could be precipitated by the addition of diethyl ether. Solids were removed by filtration and washed with 1:1 diethyl ether/dichloromethane. The combined organic layers were concentrated, and the residue was purified by silica gel chromatography to give the desired N-acyl sulfonamide.

General Procedure 4

Alternative—Acyl Benzotriazole Mediated N-Acyl Sulfonamide Formation

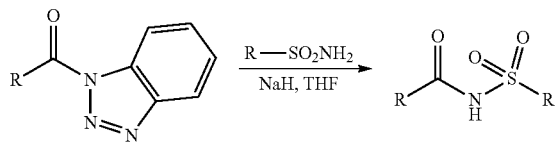

This procedure was adapted from the one described in ARKIVOC 2004 (xii), 14-22.

General Procedure 5

Trifluoroacetamide Saponification

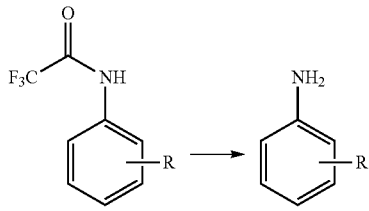

To a solution of the trifluoroacetamide-containing construct in 1,4-dioxane or methanol was added lithium hydroxide (10 equivalents) and water (10% v/v). The reaction was allowed to stir at room temperature or optionally heated to 50° C. Reaction course was monitored by HPLC-MS. Upon completion, volatiles were removed under reduced pressure and the aqueous layer was quenched with an aqueous solution of 5% w/v citric acid or 1 M hydrochloric acid. The resulting aqueous solution was washed successively with dichloromethane or ethyl acetate and the organic phases were pooled, dried over MgSO$_4$, filtered and concentrated. The reaction product was either used "as is" or purified by silica gel chromatography as necessary.

General Procedure 6

HATU Mediated Peptide Bond Formation

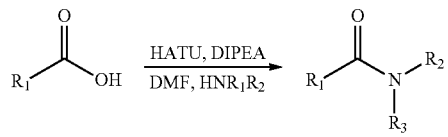

To a stirred solution of the carboxylic acid in a minimal amount of dichloromethane or N,N-dimethylformamide or mixture thereof, at 0° C. was added HATU (1.05-1.2 equivalents) and either N,N-diisopropylamine (2-4 equivalents) or 2,4,6-collidine (2-4 equivalents). Stirring was continued for a brief induction period (5-20 minutes) at which time the reaction was charged with a solution of the amine in dichloromethane. The reaction was allowed to warm to room temperature and monitored for progress by HPLC-MS. Upon completion, volatiles were removed under reduced pressure and the residual material was purified by silica gel chromatography or reverse phase HPLC to furnish amide in adequate purity.

General Procedure 7

EDCI/Cu(II) Mediated Peptide Bond Formation

To a stirred solution of the carboxylic acid in a minimal amount of 30% N,N-dimethylformamide in dichloromethane was added 1-ethyl-3-(3-dimethylaminopropyl)carbodiimide (0.95 equiv), 1-hydroxy-7-azabenzotriazole (1.0 equiv), the amine (0.33 equiv) and anhydrous copper (II) chloride (1.0 equiv) in sequence with a brief pause between each additional reagent. Stirring was continued at room temperature and progress of the reaction was monitored by HPLC-MS. Upon completion, volatiles were removed under reduced pressure and the residual material was purified by silica gel chromatography or reverse phase HPLC to furnish the desired amide in adequate purity.

General Procedure 8

FMOC Group Removal

The Fmoc-protected compound was dissolved in 20% piperidine in N,N-dimethylformamide. The reaction course was monitored by HPLC-MS. When complete, all volatiles were removed under reduced pressure to yield a residue that was either purified by silica gel chromatography or used directly in the next step.

General Procedure 9

N-Acylation of Amines Using NHS-Activated Esters

To a solution of the amine in a minimal amount of N,N-dimethylformamide was added the corresponding N-hydroxy succinimide containing ester (1.5 equivalents). The progress of the reaction was monitored by HPLC-MS (typically ~16 h) at which point all volatiles were removed under reduced pressure. The residue was then purified by either silica gel chromatography or reverse phase HPLC to give the desired amide product.

General Procedure 10

Boc Group Removal

To a solution of the Boc-protected compound in dichloromethane was added 10% v/v trifluoroacetic acid. Reaction course was monitored by HPLC-MS. Upon reaction completion, all volatiles were removed under reduced pressure. The residual material was purified either by reverse phase HPLC, silica gel chromatography or precipitation from a mixture of cold methanol/dichloromethane/diethyl ether.

General Procedure 11

Ester Saponification

To a solution of the ester containing compound in 1,4-dioxane or methanol was added lithium hydroxide (10 equivalents) and water (10% v/v). The reaction was allowed to stir at room temperature or optionally heated to 50° C. Reaction course was monitored by HPLC-MS. Upon completion, volatiles were removed under reduced pressure, the aqueous layer was pH adjusted if necessary and washed successively with dichloromethane or ethyl acetate. The organic phases were pooled, dried over MgSO4, filtered and concentrated. The reaction product was either used "as is" or purified by silica gel chromatography as necessary.

Common Reactants

Compound 1: Fmoc-Phe-Lys(Boc)-OH: (S)-2-((S)-2-(((9H-fluoren-9-yl)methoxy)carbonylamino)-3-phenylpropanamido)-6-(tert-butoxycarbonylamino) hexanoic acid; Fmoc-Phenylalanine-Lysine(Boc)-OH

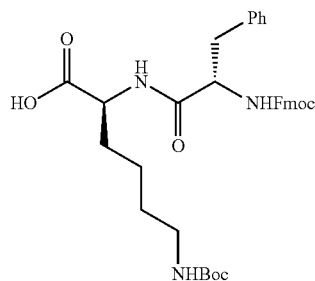

The title compound was prepared according to Walker et al., *Bioorganic Med Chem Lett,* 2004, 14, 4323-4327. $^1$H NMR (400 MHz, DMSO-$d_6$) δ 8.28 (d, J=7.7 Hz, 1H), 7.89 (d, J=7.6 Hz, 2H), 7.71-7.57 (m, 2H), 7.41 (td, J=7.6, 3.8 Hz, 2H), 7.33 (t, J=7.5 Hz, 2H), 7.30-7.23 (m, 4H), 7.19 (t, J=7.3 Hz, 1H), 6.79 (t, J=5.6 Hz, 1H), 4.37-4.24 (m, 1H), 4.24-4.07 (m, 5H), 3.02 (dd, J=13.8, 3.5 Hz, 1H), 2.95-2.83 (m, 2H), 2.83-2.71 (m, 1H), 1.82-1.68 (m, 1H), 1.68-1.51 (m, 1H), 1.46-1.22 (m, 13H). m/z calcd. for $C_{35}H_{41}N_3O_7$=615.29. Found [M+H]$^+$=616.27, [M-Boc+2H]$^+$=516.16.

Compound 2: Fmoc-Val-Lys(Boc)-OH: (S)-2-((S)-2-(((9H-fluoren-9-yl)methoxy)carbonylamino)-3-methylbutanamido)-6-(tert-butoxycarbonylamino) hexanoic acid

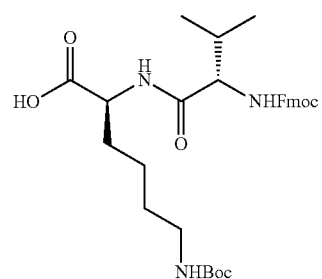

The title compound was prepared based on the above procedure from M. A. Walker, et al. *Bio. Org. Med. Chem. Lett.* 2004, 14, 4323-4327 starting with (S)-2,5-dioxopyrrolidin-1-yl 2-(((9H-fluoren-9-yl)methoxy)carbonylamino)-3-methylbutanoate. $^1$H NMR (400 MHz, Methanol-$d_4$) δ 8.28 (d, J=7.8 Hz, 1H), 7.82 (d, J=7.5 Hz, 2H), 7.69 (t, J=7.1 Hz, 2H), 7.41 (t, J=7.5 Hz, 2H), 7.33 (td, J=7.5, 1.2 Hz, 2H), 7.20 (d, J=8.5 Hz, 1H), 4.49-4.36 (m, 3H), 4.26 (t, J=7.0 Hz, 1H), 3.97 (t, J=8.0 Hz, 1H), 3.05-2.97 (m, 2H), 2.08 (dq, J=13.3, 6.6 Hz, 1H), 1.93-1.84 (m, 1H), 1.81-1.66 (m, 1H), 1.54-1.43 (m, 4H), 1.40 (s, 9H), 1.01 (d, J=6.8 Hz, 3H), 0.98 (d, J=6.8 Hz, 3H). m/z calcd. for $C_{31}H_{41}N_3O_7$=567.3. found [M-Boc+H$^+$]$^+$=468.8.

Compound 3: Boc-Val-Cit-OH: (S)-2-((S)-2-(tert-Butoxycarbonylamino)-3-methylbutanamido)-5-ureidopentanoic Acid

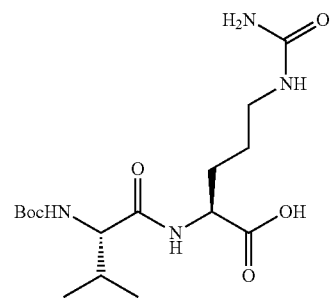 [SMILES: CC(C)[C@H](NC(=O)OC(C)(C)C)C(=O)N[C@@H](CCCNC(N)=O)C(=O)O]

The title compound was synthesized according to US2010/0233190 A1 with matching spectroscopic data.

Compound 4: H-Val-Cit-OH: (S)-2-((S)-2-Amino-3-methylbutanamido)-5-ureidopentanoic acid

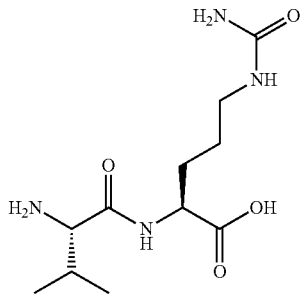 [SMILES: CC(C)[C@H](N)C(=O)N[C@@H](CCCNC(N)=O)C(=O)O]

The title compound was prepared from Boc-VC—OH according to General Procedure 10. $^1$H NMR (400 MHz, DMSO-d6) δ 8.69 (d, J=7.4 Hz, 1H), 8.21-7.97 (m, 3H), 4.24 (td, J=8.2, 4.9 Hz, 1H), 3.97 (s, OH), 3.63 (dd, J=9.2, 4.0 Hz, 1H), 2.98 (t, J=6.8 Hz, 2H), 2.60 (s, 1H), 2.10 (h, J=6.8 Hz, 1H), 1.85-1.69 (m, 1H), 1.61 (dtd, J=14.1, 9.0, 5.6 Hz, 1H), 1.45 (dtd, J=14.7, 8.2, 7.3, 3.7 Hz, 2H), 0.97 (dd, J=6.9, 5.0 Hz, 6H).

Compound 5: Fmoc-Ala(D)-Phe-Lys(Boc)-OH: (5R,8S,11S)-8-benzyl-11-(4-(tert-butoxycarbonylamino)butyl)-1-(9H-fluoren-9-yl)-5-methyl-3,6,9-trioxo-2-oxa-4,7,10-triazadodecan-12-oic acid

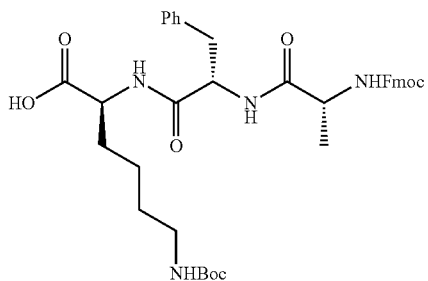

The title compound was prepared from Compound 1 by general procedure 8, followed by treatment with (R)-2,5-dioxopyrrolidin-1-yl 2-(((9H-fluoren-9-yl)methoxy)carbonylamino)propanoate per general procedure 9. $^1$H NMR (400 MHz, DMSO-d$_6$) δ 12.57 (s, 1H), 8.20 (d, J=7.6 Hz, 1H), 8.12 (d, J=8.8 Hz, 1H), 7.89 (d, J=7.5 Hz, 2H), 7.71 (t, J=6.7 Hz, 2H), 7.48-7.37 (m, 3H), 7.33 (t, J=7.4 Hz, 2H), 7.30-7.13 (m, 5H), 6.77 (t, J=5.1 Hz, 1H), 4.59 (td, J=10.8, 10.3, 3.5 Hz, 1H), 4.33-4.10 (m, 4H), 4.02 (q, J=7.1 Hz, 1H), 3.10 (dd, J=13.8, 2.8 Hz, 1H), 2.94-2.87 (m, 2H), 2.79-2.67 (m, 1H), 1.75-1.70 (m, 1H), 1.62 (s, 1H), 1.37 (s, 4H), 1.36 (s, 9H), 0.96 (d, J=7.1 Hz, 3H). m/z calcd. for C$_{31}$H$_{41}$N$_3$O$_7$=686.3. found [M+Na$^+$]$^+$=709.9.

Compound 6: Fmoc-Phe(D)-Phe-Lys-OH: (5R,8S,11S)-5,8-dibenzyl-11-(4-(tert-butoxycarbonylamino)butyl)-1-(9H-fluoren-9-yl)-3,6,9-trioxo-2-oxa-4,7,10-triazadodecan-12-oic acid

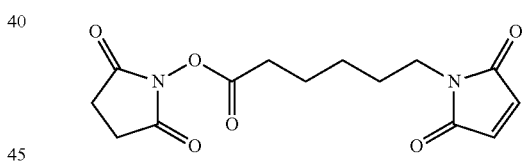

The title compound was prepared from Compound 1 by application of general procedure 8, followed by treatment with (R)-2,5-dioxopyrrolidin-1-yl 2-(((9H-fluoren-9-yl)methoxy)carbonylamino)-3-phenylpropanoate per general procedure 9. $^1$H NMR (400 MHz, DMSO-d$_6$) δ 12.59 (s, 1H), 8.39 (d, J=8.7 Hz, 1H), 8.31 (d, J=7.6 Hz, 1H), 7.88 (d, J=7.5 Hz, 2H), 7.62 (t, J=8.2 Hz, 2H), 7.47 (d, J=8.7 Hz, 1H), 7.41 (t, J=7.1 Hz, 2H), 7.35-7.10 (m, 12H), 6.77 (t, J=5.7 Hz, 1H), 4.73-4.62 (m, 1H), 4.28-4.03 (m, 5H), 3.09 (dd, J=13.7, 3.8 Hz, 1H), 2.93-2.87 (m, 2H), 2.74 (dd, J=13.7, 10.4 Hz, 1H), 2.58 (dd, J=13.8, 3.4 Hz, 1H), 2.48-2.35 (m, 1H), 1.84-1.68 (m, 1H), 1.68-1.55 (m, 1H), 1.40-1.33 (m, 13H). m/z calcd. for C$_{31}$H$_{41}$N$_3$O$_7$=762.4. found [M+Na$^+$]$^+$=785.9.

Compound 7: MC-NHS: 2,5-Dioxopyrrolidin-1-yl 6-(2,5-dioxo-2,5-dihydro-1H-pyrrol-1-yl)hexanoate To a stirred solution of 6-aminocaproic acid (10.0 g, 76.2 mmol, 1.0 eq) in acetic acid (75 mL), maleic anhydride (7.85 g, 80.0 mmol, 1.05 eq) was added. The solids took a few minutes to dissolve, then after ca. 5 min, white solids began to crash out. After an hour, the suspension thickened to a white cake. This material was scooped onto a fritted funnel and washed with toluene and dried in vacuo with heating to remove all traces of acetic acid.

The intermediate powder was taken up in toluene (250 mL), triethylamine (21.3 mL, 152 mmol, 2.0 eq) was added, and the mixture heated to reflux with a Dean-Stark trap. After 5 h of reflux, the mixture was cooled and the clear toluene layer was decanted from the rest of the sticky residue in the flask. The toluene was removed in vacuo to yield the a triethylamine salt of 6-(2,5-dioxo-2,5-dihydro-1H-pyrrol-1-yl)hexanoate. The salt was redissolved in toluene, and a small amount of acetic acid was added, then concentrated. Next, the mixture was taken up in 50% saturated sodium bicarbonate, and 1 M HCl was added to adjust the pH to 3, forming a milky precipitate. This was extracted three times with EtOAc, combined organics dried over sodium sulfate, filtered, and concentrated in vacuo to yield pure 6-(2,5-dioxo-2,5-dihydro-1H-pyrrol-1-yl)hexanoate (3.08 g, 19%).

To a stirred solution of 6-(2,5-dioxo-2,5-dihydro-1H-pyrrol-1-yl)hexanoate (3.08 g, 14.6 mmol, 1.0 eq) and N-hydroxysuccinimide (1.76 g, 15.3 mmol, 1.05 eq) in EtOAc (30 mL) at 0° C., was added dicyclohexylcarbodiimide (3.16 g, 15.3 mmol, 1.05 eq). The reaction was then allowed to warm to rt. After 20 h, the reaction was filtered and washed with EtOAc and the filtrate concentrated. The residue was purified by flash chromatography to yield the title compound (2.16 g, 48%) as a clear oil that solidified slowly to a waxy white solid. $^1$H NMR (400 MHz, Chloroform-d) δ 6.71 (s, 2H), 3.56 (t, J=7.2 Hz, 2H), 2.86 (s, 4H), 2.63 (t, J=7.4 Hz, 2H), 1.80 (p, J=7.4 Hz, 2H), 1.73-1.57 (m, 2H), 1.50-1.35 (m, 2H). m/z calcd. for $C_{14}H_{16}N_2O_6$=308.10. Found [M+H]$^+$=309.13. Rf=0.28 (50% EtOAc/Hex).

Compound 8: MT-OH: 3-(2-(2-(2-(2,5-Dioxo-2,5-dihydro-1H-pyrrol-1-yl)ethoxy)ethoxy)ethoxy)propanoic Acid

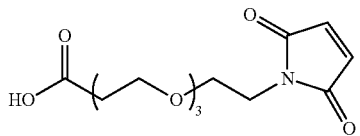

The title compound was prepared according to Warnecke, A., Kratz, F. Bioconjugate Chemistry 2003, 14, 377-387. $^1$H NMR (400 MHz, Chloroform-d) δ 6.74 (s, 2H), 3.87-3.72 (m, 4H), 3.72-3.62 (m, 10H), 2.73-2.64 (m, 2H). m/z calcd. for $C_{13}H_{29}NO_7$=301.12. Found [M+H]$^+$=302.14.

Compound 9: MT-NHS: 2,5-Dioxopyrrolidin-1-yl 3-(2-(2-(2-(2,5-dioxo-2,5-dihydro-1H-pyrrol-1-yl)ethoxy)ethoxy)ethoxy)propanoate

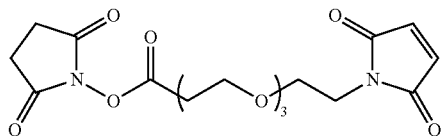

MT-OH (2.6 g, 8.6 mmol, 1.0 eq) was treated with dicyclohexylcarbodiimide (1.87 g, 9.06 mmol, 1.05 eq), and N-hydroxysuccinimide (1.04 g, 6.06 mmol, 1.05 eq) in 30 mL of 5:1 EtOAc/dioxane at rt. After 36 h, the mixture was filtered, washing with EtOAc, and the residue was purified by flash chromatography to yield the title compound (309 mg, 9.0%) as a clear oil along with starting material (1.31 g, 50% recovered). $^1$H NMR (400 MHz, Chloroform-d) δ 6.72 (s, 2H), 3.87 (t, J=6.4 Hz, 2H), 3.74 (t, J=5.6 Hz, 2H), 3.70-3.58 (m, 10H), 2.93 (t, J=6.4 Hz, 2H), 2.86 (s, 4H), 1.32-1.19 (m, 2H). m/z calcd. for $C_{17}H_{22}N_2O_9$=398.13. Found [M+H]$^+$=399.15, [M+Na]$^+$=421.14. Rf=0.59 (10% (5% AcOH/MeOH)/10% Hex/CH$_2$Cl$_2$).

Compound 10: MT-Val-Cit-OH: (14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecan-18-oic Acid

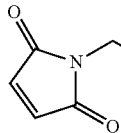

The title compound was prepared from H—VC—OH (0.50 g, 1.287 mmol)) and MT-NHS (0.512 g, 1.287 mmol) with N,N-di-isopropylethylamine (0.448 mL, 2 equiv) in dioxanes (0.50 mL). Upon consumption of the starting material (~16 h, evaluated by HPLC-MS), the reaction was concentrated in vacuo and the resulting oil was purified by preparative HPLC-MS. Lyophilization of the desired fractions afforded the title compound as a white powder (0.351 g, 63%). $^1$H NMR (400 MHz, Chloroform-d) δ 6.76 (s, 2H), 4.54-4.59 (m, 1H), 4.33-4.38 (m, J=7.6 Hz, 1H), 3.85-3.70 (m, 5H), 3.60-3.68 (m, 10H), 3.18-3.22 (m, 2H), 2.55-2.62 (m, 2H), 2.10-2.18 (m, 1H), 1.90-2.05 (m, 1H), 1.72-1.85 (m, 1H), 1.54-1.65 (m, 2H), 0.98 (t, J=6.6 Hz, 6H).

Compound 11: Boc-HTI-286-OH: (6S,9S,12S,E)-9-tert-butyl-12-isopropyl-2,2,5,11,14-pentamethyl-4,7,10-trioxo-6-(2-phenylpropan-2-yl)-3-oxa-5,8,1-triazapentadec-13-en-15-oic acid

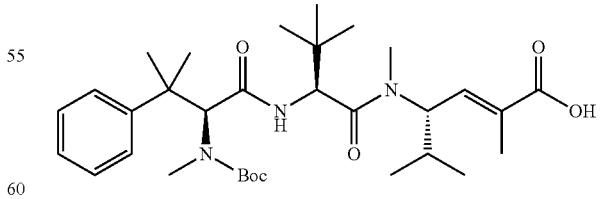

The title compound was prepared according to Nieman et al. J. Nat. Prod. 2003, 66, 183-199.
$^1$H NMR (400 MHz, Methanol-d$_4$) δ 7.57 (d, J=7.3 Hz, 2H), 7.48 (t, J=7.8 Hz, 2H), 7.38 (t, J=7.3 Hz, 1H), 6.80 (dq, J=9.8, 1.6 Hz, 1H), 5.08 (t, J=10.2 Hz, 1H), 4.95 (s, 1H), 4.37 (s, 1H), 3.17 (s, 3H), 2.53 (s, 3H), 2.15-2.02 (m, 1H), 1.94 (d, J=1.5 Hz, 3H), 1.50 (s, 3H), 1.41 (s, 3H), 1.10 (s, 9H), 0.93 (d, J=6.6 Hz, 3H), 0.92 (d, J=6.6 Hz, 3H).

$C_{32}H_{51}N_3O_6$ calcd. $[M+H]^+$ 574.38. found $[M+Na]^+$ 586.42, $[M+H]^+$ 574.46, $[M-Boc+2H]^+$ 474.39.

Compound 12: Fmoc-Val-Cit-OH: (S)-2-((S)-2-(((9H-fluoren-9-yl)methoxy)carbonylamino)-3-methylbutanamido)-5-ureidopentanoic acid, Fmoc-Valine-Citrulline-OH

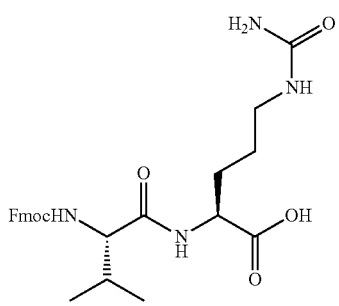

The title compound was prepared according to Dubowchik el al., *Bioconjugate Chem.*, 2002, 13, 855-869.

$^1$H NMR (400 MHz, DMSO-d$_6$) δ 12.56 (s, 1H), 8.21 (d, J=7.3 Hz, 1H), 7.90 (d, J=7.5 Hz, 2H), 7.76 (t, J=7.0 Hz, 2H), 7.49-7.39 (m, 3H), 7.38-7.23 (m, 2H), 5.96 (t, J=5.9 Hz, 1H), 5.40 (s, 2H), 4.34-4.09 (m, 4H), 3.93 (dd, J=9.1, 7.1 Hz, 1H), 3.39 (q, J=7.0 Hz, 3H), 2.96 (q, J=6.5 Hz, 2H), 1.97 (d, J=6.9 Hz, 1H), 1.86-1.63 (m, 1H), 1.57 (dtd, J=13.9, 9.0, 5.4 Hz, 1H), 1.41 (dhept, J=13.2, 6.9 Hz, 2H), 0.88 (dd, J=13.3, 6.7 Hz, 6H).). $C_{26}H_{32}N_4O_6$ calcd. $[M+H]^+$ 497.23. found $[M+H]^+$ 497.19.

Example 1

Compound A: (S,E)-N-(4-(((S)-2-((S)-2-(6-(2,5-dioxo-2,5-dihydro-1H-pyrrol-1-yl)hexanamido)-3-methylbutanamido)-5-ureidopentanamido)methyl)phenylsulfonyl)-2,5-dimethyl-4-((S)—N,3,3-trimethyl-2-((S)-3-methyl-2-(methylamino)-3-phenylbutanamido)butanamido)hex-2-enamide Compound A-1:
4-(azidomethyl)benzenesulfonamide

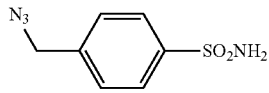

To a stirred solution of 4-(bromomethyl)benzenesulfonamide (0.50 g) in N,N-dimethylformamide (1 mL) was added sodium azide (0.20 g). The suspension was heated to 50° C. for 3 hours at which points the solvent was removed under reduced pressure. The residue was partitioned between ethyl acetate and water. The organic phase was washed with brine, dried over magnesium sulfate, filtered and concentrated to dryness to give the title compound as a syrup that solidified on standing.

$^1$H NMR (400 MHz, Chloroform-d) δ 8.06-7.91 (m, 2H), 7.58-7.44 (m, 2H), 4.96 (s, 2H), 4.48 (s, 2H).

Compound A-2:
4-(aminomethyl)benzenesulfonamide

To a solution of 4-(azidomethyl)benzenesulfonamide (0.354 g) in methanol (10 mL) in a round bottom flask equipped with a magnetic stirrer was added 10% Pd/C (~0.05 g). The flask was evacuated of gases at reduced pressure and charged with hydrogen. This evacuation and charge was repeated three times at which point the suspension was left to stir overnight. At 16 h, TLC analysis indicated complete consumption of the starting material. The reaction was diluted with methanol (40 mL), Celite® was added and the mixture was filtered through a fritted glass funnel. The resulting solution was concentrated to dryness. $^1$H NMR suggested that the material was sufficiently clean at this stage for further use without purification.

$^1$H NMR (400 MHz, DMSO-d$_6$) δ 7.77 (m, 2H), 7.53 (m, 2H), 5.76 (s, 2H), 3.76 (d, J=11.9 Hz, 2H).

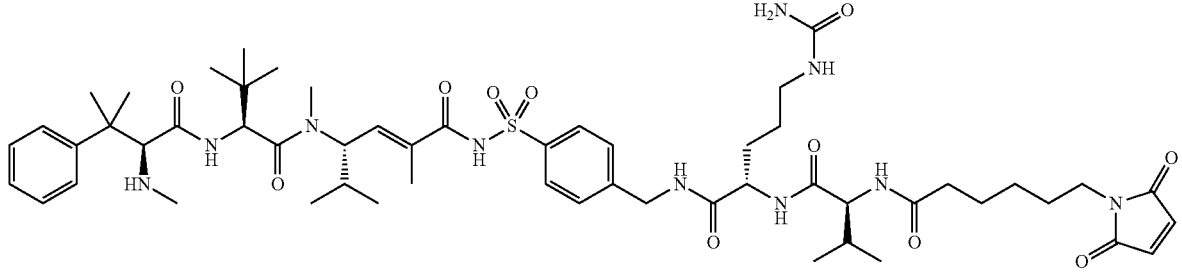 [SMILES: CN[C@H](C(=O)N[C@H](C(=O)N(C)[C@H](/C=C(\C)C(=O)NS(=O)(=O)c1ccc(CNC(=O)[C@H](CCCNC(N)=O)NC(=O)[C@@H](NC(=O)CCCCCN2C(=O)C=CC2=O)C(C)C)cc1)C(C)C)C(C)(C)C)C(C)(C)c1ccccc1]

Compound A-3:
2,2,2-trifluoro-N-(4-sulfamoylbenzyl)acetamide

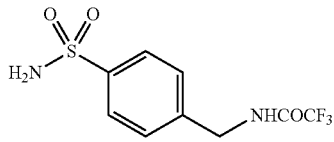

The title compound was synthesized by reaction of 4-(aminomethyl)benzenesulfonamide with TFAA according to General Procedure 2, with a $^1$H NMR spectrum that was complicated by rotamers.

$^1$H NMR (400 MHz, DMSO-d$_6$) δ 7.91-7.75 (m, 2H), 7.55-7.31 (m, 4H), 4.72 (m, 2H), 4.47 (d, J=6.0 Hz, 1H), 3.18 (s, 2H).

Compound A-4: Tert-butyl (S)-1-((S)-1-(((S,E)-2,5-dimethyl-6-oxo-6-(4-((2,2,2-trifluoroacetamido)methyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate)

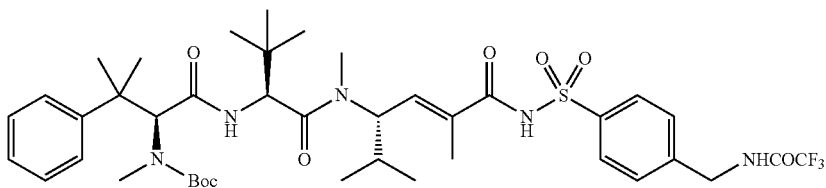

The title compound was synthesized from Boc-HTI-286-OH and Compound A-4 according to General Procedure 3.

$^1$H NMR (400 MHz, Methanol-d$_4$) δ 8.11-7.99 (m, 2H), 7.50 (dd, J=18.3, 7.9 Hz, 4H), 7.39-7.07 (m, 7H), 6.43 (d, J=9.0 Hz, 1H), 5.17 (s, 1H), 4.68 (d, J=8.9 Hz, 1H), 4.56 (s, 2H), 3.00 (d, J=33.9 Hz, 3H), 2.88 (d, J=7.6 Hz, 3H), 2.34 (s, 2H), 2.00 (d, J=13.6 Hz, 1H), 1.81 (d, J=6.4 Hz, 3H), 1.43 (s, 13H), 0.98-0.68 (m, 14H). C$_{41}$H$_{58}$F$_3$N$_5$O$_8$S calcd. [M+H]$^+$ 838.40. found [M+Na]$^+$ 860.48; [M+H]$^+$ 838.46; [M-Boc+2H]$^+$ 738.33.

Compound A-5: (S,E)-N-(4-(aminomethyl)phenylsulfonyl)-2,5-dimethyl-4-((S)—N,3,3-trimethyl-2-((S)-3-methyl-2-(methylamino)-3-phenylbutanamido)butanamido)hex-2-enamide

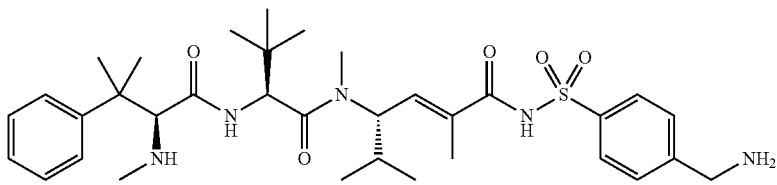 [SMILES: CN[C@H](C(=O)N[C@H](C(=O)N(C)[C@H](/C=C(\C)C(=O)NS(=O)(=O)c1ccc(CN)cc1)C(C)C)C(C)(C)C)C(C)(C)c1ccccc1]

The title compound was prepared from tert-butyl (S)-1-((S)-1-(((S,E)-2,5-dimethyl-6-oxo-6-(4-((2,2,2-trifluoroacetamido)methyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate according to General Procedures 5 and 10.

$^1$H NMR (400 MHz, Methanol-d$_4$) δ 8.13 (d, J=8.3 Hz, 2H), 7.68 (d, J=8.4 Hz, 2H), 7.59-7.41 (m, 4H), 7.37 (t, J=7.3 Hz, 1H), 6.51 (dd, J=9.4, 1.7 Hz, 1H), 5.01 (t, J=9.9 Hz, 1H), 4.37 (s, 1H), 4.24 (s, 2H), 3.17 (s, 3H), 2.51 (s, 3H), 2.12-1.96 (m, 1H), 1.84 (d, J=1.5 Hz, 3H), 1.47 (s, 3H), 1.37 (s, 3H), 1.07 (s, 9H), 0.91 (m, 6H). C$_{34}$H$_{51}$N$_5$O$_5$S calcd. [M+H]$^+$ 642.38. found [M+H]$^+$ 642.40.

Compound A-6: (9H-fluoren-9-yl)methyl (S)-1-((S)-1-(4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzylamino)-1-oxo-5-ureidopentan-2-ylamino)-3-methyl-1-oxobutan-2-ylcarbamate

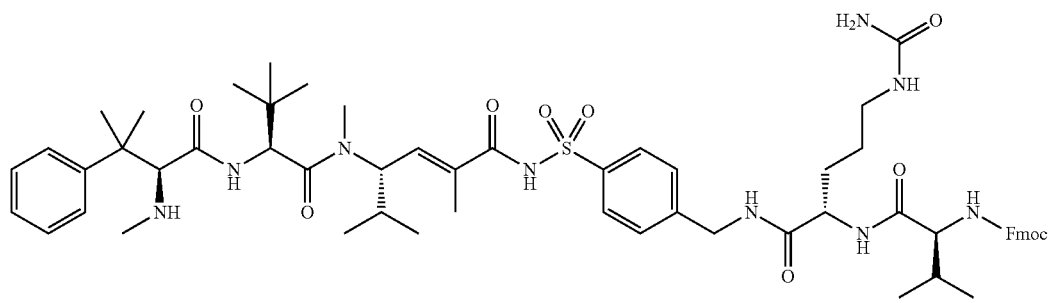

Synthesized from (S,E)-N-(4-(aminomethyl)phenylsulfonyl)-2,5-dimethyl-4-((S)—N,3,3-trimethyl-2-((S)-3-methyl-2-(methylamino)-3-phenylbutanamido)butanamido)hex-2-enamide and Fmoc-Val-Cit-OH according to General Procedure 6 with minor contamination by DIPEA and AcOH. Material used "as is" in the subsequent step.

$C_{60}H_{81}N_9O_{10}S$ calcd. $[M+H]^+$ 1120.58. found $[M+H]^+$ 1120.68.

Compound A-7: (S,E)-N-(4-(((S)-2-((S)-2-amino-3-methylbutanamido)-5-ureidopentanamido)methyl)phenylsulfonyl)-2,5-dimethyl-4-((S)—N,3,3-trimethyl-2-((S)-3-methyl-2-(methylamino)-3-phenylbutanamido)butanamido)hex-2-enamide

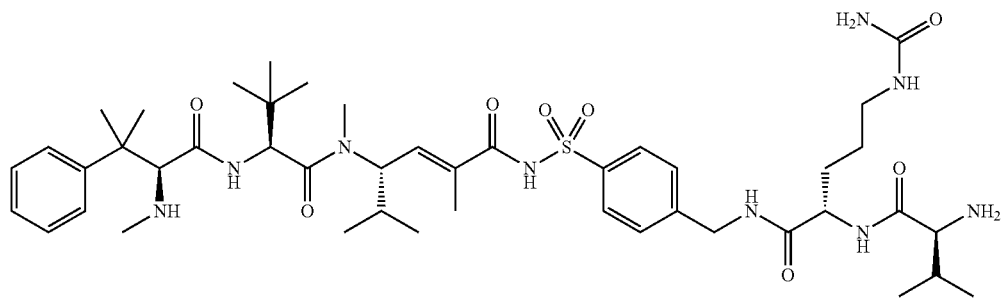 [SMILES: CN[C@H](C(=O)N[C@H](C(=O)N(C)[C@H](/C=C(\C)C(=O)NS(=O)(=O)c1ccc(CNC(=O)[C@H](CCCNC(N)=O)NC(=O)[C@@H](N)C(C)C)cc1)C(C)C)C(C)(C)C)C(C)(C)c1ccccc1]

The title compound was synthesized staring with (9H-fluoren-9-yl)methyl (S)-1-((S)-1-(4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)benzylamino)-1-oxo-5-ureidopentan-2-ylamino)-3-methyl-1-oxobutan-2-ylcarbamate according to General Procedure 8.

Compound A: (S,E)-N-(4-(((S)-2-((S)-2-(6-(2,5-dioxo-2,5-dihydro-1H-pyrrol-1-yl)hexanamido)-3-methylbutanamido)-5-ureidopentanamido)methyl)phenylsulfonyl)-2,5-dimethyl-4-((S)—N,3,3-trimethyl-2-((S)-3-methyl-2-(methylamino)-3-pheylbutanamido)butanamido)hex-2-enamide

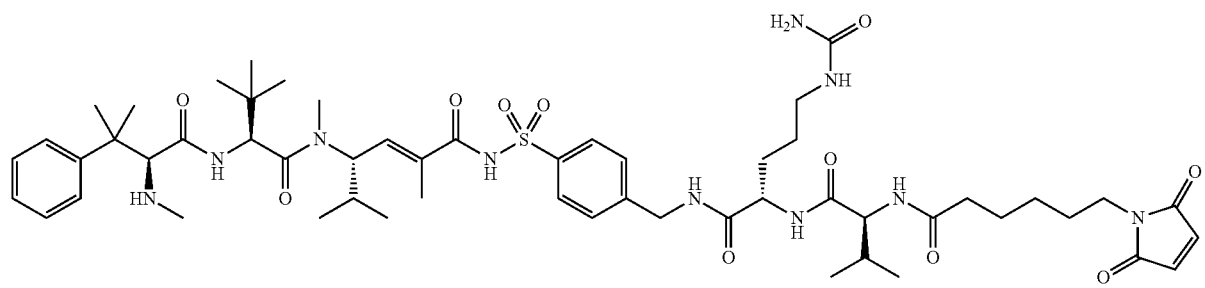 [SMILES: CN[C@H](C(=O)N[C@H](C(=O)N(C)[C@H](/C=C(\C)C(=O)NS(=O)(=O)c1ccc(CNC(=O)[C@H](CCCNC(N)=O)NC(=O)[C@@H](NC(=O)CCCCCN2C(=O)C=CC2=O)C(C)C)cc1)C(C)C)C(C)(C)C)C(C)(C)c1ccccc1]

The title compound was synthesized from Compound A-7 and MC-NHS according to General Procedure 9, purified by preparative HPLC and deprotected according to General Procedure 10.

$^1$H NMR (600 MHz, Methanol-$d_4$) δ 7.89 (d, J=8.0 Hz, 2H), 7.53-7.47 (m, 2H), 7.39 (t, J=7.5 Hz, 4H), 7.28 (t, J=7.3 Hz, 1H), 6.82 (s, 2H), 6.67 (d, J=9.3 Hz, 1H), 5.03 (t, J=10.0 Hz, 1H), 4.51-4.35 (m, 3H), 4.18 (d, J=7.4 Hz, 1H), 3.65 (s, 1H), 3.50 (t, J=7.1 Hz, 2H), 3.31 (s, 3H), 3.20-3.01 (m, 5H), 2.35-2.18 (m, 5H), 2.08 (dq, J=13.9, 6.9 Hz, 1H), 2.02-1.91 (m, 6H), 1.91-1.77 (m, 4H), 1.72 (dtd, J=14.0, 9.3, 5.2 Hz, 1H), 1.66-1.40 (m, 10H), 1.37 (s, 3H), 1.34-1.24 (m, 3H), 1.03 (s, 9H), 0.96 (dd, J=6.8, 4.0 Hz, 6H), 0.91-0.86 (m, 3H), 0.84 (d, J=6.6 Hz, 3H).

$C_{55}H_{82}N_{10}O_{11}S$ calcd. m/z [M+H]$^+$ 1091.59. found [M+H]$^+$ 1091.67.

Example 2

Compound B: (S,E)-N-(4-(((R)-6-amino-2-((R)-2-(6-(2,5-dioxo-2,5-dihydro-1H-pyrrol-1-yl)hexanamido)-3-phenylpropanamido)hexanamido)methyl)phenylsulfonyl)-2,5-dimethyl-4-((S)—N,3,3-trimethyl-2-((S)-3-methyl-2-(methylamino)-3-phenylbutanamido)butanamido)hex-2-enamide

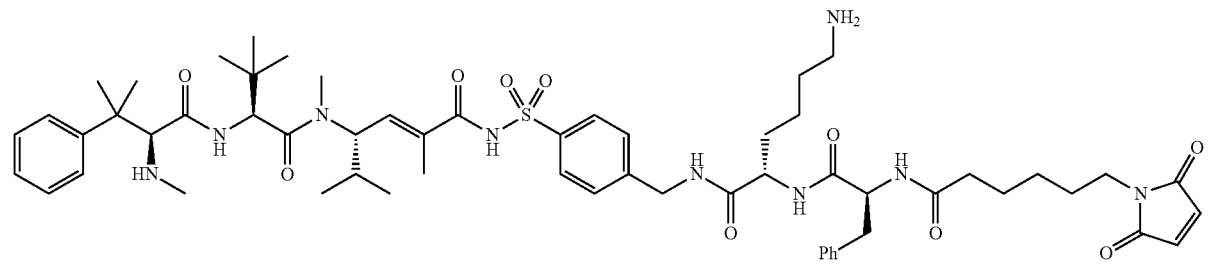 [SMILES: CN[C@H](C(=O)N[C@H](C(=O)N(C)[C@H](/C=C(\C)C(=O)NS(=O)(=O)c1ccc(CNC(=O)[C@H](CCCCN)NC(=O)[C@H](Cc2ccccc2)NC(=O)CCCCCN2C(=O)C=CC2=O)cc1)C(C)C)C(C)(C)C)C(C)(C)c1ccccc1]

Compound B-1a: Tert-butyl (S)-1-((S)-1-(((S,E)-6-(4-(aminomethyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate

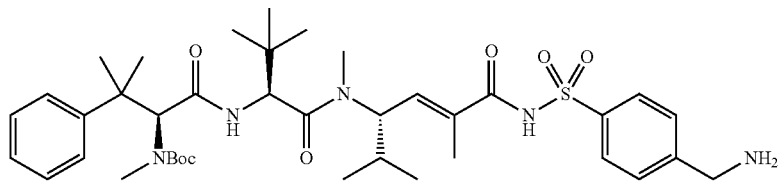 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(CN)cc1]

The title compound was prepared from tert-butyl (S)-1-((S)-1-(((S,E)-2,5-dimethyl-6-oxo-6-(4-((2,2,2-trifluoroacetamido)methyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate, Compound A-4 according to General Procedure 5.

Compound B-1

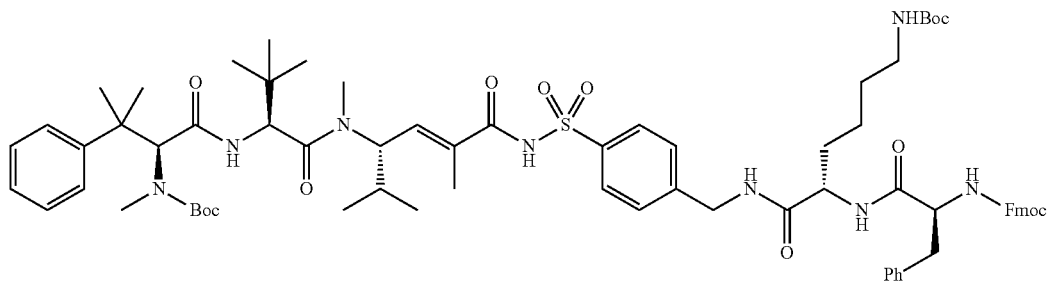

The title compound was prepared from tert-butyl (S)-1-((S)-1-(((S,E)-6-(4-(aminomethyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate and Fmoc-Phe-Lys(Boc)-OH according to General Procedure 6.

$C_{74}H_{98}N_8O_{13}S$ calcd m/z=1338.70 amu. found [M+H]$^+$=1339.86, [M+Na]$^+$=1361.88, [M+K]$^+$=1377.95, [M-Boc+2H]$^+$=1239.83, [M-2Boc+3H]$^+$=1139.72.

Compound B-2

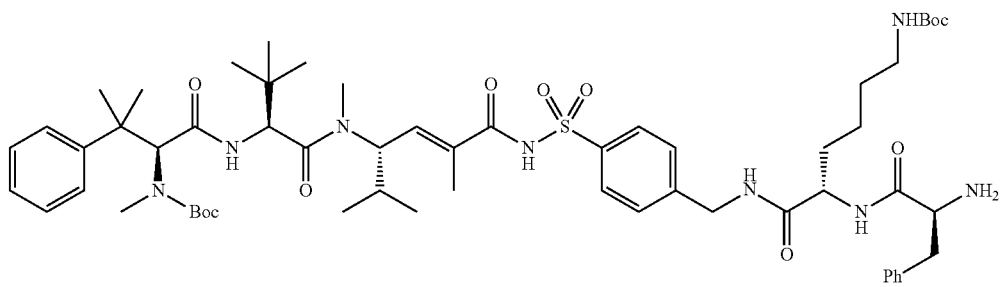 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(CNC(=O)[C@H](CCCCNC(=O)OC(C)(C)C)NC(=O)[C@@H](N)Cc2ccccc2)cc1]

The title compound was prepared from Compound B-1 according to General Procedure 8.

$C_{59}H_{88}N_8O_{11}S$ calcd m/z=1116.63 amu. found $[M+H]^+$=1117.78, $[M+Na]^+$=1139.80, $[M-Boc+2H]^+$=1017.72, $[M-2Boc+3H]^+$=917.64.

Compound B-3

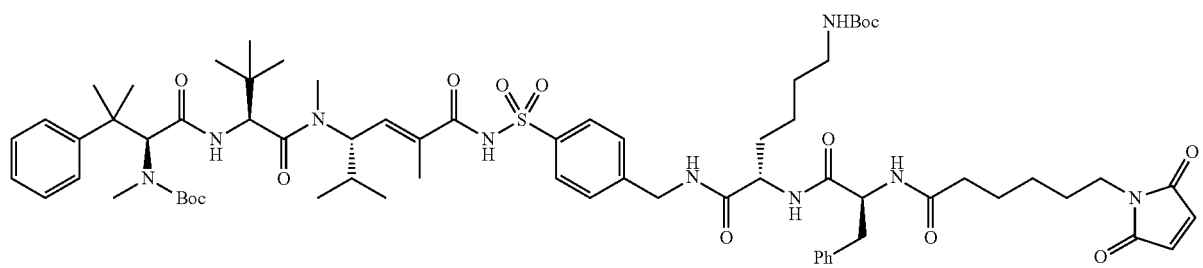 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(CNC(=O)[C@H](CCCCNC(=O)OC(C)(C)C)NC(=O)[C@H](Cc2ccccc2)NC(=O)CCCCCN2C(=O)C=CC2=O)cc1]

The title compound was prepared from Compound B-2 and MC-NHS according to General Procedure 9.

$C_{69}H_{99}N_9O_{14}S$ calcd m/z=1309.70 amu. found $[M+H]^+$=1310.89, $[M+Na]^+$=1332.91, $[M-Boc+2H]^+$=1210.86, $[M-2Boc+3H]^+$=1110.77.

Compound B: (S,E)-N-(4-(((R)-6-amino-2-((R)-2-(6-(2,5-dioxo-2,5-dihydro-1H-pyrrol-1-yl)hexanamido)-3-phenylpropanamido)hexanamido)methyl)phenylsulfonyl)-2,5-dimethyl-4-((S)—N,3,3-trimethyl-2-((S)-3-methyl-2-(methylamino)-3-phenylbutanamido)butanamido)hex-2-enamide

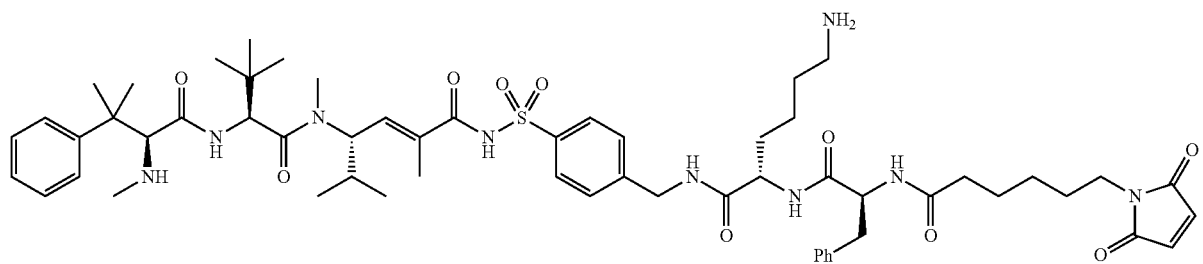 [SMILES: CN[C@H](C(=O)N[C@H](C(=O)N(C)[C@H](/C=C(\C)C(=O)NS(=O)(=O)c1ccc(CNC(=O)[C@H](CCCCN)NC(=O)[C@H](Cc2ccccc2)NC(=O)CCCCCN2C(=O)C=CC2=O)cc1)C(C)C)C(C)(C)C)C(C)(C)c1ccccc1]

The title compound was prepared from Compound B-3 according to General Procedure 10.

$C_{59}H_{83}N_9O_{10}S$ calcd m/z=1109.60 amu. found [M+H]$^+$=1110.76, [M+Na]$^+$=1132.75, [(M+2H)/2]$^{2+}$=556.11.

Example 3

Compound C: (S,E)-N-(4-(((S)-2-((S)-2-(6-(2,5-dioxo-2,5-dihydro-1H-pyrrol-1-yl)hexanamido)-3-methylbutanamido)-5-ureidopentanamido)methyl)benzylsulfonyl)-2,5-dimethyl-4-((S)—N,3,3-trimethyl-2-((S)-3-methyl-2-(methylamino)-3-phenylbutanamido)butanamido)hex-2-enamide

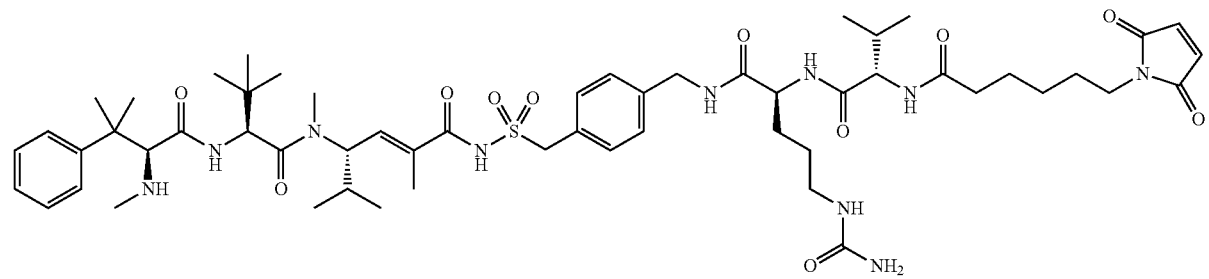 [SMILES: CN[C@H](C(=O)N[C@H](C(=O)N(C)[C@H](/C=C(\C)C(=O)NS(=O)(=O)Cc1ccc(CNC(=O)[C@H](CCCNC(N)=O)NC(=O)[C@@H](NC(=O)CCCCCN2C(=O)C=CC2=O)C(C)C)cc1)C(C)C)C(C)(C)C)C(C)(C)c1ccccc1]

Compound C-1a: 2,2,2-trifluoro-N-(4-(sulfamoylmethyl)benzyl)acetamide

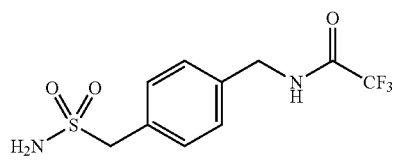 [SMILES: NS(=O)(=O)Cc1ccc(CNC(=O)C(F)(F)F)cc1]

The title compound was synthesized from commercially available (4-(aminomethyl)phenyl)methanesulfonamide and TFAA using General Procedure 2.

$^1$H NMR (400 MHz, Acetone-d$_6$) δ 9.05 (s, 1H), 7.48-7.40 (m, 2H), 7.40-7.32 (m, 2H), 6.17 (s, 1H), 4.56 (d, J=6.1 Hz, 2H), 4.35 (s, 2H).

Compound C-1

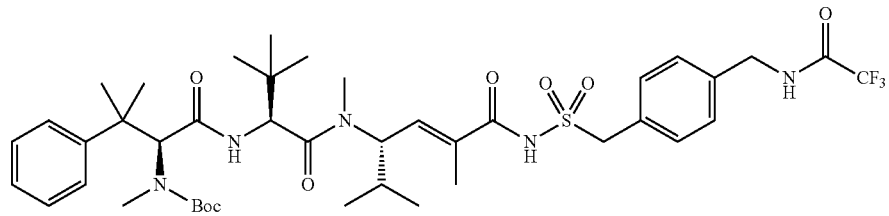 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(CNC(=O)C(F)(F)F)cc1]

The title compound was synthesized from Boc-HTI-286-OH and 2,2,2-trifluoro-N-(4-(sulfamoylmethyl)benzyl)acetamide, Compound C-1a, according to General Procedure 3.

$^1$H NMR (400 MHz, Methanol-$d_4$) δ 7.49 (d, J=7.7 Hz, 2H), 7.41-7.27 (m, 5H), 7.21 (d, J=8.0 Hz, 2H), 6.36 (d, J=9.4 Hz, 1H), 5.18 (s, 1H), 4.99 (s, 2H), 4.69 (s, 3H), 4.46 (s, 3H), 3.06-2.91 (m, 3H), 2.88 (d, J=4.7 Hz, 3H), 2.04 (d, J=1.8 Hz, 1H), 1.88 (d, J=13.5 Hz, 3H), 1.79-1.69 (m, 1H), 1.68-1.57 (m, 1H), 1.52 (d, J=8.2 Hz, 3H), 1.44 (s, 9H), 1.23-1.12 (m, 1H), 0.97 (t, J=7.4 Hz, 1H), 0.90 (d, J=6.0 Hz, 9H), 0.80 (d, J=6.8 Hz, 3H).

$C_{42}H_{60}F_3N_5O_8S$ calcd m/z=851.41 amu. found [M+H]$^+$=852.47, [M+Na]$^+$=874.47, [M-Boc+2H]$^+$=752.38.

Compound C-2

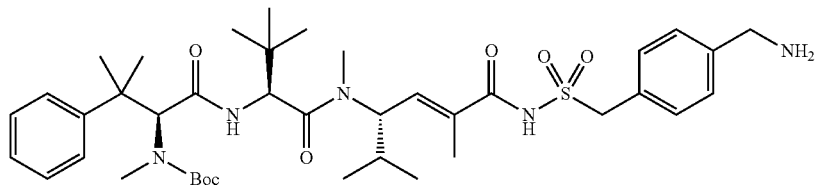 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(CN)cc1]

The title compound was prepared from Compound C-1 according to General Procedure 3.

$^1$H NMR (400 MHz, Methanol-$d_4$) δ 7.49 (t, J=8.0 Hz, 2H), 7.40-7.30 (m, 4H), 7.28 (d, J=7.9 Hz, 2H), 7.22 (q, J=7.9 Hz, 1H), 6.48 (d, J=9.4 Hz, 1H), 5.19 (s, 1H), 5.07-4.94 (m, 2H), 4.72 (s, 1H), 4.48 (s, 2H), 3.77 (s, 2H), 3.05-2.82 (m, 3H), 1.92-1.82 (m, 4H), 1.58-1.32 (m, 16H), 0.97-0.85 (m, 12H), 0.85-0.74 (m, 4H).

$C_{40}H_{61}N_5O_7S$ calcd m/z=755.43 amu. found [M+H]$^+$=756.46, [M+Na]$^+$=778.48, [M-Boc+2H]$^+$=656.39.

Compound C-3

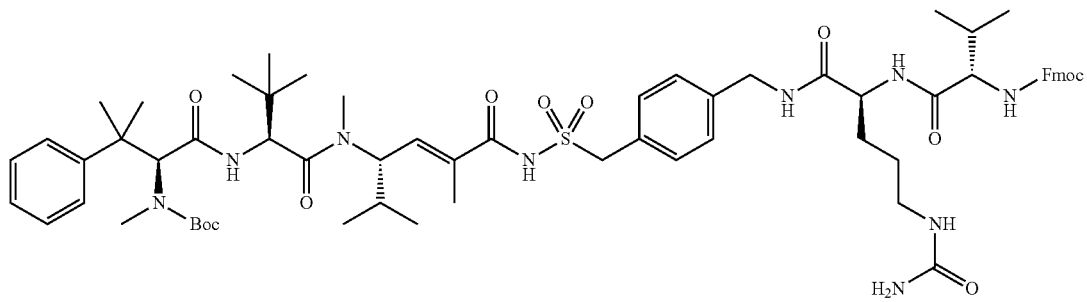

The title compound was prepared from Compound C-2 and Fmoc-Val-Cit-OH according to General Procedure 6.

$C_{66}H_{91}N_9O_{12}S$ calcd m/z=1233.65 amu. found $[M+H]^+$=1234.82, $[M+Na]^+$=1256.80, $[M-Boc+2H]^+$=1134.73.

Compound C-4

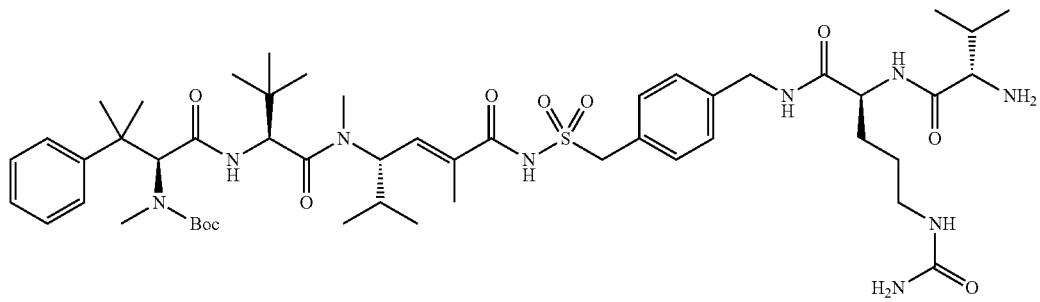 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(CNC(=O)[C@H](CCCNC(N)=O)NC(=O)[C@@H](N)C(C)C)cc1]

The title compound was prepared from Compound C-3 according to General Procedure 8.

$C_{51}H_{81}N_9O_{10}S$ calcd m/z=1011.58 amu. found $[M+H]^+$=1012.72, $[M+Na]^+$=1034.68, $[M-Boc+2H]^+$=912.66.

Compound C-5

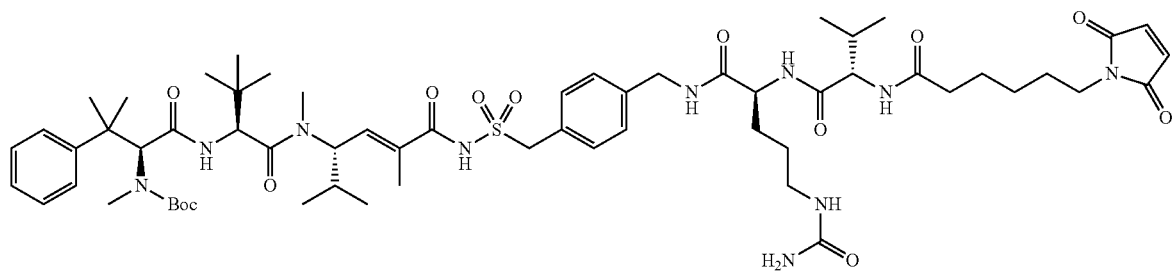 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(CNC(=O)[C@H](CCCNC(N)=O)NC(=O)[C@@H](NC(=O)CCCCCN2C(=O)C=CC2=O)C(C)C)cc1]

The title compound was prepared from Compound C-4 and MC-NHS according to General Procedure 9.

$C_{61}H_{92}N_{10}O_{13}S$ calcd m/z=1204.66 amu. found $[M+H]^+$=1205.84, $[M+Na]^+$=1227.82, $[M-Boc+2H]^+$=1105.75.

Compound C: (S,E)-N-(4-(((S)-2-((S)-2-(6-(2,5-dioxo-2,5-dihydro-H-pyrrol-1-yl)hexanamido)-3-methylbutanamido)-5-ureidopentanamido)methyl)benzylsulfonyl)-2,5-dimethyl-4-((S)—N,3,3-trimethyl-2-((S)-3-methyl-2-(methylamino)-3-phenylbutanamido)butanamido)hex-2-enamide

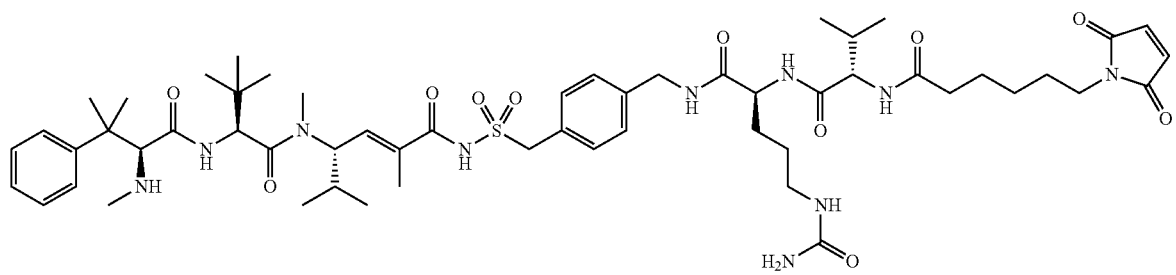 [SMILES: CN[C@H](C(=O)N[C@H](C(=O)N(C)[C@H](/C=C(\C)C(=O)NS(=O)(=O)Cc1ccc(CNC(=O)[C@H](CCCNC(N)=O)NC(=O)[C@@H](NC(=O)CCCCCN2C(=O)C=CC2=O)C(C)C)cc1)C(C)C)C(C)(C)C)C(C)(C)c1ccccc1]

The title compound was prepared from Compound C-5 according to General Procedure 10.

$C_{56}H_{84}N_{10}O_{11}S$ calcd m/z=1104.60 amu. found $[M+H]^+=1105.78$, $[M+Na]^+=1127.76$, $[(M+2H)/2]^{2+}=553.60$.

Example 4

Compound D: (S,E)-N-(4-(((R)-6-amino-2-((R)-2-(6-(2,5-dioxo-2,5-dihydro-1H-pyrrol-1-yl)hexanamido)-3-phenylpropanamido)hexanamido)methyl)benzylsulfonyl)-2,5-dimethyl-4-((S)—N,3,3-trimethyl-2-((S)-3-methyl-2-(methylamino)-3-phenylbutanamido)butanamido)hex-2-enamide

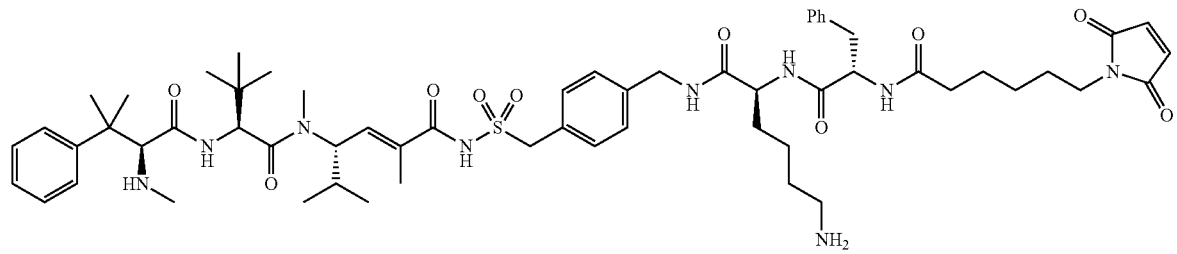 [SMILES: CN[C@H](C(=O)N[C@H](C(=O)N(C)[C@H](/C=C(\C)C(=O)NS(=O)(=O)Cc1ccc(CNC(=O)[C@H](CCCCN)NC(=O)[C@H](Cc2ccccc2)NC(=O)CCCCCN2C(=O)C=CC2=O)cc1)C(C)C)C(C)(C)C)C(C)(C)c1ccccc1]

Compound D-1

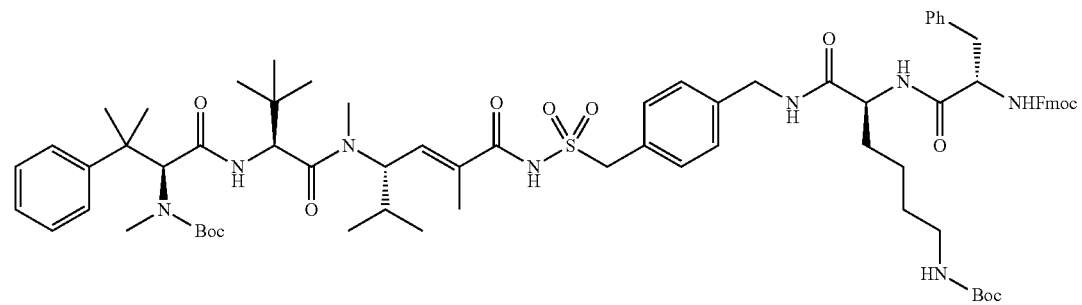

The title compound was prepared from Compound C-2 and Fmoc-Phe-Lys(Boc)-OH according to General Procedure 6.

$C_{75}H_{100}N_8O_{13}S$ calcd m/z=1352.71 amu. found $[M+H]^+=1353.96$, $[M+Na]^+=1375.83$, $[M-Boc+2H]^+=1253.78$, $[M-2Boc+H]^+=1153.70$.

Compound D-2

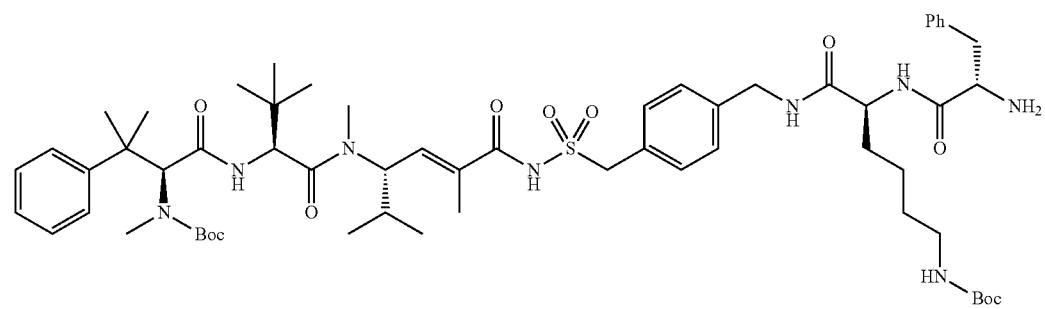 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(CNC(=O)[C@H](CCCCNC(=O)OC(C)(C)C)NC(=O)[C@@H](N)Cc2ccccc2)cc1]

The title compound was prepared from Compound D-1 according to General Procedure 8.

$C_{60}H_{90}N_8O_{11}S$ calcd m/z=1130.64 amu. found $[M+H]^+$=1131.75, $[M+Na]^+$=1153.75, $[M-Boc+2H]^+$=1031.68, $[M-2Boc+3H]^+$=931.61.

Compound D-3

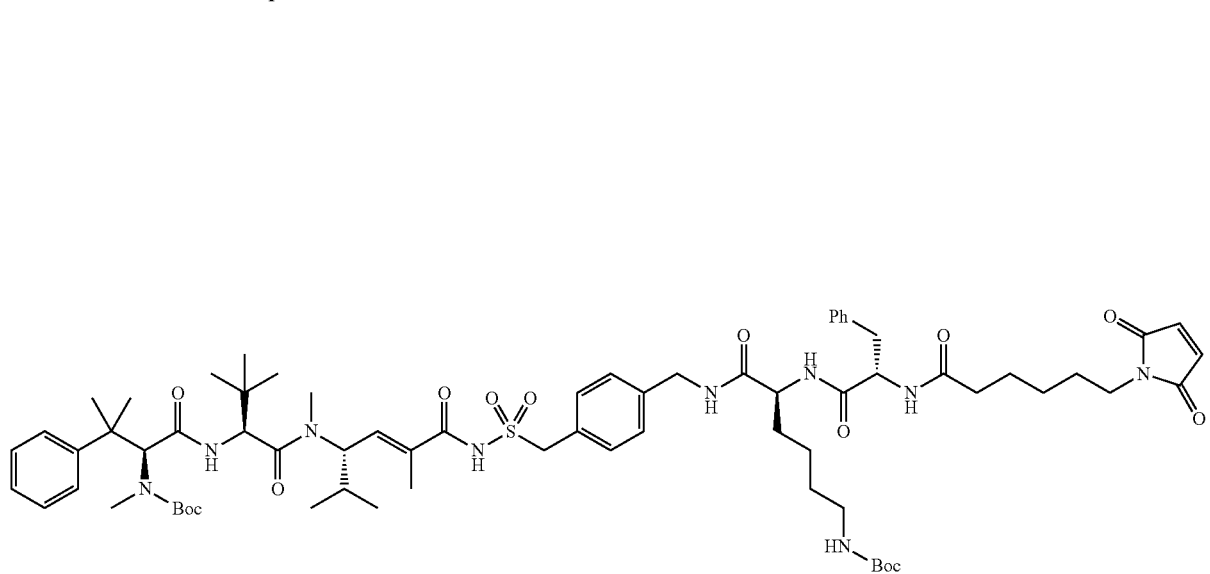

The title compound was prepared from Compound D-2 and MC-NHS according to General Procedure 9.

$C_{70}H_{101}N_9O_{14}S$ calcd m/z=1323.72 amu. found $[M+H]^+$=1324.96, $[M+Na]^+$=1346.94, $[M-Boc+2H]^+$=1224.87, $[M-2Boc+3H]^+$=1124.79.

Compound D: (S,E)-N-(4-(((R)-6-amino-2-((R)-2-(6-(2,5-dioxo-2,5-dihydro-1H-pyrrol-1-yl) hexanamido)-3-phenylpropanamido) hexanamido)methyl) benzylsulfonyl)-2,5-dimethyl-4-((S)—N,3,3-trimethyl-2-((S)-3-methyl-2-(methylamino)-3-phenylbutanamido)butanamido)hex-2-enamide

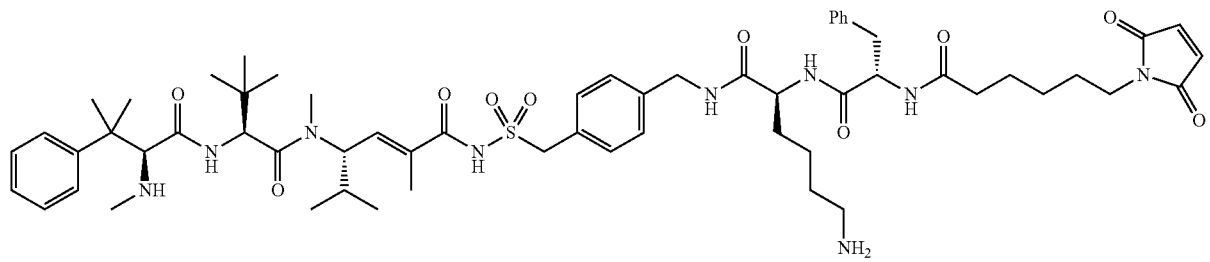 [SMILES: CN[C@H](C(=O)N[C@H](C(=O)N(C)[C@H](/C=C(\C)C(=O)NS(=O)(=O)Cc1ccc(CNC(=O)[C@H](CCCCN)NC(=O)[C@H](Cc2ccccc2)NC(=O)CCCCCN2C(=O)C=CC2=O)cc1)C(C)C)C(C)(C)C)C(C)(C)c1ccccc1]

The title compound was prepared from Compound D-3 according to General Procedure 10.

$C_{60}H_{85}N_9O_{10}S$ calcd m/z=1123.61 amu. found $[M+H]^+$=1124.75, $[M+Na]^+$=1146.77, $[(M+2H)/2]^{2+}$=563.09.

Example 5

Compound E: (S,E)-N-(4-((R)-2-((R)-2-(6-(2,5-dioxo-2,5-dihydro-1H-pyrrol-1-yl)hexanamido)-3-methylbutanamido)-5-ureidopentanamido)benzylsulfonyl)-2,5-dimethyl-4-((S)—N,3,3-trimethyl-2-((S)-3-methyl-2-(methylamino)-3-phenylbutanamido)butanamido)hex-2-enamide

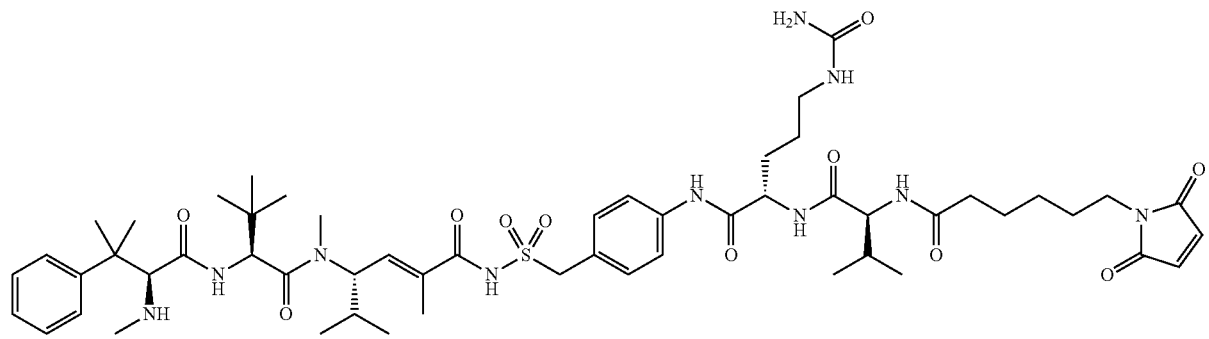 [SMILES: CN[C@H](C(=O)N[C@H](C(=O)N(C)[C@H](/C=C(\C)C(=O)NS(=O)(=O)Cc1ccc(NC(=O)[C@H](CCCNC(N)=O)NC(=O)[C@@H](NC(=O)CCCCCN2C(=O)C=CC2=O)C(C)C)cc1)C(C)C)C(C)(C)C)C(C)(C)c1ccccc1]

Compound E-1a: 2,2,2-trifluoro-N-(4-(sulfamoylmethyl)phenyl)acetamide

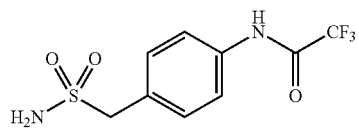 [SMILES: NS(=O)(=O)Cc1ccc(NC(=O)C(F)(F)F)cc1]

The title compound was synthesized from commercially available (4-aminophenyl)methanesulfonamide and TFAA using General Procedure 2.

$^1$H NMR (400 MHz, DMSO-d$_6$) δ 11.31 (s, 1H), 7.79-7.51 (m, 2H), 7.51-7.23 (m, 2H), 6.85 (s, 2H), 4.27 (s, 2H).

Compound E-1

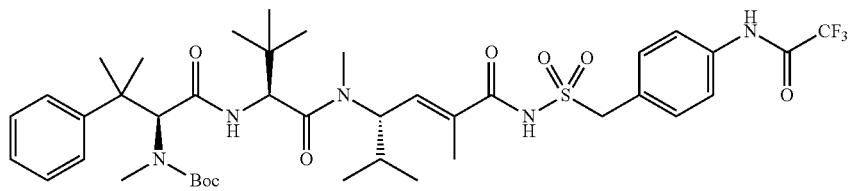 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(NC(=O)C(F)(F)F)cc1]

The title compound was synthesized from Boc-HTI-286-OH and 2,2,2-trifluoro-N-(4-(sulfamoylmethyl)phenyl)acetamide, Compound E-1a, according to General Procedure 3.

$^1$H NMR (400 MHz, Chloroform-d) δ 8.81 (s, 1H), 7.66-7.50 (m, 3H), 7.50-7.31 (m, 5H), 7.23 (t, J=7.7 Hz, 1H), 6.35 (dd, J=9.2, 1.6 Hz, 1H), 6.22 (d, J=8.8 Hz, 1H), 5.34 (s, 1H), 5.05-4.80 (m, 3H), 4.72-4.40 (m, 2H), 2.97-2.74 (m, 3H), 2.60 (s, 3H), 1.95 (m, 4H), 1.68-1.35 (m, 15H), 1.02-0.63 (m, 15H).

$C_{41}H_{58}F_3N_5O_8S$ calcd. [M+H]$^+$ 838.40. found [M+Na]$^+$ 860.48; [M+H]$^+$838.52; [M-Boc+2H]$^+$738.39.

Compound E-2

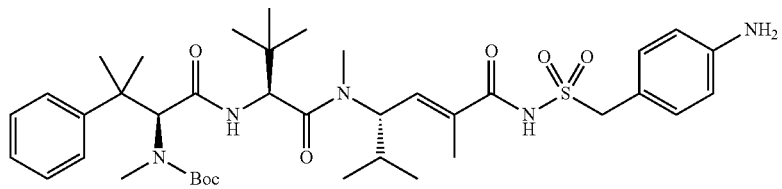 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(N)cc1]

The title compound was prepared from Compound E-1 according to General Procedure 5.

$^1$H NMR (400 MHz, Chloroform-d) δ 7.63-7.39 (m, 2H), 7.35 (t, J=7.7 Hz, 2H), 7.22 (t, J=7.3 Hz, 1H), 7.16-7.03 (m, 2H), 6.73-6.54 (m, 2H), 6.36 (dd, J=9.2, 1.6 Hz, 1H), 6.07 (s, 1H), 5.00 (m, 2H), 4.60 (s, 3H), 2.98-2.75 (m, 6H), 1.97-1.71 (m, 4H), 1.68-1.34 (m, 15H), 0.97-0.63 (m, 15H).

$C_{39}H_{59}N_5O_7S$ calcd. [M+H]$^+$ 742.41. found [M+H]$^+$ 742.47; [M-Boc+2H]$^+$642.40.

Compound E-3

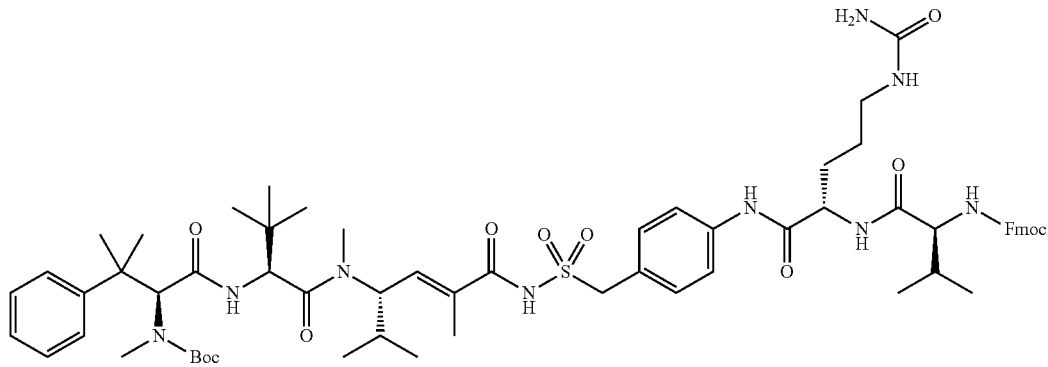

The title compound was prepared from Compound E-2 and Fmoc-Val-Cit-OH according to General Procedure 6.
$C_{65}H_{89}N_9O_{12}S$ calcd. [M+H]$^+$ 1220.64. found [M+H]$^+$ 1220.97; [M-Boc+2H]$^+$1120.87.

Compound E-4

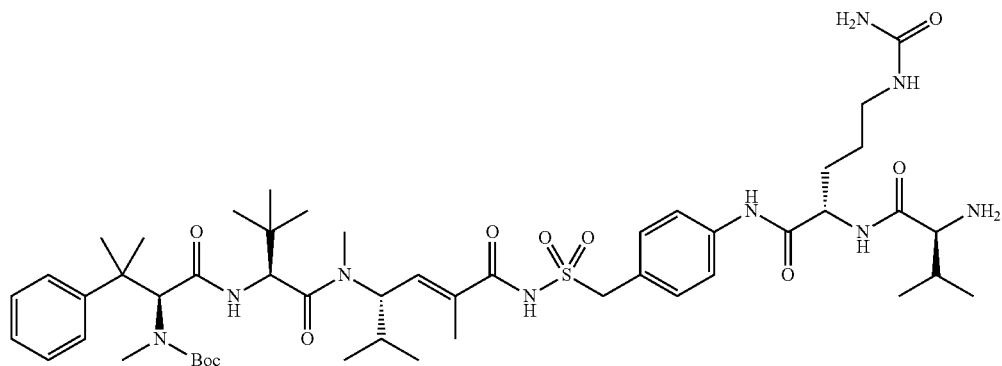 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(NC(=O)[C@H](CCCNC(N)=O)NC(=O)[C@@H](N)C(C)C)cc1]

The title compound was prepared from Compound E-3 according to General Procedure 8.
$C_{50}H_{79}N_9O_{10}S$ calcd. [M+Na]$^+$998.57. found [M+H]$^+$ 998.75; [M-Boc+H]$^+$898.69.

Compound E-5

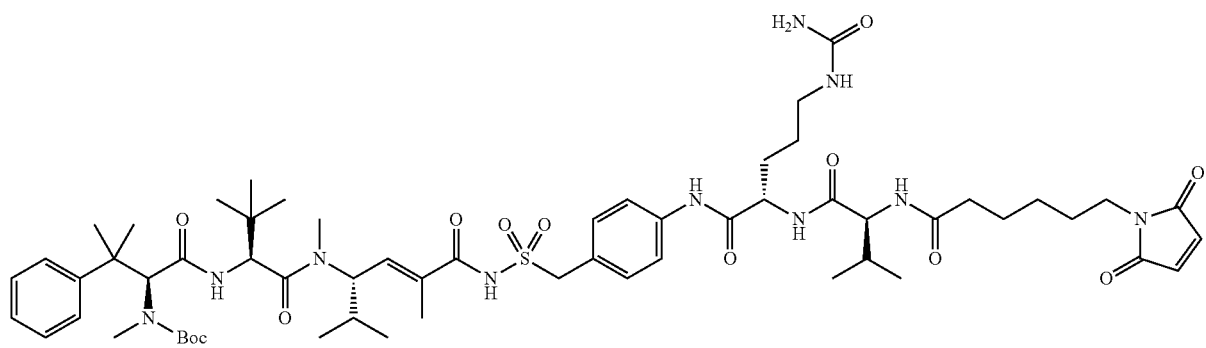 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(NC(=O)[C@H](CCCNC(N)=O)NC(=O)[C@@H](NC(=O)CCCCCN2C(=O)C=CC2=O)C(C)C)cc1]

The title compound was prepared by reaction of Compound E-4 with MC-NHS according to General Procedure 9.

$C_{60}H_{90}N_{10}O_{13}S$ calcd. [M+H]$^+$ 1191.64. found [M+H]$^+$ 1191.74; [M-Boc+2H]$^+$1091.67.

Compound E: (S,E)-N-(4-((R)-2-((R)-2-(6-(2,5-dioxo-2,5-dihydro-1H-pyrrol-1-yl)hexanamido)-3-methylbutanamido)-5-ureidopentanamido)benzylsulfonyl)-2,5-dimethyl-4-((S)—N,3,3-trimethyl-2-((S)-3-methyl-2-(methylamino)-3-phenylbutanamido)butanamido)hex-2-enamide

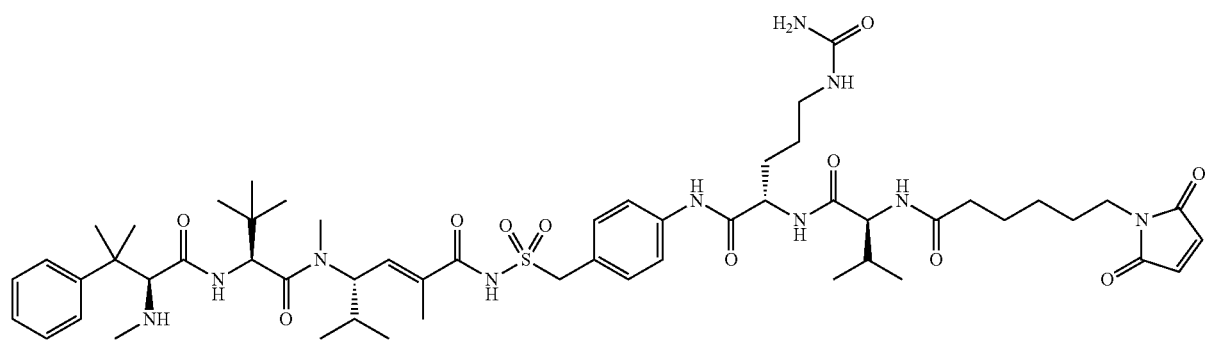 [SMILES: CN[C@H](C(=O)N[C@H](C(=O)N(C)[C@H](/C=C(\C)C(=O)NS(=O)(=O)Cc1ccc(NC(=O)[C@H](CCCNC(N)=O)NC(=O)[C@@H](NC(=O)CCCCCN2C(=O)C=CC2=O)C(C)C)cc1)C(C)C)C(C)(C)C)C(C)(C)c1ccccc1]

The title compound was prepared from Compound E-5 according to General Procedure 10.

$C_{55}H_{82}N_{10}O_{11}S$ calcd. $[M+H]^+$ 1091.59. found $[M+H]^+$ 1091.67.

Example 6

Compound F: -(4-(((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)benzylsulfonyl)-2,5-dimethyl-4-((S)—N,3,3-trimethyl-2-((S)-3-methyl-2-(methylamino)-3-phenylbutanamido)butanamido)hex-2-enamide

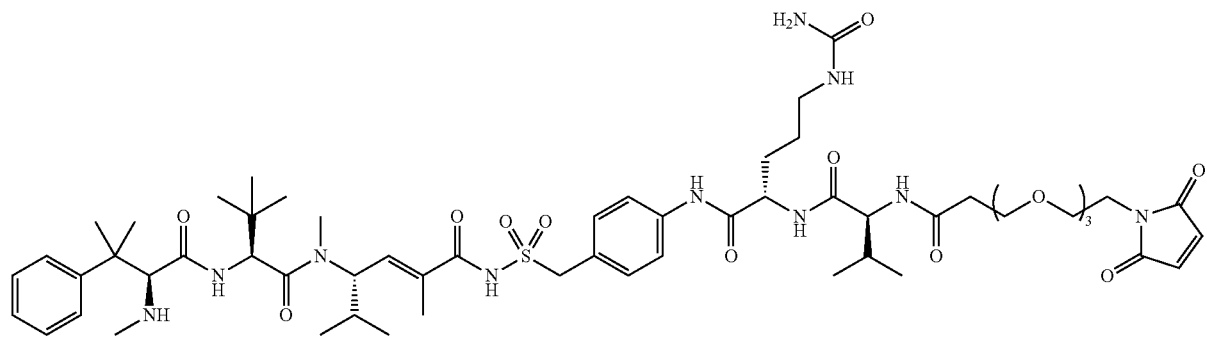

Compound F-1

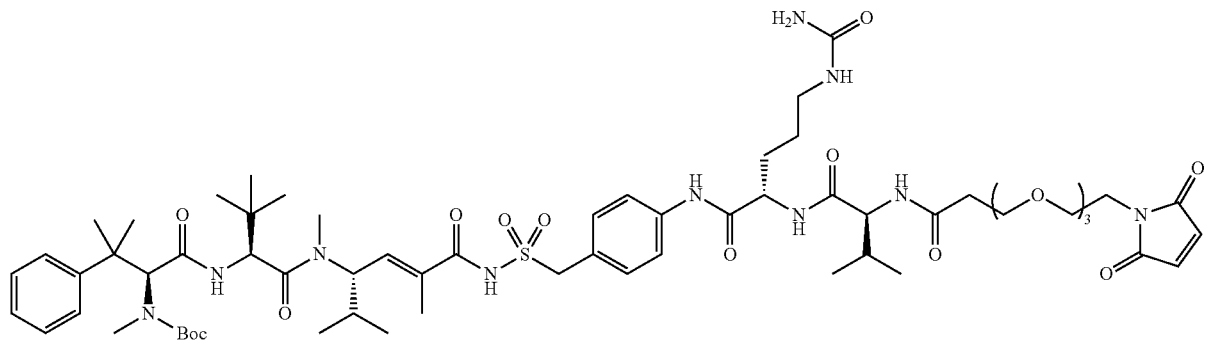

To a stirred solution of Compound E-4 (40.0 mg, 0.040 mmol, 1.0 eq) in CH$_2$Cl$_2$ (0.5 mL) was added MT-OH (18.1 mg, 0.060 mmol, 1.5 eq). Next, triethylamine (0.017 mL, 0.120 mmol, 3.0 eq) then Mukiyama's reagent (15.4 mg, 0.060 mmol, 1.5 eq) were added. After 3 h, approximately one equivalent of acid, triethylamine, and Mukiyama's reagent was added, and after 30 more min, HPLC indicated consumption of starting material Compound E-4. The reaction mixture was diluted with 0.25 mL hexanes and loaded directly onto flash chromatography to yield the title compound (29.3 mg, 57%) as a clear yellow film.

C$_{63}$H$_{96}$N$_{10}$O$_{16}$S calcd. m/z=1280.67. Found [M+H]$^+$=1281.94, [M+Na]$^+$=1303.91, [M-Boc+2H]$^+$=1181.86. R$_f$=0.45 (10% (5% AcOH/MeOH)/10% Hex/CH$_2$Cl$_2$).

Compound F(S,E)-N-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)benzylsulfonyl)-2,5-dimethyl-4-((S)—N,3,3-trimethyl-2-((S)-3-methyl-2-(methylamino)-3-phenylbutanamido)butanamido)hex-2-enamide

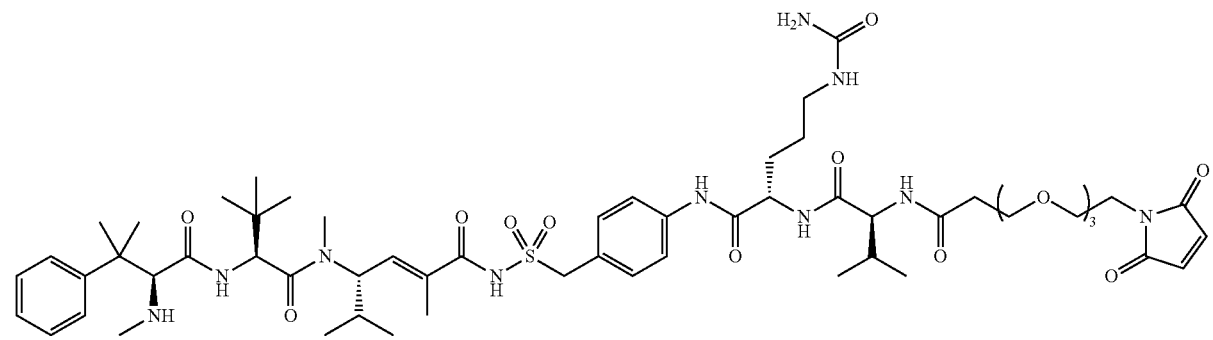

The title compound was prepared according to General Procedure 10 from Compound F-1.
$C_{58}H_{88}N_{10}O_{14}S$ calcd. m/z for =1180.62. Found $[M+H]^+$=1181.82, $[(M+2H)/2]^{2+}$=591.60.
Example 7
Compound G: (S,E)-N-(4-((R)-6-amino-2-((R)-2-(6-(2,5-dioxo-2,5-dihydro-1H-pyrrol-1-yl)hexanamido)-3-phenylpropanamido)hexanamido)benzylsulfonyl)-2,5-dimethyl-4-((S)—N,3,3-trimethyl-2-((S)-3-methyl-2-(methylamino)-3-phenylbutanamido)butanamido)hex-2-enamide
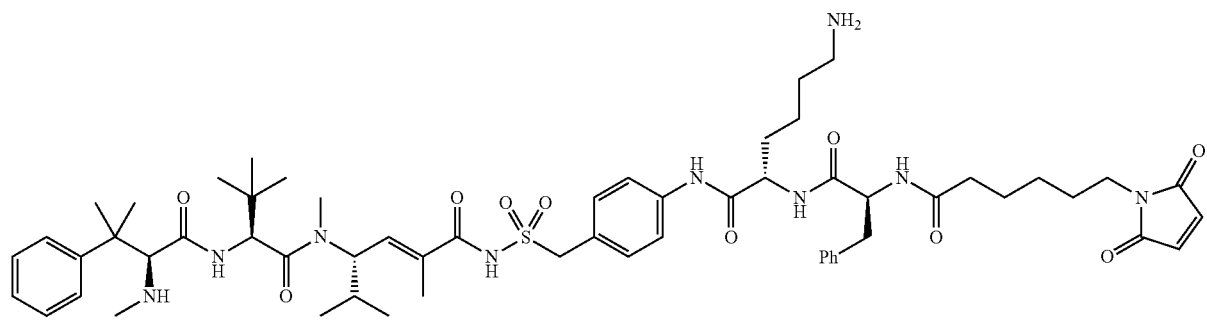 [SMILES: CN[C@H](C(=O)N[C@H](C(=O)N(C)[C@H](/C=C(\C)C(=O)NS(=O)(=O)Cc1ccc(NC(=O)[C@H](CCCCN)NC(=O)[C@H](Cc2ccccc2)NC(=O)CCCCCN2C(=O)C=CC2=O)cc1)C(C)C)C(C)(C)C)C(C)(C)c1ccccc1]
Compound G-1
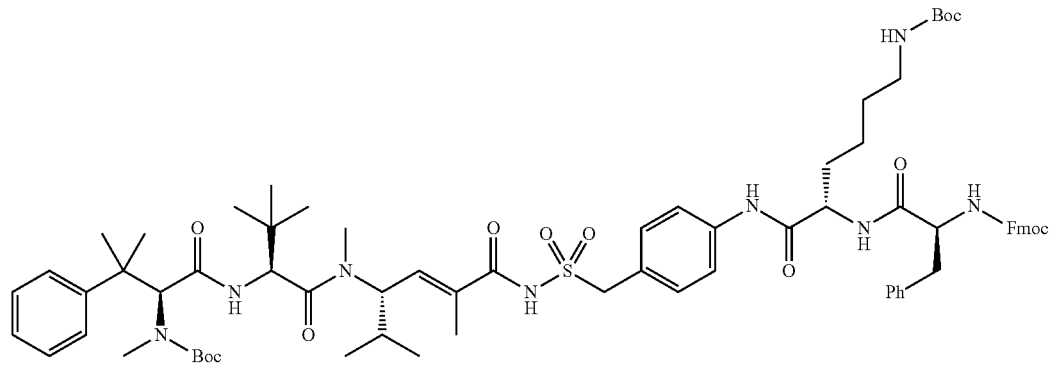

The title compound was prepared from Compound E-2 and Fmoc-Phe-Lys(Boc)-OH according to General Procedure 6.

$C_{74}H_{98}N_8O_{13}S$ calcd m/z=1338.70 amu. found $[M+H]^+$=1339.96, $[M+Na]^+$=1361.92, $[M-Boc+2H]^+$=1239.85, $[M-2Boc+H]^+$=1139.77.

Compound G-2

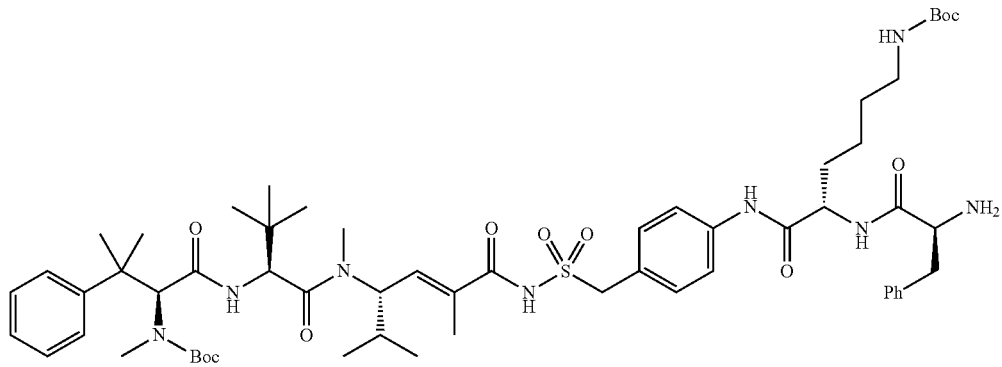 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(NC(=O)[C@H](CCCCNC(=O)OC(C)(C)C)NC(=O)[C@@H](N)Cc2ccccc2)cc1]

The title compound was prepared from Compound G-1 according to General Procedure 8.

$C_{59}H_{88}N_8O_{11}S$ calcd m/z=1116.63 amu. found $[M+H]^+$=1117.78, $[M+Na]^+$=1139.80, $[M-Boc+2H]^+$=1017.72, $[M-2Boc+H]^+$=917.64.

Compound G-3

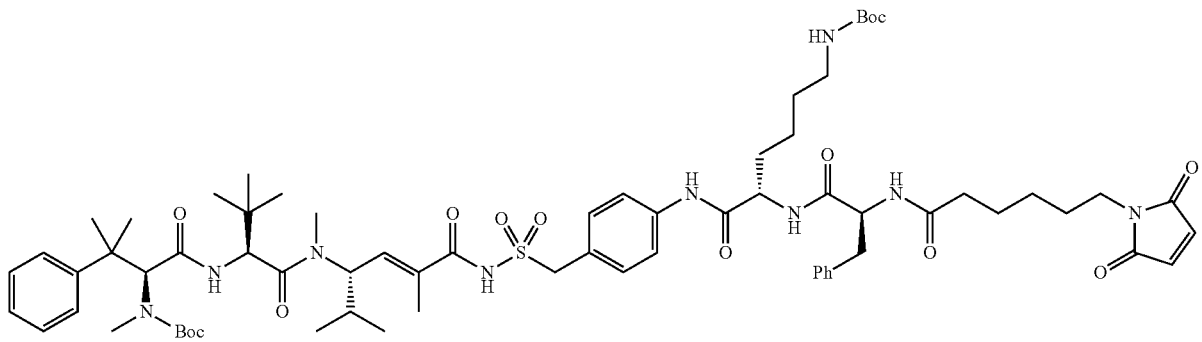 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(NC(=O)[C@H](CCCCNC(=O)OC(C)(C)C)NC(=O)[C@H](Cc2ccccc2)NC(=O)CCCCCN2C(=O)C=CC2=O)cc1]

The title compound was prepared from Compound G-2 and MC-NHS according to General Procedure 9.

$C_{69}H_{99}N_9O_{14}S$ calcd m/z=1309.70 amu. found $[M+H]^+$=1310.93, $[M+Na]^+$=1332.89, $[M-Boc+2H])/2$=1210.84, $[M-2Boc+3H]^+$=1110.76.

Compound G: (S,E)-N-(4-((R)-6-amino-2-((R)-2-(6-(2,5-dioxo-2,5-dihydro-1H-pyrrol-1-yl) hexanamido)-3-phenylpropanamido) hexanamido)benzylsulfonyl)-2,5-dimethyl-4-((S)—N,3,3-trimethyl-2-((S)-3-methyl-2-(methylamino)-3-phenylbutanamido)butanamido)hex-2-enamide

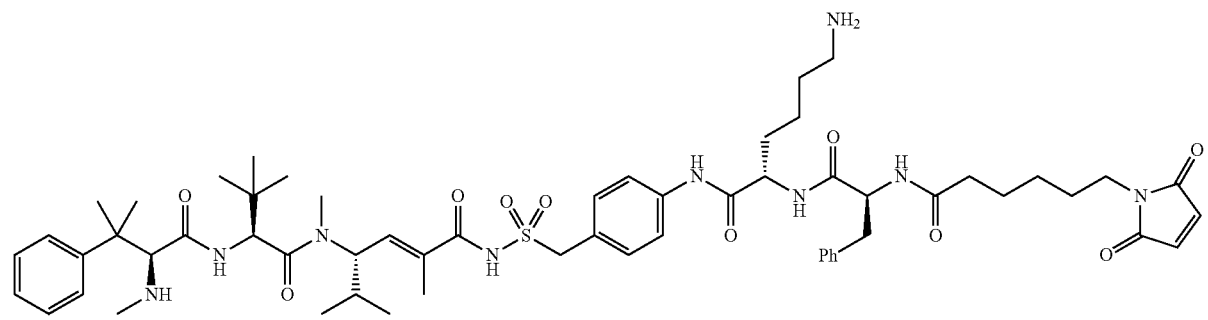 [SMILES: CN[C@H](C(=O)N[C@H](C(=O)N(C)[C@H](/C=C(\C)C(=O)NS(=O)(=O)Cc1ccc(NC(=O)[C@H](CCCCN)NC(=O)[C@H](Cc2ccccc2)NC(=O)CCCCCN2C(=O)C=CC2=O)cc1)C(C)C)C(C)(C)C)C(C)(C)c1ccccc1]

The title compound was prepared from Compound G-3 according to General Procedure 10.

$C_{59}H_{83}N_9O_{10}S$ calcd m/z=1109.60 amu. found $[M+H]^+$=1110.71, $[M+Na]^+$=1132.74, $[(M+2H)/2]^{2+}$=556.18.

Example 8

Compound H: (S,E)-N-(4-((S)-2-((S)-2-(6-(2,5-dioxo-2,5-dihydro-1H-pyrrol-1-yl)hexanamido)-3-methylbutanamido)-5-ureidopentanamido)phenylsulfonyl)-2,5-dimethyl-4-((S)—N,3,3-trimethyl-2-((S)-3-methyl-2-(methylamino)-3-phenylbutanamido)butanamido)hex-2-enamide

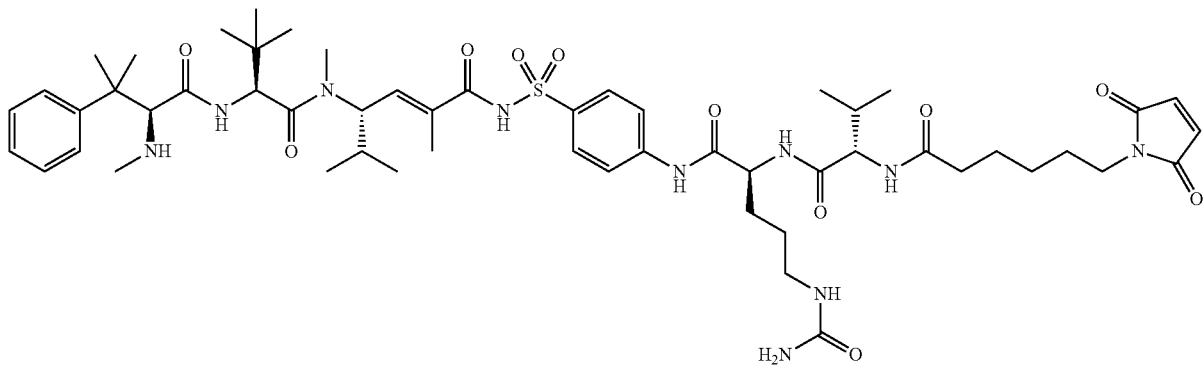 [SMILES: CN[C@H](C(=O)N[C@H](C(=O)N(C)[C@H](/C=C(\C)C(=O)NS(=O)(=O)c1ccc(NC(=O)[C@H](CCCNC(N)=O)NC(=O)[C@@H](NC(=O)CCCCCN2C(=O)C=CC2=O)C(C)C)cc1)C(C)C)C(C)(C)C)C(C)(C)c1ccccc1]

Compound H-1a:
2,2,2-trifluoro-N-(4-sulfamoylphenyl)acetamide

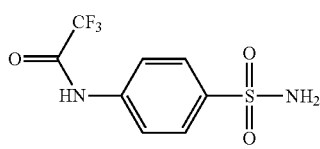 [SMILES: NS(=O)(=O)c1ccc(NC(=O)C(F)(F)F)cc1]

The title compound was synthesized from commercially available sulfanilamide and TFAA using General Procedure 2 in near quantitative yield.

Compound H-1b: Tert-butyl (S)-1-((S)-1-(((S,E)-2,5-dimethyl-6-oxo-6-(4-(2,2,2-trifluoroacetamido)phenylsulfonamido) hex-4-en-3-yl)(methyl)amino)-3,3-dimethyl-1-oxobutan-2-ylamino)-3-methyl-1-oxo-3-phenylbutan-2-yl(methyl)carbamate

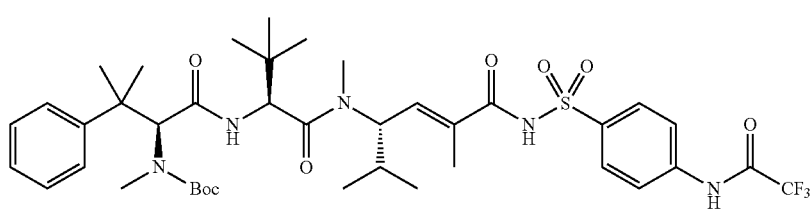 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(NC(=O)C(F)(F)F)cc1]

To a stirred solution of Boc-HTI-286-OH (0.400 g, 0.7 mmol) and 2,2,2-trifluoro-N-(4-sulfamoylphenyl)acetamide (0.244, 1.3 equiv) in ethyl acetate (10 mL) was added N,N-dicyclohexylcarbodiimide (0.202 g, 1.4 equiv) and N,N-dimethyl-4-aminopyridine (0.119 g, 1.4 equiv). Stirring was continued overnight at which point the reaction was diluted with diethyl ether (60 mL), the solids were filtered off, washed with diethyl ether (30 mL) and the filtrate concentrated to give a colourless oil. The oil was purified by silica gel chromatography using 5-50% EtOAc (containing 5% AcOH) in hexanes on a 25 g Isolera™ column over 25 column volumes. Fractions containing the desired material were pooled and concentrated to give the title compound (0.504 g, 86%) as a colourless foam.

$^1$H NMR (400 MHz, Methanol-$d_4$) δ 8.14-8.03 (m, 2H), 7.98-7.83 (m, 3H), 7.47 (d, J=7.6 Hz, 2H), 7.32 (d, J=7.6, 2H), 7.20 (q, J=7.4, 6.2 Hz, 2H), 6.44 (d, J=9.1 Hz, 1H), 5.16 (s, 1H), 4.68 (d, J=9.0 Hz, 1H), 3.08-2.95 (m, 3H), 2.87 (d, J=6.4 Hz, 3H), 2.01 (m, 6H), 1.80 (d, J=11.7 Hz, 3H), 1.62 (d, J=6.4 Hz, 1H), 1.52-1.36 (m, 14H), 1.26 (m, 1H), 0.98-0.72 (m, 15H). $C_{40}H_{56}F_3N_5O_8S$ calcd. m/z [M+H]$^+$ 824.38. found [M+Na]$^+$846.43; [M+H]$^+$ 824.40; [M-Boc+2H]$^+$724.34.

Compound H-1c: Tert-butyl (S)-1-((S)-1-(((S,E)-6-(4-aminophenylsulfonamido)-2,5-dimethyl-6-oxo-hex-4-en-3-yl)(methyl)amino)-3,3-dimethyl-1-oxobutan-2-ylamino)-3-methyl-1-oxo-3-phenylbutan-2-yl(methyl)carbamate

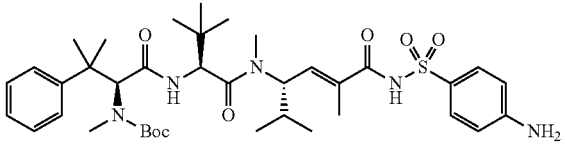 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(N)cc1]

The title compound was prepared from Compound H-1b according to General Procedure 5.

Compound H-1

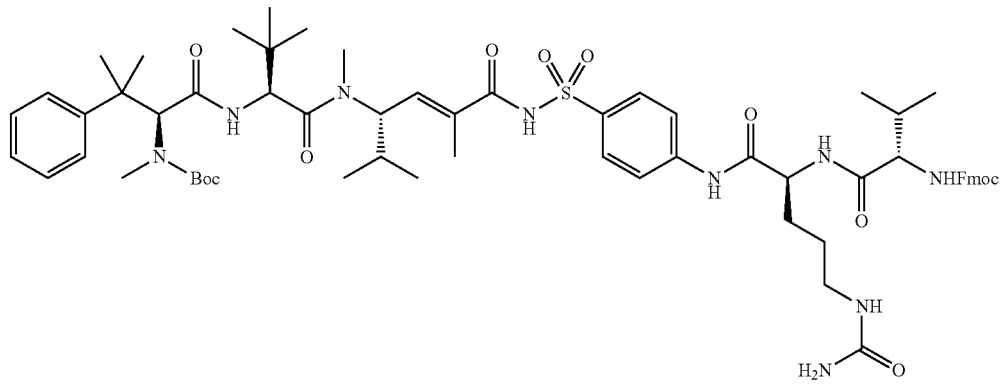

Synthesized from tert-butyl (S)-1-((S)-1-(((S,E)-6-(4-aminophenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate and Fmoc-Val-Cit-OH according to General Procedure 6.

$C_{64}H_{87}N_9O_{12}S$ calcd. m/z [M+H]$^+$ 1206.62. found [M+Na]$^+$1230.81; [M+H]$^+$1206.73; [M-Boc+2H]$^+$1106.63.

Compound H-2: Tert-butyl (S)-1-((S)-1-(((S,E)-6-(4-((S)-2-((S)-2-amino-3-methylbutanamido)-5-ureidopentanamido)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate

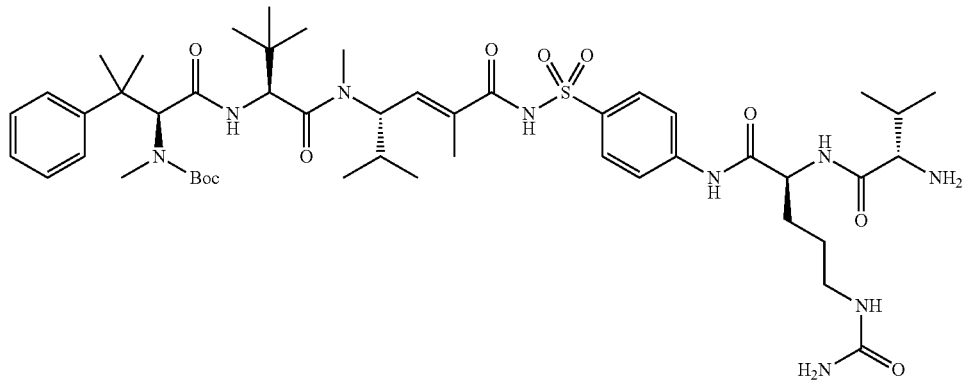 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(NC(=O)[C@H](CCCNC(N)=O)NC(=O)[C@@H](N)C(C)C)cc1]

The title compound was prepared from Compound H-1 according to General Procedure 8.

$C_{49}H_{77}N_9O_{10}S$ calcd. m/z [M+H]$^+$ 984.55. found [M+H]$^+$ 984.63; [M-Boc+2H]$^+$ 884.57.

Compound H-3: Tert-butyl (S)-1-((S)-1-(((S,E)-6-(4-((S)-2-((S)-2-(6-(2,5-dioxo-2,5-dihydro-1H-pyrrol-1-yl)hexanamido)-3-methylbutanamido)-5-ureidopentanamido)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate

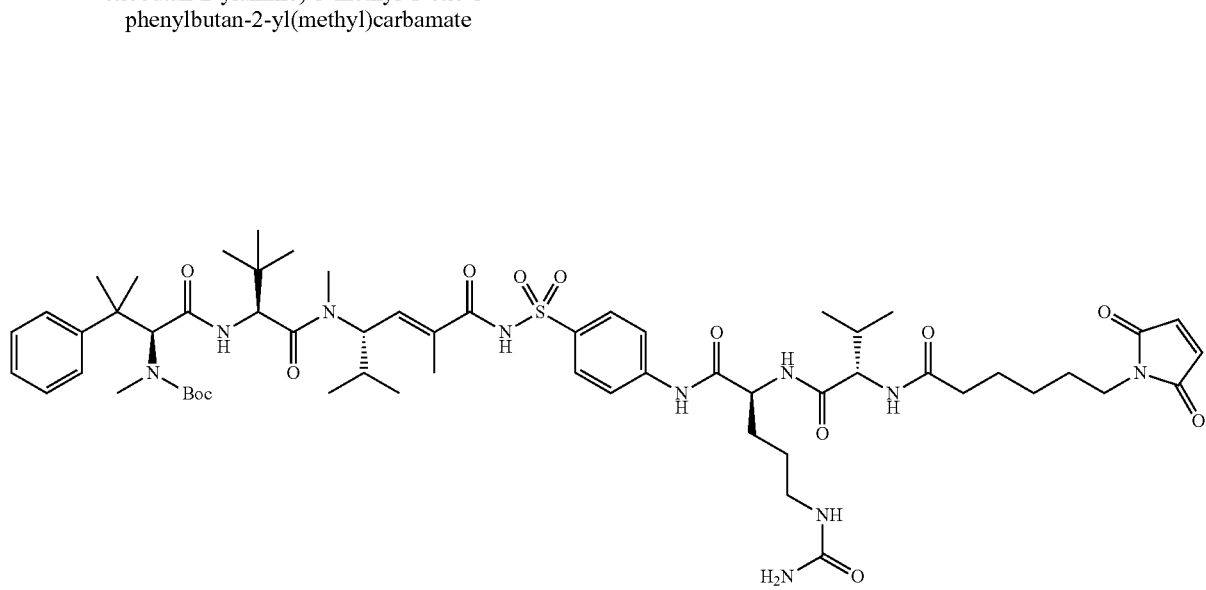

The title compound was prepared from tert-butyl (S)-1-((S)-1-(((S,E)-6-(4-((S)-2-((S)-2-amino-3-methylbutanamido)-5-ureidopentanamido)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate and MC-NHS according to General Procedure 9.

$C_{59}H_{88}N_{10}O_{13}S$ calcd. m/z [M+H]$^+$ 1177.63. found [M+Na]$^+$ 1199.74; [M+H]$^+$ 1177.85; [M-Boc+2H]$^+$ 1077.68.

Compound H: (S,E)-N-(4-((S)-2-((S)-2-(6-(2,5-dioxo-2,5-dihydro-1H-pyrrol-1-yl)hexanamido)-3-methylbutanamido)-5-ureidopentanamido)phenylsulfonyl)-2,5-dimethyl-4-((S)—N,3,3-trimethyl-2-((S)-3-methyl-2-(methylamino)-3-phenylbutanamido)butanamido)hex-2-enamide

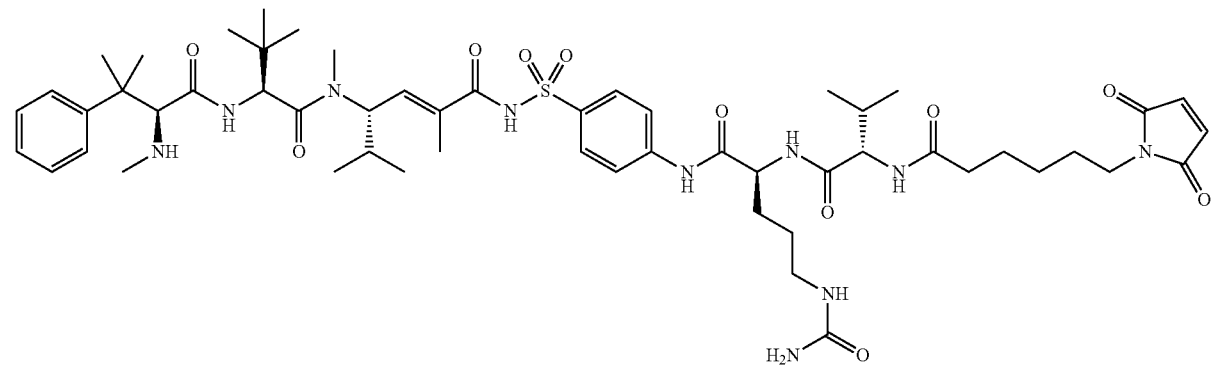 [SMILES: CN[C@H](C(=O)N[C@H](C(=O)N(C)[C@H](/C=C(\C)C(=O)NS(=O)(=O)c1ccc(NC(=O)[C@H](CCCNC(N)=O)NC(=O)[C@@H](NC(=O)CCCCCN2C(=O)C=CC2=O)C(C)C)cc1)C(C)C)C(C)(C)C)C(C)(C)c1ccccc1]

The title compound was prepared from tert-butyl (S)-1-((S)-1-(((S,E)-6-(4-((S)-2-((S)-2-(6-(2,5-dioxo-2,5-dihydro-1H-pyrrol-1-yl)hexanamido)-3-methylbutanamido)-5-ureidopentanamido)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl (methyl)carbamate according to General Procedure 10.

$C_{54}H_{80}N_{10}O_{11}S$ calcd. m/z $[M+H]^+$ 1077.63. found $[M+H]^+$ 1077.68.

Example 9

Compound I: (S,E)-N-((4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenyl)sulfonyl)-2,5-dimethyl-4-((S)—N,3,3-trimethyl-2-((S)-3-methyl-2-(methylamino)-3-phenylbutanamido)butanamido)hex-2-enamide

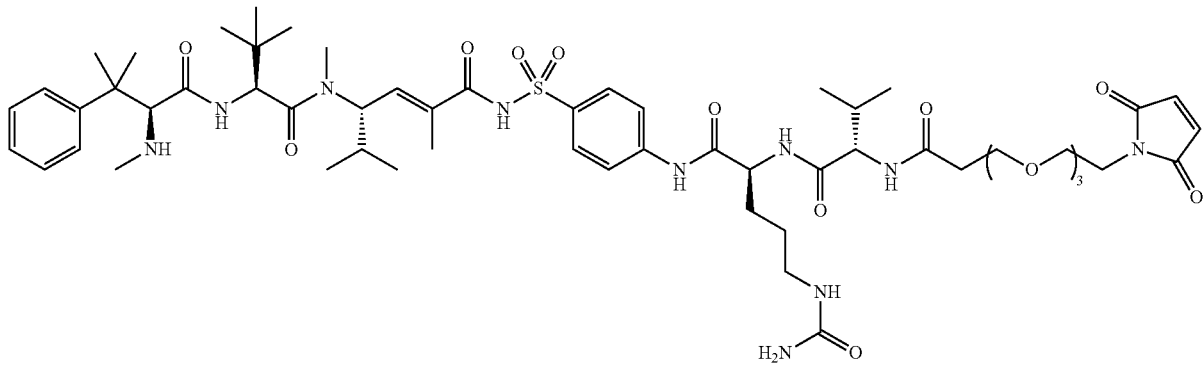

Compound I-1: tert-butyl ((S)-1-(((S)-1-(((S,E)-6-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl)(methyl)carbamate

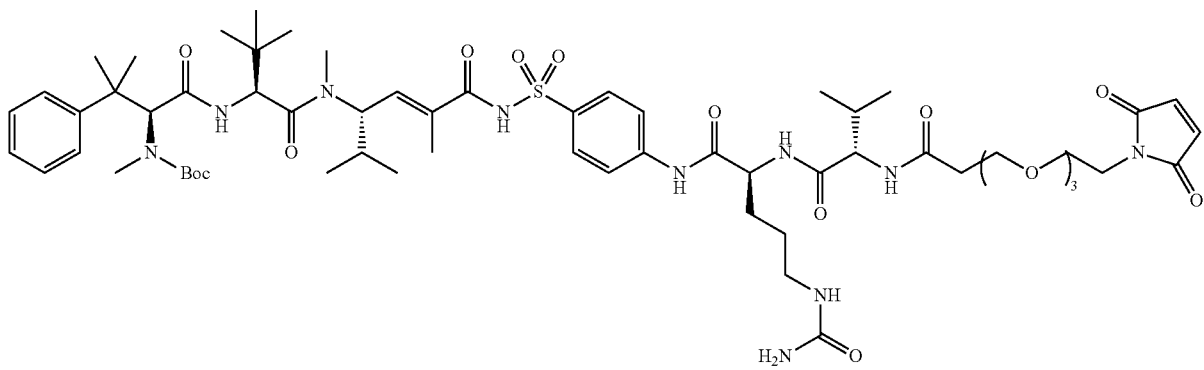

The title compound was prepared according to General Procedure 9 from tert-butyl (S)-1-((S)-1-(((S,E)-6-(4-((S)-2-((S)-2-amino-3-methylbutanamido)-5-ureidopentanamido)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate (Compound H-2) and MT-NHS.

m/z calcd. for $C_{62}H_{94}N_{10}O_{16}S$=1266.66. Found [M+H]$^+$=1267.87 [M+Na]$^+$=1289.86, [M-Boc+2H]$^+$=1167.82. $R_f$=0.49 (10% (5% AcOH/MeOH)/CH$_2$Cl$_2$).

Compound I: (S,E)-N-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonyl)-2,5-dimethyl-4-((S)—N,3,3-trimethyl-2-((S)-3-methyl-2-(methylamino)-3-phenylbutanamido)butanamido)hex-2-enamide

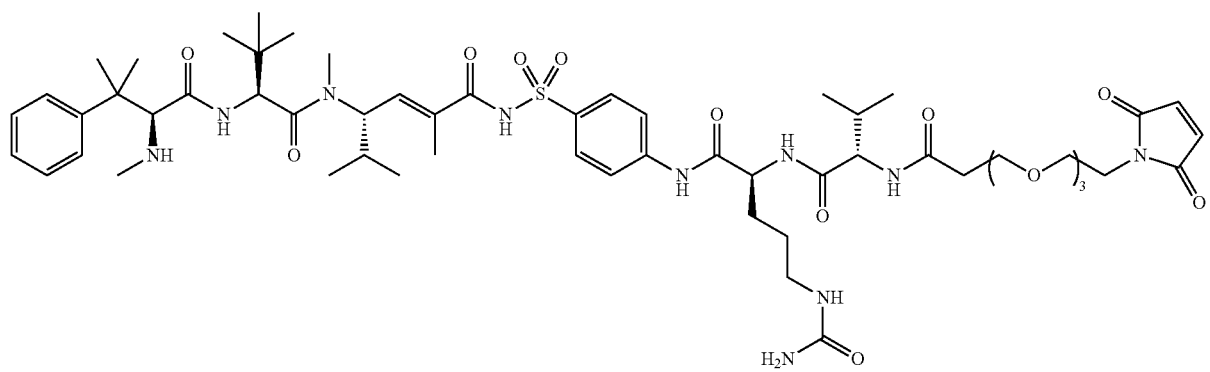

The title compound was prepared according to General Procedure 10 from tert-butyl ((S)-1-(((S)-1-(((S,E)-6-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3,3-dimethyl-1-oxobutan-2-yl)amino)-3-methyl-1-oxo-3-phenylbutan-2-yl)(methyl)carbamate (Compound I-1).

m/z calcd. for $C_{57}H_{86}N_{10}O_{14}S$=1166.60. Found [M+H]$^+$=1167.67, [(M+2H)/2]$^{2+}$=584.57.

Example 10

Compound J: (S,E)-N-(4-(1-((R)-2-((R)-2-(6-(2,5-dioxo-2,5-dihydro-1H-pyrrol-1-yl)hexanamido)-3-methylbutanamido)-5-ureidopentanamido)cyclopropyl)benzylsulfonyl)-2,5-dimethyl-4-((S)—N,3,3-trimethyl-2-((S)-3-methyl-2-(methylamino)-3-phenylbutanamido)butanamido)hex-2-enamide

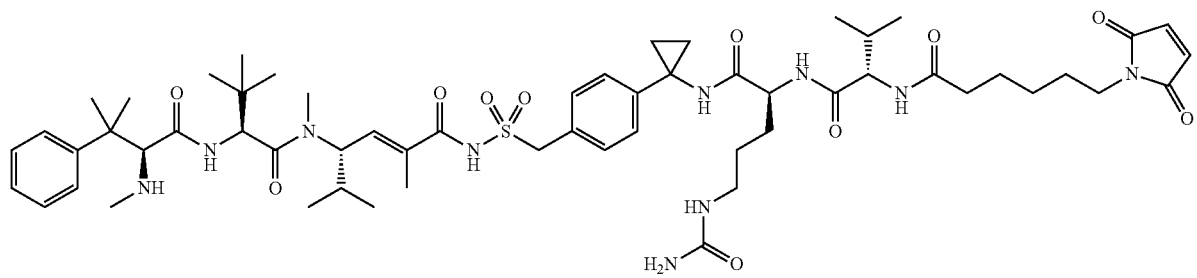 [SMILES: CN[C@H](C(=O)N[C@H](C(=O)N(C)[C@H](/C=C(\C)C(=O)NS(=O)(=O)Cc1ccc(C2(NC(=O)[C@H](CCCNC(N)=O)NC(=O)[C@@H](NC(=O)CCCCCN3C(=O)C=CC3=O)C(C)C)CC2)cc1)C(C)C)C(C)(C)C)C(C)(C)c1ccccc1]

Compound J-1a: 4-(tritylthiomethyl)benzonitrile

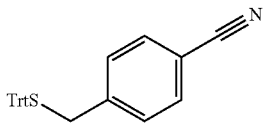

Tritylmercaptan (1.48 g, 5.36 mmol, 1.05 eq) in THF (5 mL) was added dropwise to a stirred suspension of sodium hydride (60% dispersion in mineral oil, 214 mg, 5.36 mmol, 1.05 eq) in THF (5 mL) under $N_2$ at 0° C. After 15 min, 4-(bromomethyl)benzonitrile (1.00 g, 5.10 mmol, 1.0 eq) in THF (5 mL) was added and the reaction was allowed to come to rt. After 1 h, TLC indicated complete conversion of starting material. The reaction was quenched by adding saturated ammonium chloride, then some $dH_2O$. The mixture was extracted three times with ether, washed with saturated brine, dried over sodium sulfate, and concentrated to a viscous yellow oil. Purification by flash chromatography gave the title compound (1.76 g, 88%) as a light white powder.

$^1$H NMR (400 MHz, Chloroform-d) δ 7.52 (d, J=8.2 Hz, 2H), 7.47 (d, J=7.1 Hz, 6H), 7.33 (t, J=7.5 Hz, 6H), 7.26 (t, J=7.2 Hz, 3H), 7.19 (d, J=8.2 Hz, 2H), 3.40 (s, 2H). m/z calcd. for $C_{27}H_{21}NS$=391.14. Found [M+Na]$^+$=414.13. $R_f$=0.32 (10% EtOAc/Hex).

Compound J-1b: 1-(4-(tritylthiomethyl)phenyl)cyclopropanamine

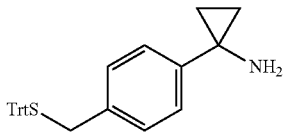

4-(tritylthiomethyl)benzonitrile (1.47 g, 3.75 mmol, 1.0 eq) was taken up in 40 mL THF, under $N_2$ atmosphere, then cooled to −78° C. To this solution was added Ti(O-iPr)$_4$ (1.21 mL, 4.13 mmol, 1.1 eq), then ethylmagnesium bromide (3 M, 2.75 mL, 8.26 mmol, 2.2 eq) was added dropwise over 5 min. The dry-ice bath was removed, allowing the solution to reach rt. After 45 min at rt, $BF_3$-$Et_2O$ (0.93 mL, 7.51 mmol, 2.0 eq) was added to the now very dark reaction mixture. After stirring for an additional 2.5 h, the reaction was quenched with 5 mL of 2 M HCl, followed by pH adjustment to strong base with about 15 mL 2 M NaOH. Some water was added to the mixture, then it was extracted three times with 75 mL EtOAc, washed once with $dH_2O$, once with saturated brine, dried over sodium sulfate, and concentrated to a clear oil. The material was purified by flash chromatography to afford the title compound (680 mg, 36%) as a clear oil.

$^1$H NMR (400 MHz, Chloroform-d) δ 7.49 (d, J=7.8 Hz, 6H), 7.33 (t, J=7.7 Hz, 6H), 7.26 (t, J=7.2 Hz, 3H), 7.20 (d, J=8.2 Hz, 2H), 7.11 (d, J=8.2 Hz, 2H), 3.32 (s, 2H), 1.06 (dd, J=7.9, 5.0 Hz, 2H), 0.95 (dd, J=7.9, 4.7 Hz, 2H). m/z calcd. for $C_{29}H_{27}NS$=421.19. Found [M+H]$^+$=422.19. Rf=0.21 (50% EtOAc/Hex).

Compound J-1c: 2,2,2-trifluoro-N-(1-(4-(tritylthiomethyl)phenyl)cyclopropyl)acetamide

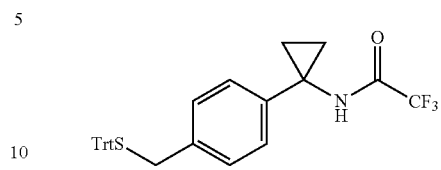

To a stirred solution of 1-(4-(tritylthiomethyl)phenyl)cyclopropanamine (680 mg, 1.61 mmol, 1.0 eq) in $CH_2Cl_2$ was added trifluoroacetic anhydride (0.448 mL, 3.22 mmol, 2.0 eq) and triethylamine (0.45 mL, 3.22 mmol, 2.0 eq). After two hours, TLC and HPLC indicated complete conversion of starting material. The reaction was quenched by the addition of 3 mL $NaHCO_3$, then some $dH_2O$ was added, and the mixture was extracted three times with $CH_2Cl_2$. The combined organics were washed with saturated brine, dried over sodium sulfate, and concentrated to a yellow foam, giving the title compound (715 mg, 86%) in sufficient purity to move to the next step.

$^1$H NMR (400 MHz, Chloroform-d) δ 7.48 (d, J=7.7 Hz, 6H), 7.32 (t, J=7.6 Hz, 6H), 7.25 (t, J=7.2 Hz, 3H), 7.19 (d, J=8.2 Hz, 2H), 7.10 (d, J=8.3 Hz, 2H), 6.83 (s, 1H), 3.31 (s, 2H), 1.40-1.24 (m, 4H). m/z calcd. for $C_{31}H_{26}F_3NOS$=517.17. Found [M+Na]$^+$=540.25. $R_f$=0.71 (50% EtOAc/Hex).

Compound J-1d: 2,2,2-trifluoro-N-(1-(4-(mercaptomethyl)phenyl)cyclopropyl)acetamide

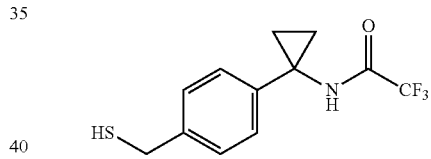

2,2,2-trifluoro-N-(1-(4-(tritylthiomethyl)phenyl)cyclopropyl)acetamide (715 mg, 1.38 mmol, 1.0 eq) in 5 mL $CH_2Cl_2$ was treated with 2.5 mL TFA. After 1 min, TIPSH (0.42 mL, 2.1 mmol, 1.5 eq) was added, causing the yellow color to fade. After 30 min, TLC indicated the reaction to be complete. The mixture was concentrated, then co-evaporated once with $CH_2Cl_2$ and twice with toluene. The residue was purified by flash chromatography to afford the title compound (261 mg, 69%) as a white solid. $^1$H NMR (400 MHz, Chloroform-d) δ 7.35-7.23 (m, 4H), 6.87 (s, 1H), 3.74 (d, J=7.6 Hz, 2H), 1.77 (t, J=7.6 Hz, 1H), 1.36 (s, 4H). $R_f$=0.47 (20% EtOAc/Hex).

Compound J-1e: 2,2,2-trifluoro-N-(1-(4-(sulfamoylmethyl)phenyl)cyclopropyl)acetamide

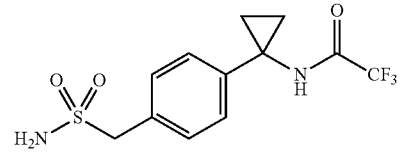 [SMILES: NS(=O)(=O)Cc1ccc(C2(NC(=O)C(F)(F)F)CC2)cc1]

To a stirred solution of 2,2,2-trifluoro-N-(1-(4-(mercaptomethyl)phenyl)cyclopropyl)acetamide (220 mg, 0.799 mmol, 1.0 eq) in acetonitrile were added dH$_2$O (0.029 mL, 1.6 mmol, 2.0 eq), tetrabutylammonium chloride (110 mg, 0.40 mmol, 0.5 eq), then N-chlorosuccinimide (320 mg, 2.40 mmol, 3.0 eq). After 20 minutes, no starting material was visible by TLC. After 90 min, concentrated NH$_4$OH (0.18 mL, 3.2 mmol, 4.0 eq) was added. After 10 minutes, 1 mL of NH$_4$Cl was added, and the mixture was extracted three times with EtOAc. The combined organics were washed twice with dH$_2$O, once with saturated brine, dried over sodium sulfate, and concentrated to a clear oil. The residue was purified by flash chromatography to afford the title compound (192 mg, 74%) as a white solid.

$^1$H NMR (400 MHz, DMSO-d$_6$) δ 10.21 (s, 1H), 7.31 (d, J=8.2 Hz, 2H), 7.16 (d, J=8.3 Hz, 2H), 6.85 (s, 2H), 4.23 (s, 2H), 1.27 (dt, J=6.1, 2.3 Hz, 4H). R$_f$=0.26 (50% EtOAc/Hex).

Compound J-1

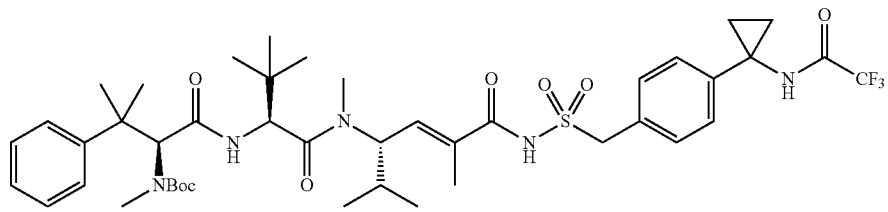 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(C2(NC(=O)C(F)(F)F)CC2)cc1]

The title compound was prepared according to General Procedure 3 from 2,2,2-trifluoro-N-(1-(4-(sulfamoylmethyl)phenyl)cyclopropyl)acetamide (Compound J-1e) and Boc-HTI-286-OH.

$^1$H NMR (400 MHz, Chloroform-d) δ 8.54 (s, 1H), 7.78 (s, 1H), 7.36 (d, J=7.1 Hz, 2H), 7.31-7.23 (m, 2H), 7.23-7.11 (m, 5H), 6.33 (d, J=9.3 Hz, 1H), 6.28-6.14 (m, 1H), 5.35 (s, 1H), 4.97 (t, J=10.3 Hz, 1H), 4.84 (d, J=13.7 Hz, 1H), 4.70-4.56 (m, 1H), 4.50 (d, J=8.9 Hz, 1H), 2.90 (s, 3H), 2.59 (s, 3H), 1.90 (s, 3H), 1.82-1.72 (m, 1H), 1.62-1.57 (m, 3H), 1.55 (s, 3H), 1.47 (s, 9H), 1.45-1.34 (m, 41H), 0.85 (d, J=6.5 Hz, 2H), 0.82-0.67 (m, 12H). m/z calcd. for C$_{44}$H$_{62}$F$_3$N$_5$O$_8$S=877.43. Found [M+Na]$^+$=900.67. R$_f$=0.34 (50% (2% AcOH/EtOAc)/Hex).

Compound J-2

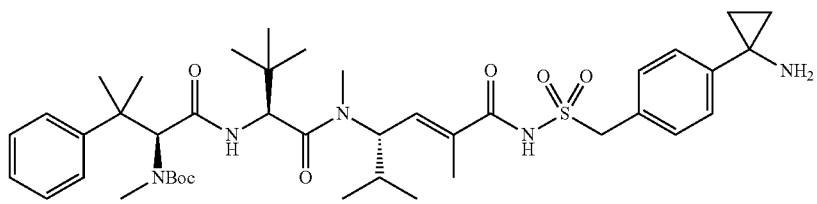 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(C2(N)CC2)cc1]

The title compound was prepared according to General Procedure 5 in MeOH/H$_2$O from Compound J-1.

$^1$H NMR (400 MHz, Chloroform-d) δ 7.62-7.48 (m, 4H), 7.35 (t, J=7.6 Hz, 2H), 7.31-7.12 (m, 3H), 6.51 (d, J=6.8 Hz, 1H), 6.36-6.18 (m, 1H), 5.29 (s, 1H), 5.00-4.86 (m, 1H), 4.67 (s, 2H), 4.60 (d, J=9.3 Hz, 1H), 3.07-2.73 (m, 6H), 2.02-1.84 (m, 4H), 1.68-1.51 (m, 6H), 1.47 (s, 9H), 1.45-1.38 (m, 2H), 1.16 (s, 2H), 0.89-0.81 (m, 12H), 0.80 (d, J=6.7 Hz, 3H). m/z calcd. for C$_{42}$H$_{63}$N$_5$O$_7$S=781.44. Found [M+H]$^+$=782.63.

Compound J-3

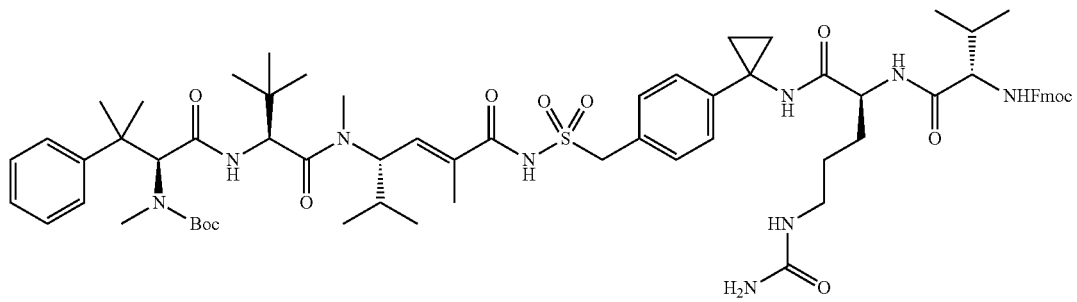

The title compound was prepared according to General Procedure 6 from Compound J-2 and Fmoc-Val-Cit-OH.

m/z calcd. for C$_{68}$H$_{93}$N$_9$O$_{12}$S=1259.67. Found [M+H]$^+$=1261.11, [M+Na]$^+$=1283.06, [M-Boc+2H]$^+$=1160.97. R$_f$=0.54 (5% MeOH/(2% AcOH/EtOAc)).

Compound J-4

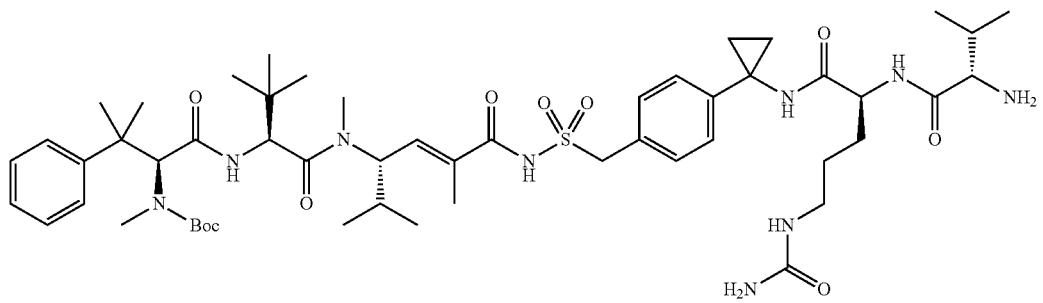 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(C2(NC(=O)[C@H](CCCNC(N)=O)NC(=O)[C@@H](N)C(C)C)CC2)cc1]

The title compound was prepared according to General Procedure 8 from Compound J-3.

m/z calcd. for C$_{53}$H$_{83}$N$_9$O$_{10}$S=1037.60. Found [M+H]$^+$=1038.90, [M-Boc+2H]$^+$=938.78. R$_f$~0.1 (25% MeOH/CH$_2$Cl$_2$).

Compound J-5

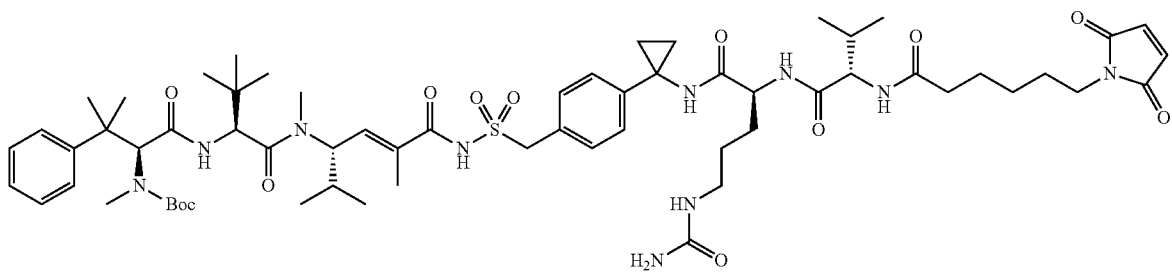 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)Cc1ccc(C2(NC(=O)[C@H](CCCNC(N)=O)NC(=O)[C@@H](NC(=O)CCCCCN3C(=O)C=CC3=O)C(C)C)CC2)cc1]

The title compound was prepared according to General Procedure 9 from Compound J-4 and MC-NHS.
m/z calcd. for $C_{63}H_{94}N_{10}O_{13}S=1230.67$. Found $[M+H]^+=1232.11$, $[M+Na]^+=1254.09$, $[M-Boc+2H]^+=1132.01$. $R_f=0.44$ (10% (5% AcOH/MeOH)/$CH_2Cl_2$).

Compound J: (S,E)-N-(4-(1-((R)-2-((R)-2-(6-(2,5-dioxo-2,5-dihydro-1H-pyrrol-1-yl)hexanamido)-3-methylbutanamido)-5-ureidopentanamido)cyclopropyl)benzylsulfony)-2,5-dimethyl-4-((S)—N,3,3-trimethyl-2-((S)-3-methyl-2-(methylamino)-3-phenylbutanamido)butanamido)hex-2-enamide

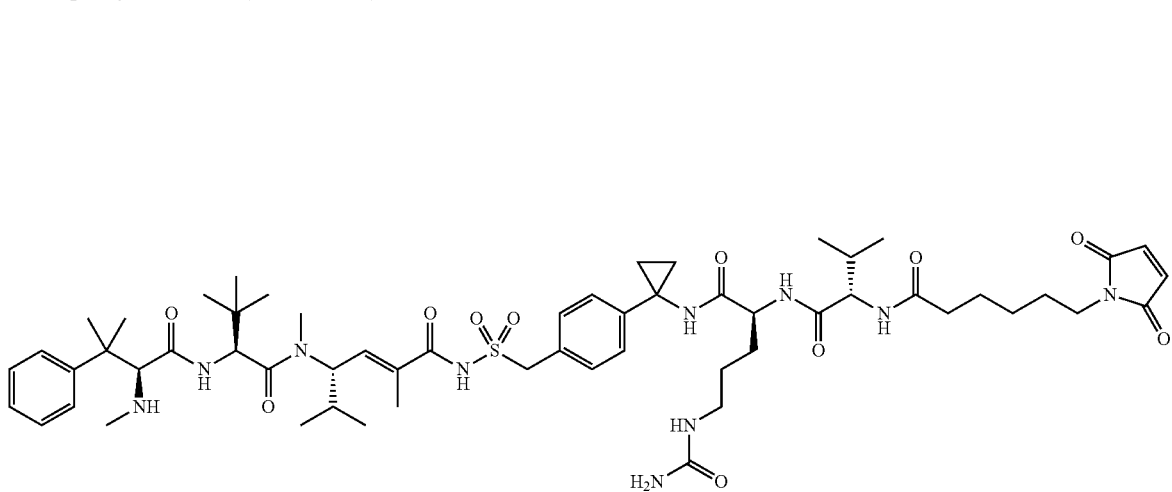 [SMILES: CN[C@H](C(=O)N[C@H](C(=O)N(C)[C@H](/C=C(\C)C(=O)NS(=O)(=O)Cc1ccc(C2(NC(=O)[C@H](CCCNC(N)=O)NC(=O)[C@@H](NC(=O)CCCCCN3C(=O)C=CC3=O)C(C)C)CC2)cc1)C(C)C)C(C)(C)C)C(C)(C)c1ccccc1]

The title compound was prepared according to General Procedure 10 from Compound J-5.
m/z calcd. for $C_{58}H_{86}N_{10}O_{11}S=1130.62$. Found $[M+H]^+=1131.95$, $[(M+2H)/2]^{2+}=566.69$.

Example 11

Compound K: (S,E)-N-(4-(1-((R)-2-((R)-2-(6-(2,5-dioxo-2,5-dihydro-1H-pyrrol-1-yl)hexanamido)-3-methylbutanamido)-5-ureidopentanamido)cyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide

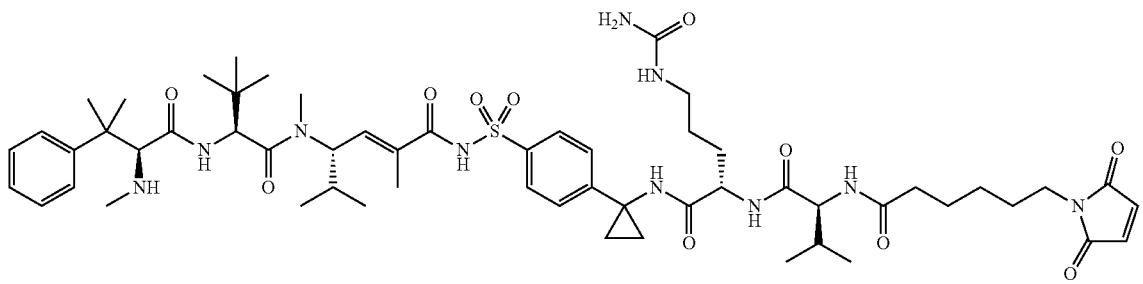 [SMILES: CN[C@H](C(=O)N[C@H](C(=O)N(C)[C@H](/C=C(\C)C(=O)NS(=O)(=O)c1ccc(C2(NC(=O)[C@H](CCCNC(N)=O)NC(=O)[C@@H](NC(=O)CCCCCN3C(=O)C=CC3=O)C(C)C)CC2)cc1)C(C)C)C(C)(C)C)C(C)(C)c1ccccc1]

Compound K-1a: 1-phenylcyclopropanamine

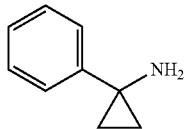

The title compound was prepared as described in Bertus, P., Szymoniak, J. *J. Org. Chem.*, 2003, 68, 7133-7136 from benzonitrile (1.0 mL, 9.7 mmol) to give 270 mg (21%).

$^1$H NMR (400 MHz, Chloroform-d) δ 7.44-7.28 (m, 4H), 7.27-7.15 (m, 1H), 1.18-1.06 (m, 2H), 1.07-0.95 (m, 2H). Rf=0.28 (5% (5% NH$_4$OH/MeOH)/CH$_2$Cl$_2$).

Compound K-1b: 2,2,2-trifluoro-N-(1-phenylcyclopropyl)acetamide

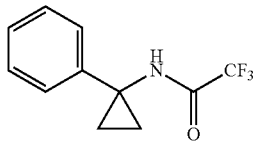 [SMILES: O=C(NC1(c2ccccc2)CC1)C(F)(F)F]

To a stirred solution of 1-phenylcyclopropanamine (270 mg, 2.03 mmol, 1.0 eq) in dioxane (5 mL), was added trifluoroacetic anhydride (0.310 mL, 2.23 mmol, 1.1 eq). After 5 min, TLC indicated complete conversion of starting material. The mixture was concentrated, then coevaporated once with CH$_2$Cl$_2$ and once with toluene to yield the title compound (453 mg, 97%) as a flaky white powder.

$^1$H NMR (400 MHz, Chloroform-d) δ 7.47-7.15 (m, 5H), 6.88 (s, 1H), 1.65 (s, 4H). m/z calcd. for C$_{11}$H$_{10}$F$_3$NO=229.07. Found [M+H]$^+$=230.14. R$_f$=0.82 (5% (5% NH$_4$OH/MeOH)/CH$_2$Cl$_2$).

Compound K-1c: 2,2,2-trifluoro-N-(1-(4-sulfamoylphenyl)cyclopropyl)acetamide

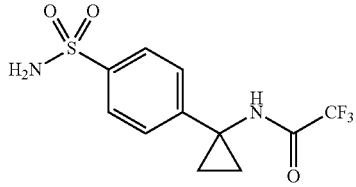 [SMILES: NS(=O)(=O)c1ccc(C2(NC(=O)C(F)(F)F)CC2)cc1]

To stirred chlorosulfonic acid (0.78 mL, 11.8 mmol, 6.0 eq) at 0° C., was added solid 2,2,2-trifluoro-N-(1-phenylcyclopropyl)acetamide (450 mg, 1.96 mmol, 1.0 eq) portionwise, keeping the temperature low. After complete addition, the mixture was heated to 50° C. After 1-minutes, gas evolution ceased, and the reaction was allowed to cool. The mixture was added slowly to a beaker of ice, being mindful of splattering. The solid that was left in the ice was filtered off. This solid was dried in vacuo and then taken up in THF (4 mL). Concentrated NH$_4$OH (0.44 mL, 7.85 mmol, 4.0 eq) was added, turning the solution green-black. After 2 min, TLC indicated complete consumption of the sulfonylchloride intermediate. 2M HCl was added until the color faded, then the mixture was extracted three times with EtOAc, washed once with saturated NaHCO$_3$, once with saturated brine, dried over sodium sulfate, and concentrated to a flaky solid. The crude material was purified by flash chromatography to yield the title compound (235 mg, 39%) as a white solid.

$^1$H NMR (400 MHz, DMSO-d$_6$) δ 10.28 (s, 1H), 7.76 (d, J=8.5 Hz, 2H), 7.32 (d, J=8.1 Hz, 2H), 7.31 (s, 2H), 1.42-1.35 (m, 2H), 1.35-1.27 (m, 2H). m/z calcd. for C$_{11}$H$_{11}$F$_3$N$_2$O$_3$S=308.04. Found [M+H]$^+$=309.07. Rf=0.27 (50% EtOAc/Hex).

Compound K-1d: Tert-butyl (S)-1-((S)-1-(((S,E)-2,5-dimethyl-6-oxo-6-(4-(1-(2,2,2-trifluoroacetamido)cyclopropyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate

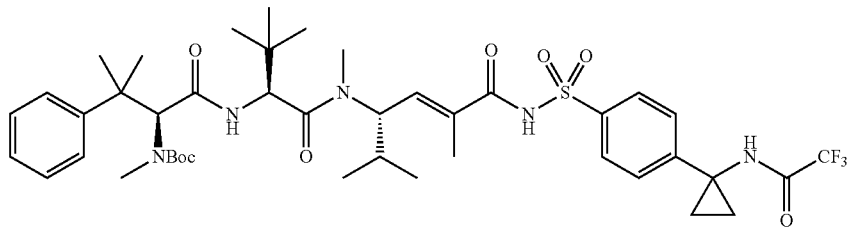 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(C2(NC(=O)C(F)(F)F)CC2)cc1]

The title compound was prepared according to General Procedure 3 from 2,2,2-trifluoro-N-(1-(4-sulfamoylphenyl)cyclopropyl)acetamide (Compound K-1c) and Boc-HTI-286—OH.

$^1$H NMR (400 MHz, Chloroform-d) δ 8.51 (s, 1H), 8.08 (d, J=8.6 Hz, 2H), 7.42-7.32 (m, 2H), 7.32-7.23 (m, 2H), 7.23-7.10 (m, 3H), 6.46 (d, J=9.0 Hz, 1H), 6.17-6.08 (m, 1H), 5.29 (s, 1H), 4.97-4.76 (m, 1H), 4.56 (d, J=8.8 Hz, 1H), 2.90 (d, J=10.4 Hz, 6H), 2.01-1.79 (m, 4H), 1.62 (s, 3H), 1.53 (s, 3H), 1.49 (s, 4H), 1.46 (s, 9H), 0.86 (t, J=6.9 Hz, 3H), 0.81 (d, J=6.8 Hz, 3H), 0.77 (s, 9H). m/z calcd. for C$_{43}$H$_{60}$F$_3$N$_5$O$_8$S=863.41. Found [M+H]$^+$=864.56, [M+Na]$^+$=886.52, [M-Boc+2H]$^+$=764.44. R$_f$=0.34 (50% (2% AcOH/EtOAc)/Hex).

Compound K-1e: Tert-butyl (S)-1-((S)-1-(((S,E)-6-(4-(1-aminocyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate

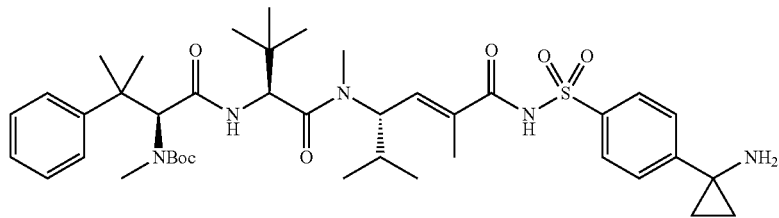 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(C2(N)CC2)cc1]

The title compound was prepared according to General Procedure 5 in dioxanes from compound tert-butyl (S)-1-((S)-1-(((S,E)-2,5-dimethyl-6-oxo-6-(4-(1-(2,2,2-trifluoroacetamido)cyclopropyl)phenylsulfonamido)hex-4-en-3-yl)(methyl)amino)-3,3-dimethyl-1-oxobutan-2-ylamino)-3-methyl-1-oxo-3-phenylbutan-2-yl(methyl)carbamate.

$^1$H NMR (400 MHz, Methanol-$d_4$) δ 7.97 (d, J=8.5 Hz, 2H), 7.52 (d, J=8.5 Hz, 2H), 7.51-7.43 (m, 2H), 7.32 (t, J=7.5 Hz, 2H), 7.20 (t, J=8.4 Hz, 1H), 6.55 (d, J=9.0 Hz, 1H), 5.17 (s, 1H), 5.03-4.94 (m, 1H), 4.70 (d, J=9.0 Hz, 1H), 2.94 (s, 3H), 2.88 (s, 3H), 1.94-1.89 (m, 1H), 1.80 (s, 3H), 1.53 (s, 3H), 1.51 (s, 3H), 1.43 (s, 9H), 1.40-1.37 (m, 2H), 1.36-1.32 (m, 2H), 0.87 (d, J=6.0 Hz, 12H), 0.82-0.76 (m, 3H). m/z calcd. for $C_{41}H_{61}N_5O_7S$=767.43. Found [M+H]$^+$=768.51 [M-Boc+2H]$^+$=668.38. $R_f$=0.32 (10% EtOAc/Hex).

Compound K-1

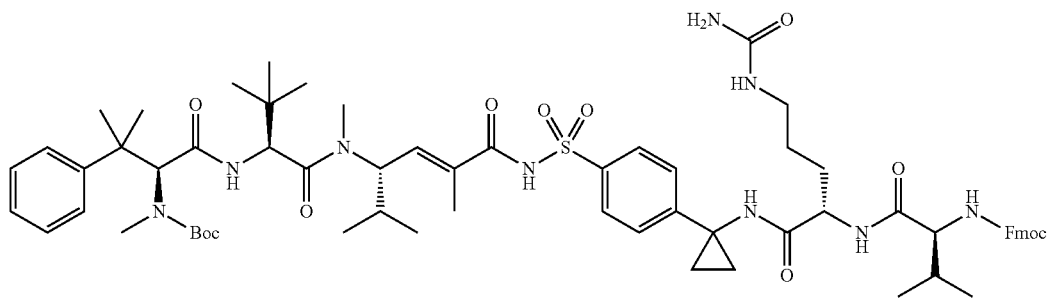

The title compound was prepared according to General Procedure 6 from tert-butyl (S)-1-((S)-1-(((S,E)-6-(4-(1-aminocyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate and Fmoc-Val-Cit-OH.

m/z calcd. for $C_{67}H_{91}N_9O_{12}S$=1245.65. Found [M+H]$^+$=1246.89, [M+Na]$^+$=1268.88, [M-Boc+2H]$^+$=1146.82. $R_f$=0.52 (5% MeOH/(2% AcOH/EtOAc)).

Compound K-2: Tert-butyl (S)-1-((S)-1-(((S,E)-6-(4-(1-((R)-2-((R)-2-amino-3-methylbutanamido)-5-ureidopentanamido)cyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate

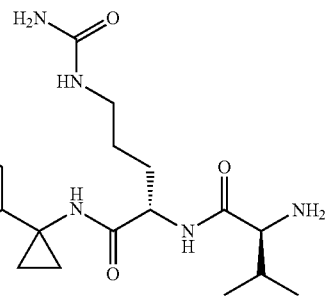

The title compound was prepared according to General Procedure 8 from Compound K-1.

m/z calcd. for $C_{52}H_{81}N_9O_{10}S$=1023.58. Found [M+H]$^+$=1024.72, [M-Boc+2H]$^+$=924.66.

Compound K-3: 1-((S)-1-(((S,E)-6-(4-(1-((R)-2-((R)-2-(6-(2,5-dioxo-2,5-dihydro-1H-pyrrol-1-yl)hexanamido)-3-methylbutanamido)-5-ureidopentanamido)cyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate

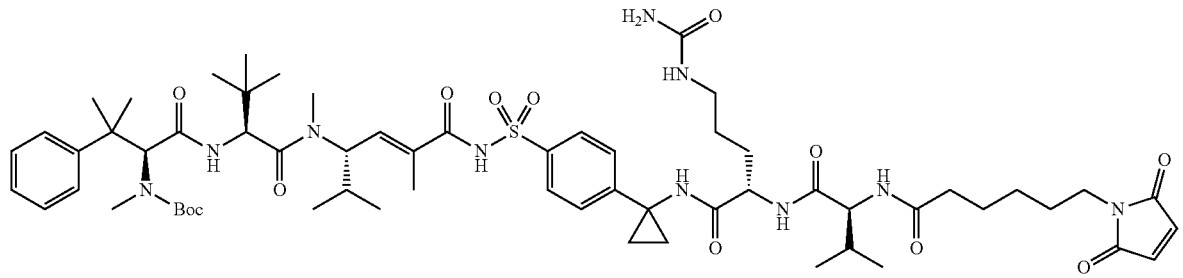 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccc(C2(NC(=O)[C@H](CCCNC(N)=O)NC(=O)[C@@H](NC(=O)CCCCCN3C(=O)C=CC3=O)C(C)C)CC2)cc1]

The title compound was prepared according to General Procedure 9 from tert-butyl (S)-1-((S)-1-(((S,E)-6-(4-(1-((R)-2-((R)-2-amino-3-methylbutanamido)-5-ureidopentanamido)cyclopropyl)phenylsulfonamido)-2,5-dimethyl-6-oxohex-4-en-3-yl)(methyl)amino)-3,3-dimethyl-1-oxobutan-2-ylamino)-3-methyl-1-oxo-3-phenylbutan-2-yl(methyl)carbamate and MC-NHS.

m/z calcd. for $C_{62}H_{92}N_{10}O_{13}S$=1216.66. Found [M+H]$^+$=1217.89, [M+Na]$^+$=1239.94, [M-Boc+2H]$^+$=1117.82. $R_f$=0.39 (10% (5% AcOH/MeOH)/CH$_2$Cl$_2$).

Compound K: (S,E)-N-(4-(1-((R)-2-((R)-2-(6-(2,5-dioxo-2,5-dihydro-1H-pyrrol-1-yl)hexanamido)-3-methylbutanamido)-5-ureidopentanamido)cyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide

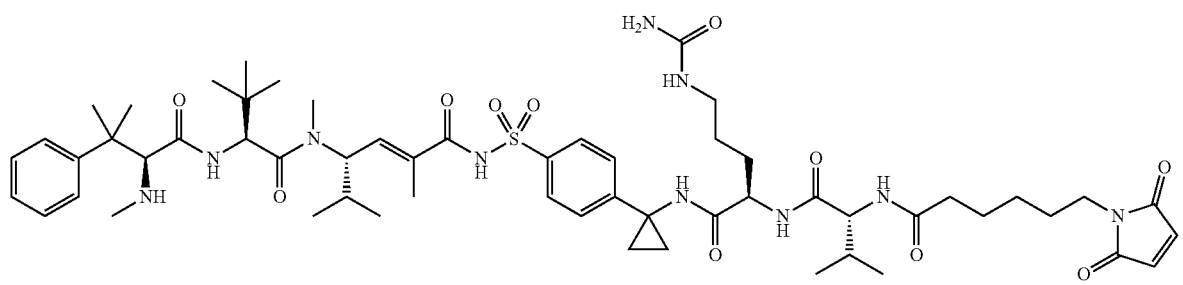 [SMILES: CN[C@H](C(=O)N[C@H](C(=O)N(C)[C@H](/C=C(\C)C(=O)NS(=O)(=O)c1ccc(C2(NC(=O)[C@@H](CCCNC(N)=O)NC(=O)[C@H](NC(=O)CCCCCN3C(=O)C=CC3=O)C(C)C)CC2)cc1)C(C)C)C(C)(C)C)C(C)(C)c1ccccc1]

The title compound was prepared according to General Procedure 10 from Compound K-3. m/z calcd. for $C_{57}H_{84}N_{10}O_{11}S$=1116.60. Found $[M+H]^+$=1117.77, $[(M+2H)/2]^{2+}$=559.56.

Example 12

Compound KK: (S,E)-N-(4-(1-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)cyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide

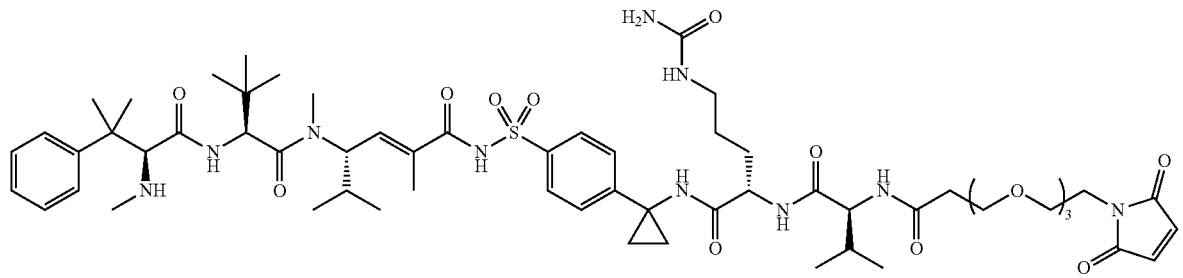

Compound KK-1: (S,E)-N-(4-(1-((S)-2-((S)-2-amino-3-methylbutanamido)-5-ureidopentanamido)cyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide

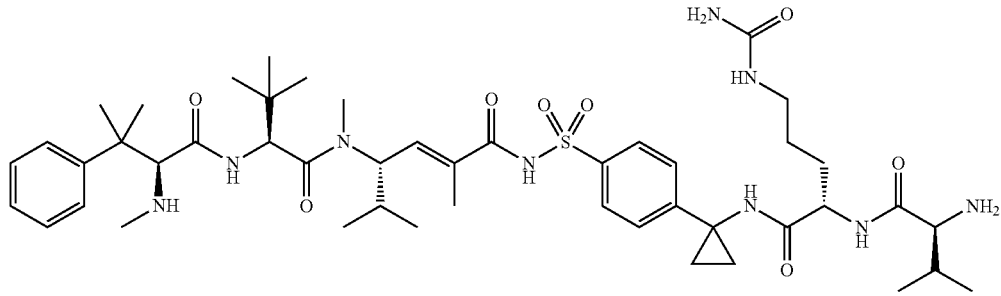 [SMILES: CN[C@H](C(=O)N[C@H](C(=O)N(C)[C@H](/C=C(\C)C(=O)NS(=O)(=O)c1ccc(C2(NC(=O)[C@H](CCCNC(N)=O)NC(=O)[C@@H](N)C(C)C)CC2)cc1)C(C)C)C(C)(C)C)C(C)(C)c1ccccc1]

The title compound was synthesized from Compound K-2 according to General Procedure 10. $^1$H NMR (400 MHz, Methanol-$d_4$) δ 7.97-7.90 (m, 2H), 7.59-7.51 (m, 2H), 7.47 (dd, J=8.5, 6.9 Hz, 2H), 7.44-7.34 (m, 3H), 6.46 (dd, J=9.4, 1.7 Hz, 1H), 5.02 (t, J=10.0 Hz, 1H), 4.93 (s, 1H), 4.43 (dd, J=8.6, 5.8 Hz, 1H), 4.35 (s, 1H), 3.71 (d, J=5.7 Hz, 1H), 3.23-3.09 (m, 5H), 2.51 (s, 3H), 2.22 (dt, J=13.4, 6.7 Hz, 1H), 2.04 (q, J=8.8, 7.8 Hz, 1H), 1.89-1.68 (m, 4H), 1.58 (dq, J=14.5, 8.7, 8.3 Hz, 2H), 1.48 (s, 4H), 1.36 (d, J=14.3 Hz, 5H), 1.15-0.99 (m, 16H), 0.90 (dd, J=6.6, 3.4 Hz, 6H). m/z calcd. for $C_{47}H_{73}N_9O_8S$=923.53. Found $[M+H]^+$=924.8.

Compound KK: (S,E)-N-(4-(1-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)cyclopropyl)phenylsulfonyl)-2,5-dimethyl-4-((S)—N,3,3-trimethyl-2-((S)-3-methyl-2-(methylamino)-3-phenylbutanamido)butanamido)hex-2-enamide

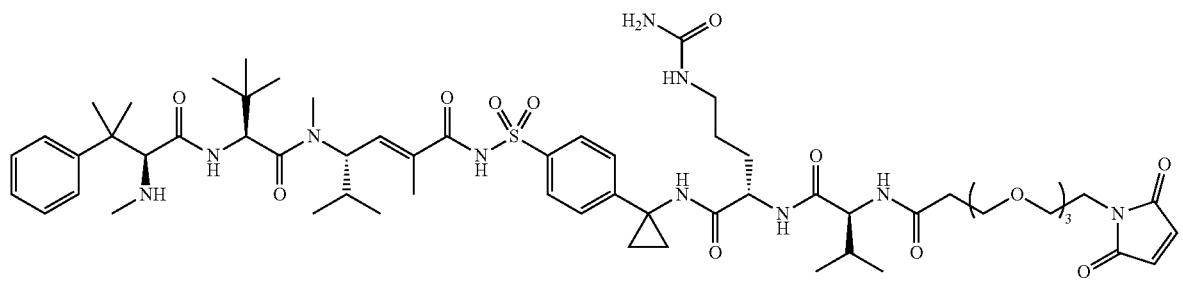

The title compound was synthesized from KK-1 and MT-NHS according to General Procedure 9 prior to purification by preparative HPLC-MS. $^1$H NMR (400 MHz, Methanol-$d_4$) δ 7.99-7.91 (m, 2H), 7.60-7.52 (m, 2H), 7.48 (t, J=7.7 Hz, 2H), 7.44-7.31 (m, 3H), 6.84 (s, 2H), 6.45 (dd, J=9.3, 1.7 Hz, 1H), 5.00 (t, J=10.0 Hz, 1H), 4.94 (s, 1H), 4.35 (d, J=5.3 Hz, 2H), 4.21 (d, J=6.9 Hz, 1H), 3.81-3.67 (m, 4H), 3.67-3.54 (m, 10H), 3.25-3.05 (m, 5H), 2.64-2.47 (m, 5H), 2.20-1.99 (m, 2H), 1.85 (d, J=1.3 Hz, 4H), 1.73 (dq, J=9.5, 4.5 Hz, 1H), 1.66-1.28 (m, 11H), 1.12-0.94 (m, 16H), 0.90 (dd, J=6.6, 4.9 Hz, 6H). m/z calcd. for $C_{60}H_{90}N_{10}O_{14}S$=1206.64. Found $[M+H]^+$=1207.9.

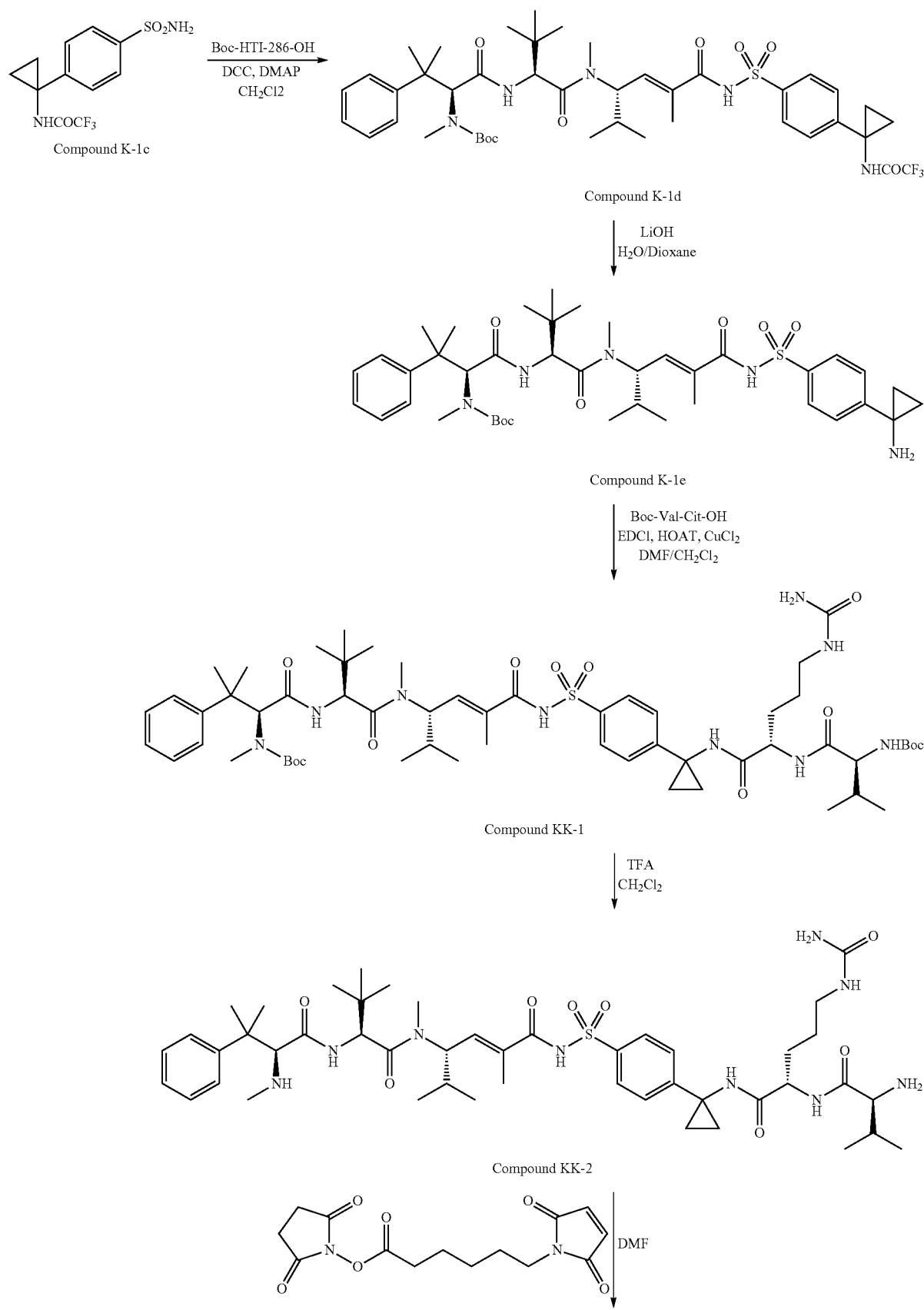

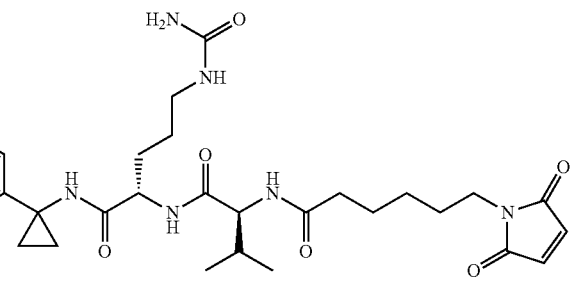

Compound KK

Example 13

Compound L: (R)—N-((2S,3S)-1-(((S,E)-6-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3-methyl-1-oxopentan-2-yl)-1-methylpiperidine-2-carboxamide

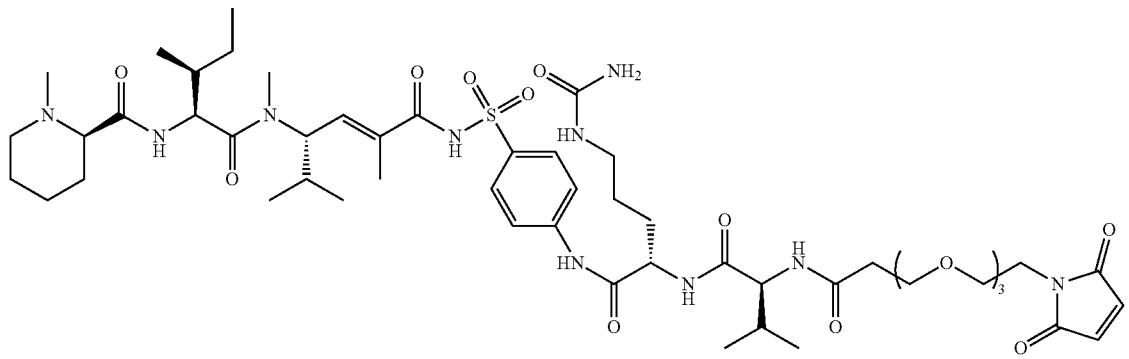

Compound L-1: (S,E)-Ethyl 4-(tert-Butoxycarbonyl(methyl)amino)-2,5-dimethylhex-2-enoate, Boc-ICD-OEt

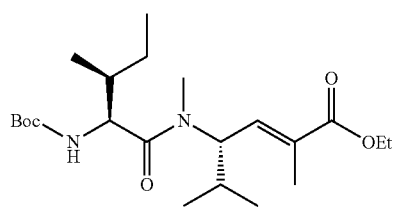

The title compound was synthesized from (S,E)-ethyl 2,5-dimethyl-4-(methylamino)hex-2-enoate (synthesized according to U.S. Pat. No. 7,579,323 B1) and Boc-Isoleucine-OH and using General Procedure 6. NMR provided for a sample treated with TFA to remove the Boc group and resolve rotamers in the spectrum. $^1$H NMR (400 MHz, Chloroform-d) δ 6.68 (dd, J=9.5, 1.8 Hz, 1H), 5.33 (s, OH), 4.97 (t, J=9.9 Hz, 1H), 4.36 (d, J=4.1 Hz, 1H), 4.25 (q, J=7.1 Hz, 2H), 3.56 (s, 1H), 2.96 (s, 3H), 2.07-1.83 (m, 5H), 1.53 (s, 1H), 1.34 (t, J=7.1 Hz, 3H), 1.12 (d, J=7.0 Hz, 3H), 1.00-0.83 (m, 9H).

Compound L-2: (S,E)-4-((2S,3R)-2-(tert-butoxycarbonylamino)-N,3-dimethylpentanamido)-2,5-dimethylhex-2-enoic acid

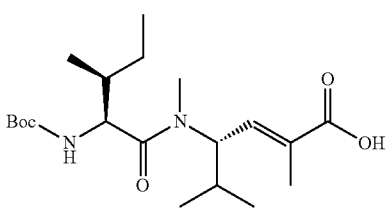 [SMILES: CCOC(=O)/C(C)=C/[C@H](C(C)C)N(C)C(=O)[C@@H](NC(=O)OC(C)(C)C)[C@@H](C)CC]

The title compound was generated from Boc-ICD-OEt using General Procedure 11. $^1$H NMR (400 MHz, Chloroform-d) δ 6.79 (dd, J=9.3, 1.7 Hz, 1H), 5.28 (d, J=9.7 Hz, 1H), 5.11 (dd, J=10.6, 9.2 Hz, 1H), 4.46-4.34 (m, 1H), 3.01 (s, 3H), 1.94 (s, J=1.5 Hz, 4H), 1.77-1.54 (m, 2H), 1.44 (s, 9H), 1.14 (dt, J=15.8, 8.0 Hz, 1H), 0.97-0.81 (m, 12H).

Compound L-3: (S,E)-4-((2S,3S)—N,3-dimethyl-2-((R)-1-methylpiperidine-2-carboxamido)pentanamido)-2,5-dimethylhex-2-enoic acid

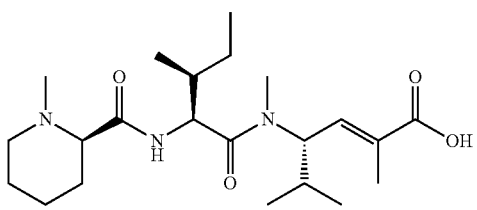 [SMILES: CC[C@H](C)[C@H](NC(=O)[C@H]1CCCCN1C)C(=O)N(C)[C@H](/C=C(\C)C(=O)O)C(C)C]

The title compound was synthesized from Compound L-1 according to General Procedure 10 and reacting the liberated amine with D-(N-methyl)-pipecolic acid using General Procedure 6. Finally, the C-terminal carboxylate was liberated using General Procedure 11 prior to purification by preparative scale HPLC. $^1$H NMR (400 MHz, Methanol-$d_4$) δ 6.77 (dd, J=9.5, 1.4 Hz, 1H), 5.04 (t, J=10.1 Hz, 1H), 4.65-4.56 (m, 1H), 3.79-3.69 (m, 1H), 3.54-3.45 (m, 1H), 3.12 (s, 3H), 3.10-3.06 (m, 1H), 2.76 (s, 3H), 2.21-2.10 (m, 1H), 2.08-2.00 (m, 1H), 2.01-1.92 (m, 2H), 1.90 (d, J=1.5 Hz, 3H), 1.88-1.72 (m, 3H), 1.69-1.52 (m, 2H), 1.31-1.16 (m, 1H), 0.98-0.86 (m, 12H). $C_{22}H_{39}N_3O_4$ calcd. m/z=409.29. found [M+H]$^+$=410.91.

Compound L-4: (S,E)-4-((2S,3S)-2-Amino-N,3-dimethylpentanamido)-2,5-dimethyl-N-(4-(2,2,2-trifluoroacetamido)phenylsulfonyl) hex-2-enamide

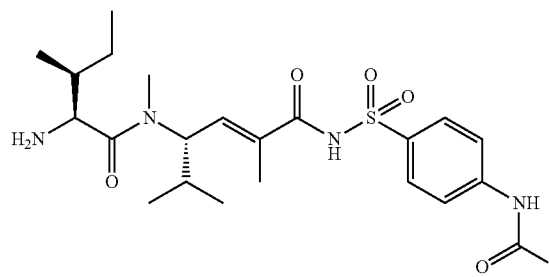

The title compound was prepared from Compound L-2 according to General Procedure 11, followed by N-acyl sulfonamide generation with 2,2,2-trifluoro-N-(4-sulfamoylphenyl)acetamide according to General Procedure 2, followed by General Procedure 10. $^1$H NMR (400 MHz, Chloroform-d) δ 8.00-7.85 (m, 2H), 7.76 (d, J=8.8 Hz, 2H), 6.39 (dd, J=9.2, 1.8 Hz, 1H), 4.45-4.30 (m, 1H), 4.14 (d, J=4.1 Hz, 1H), 2.82 (s, 3H), 2.08-1.91 (m, 1H), 1.67 (s, J=1.5 Hz, 3H), 1.41-1.35 (m, J=13.3, 7.6, 3.2 Hz, 1H), 1.10-0.88 (m, 4H), 0.77 (ddd, J=17.2, 9.0, 5.4 Hz, 9H).

Compound L-5: (R)—N-((2S,3S)-1-(((S,E)-2,5-Dimethyl-6-oxo-6-(4-(2,2,2-trifluoroacetamido)phenylsulfonamido) hex-4-en-3-yl)(methyl)amino)-3-methyl-1-oxopentan-2-yl)-1-methylpiperidine-2-carboxamide

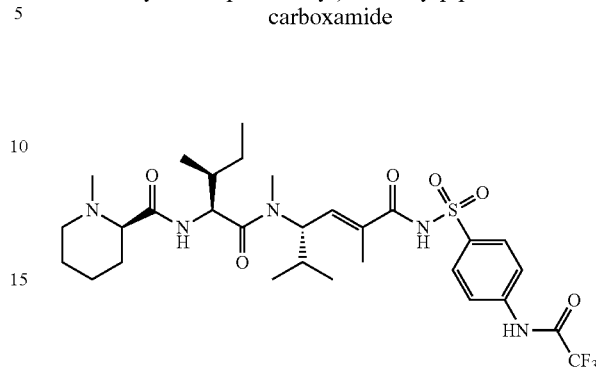

The title compound was prepared from Compound L-4 and N-methyl-D-pipecolic acid according to General Procedure 6. $^1$H NMR (400 MHz, Methanol-d4) δ 7.97 (d, 2H), 7.77 (d, 2H), 7.67 (d, J=8.6 Hz, 0H), 6.60 (d, J=9.2 Hz, 1H), 4.96 (t, J=9.9 Hz, 1H), 4.61 (d, J=8.8 Hz, 1H), 3.75 (hept, J=6.6 Hz, 1H), 3.19-3.10 (m, 1H), 3.06 (s, 3H), 2.45 (s, 2H), 2.39 (s, 3H), 2.01-1.88 (m, 3H), 1.84 (d, J=1.4 Hz, 3H), 1.78-1.54 (m, 5H), 1.25-1.13 (m, 1H), 0.92 (s, 1H), 0.91-0.86 (m, 8H), 0.83 (d, J=6.6 Hz, 3H). $C_{30}H_{44}F_3N_5O_6S$ calcd. m/z=659.30. found [M+H]+=660.88.

Compound L-6: (R)—N-((2S,3S)-1-(((S,E)-6-(4-Aminophenylsulfonamido)-2,5-dimethyl-6-oxohex-4-en-3-yl)(methyl)amino)-3-methyl-1-oxopentan-2-yl)-1-methylpiperidine-2-carboxamide

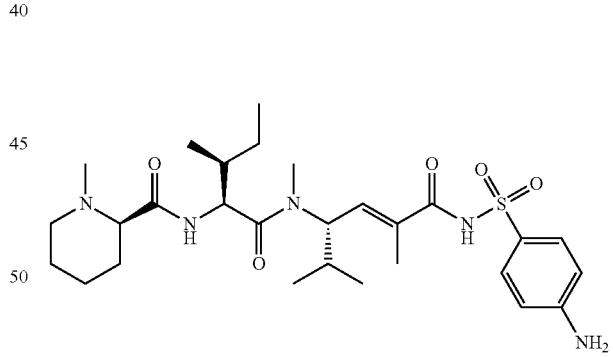

The title compound was prepared from Compound L-5 according to General Procedure 5. $^1$H NMR (400 MHz, Methanol-$d_4$) δ 7.72 (d, 2H), 6.69 (d, 2H), 6.42 (dd, J=9.2, 1.7 Hz, 1H), 4.61-4.55 (m, 1H), 3.72 (dd, J=12.2, 3.2 Hz, 1H), 3.52-3.44 (m, 1H), 3.37 (s, 3H), 3.12 (s, 3H), 3.09-3.03 (m, 1H), 2.71 (s, 3H), 2.20-1.92 (m, 3H), 1.84 (d, J=1.4 Hz, 3H), 1.80-1.72 (m, 2H), 1.67-1.53 (m, 2H), 1.29-1.16 (m, 1H), 0.96-0.85 (m, 12H). $C_{28}H_{45}N_5O_5S$ calcd. m/z=563.31. found [M+H]$^+$=564.93.

Compound L: (R)—N-((2S,3S)-1-(((S,E)-6-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3-methyl-1-oxopentan-2-yl)-1-methylpiperidine-2-carboxamide

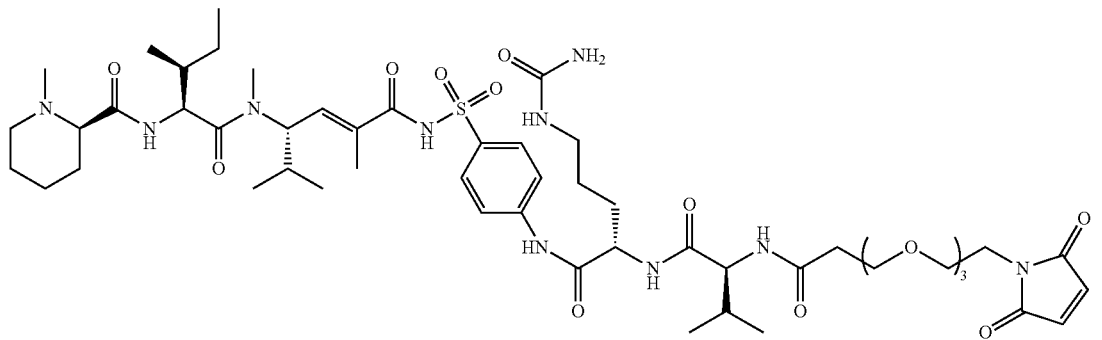

The title compound was prepared from Compound L-6 and MT-Val-Cit-OH according to General Procedure 7. $^1$H NMR (400 MHz, Methanol-d4) δ 8.00 (d, 2H), 7.88 (d, 2H), 6.83 (s, 2H), 6.46 (dd, J=9.1, 1.6 Hz, 1H), 4.57 (d, J=8.3 Hz, 1H), 4.55-4.52 (m, 1H), 4.22 (d, J=6.9 Hz, 1H), 3.80-3.73 (m, 3H), 3.73-3.66 (m, 2H), 3.66-3.60 (m, 2H), 3.58 (d, J=2.2 Hz, 8H), 3.52-3.43 (m, 1H), 3.26-3.19 (m, 1H), 3.17-3.13 (m, 2H), 3.12 (s, 4H), 2.71 (s, 3H), 2.61-2.55 (m, 2H), 2.21-2.01 (m, 3H), 2.00-1.88 (m, 3H), 1.83 (d, J=1.4 Hz, 3H), 1.81-1.71 (m, 4H), 1.68-1.52 (m, 4H), 1.29-1.14 (m, 1H), 1.01 (t, J=6.8 Hz, 6H), 0.94-0.86 (m, 12H).

$C_{52}H_{82}N_{10}O_{14}S$ calcd. m/z=1102.57. found [M+H]$^+$=1104.22.

Example 14

Compound M: (R)—N—((S)-1-(((S,E)-6-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3,3-dimethyl-1-oxobutan-2-yl)-1-methylpiperidine-2-carboxamide

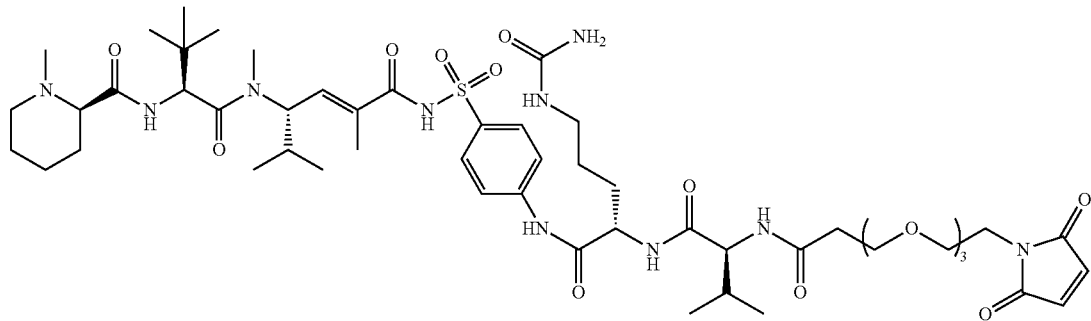

187

Compound M-1: (S,E)-2,5-Dimethyl-4-((S)—N,3,3-trimethyl-2-((R)-1-methylpiperidine-2-carboxamido)butanamido)hex-2-enoic acid

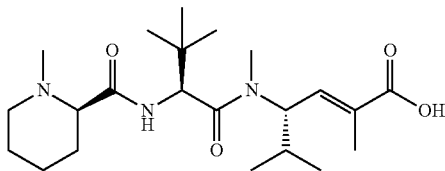 [SMILES: C/C(=C\[C@H](C(C)C)N(C)C(=O)[C@@H](NC(=O)[C@H]1CCCCN1C)C(C)(C)C)C(=O)O]

The title compound was prepared from (S,E)-ethyl 4-((S)-2-amino-N,3,3-trimethylbutanamido)-2,5-dimethylhex-2-enoate (synthesized according to U.S. Pat. No. 7,579,323 B1) and D-N-methyl-pipecolic acid according to General Procedures 6 and 11. $^1$H NMR (400 MHz, Methanol-d4) δ 6.60 (dd, J=9.4, 1.7 Hz, 1H), 5.04 (t, J=10.0 Hz, 1H), 4.77 (s, 1H), 4.62 (s, 1H), 3.30-3.23 (m, 1H), 3.10 (s, 3H), 2.68 (t, J=12.2 Hz, 1H), 2.52 (s, 3H), 2.04 (s, 1H), 2.02-1.93 (m, 2H), 1.90 (d, J=1.4 Hz, 3H), 1.88-1.79 (m, 1H), 1.77-1.62 (m, 2H), 1.56-1.43 (m, 1H), 1.04 (s, 9H), 0.92 (d, J=6.6 Hz, 3H), 0.85 (d, J=6.6 Hz, 3H). $C_{22}H_{39}N_3O_4$ calcd. m/z=409.29. found [M+H]$^+$=410.92.

Compound M-2: (R)—N—((S)-1-(((S,E)-2,5-Dimethyl-6-oxo-6-(4-(2,2,2-trifluoroacetamido)phenylsulfonamido) hex-4-en-3-yl)(methyl)amino)-3,3-dimethyl-1-oxobutan-2-yl)-1-methylpiperidine-2-carboxamide

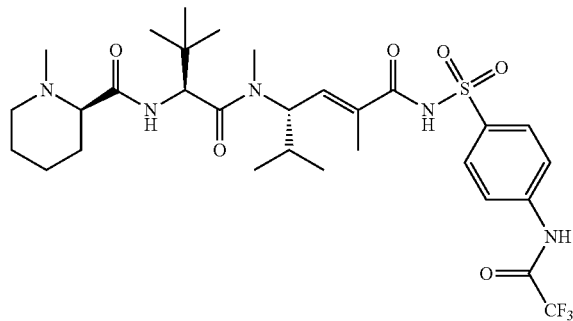 [SMILES: C/C(=C\[C@H](C(C)C)N(C)C(=O)[C@@H](NC(=O)[C@H]1CCCCN1C)C(C)(C)C)C(=O)NS(=O)(=O)c1ccc(NC(=O)C(F)(F)F)cc1]

188

The title compound was prepared from Compound M-1 and 2,2,2-trifluoro-N-(4-sulfamoylphenyl)acetamide using General Procedure 3. $^1$H NMR (400 MHz, Methanol-d4) δ 8.08 (d, J=8.8 Hz, 2H), 7.92 (d, J=8.9 Hz, 2H), 6.47 (d, J=9.0 Hz, 1H), 5.01-4.92 (m, 1H), 4.70 (s, 1H), 3.82 (d, J=12.3 Hz, 1H), 3.53-3.43 (m, 1H), 3.13 (s, 3H), 2.72 (s, 3H), 2.22-1.90 (m, 4H), 1.85 (d, J=1.4 Hz, 5H), 1.60 (m, 1H), 1.40-1.22 (m, 4H), 1.03 (s, 9H), 0.89 (dd, J=17.1, 6.5 Hz, 6H). $C_{30}H_{44}F_3N_5O_6S$ calcd. m/z=659.76. found [M+H]$^+$=660.95.

Compound M-3: (R)—N—((S)-1-(((S,E)-6-(4-Aminophenylsulfonamido)-2,5-dimethyl-6-oxohex-4-en-3-yl)(methyl)amino)-3,3-dimethyl-1-oxobutan-2-yl)-1-methylpiperidine-2-carboxamide

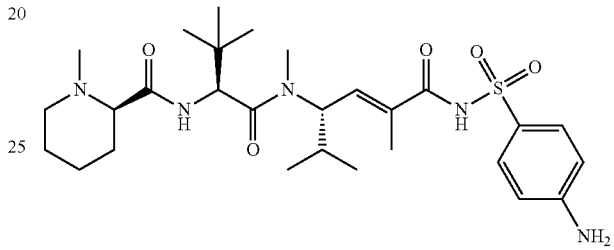

The title compound was prepared from Compound M-2 according to General Procedure 5. $^1$H NMR (400 MHz, Methanol-d4) δ 7.76-7.66 (m, 2H), 6.74-6.64 (m, 2H), 6.42 (dd, J=8.9, 1.7 Hz, 1H), 4.94 (m, 1H), 4.70 (s, 1H), 3.82 (dd, J=12.2, 3.1 Hz, 1H), 3.54-3.42 (m, 1H), 3.13 (s, 4H), 2.70 (s, 3H), 2.16 (d, J=14.6 Hz, 1H), 2.11-2.01 (m, 1H), 1.96 (d, J=12.9 Hz, 2H), 1.89-1.51 (m, 6H), 1.03 (s, 9H), 0.89 (dd, J=16.3, 6.5 Hz, 6H). $C_{28}H_{45}N_5O_5S$ calcd. m/z=563.31. found [M+H]$^+$=564.93.

Compound M: (R)—N—((S)-1-(((S,E)-6-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3,3-dimethyl-1-oxobutan-2-yl)-1-methylpiperidine-2-carboxamide

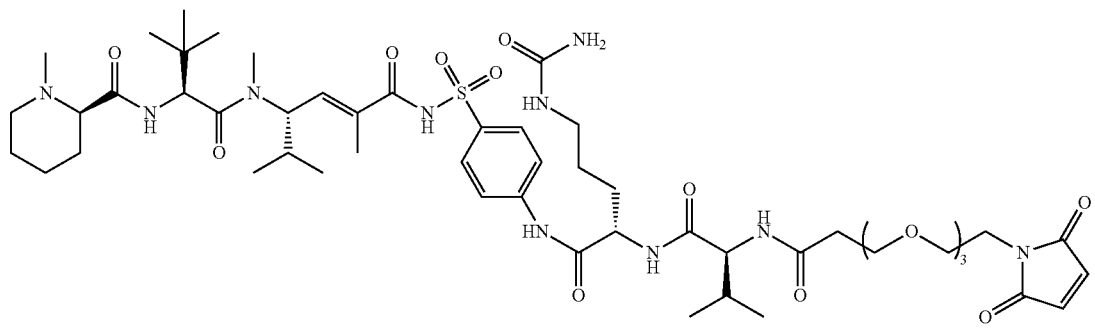

The title compound was prepared from Compound M-3 and MT-Val-Cit-OH according to General Procedure 7. $^1$H NMR (400 MHz, Methanol-d4) δ 8.00 (d, J=8.9 Hz, 2H), 7.88 (d, J=8.7 Hz, 2H), 6.83 (s, 2H), 6.46 (d, J=9.1 Hz, 1H), 4.96-4.91 (m, 1H), 4.72-4.68 (m, 1H), 4.58-4.51 (m, 1H), 4.22 (t, J=7.2 Hz, 1H), 3.83-3.73 (m, 3H), 3.72-3.67 (m, 2H), 3.65-3.61 (m, 2H), 3.61-3.55 (m, 8H), 3.52-3.46 (m, 1H), 3.27-3.19 (m, 1H), 3.13 (s, 3H), 3.09-3.03 (m, 1H), 2.69 (s, 3H), 2.58 (t, J=6.0 Hz, 2H), 2.19-2.01 (m, 4H), 2.00-1.90 (m, 3H), 1.84 (d, J=1.4 Hz, 3H), 1.83-1.72 (m, 3H), 1.61 (d, J=9.0 Hz, 3H), 1.03 (s, 11H), 1.00 (d, J=6.8 Hz, 4H), 0.91 (d, J=6.5 Hz, 3H), 0.87 (d, J=6.6 Hz, 3H). $C_{52}H_{82}N_{10}O_{14}S$ calcd. m/z=1102.57. found [M+H]$^+$=1104.30.

Example 15

Compound N: (R)—N—((S)-1-(((S,E)-6-(4-((14S, 17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido) phenylsulfonamido)-2,5-dimethyl-6-oxohex-4-en-3-yl)(methyl)amino)-3,3-dimethyl-1-oxobutan-2-yl)-1-isopropylpiperidine-2-carboxamide

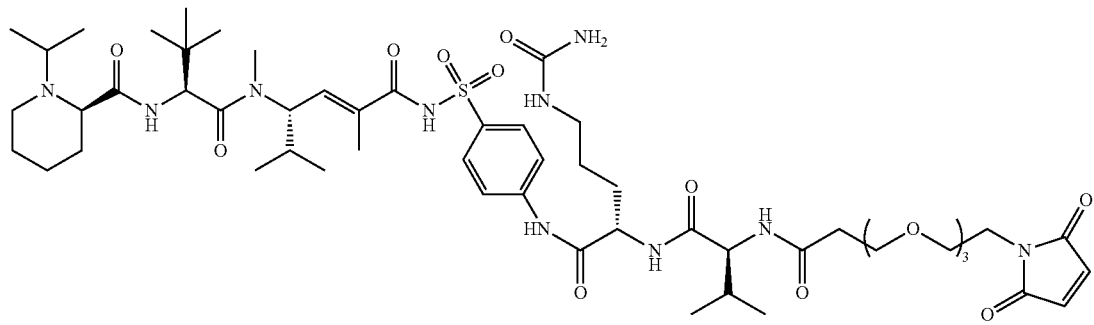

Compound N-1: (R)—N—((S)-1-(((S,E)-2,5-dimethyl-6-oxo-6-(4-(2,2,2-trifluoroacetamido)phenylsulfonamido)hex-4-en-3-yl)(methyl)amino)-3,3-dimethyl-1-oxobutan-2-yl)-1-isopropylpiperidine-2-carboxamide

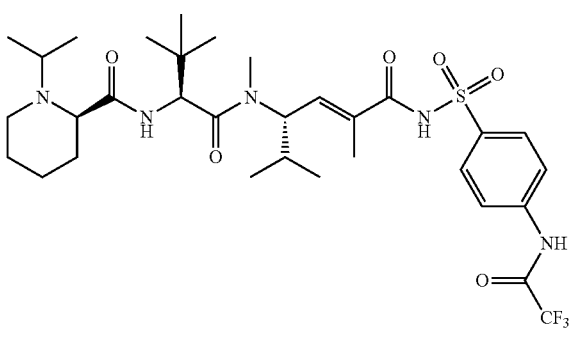 [SMILES: C/C(=C\[C@H](C(C)C)N(C)C(=O)[C@@H](NC(=O)[C@H]1CCCCN1C(C)C)C(C)(C)C)C(=O)NS(=O)(=O)c1ccc(NC(=O)C(F)(F)F)cc1]

The title compound was prepared from (S,E)-4-((S)-2-((R)-1-isopropylpiperidine-2-carboxamido)-N,3,3-trimethylbutanamido)-2,5-dimethylhex-2-enoic acid (prepared according to US 2012/0309938 A1) and 2,2,2-trifluoro-N-(4-sulfamoylphenyl)acetamide using General Procedure 3. $^1$H NMR (400 MHz, Methanol-d$_4$) δ 8.00 (d, J=8.8 Hz, 2H), 7.83 (d, J=8.8 Hz, 2H), 6.56 (d, J=9.1 Hz, 1H), 4.69 (s, 1H), 4.12 (dd, J=11.6, 3.3 Hz, 1H), 3.95 (hept, J=6.2 Hz, 1H), 3.54-3.41 (m, 2H), 3.37 (s, 3H), 3.08 (s, 3H), 3.04-2.89 (m, 1H), 2.13 (dd, J=17.2, 6.4 Hz, 1H), 2.00-1.88 (m, 4H), 1.84 (d, J=1.5 Hz, 4H), 1.71-1.52 (m, 1H), 1.29 (dd, J=28.0, 6.7 Hz, 8H), 1.17 (d, J=6.1 Hz, 6H), 1.01 (s, 10H), 0.86 (dd, J=28.2, 6.5 Hz, 7H). $C_{32}H_{48}F_3N_5O_6S$ calcd. m/z=687.33. found [M+H]$^+$=688.9.

Compound N-2: (R)—N—((S)-1-(((S,E)-6-(4-aminophenylsulfonamido)-2,5-dimethyl-6-oxohex-4-en-3-yl)(methyl)amino)-3,3-dimethyl-1-oxobutan-2-yl)-1-isopropylpiperidine-2-carboxamide

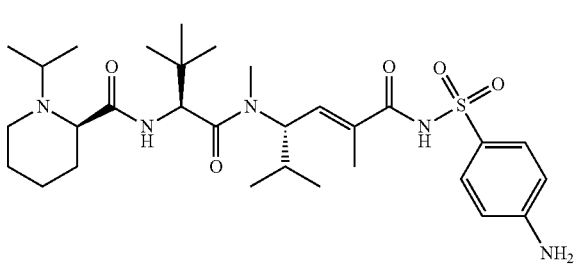 [SMILES: C/C(=C\[C@H](C(C)C)N(C)C(=O)[C@@H](NC(=O)[C@H]1CCCCN1C(C)C)C(C)(C)C)C(=O)NS(=O)(=O)c1ccc(N)cc1]

The title compound was prepared from Compound N-1 according to General Procedure 5. $^1$H NMR (400 MHz, Methanol-$d_4$) δ 7.75-7.62 (m, 2H), 6.74-6.62 (m, 2H), 6.59-6.35 (m, 1H), 4.70 (s, 1H), 4.09 (dd, J=11.7, 3.3 Hz, 1H), 3.52-3.38 (m, 2H), 3.10 (s, 3H), 3.02-2.87 (m, 1H), 2.12 (d, J=11.9 Hz, 1H), 2.06-1.73 (m, 11H), 1.70-1.50 (m, 1H), 1.28 (dd, J=28.8, 6.7 Hz, 6H), 1.02 (s, 9H), 0.87 (dd, J=27.7, 6.5 Hz, 6H). $C_{30}H_{49}N_5O_5S$ calcd. m/z=591.35. found [M+H]$^+$=593.0.

Compound N-3: tert-butyl (S)-1-((S)-1-(4-(N—((S,E)-4-((S)-2-((R)-1-isopropylpiperidine-2-carboxamido)-N,3,3-trimethylbutanamido)-2,5-dimethylhex-2-enoyl)sulfamoyl)phenylamino)-1-oxo-5-ureidopentan-2-ylamino)-3-methyl-1-oxobutan-2-ylcarbamate

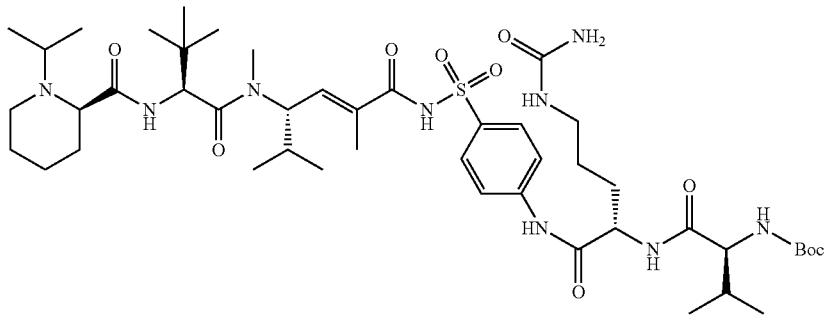 [SMILES: C/C(=C\[C@H](C(C)C)N(C)C(=O)[C@@H](NC(=O)[C@H]1CCCCN1C(C)C)C(C)(C)C)C(=O)NS(=O)(=O)c1ccc(NC(=O)[C@H](CCCNC(N)=O)NC(=O)[C@@H](NC(=O)OC(C)(C)C)C(C)C)cc1]

The title compound was synthesized from Compound N-2 and Boc-Val-Cit-OH according to General Procedure 7. $C_{46}H_{77}N_9O_{10}S$ calcd. m/z=947.55. found [M+H]$^+$=949.2.

Compound N: (R)—N—((S)-1-(((S,E)-6-(4-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonamido)-2,5-dimethyl-6-oxohex-4-en-3-yl)(methyl)amino)-3,3-dimethyl-1-oxobutan-2-yl)-1-isopropylpiperidine-2-carboxamide

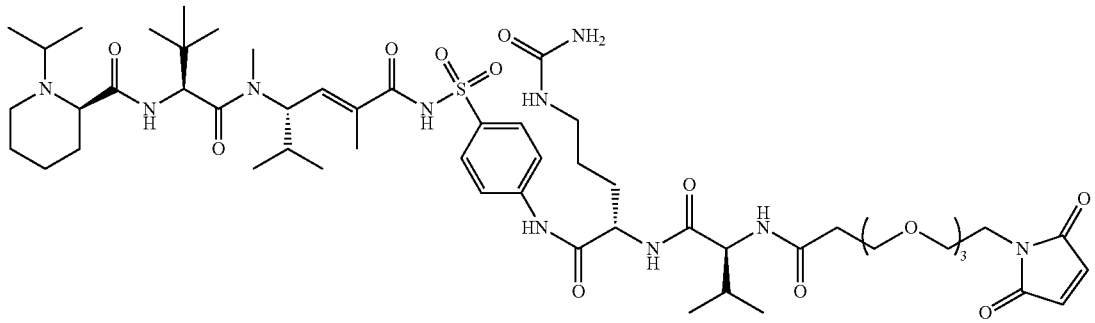

The title compound was prepared from Compound N-3 and MT-NHS according to General Procedure 10 and 9 and purified by preparative HPLC-MS.

$C_{54}H_{86}N_{10}O_{14}S$ calcd. m/z=1130.60. found [M+H]$^+$=1132.5.

Example 16

Compound O: (R)—N-(4-(N-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)phenyl)-2-((S)-1-(2>5-dioxo-2,5-dihydro-1H-pyrrol-1-yl)-14-isopropyl-12-oxo-3,6,9-trioxa-13-azapentadecanamido)-5-ureidopentanamide

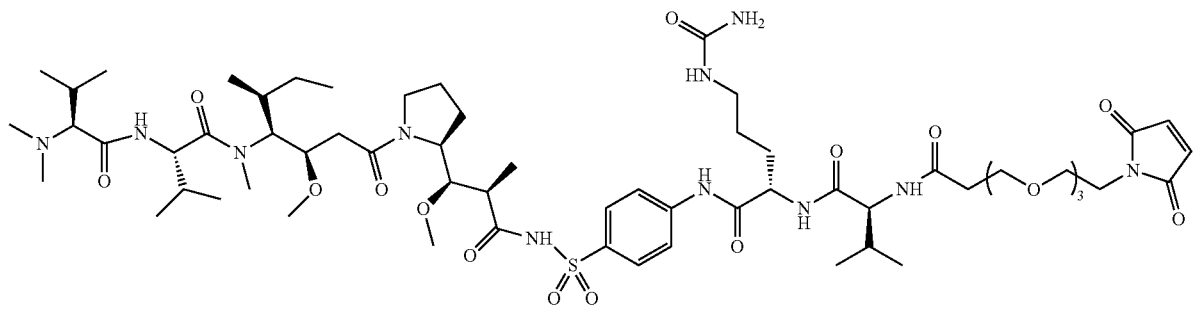

Compound O-1: tert-Butyl (S)-1-(((3R,4S,5R)-3-Methoxy-1-((S)-2-((1R,2R)-1-methoxy-2-methyl-3-oxo-3-(4-(2,2,2-trifluoroacetamido)phenylsulfonamido)propyl)pyrrolidin-1-yl)-5-methyl-1-oxoheptan-4-yl)(methyl)amino)-3-methyl-1-oxobutan-2-ylcarbamate

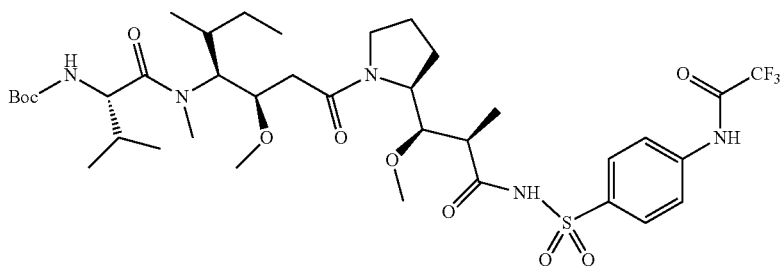 [SMILES: CCC(C)[C@@H]([C@@H](CC(=O)N1CCC[C@H]1[C@H](OC)[C@@H](C)C(=O)NS(=O)(=O)c1ccc(NC(=O)C(F)(F)F)cc1)OC)N(C)C(=O)[C@@H](NC(=O)OC(C)(C)C)C(C)C]

The title compound was synthesized from commercially available Boc-Val-Dip-Dap-OH (0.08 g, 0.14 mmol) and 2,2,2-trifluoro-N-(4-sulfamoylphenyl)acetamide (0.045 g, 1.2 equiv) using dicyclohexylcarbodiimide (0.0347 g, 1.2 equiv), N,N-dimethyl-4-aminopyridine (0.0205 g, 1.2 equiv) in CH$_2$Cl$_2$/DMF(2 mL, 10:1, v/v) according to General Procedure 3. The title compound was isolated by silica gel chromatography using 10-45% EtOAc (containing 2% AcOH) in Hexanes over 10 column volumes. (0.112 g, 98%). $C_{37}H_{58}F_3N_5O_{10}S$ calcd. m/z=821.39. found [M+H]$^+$=823.04.

Compound O-2: (S)-2-((S)-2-(Dimethylamino)-3-methylbutanamido)-N-((3R,4S,5R)-3-methoxy-1-((S)-2-((1R,2R)-1-methoxy-2-methyl-3-oxo-3-(4-(2,2,2-trifluoroacetamido)phenylsulfonamido)propyl)pyrrolidin-1-yl)-5-methyl-1-oxoheptan-4-yl)-N,3-dimethylbutanamide

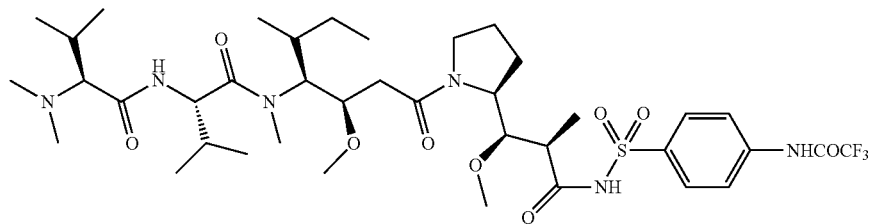

The title compound was prepared by treating Compound O-1 (0.111 g, 0.133 mmol) with trifluoroacetic acid, according to General Procedure 10, followed by activation of N,N-dimethyl valine (0.029 g, 0.20 mmol, 1.5 equiv) with HATU (0.076 g, 1.5 equiv) and N,N-di-isopropylethylamine (0.093 mL, 4 equiv) in $CH_2Cl_2$ and introduction of the TFA salt generated above according to General Procedure 6. The crude reaction was concentrated to dryness, dissolved in a minimal amount of $CH_2Cl_2$ and purified by silica gel chromatography (3-20% $MeOH/CH_2Cl_2$ over 10 column volumes, 25 g column) to give the title compound as a colourless oil (0.108 g, 97%) $C_{39}H_{63}F_3N_6O_9S$ calc'd m/z=848.43. found $[M+H]^+$ 850.11.

Compound O-3: (S)—N-((3R,4S,5R)-1-((S)-2-((1R,2R)-3-(4-Aminophenylsulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide

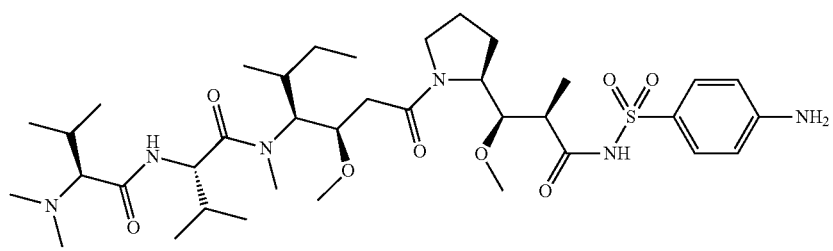 [SMILES: CCC(C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)[C@H](C(C)C)N(C)C)C(C)C]

The title compound was prepared according to General Procedure 5 from Compound O-2 (0.114 g, 0.13 mmol) with lithium hydroxide (0.671 mL, 1M, 5 equiv) in dioxanes (5.0 mL) at room temperature for 16 h. The solution was adjusted to pH 7 with saturated $NH_4Cl$, concentrated under reduced pressure to yield a milky suspension and extracted repeatedly (3×20 mL, EtOAc). The organic phases were pooled, dried over $MgSO_4$, filtered, concentrated and used without further purification (0.097 g, 96%). $C_{37}H_{64}N_6O_8S$ calc'd m/z=752.45. found $[M+H]^+$ 754.16.

Compound O: (R)—N-(4-(N-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide

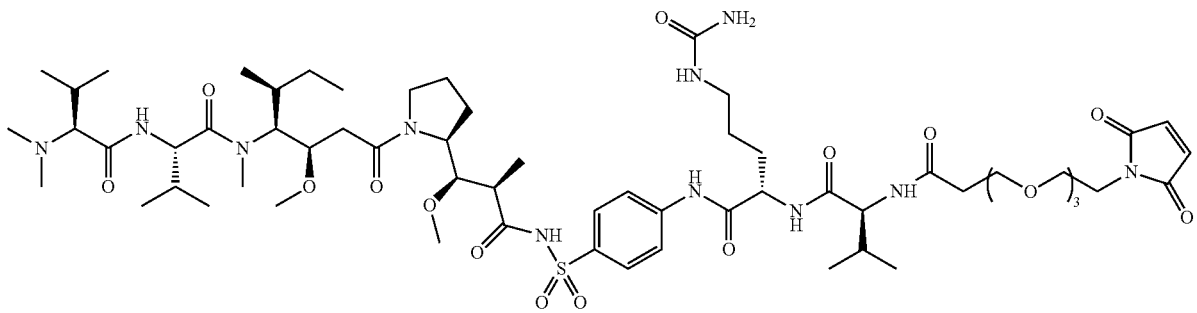

The title compound was synthesized using General Procedure 7 from MT-VAL-CIT-OH (0.0394 g, 0.071 mmol, 2 equiv) and Compound O-3 (0.030 g, 0.035 mmol) with EDCI (0.0115 g, 2.1 equiv), hydroxybenzotriazole (0.0101 g, 2.1 equiv) and copper (II) chloride (0.010 g, 2.1 equiv) in a mixture of dichloromethane/DMF (7:1 v/v). Upon reaction completion, the reaction was concentrated and treated with a methanolic solution of TMEDA before being concentrated in vacuo. The blue residue was dissolved in methanol and purified by preparative scale HPLC-MS to give the title compound (4.65 mg) as a fluffy white hygroscopic solid after lyophilization of the product containing fractions. $C_{61}H_{101}N_{11}O_{17}S$ calc'd m/z=1291.71 found $[M+H]^+$ 1292.89.

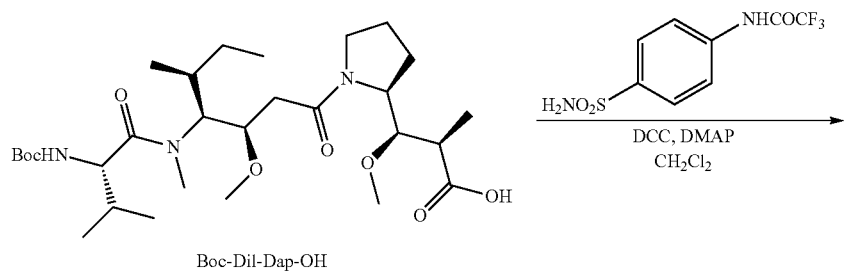

Boc-Dil-Dap-OH

DCC, DMAP
CH$_2$Cl$_2$

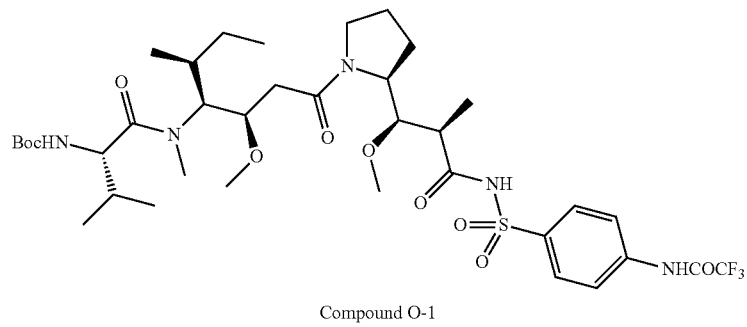

Compound O-1

1. TFA, CH$_2$Cl$_2$
2. HATU, DIPEA
   Me$_2$-Val-OH
   DCM

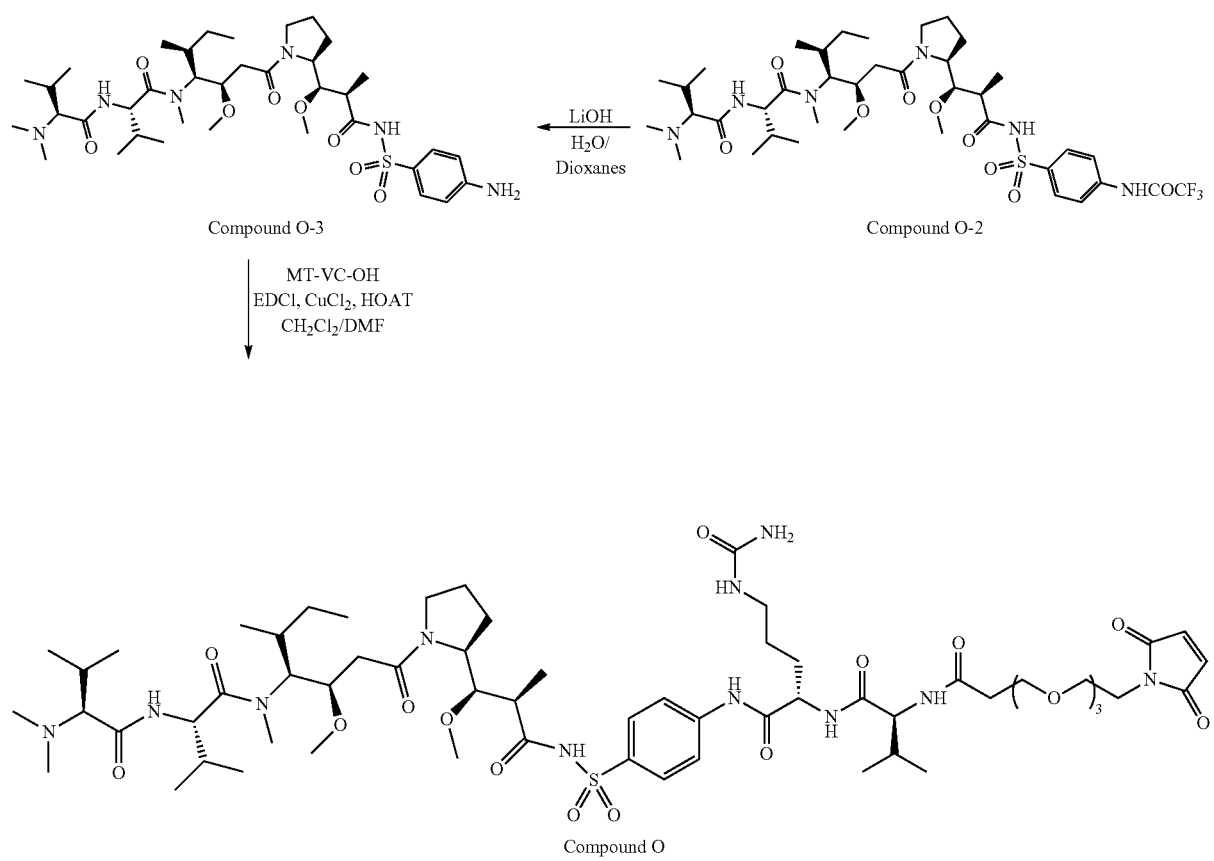
Example 17
Compound P: (S)—N-(4-((N-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)methyl) Phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide
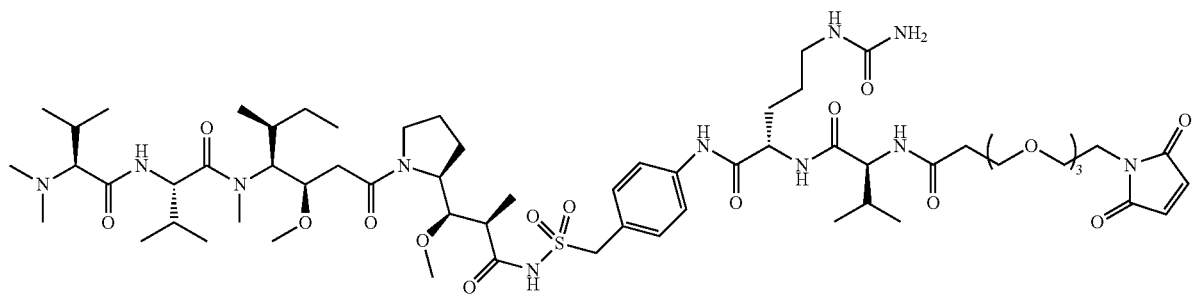

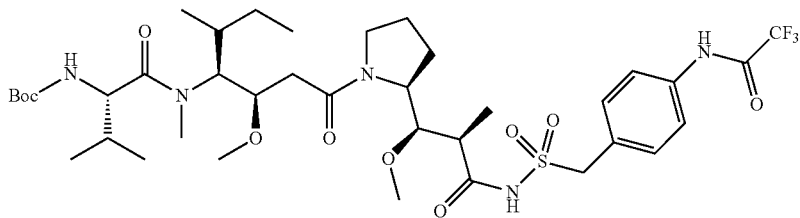 [SMILES: CCC(C)[C@@H]([C@@H](CC(=O)N1CCC[C@H]1[C@H](OC)[C@@H](C)C(=O)NS(=O)(=O)Cc1ccc(NC(=O)C(F)(F)F)cc1)OC)N(C)C(=O)[C@@H](NC(=O)OC(C)(C)C)C(C)C]

The title compound was prepared from commercially available Boc-Val-Dil-Dap-OH and 2,2,2-trifluoro-N-(4-(sulfamoylmethyl)phenyl)acetamide through general procedure 3. $C_{38}H_{60}F_3N_5O_{10}S$ calc'd m/z=835.40. found $[M+H]^+$=836.7.

Compound P-2: (S)-2-((S)-2-(Dimethylamino)-3-methylbutanamido)-N-((3R,4S,5R)-3-methoxy-1-((S)-2-((1R,2R)-1-methoxy-2-methyl-3-oxo-3-((4-(2,2,2-trifluoroacetamido)phenyl)methylsulfonamido)propy)pyrrolidin-1-yl)-5-methyl-1-oxoheptan-4-yl)-N,3-dimethylbutanamide

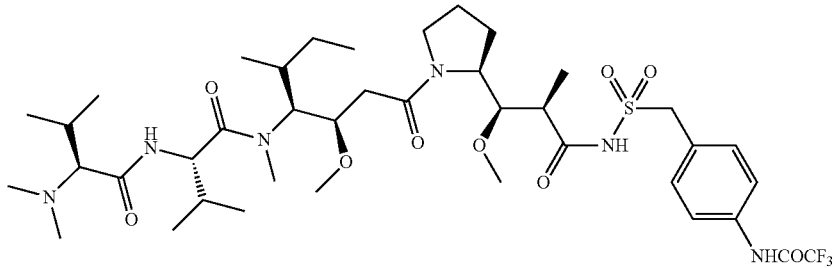

The title compound was prepared from Compound P-1 and N,N-dimethylvaline according to General Procedure 6. $C_{40}H_{65}F_3N_6O_9S$ calc'd m/z=862.45. found $[M+H]^+$=863.2.

Compound P-3: (S)—N-((3R,4S,5R)-1-((S)-2-((1R,2R)-3-((4-Aminophenyl)methylsulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide

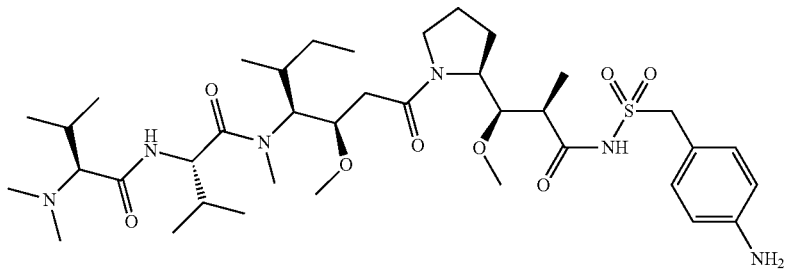 [SMILES: CCC(C)[C@@H]([C@@H](CC(=O)N1CCC[C@H]1[C@H](OC)[C@@H](C)C(=O)NS(=O)(=O)Cc1ccc(N)cc1)OC)N(C)C(=O)[C@@H](NC(=O)[C@H](C(C)C)N(C)C)C(C)C]

The title compound was prepared from Compound P-2 by following General Procedure 5. $C_{38}H_{66}N_6O_8S$ calc'd m/z=766.47. found $[M-C_7H_8O_2S+H]^+$=599.0 (Quinone methide fragmentation and loss of 4-aminobenzylsulfonate).

Compound P: (S)—N-(4-((N-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)methyl)phenyl)-2-((S)-1-(2, 5-dioxo-2, 5-dihydro-1H-pyrrol-1-yl)-14-isopropyl-12-oxo-3,6,9-trioxa-13-azapentadecanamido)-5-ureidopentanamide

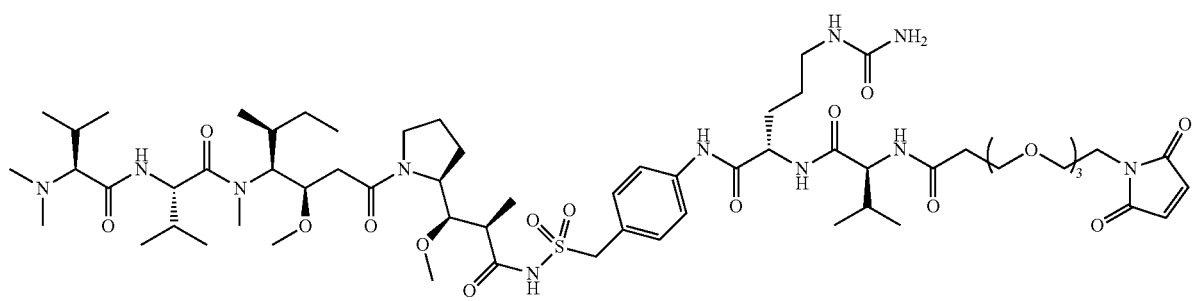

The title compound was synthesized using General Procedure 5 from MT-VAL-CIT-OH and Compound P-3 and purified by preparative HPLC chromatography. $C_{61}H_{101}N_{11}O_{17}S$ calc'd m/z=1305.73. found $[M+H]^+$=1306.9.

Example 18

Compound Q: (S)—N-(4-(N—((S)-2-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-3-phenylpropanoyl)sulfamoyl)phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide Compound Q-1: (S)-2-Amino-3-phenyl-N-(4-(2,2,2-trifluoroacetamido)phenylsulfonyl)propanamide

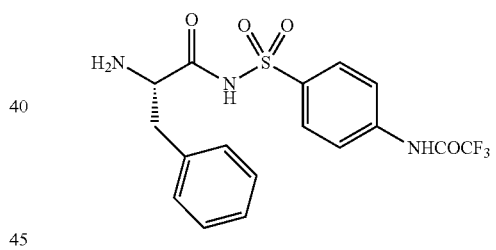

Prepared from Boc-phenylalanine and 2,2,2-trifluoro-N-(4-sulfamoylphenyl)acetamide according to General Proce-

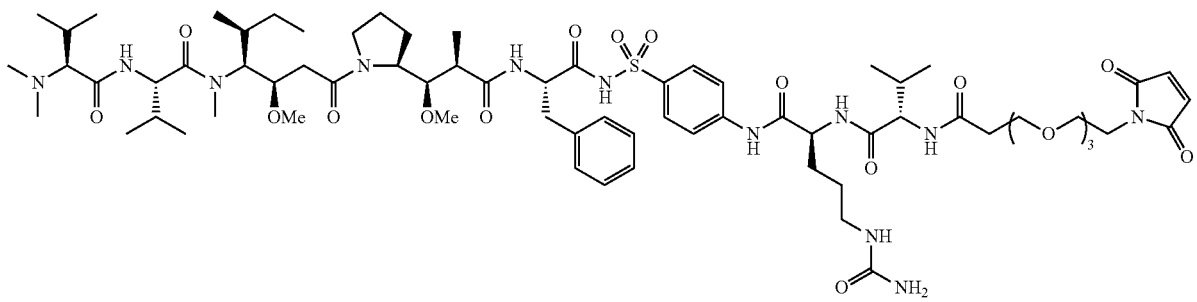

dures 3 and 10. $^1$H NMR (400 MHz, DMSO-d6) δ 11.42 (s, 1H), 7.84 (d, J=8.7 Hz, 2H), 7.73-7.64 (m, 1H), 7.69 (d, J=8.7 Hz, 2H), 7.24-7.14 (m, 3H), 7.13-7.06 (m, 2H), 3.65-3.60 (m, 1H), 3.06 (dd, J=14.2, 5.1 Hz, 1H), 2.91 (dd, J=14.1, 7.1 Hz, 1H). $C_{17}H_{16}F_3N_3O_4S$ calcd. m/z=415.08. found [M+H]$^+$=416.5.

Compound Q-2: tert-Butyl (S)-1-(((3R,4S,5R)-3-Methoxy-1-((S)-2-((1R,2R)-1-methoxy-2-methyl-3-oxo-3-((S)-1-oxo-3-phenyl-1-(4-(2,2,2-trifluoroacet-amido)phenylsulfonamido)propan-2-ylamino)propyl)pyrrolidin-1-yl)-5-methyl-1-oxoheptan-4-yl)(methyl)amino)-3-methyl-1-oxobutan-2-ylcarbamate

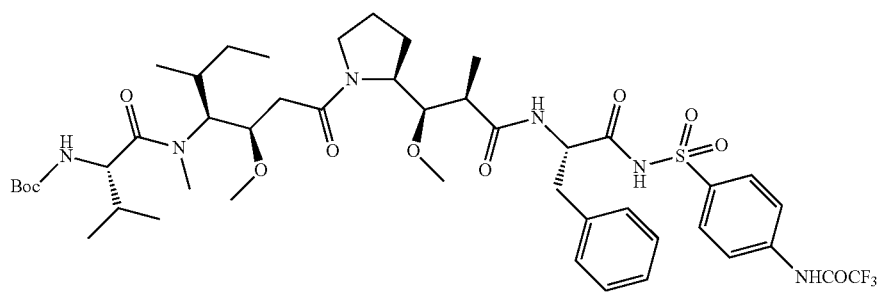

The title compound was synthesized from commercially available Boc-Val-Dip-Dap-OH (0.07 g) and Compound Q-1 using General Procedure 6. $C_{46}H_{67}F_3N_6O_{11}S$ calcd. m/z=968.45. found [M+Na]$^+$=992.1.

Compound Q-3: (S)-2-((S)-2-(Dimethylamino)-3-methylbutanamido)-N-((3R,4S,5R)-3-methoxy-1-((S)-2-((1R,2R)-1-methoxy-2-methyl-3-oxo-3-((S)-1-oxo-3-phenyl-1-(4-(2,2,2-trifluoroacetamido)phenylsulfonamido)propan-2-ylamino)propyl)pyrrolidin-1-yl)-5-methyl-1-oxoheptan-4-yl)-N,3-dimethylbutanamide

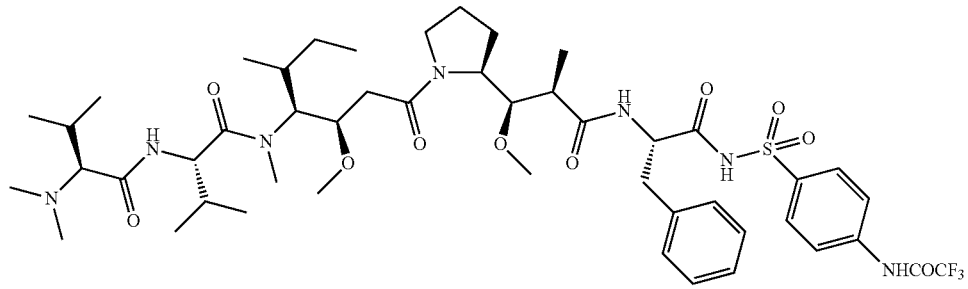

The title compound was prepared from Compound Q-2 (110 mg) and N,N-dimethyl valine using General Procedures 10 and 6. $C_{48}H_{72}F_3N_7O_{10}S$ calc'd m/z=995.50 found [M+H]$^+$ 997.3.

Compound Q-4: (S)—N-((3R,4S,5R)-1-((S)-2-((1R,2R)-3-((S)-1-(4-Aminophenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide

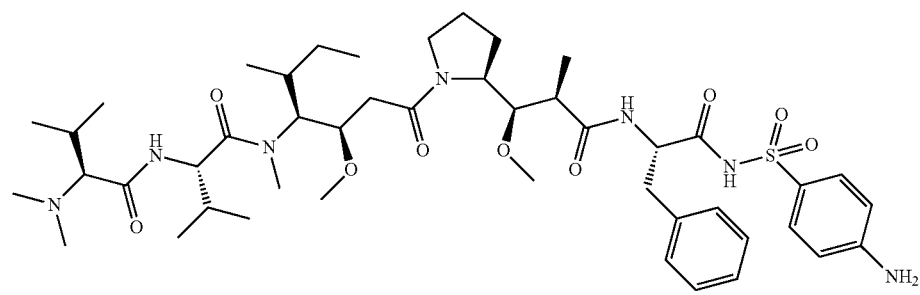 [SMILES: CCC(C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(N)cc1)OC)N(C)C(=O)[C@@H](NC(=O)[C@H](C(C)C)N(C)C)C(C)C]

The title compound was prepared from Compound Q-3 (100 mg) using General Procedure 5. $C_{46}H_{73}N_7O_9S$ calc'd m/z=899.52. found [M+H]$^+$ 901.3.

Compound Q: (S)—N-(4-(N—((S)-2-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-3-phenylpropanoyl)sulfamoyl)phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide

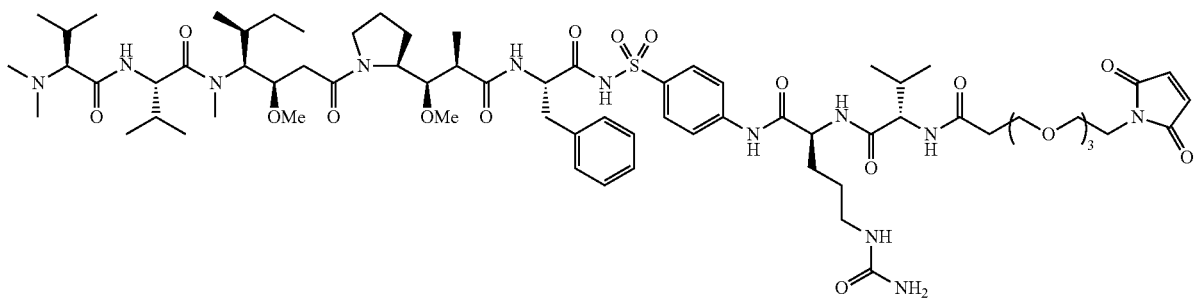

The title compound was prepared from Compound Q-4 (25 mg) and MT-Val-Cit-OH (63 mg) using General Procedure 7. $C_{70}H_{110}N_{12}O_{18}S$ calcd m/z=1438.8 amu. found [M+H]$^+$=1440.2, [(M+2H)/2]$^{2+}$=720.5.

Example 19

Compound R: (S)—N-(4-(N—((S)-2-((2R,3R)-3-((S)-1-((3R,4S,5S)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanamido)-3-phenylpropanoyl)sulfamoyl)methylphenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide

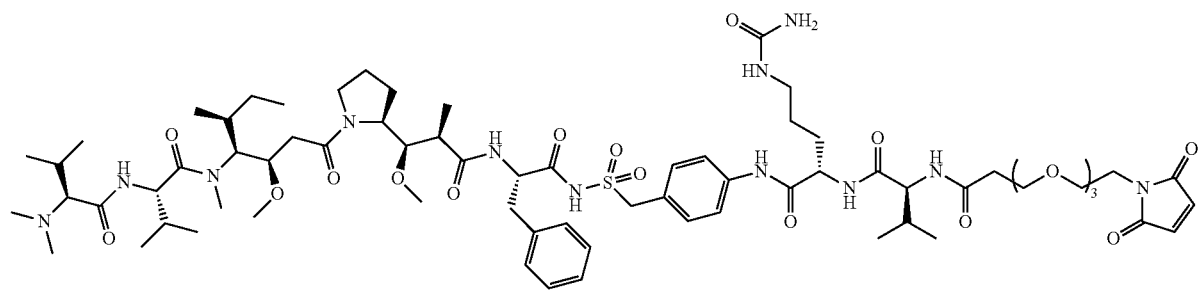

Compound R-1: (S)-2-amino-3-phenyl-N-(4-(2,2,2-trifluoroacetamido)benzylsulfonyl)propanamide

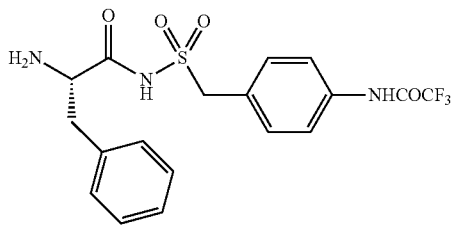

Prepared from Boc-phenylalanine and 2,2,2-trifluoro-N-(4-sulfamoylphenyl)acetamide according to General Procedures 4 and 10 (S)-tert-butyl 1-oxo-3-phenyl-1-(phenylmethylsulfonamido)propan-2-ylcarbamate $^1$H NMR (400 MHz, DMSO-d6) δ 7.76-7.71 (m, 2H), 7.58 (d, J=8.4 Hz, 2H), 7.36-7.21 (m, 8H), 4.34 (d, J=13.1 Hz, 1H), 4.30 (d, J=13.1 Hz, 1H), 3.62 (dd, J=8.2, 4.6 Hz, 1H), 3.21-3.09 (m, 1H), 2.89 (dd, J=14.3, 8.3 Hz, 1H). $C_{18}H_{18}F_3N_3O_4S$ calcd. m/z=429.10. found [M+H]$^+$=430.7.

Compound R-2: tert-Butyl (S)-1-(((3R,4S,5R)-3-Methoxy-1-((S)-2-((1R,2R)-1-methoxy-2-methyl-3-oxo-3-((S)-1-oxo-3-phenyl-1-(4-(2,2,2-trifluoroacetamido)phenylmethylsulfonamido)propan-2-ylamino)propyl)pyrrolidin-1-yl)-5-methyl-1-oxoheptan-4-yl)(methyl)amino)-3-methyl-1-oxobutan-2-ylcarbamate

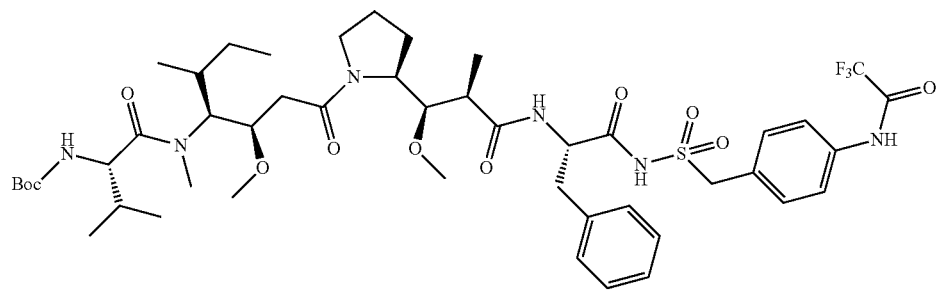 [SMILES: CCC(C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(NC(=O)C(F)(F)F)cc1)OC)N(C)C(=O)[C@@H](NC(=O)OC(C)(C)C)C(C)C]

The title compound was prepared from commercially available Boc-Val-Dil-Dap-OH and Compound R-1 by following general procedure 6. $C_{47}H_{69}F_3N_6O_{11}S$ calc'd m/z=982.47. found [M+Na]⁺=1006.2.

Compound R-3: (S)-2-((S)-2-(Dimethylamino)-3-methylbutanamido)-N-((3R,4S,5R)-3-methoxy-1-((S)-2-((1R,2R)-1-methoxy-2-methyl-3-oxo-3-((S)-1-oxo-3-phenyl-1-(4-(2,2,2-trifluoroacetamido)phenylmethylsulfonamido)propan-2-ylamino)propyl)pyrrolidin-1-yl)-5-methyl-1-oxoheptan-4-yl)-N,3-dimethylbutanamide

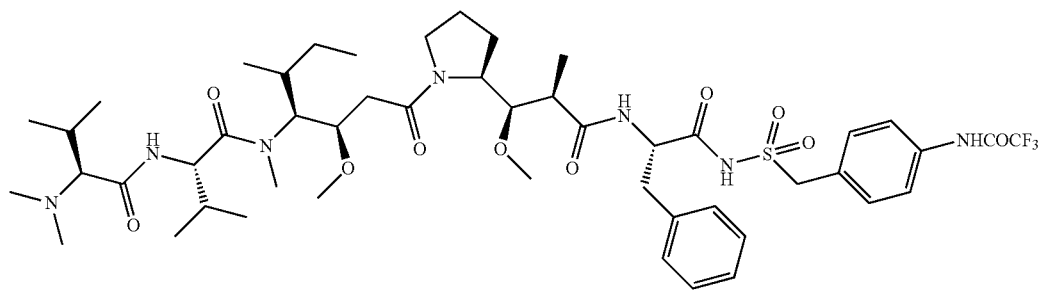

The title compound was prepared from Compound R-2 and N,N-dimethylvaline according to general procedures 10 and 6. $C_{49}H_{74}F_3N_7O_{10}S$ calc'd m/z=1009.52. found [M+H]⁺=1011.0.

Compound R-4: (S)—N-((3R,4S,5R)-1-((S)-2-((1R,2R)-3-((S)-1-(4-Aminophenylmethylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide

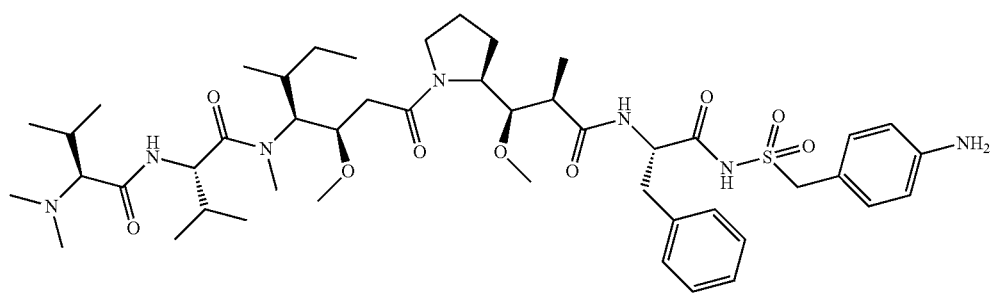 [SMILES: CCC(C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(N)cc1)OC)N(C)C(=O)[C@@H](NC(=O)[C@H](C(C)C)N(C)C)C(C)C]

The compound was prepared from Compound R-3 according to General Procedure 5. $C_{47}H_{75}N_7O_9S$ calc'd m/z=913.53. found [M-$C_7H_8O_2S$+Na]⁺=768.1 (Quinone methide fragmentation and loss of 4-aminobenzylsulfonate).

Compound R: (S)—N-(4-(N—((S)-2-((2R,3R)-3-((S)-1-((3R,4S,5S)-4-((S)-2-((S)-2-(Dimethyl-amino)-3-methylbutanamido)-N,3-dimethylbutana-mido)-3-methoxy-5-methylheptanoyl)pyrrolidin-2-yl)-3-methoxy-2-methylpropanamido)-3-phenylpropanoyl)sulfamoyl)methylphenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide

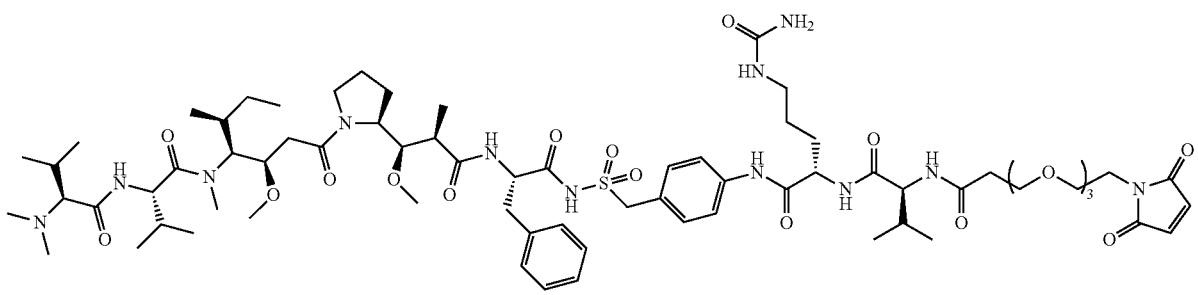

The compound was prepared from Compound R-4 and MT-Val-Cit-OH according to General Procedure 7, followed by purification by preparative HPLC. m/z calcd. for $C_{71}H_{112}N_{12}O_{18}S$=1452.8. found $[M+H^+]^+$=1454.6.

Example 20

Compound S: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diaz-aoctadecanamido)-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide

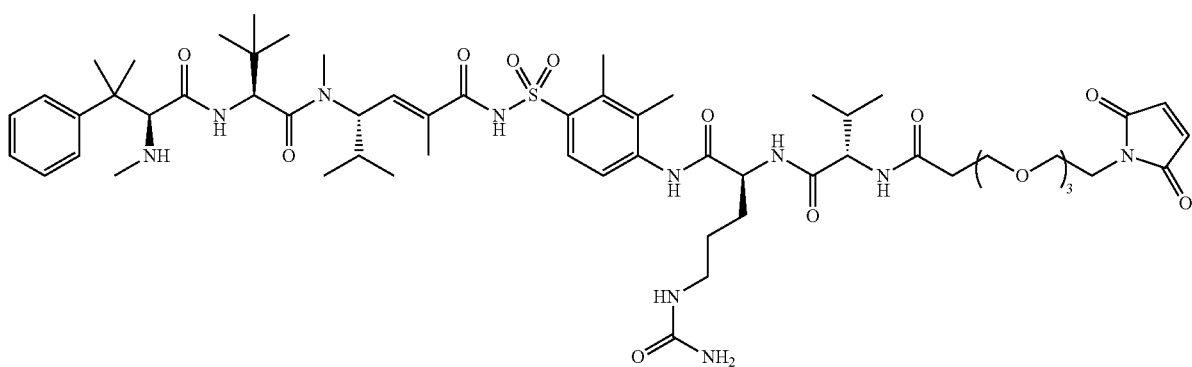

Compound S-1: N-(2,3-dimethyl-4-sulfamoylphenyl)-2,2,2-trifluoroacetamide

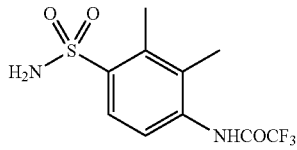

Synthesized from 2,3-dimethylaniline according to general procedure 1.

$^1$H NMR (400 MHz, DMSO-d$_6$) δ 11.25 (s, 1H), 7.79 (d, J=8.5 Hz, 1H), 7.48 (s, 2H), 7.29 (d, J=8.5 Hz, 1H), 2.55 (s, 3H), 2.14 (s, 3H).

Compound S-2: (S,E)-N-(4-amino-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide

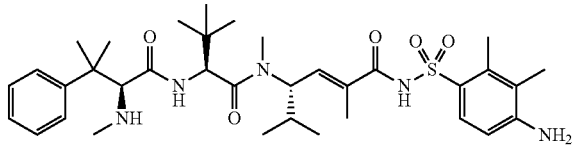 [SMILES: CN[C@H](C(=O)N[C@H](C(=O)N(C)[C@H](/C=C(\C)C(=O)NS(=O)(=O)c1ccc(N)c(C)c1C)C(C)C)C(C)(C)C)C(C)(C)c1ccccc1]

Synthesized from Boc-HTI-286-OH and Compound S-1 using general procedures 3, 5 and 10.

$^1$H NMR (400 MHz, Methanol-d$_4$) δ 7.75 (d, J=8.8 Hz, 1H), 7.55 (d, J=7.9 Hz, 2H), 7.47 (t, J=7.7 Hz, 2H), 7.37 (t, J=6.9 Hz, 1H), 6.63 (d, J=8.8 Hz, 1H), 6.46 (d, J=9.7 Hz, 1H), 5.00 (t, J=10.0 Hz, 1H), 4.93 (s, 1H), 4.32 (s, 1H), 3.17 (s, 3H), 2.54 (s, 3H), 2.49 (s, 3H), 2.09 (s, 3H), 2.08-2.02 (m, 1H), 1.87 (d, J=1.4 Hz, 3H), 1.47 (s, 3H), 1.37 (s, 3H), 1.07 (s, 9H), 0.92 (dd, J=6.8, 6.5 Hz, 6H).

$C_{35}H_{53}N_5O_5S$ calcd m/z=655.38. found [M+H]$^+$=656.4.

Compound S: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-2,3-dimethylphenylsulfonyl)-2,5-dimethyl-4-((S)—N,3,3-trimethyl-2-((S)-3-methyl-2-(methylamino)-3-phenylbutanamido)butanamido)hex-2-enamide

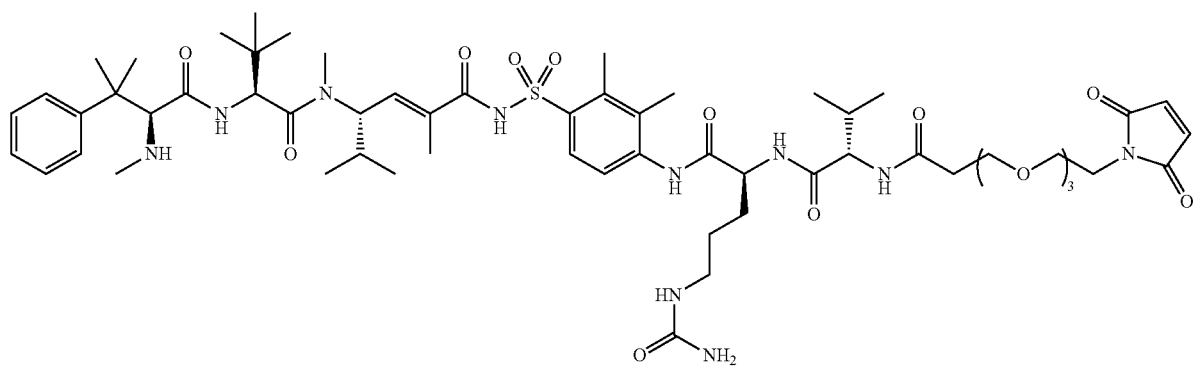

Synthesized from Compound S-2 and MT-NHS according to General Procedure 9.

$^1$H NMR (400 MHz, Methanol-d$_4$) δ 8.01 (dd, J=11.0, 8.2 Hz, 2H), 7.60-7.51 (m, 2H), 7.47 (dd, J=8.5, 6.8 Hz, 3H), 7.41-7.31 (m, 1H), 6.83 (s, 2H), 6.50 (dd, J=9.5, 1.8 Hz, 1H), 5.01 (t, J=10.0 Hz, 1H), 4.93 (t, J=4.1 Hz, 1H), 4.60 (m, 1H), 4.36 (s, 1H), 4.30-4.17 (m, 1H), 3.80-3.67 (m, 4H), 3.64 (td, J=5.5, 1.2 Hz, 2H), 3.60 (d, J=3.2 Hz, 7H), 3.29-3.13 (m, 5H), 2.67-2.46 (m, 9H), 2.24 (s, 3H), 2.20-1.92 (m, 4H), 1.93-1.75 (m, 3H), 1.65 (dp, J=16.0, 7.8 Hz, 2H), 1.43 (d, J=38.9 Hz, 6H), 1.14-0.96 (m, 16H), 0.92 (t, J=6.8 Hz, 6H). m/z calcd. for $C_{59}H_{90}N_{10}O_{14}S$=1194.64. found [M+H]$^+$ 1195.51; [(M+2H)/2]$^+$599.09.

Example 21

Compound T: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide

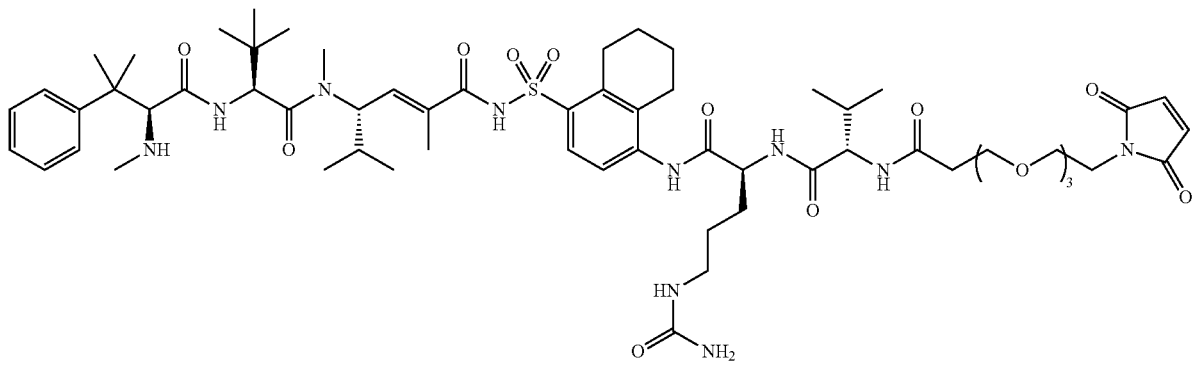

Compound T-1: 2,2,2-trifluoro-N-(4-sulfamoyl-5,6,7,8-tetrahydronaphthalen-1-yl)acetamide

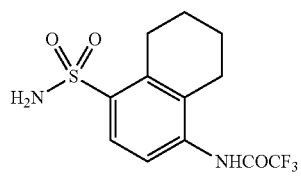

Synthesized from 5,6,7,8-tetrahydronaphthalen-1-amine according to general procedure 1.

$^1$H NMR (400 MHz, DMSO-d$_6$) δ 11.04 (s, 1H), 7.79 (d, J=8.4 Hz, 1H), 7.46 (s, 2H), 7.30 (d, J=8.4 Hz, 1H), 3.14 (s, 1H), 2.77 (d, J=15.4 Hz, 1H), 2.72-2.57 (m, 4H), 1.73 (p, J=3.3 Hz, 4H).

Compound T-2: (S,E)-N-(4-amino-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide

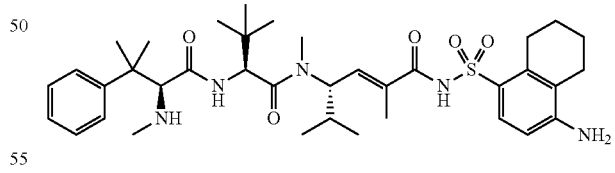

Synthesized from Boc-HTI-286-OH and Compound T-1 using general procedures 3, 5 and 10.

$^1$H NMR (400 MHz, Methanol-d$_4$) δ 7.74 (d, J=8.7 Hz, 1H), 7.55 (d, J=7.9 Hz, 2H), 7.48 (t, J=7.6 Hz, 2H), 7.38 (t, J=7.2 Hz, 1H), 6.60 (d, J=8.7 Hz, 1H), 6.46 (d, J=9.2 Hz, 1H), 5.00 (t, J=10.0 Hz, 1H), 4.95-4.91 (m, 1H), 4.36 (s, 1H), 3.17 (s, 3H), 3.10-3.05 (m, 2H), 2.51 (s, 3H), 2.46 (t, J=6.5 Hz, 2H), 2.10-2.02 (m, 1H), 1.88 (s, 3H), 1.87-1.75 (m, 4H), 1.47 (s, 3H), 1.38 (s, 3H), 1.07 (s, 9H), 0.92 (dd, J=7.1 Hz, 6H).

$C_{37}H_{55}N_5O_5S$ calcd m/z=681.39. found [M+H]$^+$=682.4.

Compound T: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-5,6,7,8-tetrahydronaphthalen-1-ylsulfonyl)-2,5-dimethyl-4-((S)—N,3,3-trimethyl-2-((S)-3-methyl-2-(methylamino)-3-phenylbutanamido)butanamido)hex-2-enamide

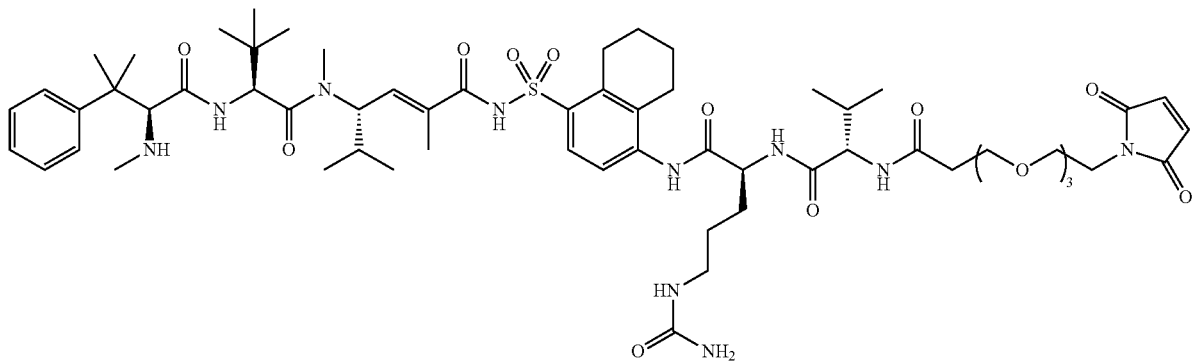

Synthesized from Compound T-2 and MT-NHS according to General Procedure 9.

¹H NMR (400 MHz, Methanol-d4) δ 7.98 (d, J=8.7 Hz, 1H), 7.62 (d, J=8.7 Hz, 1H), 7.59-7.51 (m, 2H), 7.47 (dd, J=8.5, 6.8 Hz, 2H), 7.42-7.30 (m, 1H), 6.83 (s, 2H), 6.50 (dd, J=9.5, 1.8 Hz, 1H), 5.01 (t, J=10.0 Hz, 1H), 4.93 (t, J=4.1 Hz, 1H), 4.62 (td, J=8.1, 7.5, 5.0 Hz, 1H), 4.37 (s, 1H), 4.29-4.18 (m, 1H), 3.75 (t, J=6.0 Hz, 2H), 3.72-3.67 (m, 2H), 3.64 (td, J=5.9, 1.5 Hz, 2H), 3.29-3.08 (m, 7H), 2.74 (d, J=6.0 Hz, 2H), 2.62-2.46 (m, 5H), 2.20-1.94 (m, 4H), 1.91-1.75 (m, 7H), 1.70-1.58 (m, 2H), 1.48 (s, 3H), 1.38 (s, 3H), 1.07 (s, 9H), 1.00 (dd, J=6.8, 3.4 Hz, 6H), 0.92 (t, J=6.6 Hz, 6H). m/z calcd. for $C_{61}H_{92}N_{10}O_{14}S$=1220.65. found [M+H]⁺ 1221.48; [(M+2H)/2]⁺611.39.

Example 22

Compound U: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide

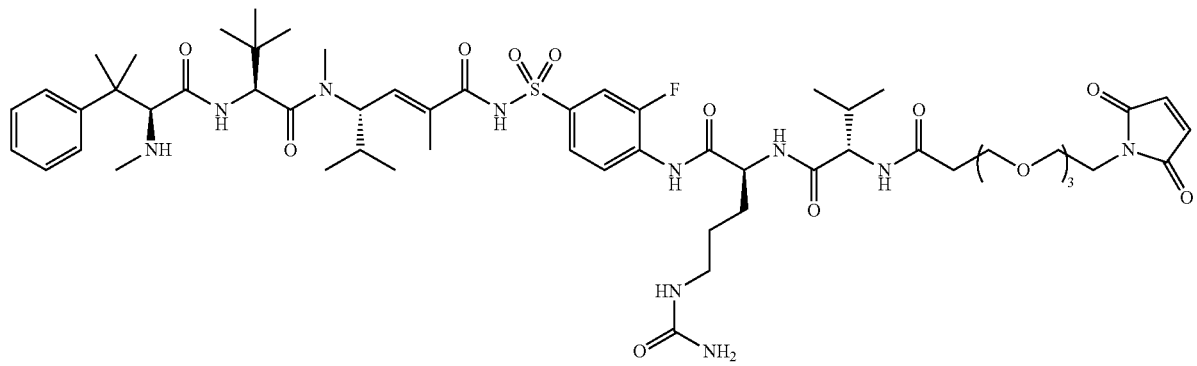

221

Compound U-1: 2,2,2-trifluoro-N-(2-fluoro-4-sulfamoylphenyl)acetamide

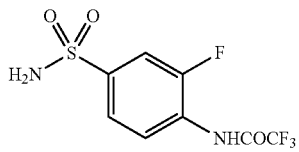

Synthesized from 2-fluoroaniline according to general procedure 1.

$^1$H NMR (400 MHz, DMSO-d$_6$) δ 11.58 (s, 1H), 7.85-7.66 (m, 3H), 7.56 (s, 2H).

Compound U-2: (S,E)-N-(4-amino-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide

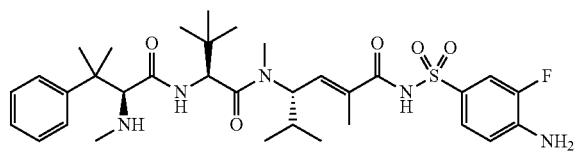 [SMILES: CN[C@H](C(=O)N[C@H](C(=O)N(C)[C@H](/C=C(\C)C(=O)NS(=O)(=O)c1ccc(N)c(F)c1)C(C)C)C(C)(C)C)C(C)(C)c1ccccc1]

222

Synthesized from Boc-HTI-286-OH and Compound U-1 using general procedures 3, 5 and 10.

$^1$H NMR (400 MHz, Methanol-d$_4$) δ 7.62-7.55 (m, 3H), 7.54 (s, 1H), 7.48 (t, J=7.7 Hz, 2H), 7.37 (t, J=7.3 Hz, 1H), 6.85 (t, J=8.6 Hz, 1H), 6.45 (d, J=9.3 Hz, 1H), 4.98 (t, J=9.9 Hz, 1H), 4.92 (s, 1H), 4.34 (s, 1H), 3.16 (s, 3H), 2.50 (s, 3H), 2.12-2.00 (m, 1H), 1.88 (d, J=1.4 Hz, 3H), 1.46 (s, 3H), 1.37 (s, 3H), 1.07 (s, 9H), 0.91 (dd, J=6.8 Hz, 6H).

C$_{33}$H$_{48}$FN$_5$O$_5$S calcd m/z=645.34 [M+H]$^+$=646.4

Compound U: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-3-fluorophenylsulfonyl)-2,5-dimethyl-4-((S)—N,3,3-trimethyl-2-((S)-3-methyl-2-(methylamino)-3-phenylbutanamido)butanamido)hex-2-enamide

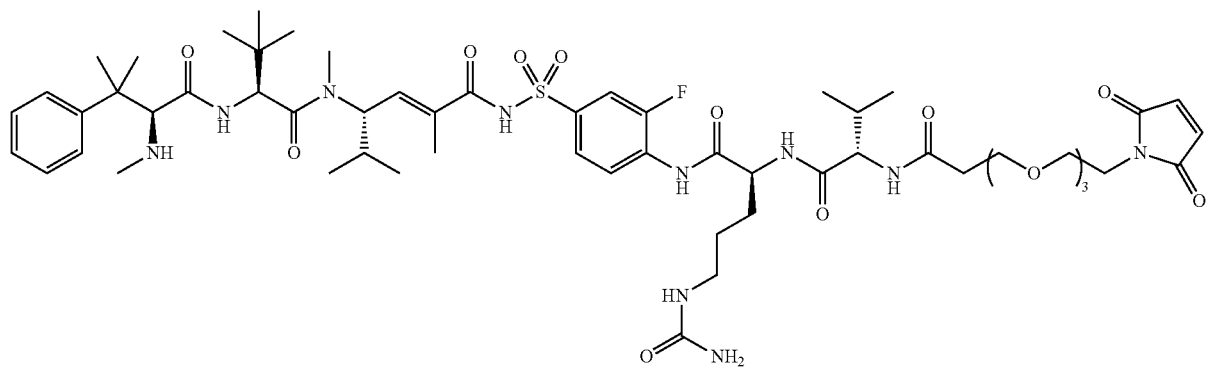

Synthesized from Compound U-2 and MT-NHS according to General Procedure 9.

$^1$H NMR (400 MHz, Methanol-d4) δ 8.42-8.28 (m, 1H), 7.91-7.77 (m, 2H), 7.58-7.51 (m, 2H), 7.47 (t, J=7.8 Hz, 2H), 7.42-7.32 (m, 1H), 6.84 (s, 2H), 6.50 (dd, J=9.3, 1.8 Hz, 1H), 5.02-4.90 (m, 2H), 4.67 (td, J=7.9, 7.2, 4.8 Hz, 1H), 4.35 (s, 1H), 4.26 (t, J=7.5 Hz, 1H), 3.76 (t, J=6.1 Hz, 2H), 3.70 (td, J=5.5, 1.2 Hz, 2H), 3.67-3.53 (m, 10H), 3.28-3.06 (m, 51H), 2.61-2.47 (m, 5H), 2.19-2.01 (m, 2H), 2.01-1.71 (m, 4H), 1.61 (dt, J=15.2, 7.1 Hz, 2H), 1.46 (s, 3H), 1.36 (s, 3H), 1.13-0.95 (m, 16H), 0.91 (dd, J=6.6, 4.9 Hz, 6H).

m/z calcd. for C$_{57}$H$_{85}$FN$_{10}$O$_{14}$S=1184.60. found [M+H]$^+$ 1185.47; [(M+2H)/2]$^+$593.41.

Example 23

Compound V: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide

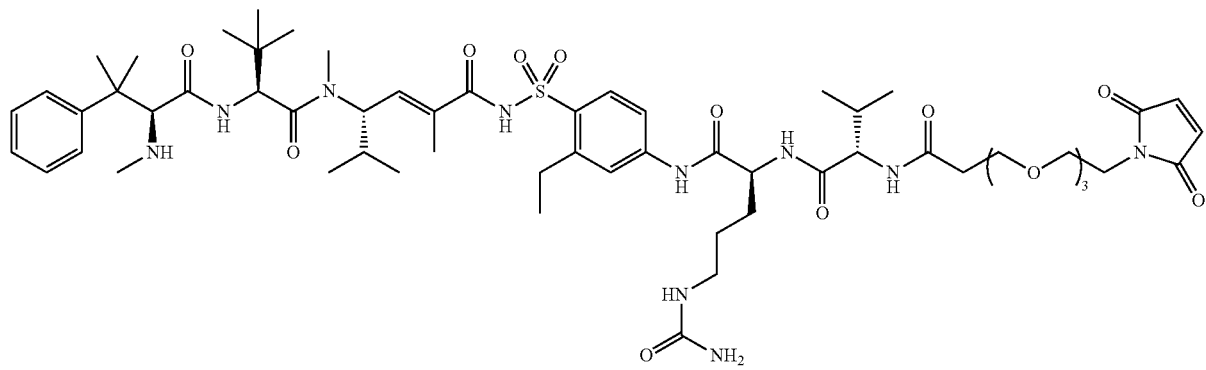

Compound V-1: N-(3-ethyl-4-sulfamoylphenyl)-2,2,2-trifluoroacetamide

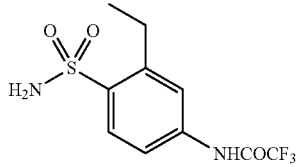

Synthesized from 3-ethylaniline according to general procedure 1.

$^1$H NMR (400 MHz, DMSO-$d_6$) δ 11.48 (s, 1H), 7.89 (d, J=8.5 Hz, 1H), 7.75-7.63 (m, 2H), 7.45 (s, 2H), 3.02 (q, J=7.5 Hz, 2H), 1.24 (t, J=7.4 Hz, 3H).

Compound V-2: (S,E)-N-(4-amino-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide

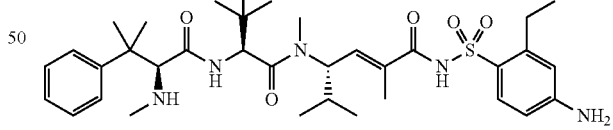

Synthesized from Boc-HTI-286-OH and Compound V-1 using general procedures 3, 5 and 10.

$^1$H NMR (400 MHz, Methanol-$d_4$) δ 7.79 (d, J=8.7 Hz, 1H), 7.55 (d, J=7.9 Hz, 2H), 7.48 (t, J=7.6 Hz, 2H), 7.37 (t, J=7.4 Hz, 1H), 6.57 (d, J=2.3 Hz, 1H), 6.54 (dd, J=8.8, 2.4 Hz, 1H), 6.46 (d, J=9.4 Hz, 1H), 5.01 (t, J=10.0 Hz, 1H), 4.92 (s, 1H), 4.34 (s, 1H), 3.16 (s, 3H), 2.99-2.90 (m, 2H), 2.50 (s, 3H), 2.11-2.00 (m, 1H), 1.87 (d, J=1.4 Hz, 3H), 1.47 (s, 3H), 1.38 (s, 3H), 1.22 (t, J=7.5 Hz, 3H), 1.06 (s, 9H), 0.91 (dd, J=6.6 Hz, 6H).

$C_{35}H_{53}N_5O_5S$ calcd m/z=655.38 [M+H]$^+$=656.4.

Compound V: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-2-ethylphenylsulfonyl)-2,5-dimethyl-4-((S)—N,3,3-trimethyl-2-((S)-3-methyl-2-(methylamino)-3-phenylbutanamido)butanamido)hex-2-enamide

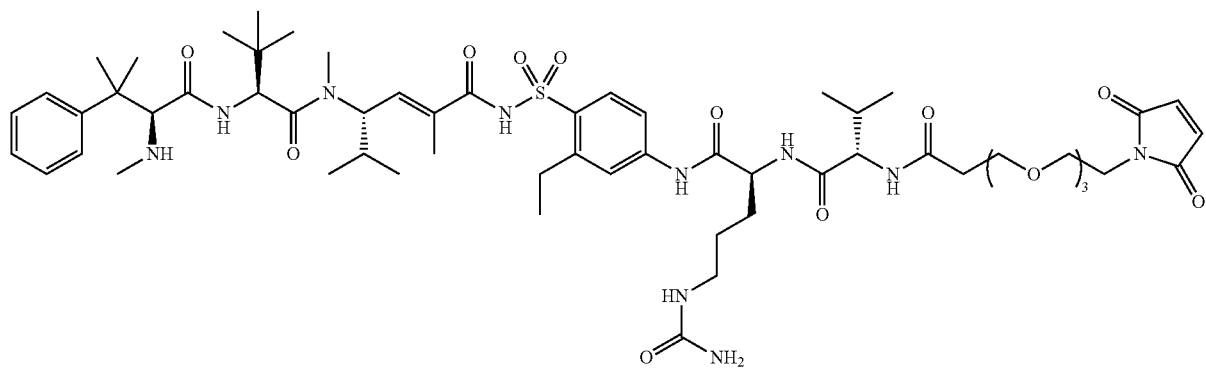

Synthesized from Compound V-2 and MT-NHS according to General Procedure 9.

$^1$H NMR (400 MHz, Methanol-$d_4$) δ 8.04 (d, J=8.8 Hz, 1H), 7.77 (d, J=2.2 Hz, 1H), 7.67 (dd, J=8.8, 2.2 Hz, 1H), 7.54 (d, J=7.6 Hz, 2H), 7.46 (t, J=7.7 Hz, 2H), 7.36 (t, J=7.3 Hz, 1H), 6.83 (s, 2H), 6.51 (dd, J=9.5, 1.9 Hz, 1H), 5.01 (t, J=10.0 Hz, 1H), 4.92 (d, J=8.4 Hz, 2H), 4.60-4.47 (m, 1H), 4.37 (s, 1H), 4.23 (d, J=6.9 Hz, 1H), 3.82-3.72 (m, 2H), 3.69 (dd, J=6.0, 4.5 Hz, 2H), 3.66-3.52 (m, 10H), 3.28-3.10 (m, 5H), 3.06 (q, J=7.4 Hz, 2H), 2.58 (t, J=6.0 Hz, 2H), 2.52 (s, 3H), 2.20-1.90 (m, 3H), 1.87 (s, 3H), 1.84-1.72 (m, 1H), 1.64-1.55 (m, 2H), 1.47 (s, 3H), 1.37 (s, 3H), 1.26 (t, J=7.5 Hz, 3H), 1.10-0.96 (m, 15H), 0.91 (dd, J=6.6, 4.0 Hz, 6H).

m/z calcd. for $C_{59}H_{90}N_{10}O_{14}S$=1194.64. found [M+H]$^+$ 1195.57; [(M+2H)/2]$^+$599.12.

Example 24

Compound W: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-3-ethylphenylsulfonyl)-2,5-dimethyl-4-((S)—N,3,3-trimethyl-2-((S)-3-methyl-2-(methylamino)-3-phenylbutanamido)butanamido)hex-2-enamide

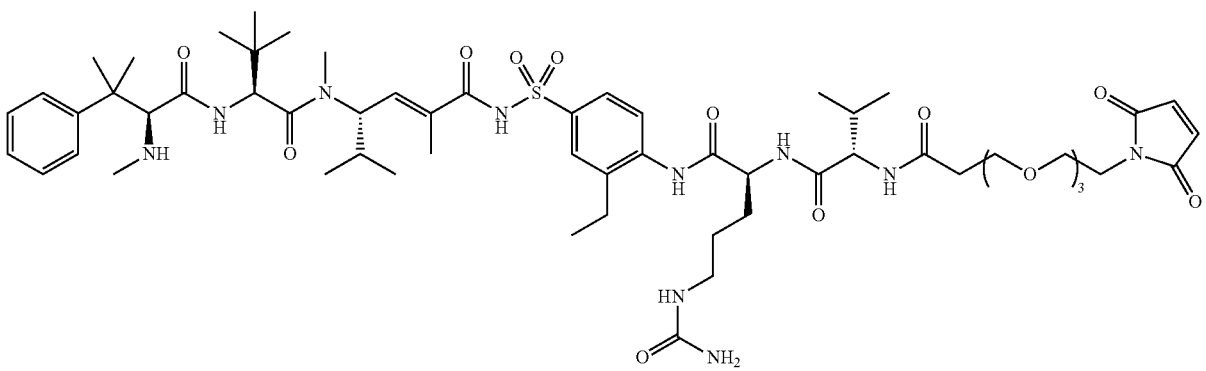

Compound W-1: N-(2-ethyl-4-sulfamoylphenyl)-2,2,2-trifluoroacetamide

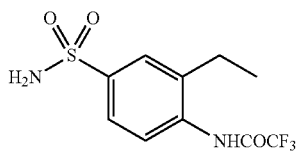

Synthesized from 2-ethylaniline according to general procedure 1.

¹H NMR (400 MHz, DMSO-d$_6$) δ 11.21 (s, 1H), 7.80 (d, J=2.1 Hz, 1H), 7.72 (dd, J=8.2, 2.2 Hz, 1H), 7.48 (d, J=8.3 Hz, 1H), 7.41 (s, 2H), 2.64 (q, J=7.6 Hz, 2H), 1.16 (t, J=7.5 Hz, 3H).

Compound W-2: (S,E)-N-(4-amino-3-ethylphenylsulfonyl)-2,5-dimethyl-4-((S)—N,3,3-trimethyl-2-((S)-3-methyl-2-(methylamino)-3-phenylbutanamido)butanamido)hex-2-enamide

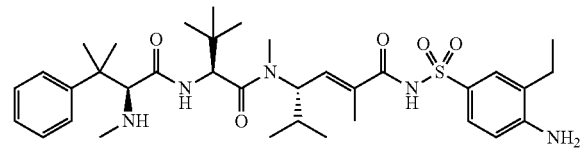

Synthesized from Boc-HTI-286-OH and Compound W-1 using general procedures 3, 5 and 10.

¹H NMR (400 MHz, Methanol-d$_4$) δ 7.66 (d, J=2.3 Hz, 1H), 7.61 (dd, J=8.6, 2.3 Hz, 1H), 7.55 (d, J=7.6 Hz, 2H), 7.48 (t, J=7.7 Hz, 2H), 7.37 (t, J=7.3 Hz, 1H), 6.71 (d, J=8.5 Hz, 1H), 6.43 (dd, J=9.3, 1.7 Hz, 1H), 4.96 (t, J=9.9 Hz, 1H), 4.92 (s, 1H), 4.35 (s, 1H), 3.16 (s, 3H), 2.54 (dd, J=7.4, 2.2 Hz, 2H), 2.51 (s, 3H), 2.12-1.99 (m, 1H), 1.87 (d, J=1.4 Hz, 3H), 1.46 (s, 3H), 1.36 (s, 3H), 1.27 (t, J=7.5 Hz, 3H), 1.07 (s, 9H), 0.91 (dd, J=6.4 Hz, 6H) $C_{35}H_{53}N_5O_5S$ calcd m/z=655.38 [M+H]$^+$=656.5.

Compound W: (S,E)-N-(4-((14R,17R)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)-3-ethylphenylsulfonyl)-2,5-dimethyl-4-((S)—N,3,3-trimethyl-2-((S)-3-methyl-2-(methylamino)-3-phenylbutanamido)butanamido)hex-2-enamide

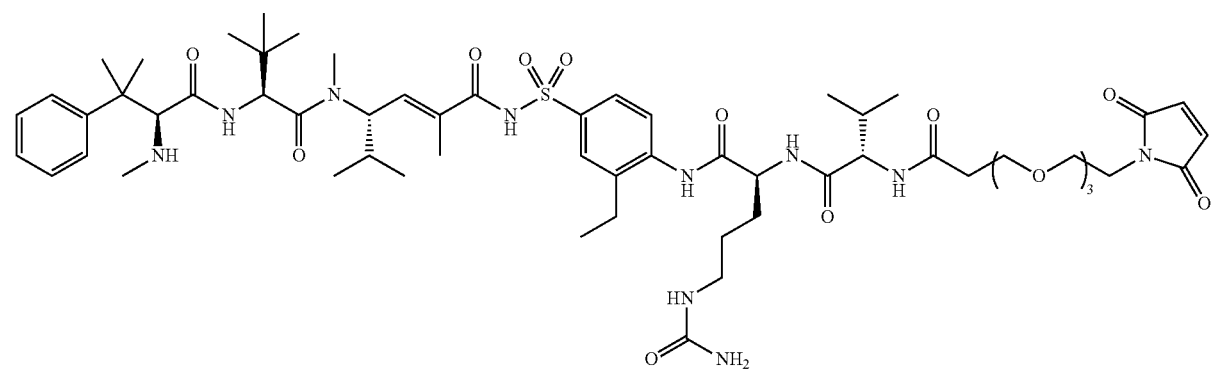

Synthesized from Compound W-2 and MT-NHS according to General Procedure 9.

¹H NMR (400 MHz, Methanol-d$_4$) δ 7.97 (d, J=2.3 Hz, 1H), 7.87 (dd, J=8.5, 2.3 Hz, 1H), 7.77 (d, J=8.5 Hz, 1H), 7.59-7.51 (m, 2H), 7.51-7.42 (m, 2H), 7.41-7.34 (m, 1H), 6.84 (s, 2H), 6.48 (dd, J=9.4, 1.8 Hz, 1H), 4.98 (t, J=9.9 Hz, 1H), 4.92 (d, J=8.4 Hz, 1H), 4.64 (td, J=8.4, 7.6, 3.7 Hz, 1H), 4.36 (s, 1H), 4.25 (d, J=7.0 Hz, 1H), 3.82-3.67 (m, 4H), 3.67-3.53 (m, 10H), 3.29-3.09 (m, 5H), 2.77 (q, J=7.5 Hz, 2H), 2.62-2.46 (m, 5H), 2.20-1.95 (m, 4H), 1.91-1.74 (m, 4H), 1.72-1.60 (m, 2H), 1.47 (s, 3H), 1.37 (s, 3H), 1.27 (t, J=7.5 Hz, 3H), 1.12-0.95 (m, 16H), 0.91 (dd, J=6.6, 4.6 Hz, 6H).

m/z calcd. for $C_{59}H_{90}N_{10}O_{14}S$=1194.64. found [M+H]$^+$ 1195.54; [(M+2H)/2]$^+$599.09.

Example 25

Compound X: (S)—N-(4-(N—((S,E)-2,5-dimethyl-4-((S)—N,3,3-trimethyl-2-((S)-3-methyl-2-(methylamino)-3-phenylbutanamido)butanamido)hex-2-enoyl)sulfamoyl)phenyl)-1-((S)-1-(2,5-dioxo-2,5-dihydro-1H-pyrrol-1-yl)-14-methyl-12-oxo-3,6,9-trioxa-13-azapentadecane)pyrrolidine-2-carboxamide

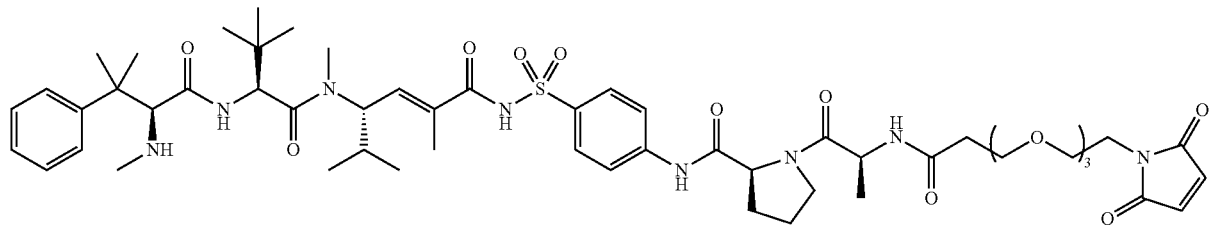

Synthesized from Compound H-1c and Boc-Ala-Pro-OH according to General Procedure 7, followed by Boc-removal according to General Procedure 10 and MT-NHS installation according to General Procedure 9 prior to purification by preparative HPLC.

$^1$H NMR (400 MHz, Methanol-$d_4$) δ 7.99 (d, J=8.9 Hz, 2H), 7.81 (d, J=8.5 Hz, 2H), 7.55 (d, J=7.5 Hz, 2H), 7.48 (t, J=7.7 Hz, 2H), 7.38 (t, J=7.3 Hz, 1H), 6.84 (s, 2H), 6.54-6.42 (m, 1H), 5.07-4.95 (m, 2H), 4.67 (t, J=6.8 Hz, 1H), 4.57 (dd, J=8.4, 4.6 Hz, 1H), 4.35 (s, 1H), 3.95-3.83 (m, 1H), 3.80-3.66 (m, 5H), 3.61 (dd, J=18.6, 4.6 Hz, 10H), 3.16 (s, 3H), 2.58-2.42 (m, 5H), 2.36 (d, J=18.0 Hz, 1H), 2.23-1.98 (m, 4H), 1.86 (d, J=1.4 Hz, 3H), 1.46 (s, 3H), 1.43-1.31 (m, 6H), 1.07 (s, 10H), 0.91 (t, J=6.3 Hz, 6H). m/z calcd. for $C_{59}H_{90}N_{10}O_{14}S$=1078.54. found [M+H]$^+$ 1079.48; [(M+2H)/2]$^+$540.27.

Example 26

Compound Z: (S,E)-N-(4-((14S,17S)-17-(4-aminobutyl)-14-benzyl-1-(2,5-dioxo-2,5-dihydro-1H-pyrrol-1-yl)-12,15-dioxo-3,6,9-trioxa-13,16-diazaoctadecanamido)phenylsulfonyl)-2,5-dimethyl-4-((S)—N,3,3-trimethyl-2-((S)-3-methyl-2-(methylamino)-3-phenylbutanamido)butanamido)hex-2-enamide

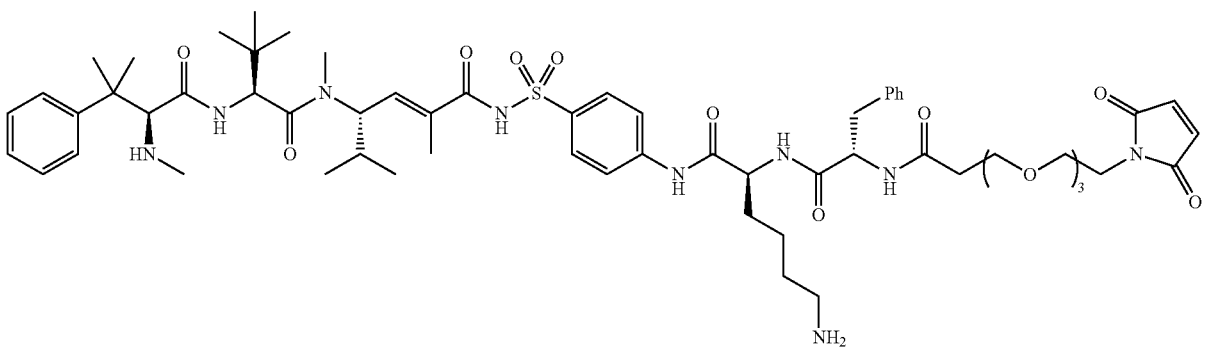

The title compound was prepared from Compound H-1c and Fmoc-Phe-Lys(Boc)-OH according to General Procedure 7, followed by Fmoc removal according to General Procedure 8, acylation with MT-NHS according to General Procedure 9 and deprotection according to General Procedure 10 prior to purification by preparative HPLC. m/z calcd. for $C_{61}H_{87}N_9O_{13}S$=1185.6. found $[M+H+]^+$=1186.6 and $[(M+2H+)/2]^{2+}$=593.9.

Example 27

Compound AA: (S,E)-N-(4-((14S,17S)-17-(4-aminobutyl)-1-(2,5-dioxo-2,5-dihydro-1H-pyrrol-1-yl)-14-isopropyl-12,15-dioxo-3,6,9-trioxa-13,16-diazaoctadecanamido)phenylsulfonyl)-2,5-dimethyl-4-((S)—N,3,3-trimethyl-2-((S)-3-methyl-2-(methylamino)-3-phenylbutanamido)butanamido)hex-2-enamide

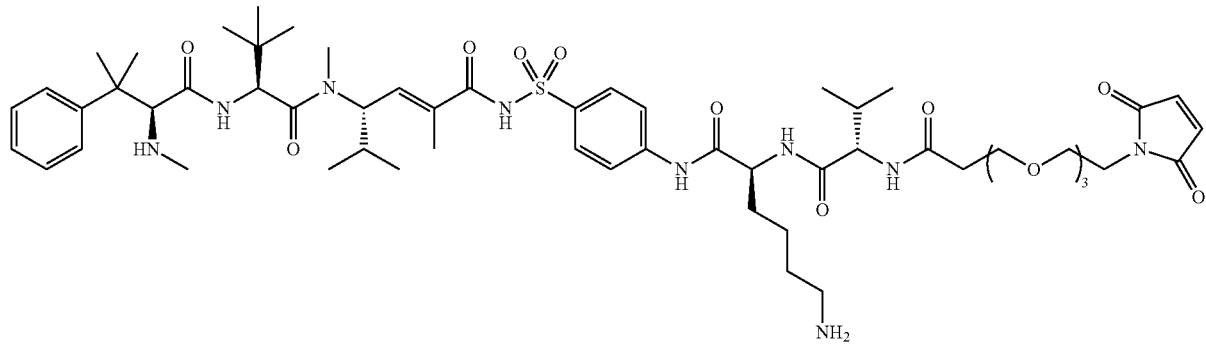

The title compound was prepared from Compound H-1c and Fmoc-Val-Lys(Boc)-OH according to General Procedure 7, followed by Fmoc removal according to General Procedure 8, acylation with MT-NHS according to General Procedure 9 and deprotection according to General Procedure 10 prior to purification by preparative HPLC. m/z calcd. for $C_{57}H_{87}N_9O_{13}S$=1137.6. found $[M+H^+]^+$=1138.5 and $[(M+2H+)/2]^{2+}$=569.8.

Example 28

Compound BB: (S,E)-N-(4-((2S,5S,8R)-2-(4-aminobutyl)-5-benzyl-21-(2,5-dioxo-2,5-dihydro-1H-pyrrol-1-yl)-8-methyl-4,7,10-trioxo-13,16,19-trioxa-3,6,9-triazahenicosanamido)phenylsulfonyl)-2,5-dimethyl-4-((S)—N,3,3-trimethyl-2-((S)-3-methyl-2-(methylamino)-3-phenylbutanamido)butanamido)hex-2-enamide

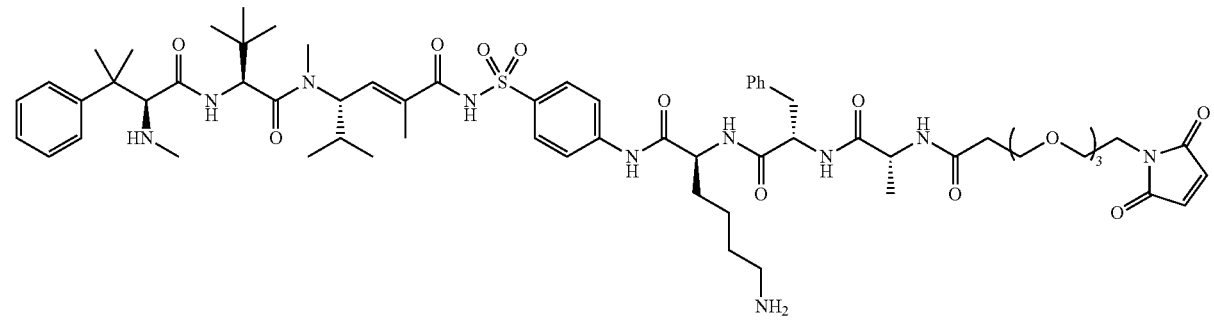

The title compound was prepared from Compound H-1c and Fmoc-Ala-Phe(D)-Lys(Boc)-OH according to general procedure 7. The resulting material, purified by flash chromatography was then subject to general procedure 8 to remove the Fmoc protecting group, followed by treatment with MT-NHS according to general procedure 9 and deprotection according to General Procedure 10 prior to purification by preparative HPLC. m/z calcd. for $C_{64}H_{92}N_{10}O_{14}S$=1256.7. found $[M+H^+]^+$=1258.3 and $[(M+2H+)/2]^{2+}$=630.2.

Example 29

Compound CC: (S,E)-N-(4-((2S,5S,8R)-2-(4-aminobutyl)-5,8-dibenzyl-21-(2,5-dioxo-2,5-dihydro-1H-pyrrol-1-yl)-4,7,10-trioxo-13,16,19-trioxa-3,6,9-triazahenicosanamido)phenylsulfonyl)-2,5-dimethyl-4-((S)—N,3,3-trimethyl-2-((S)-3-methyl-2-(methylamino)-3-phenylbutanamido)butanamido)hex-2-enamide

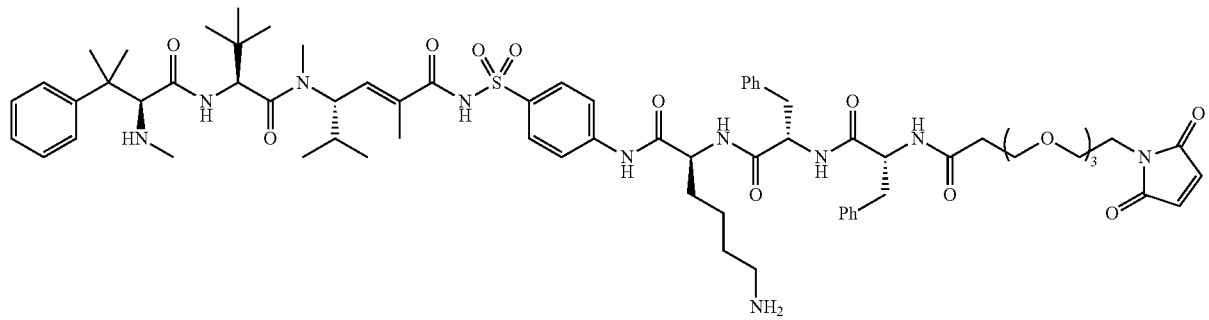

The title compound was prepared from Compound H-1c and Fmoc-Phe-Phe(D)-Lys(Boc)-OH according to General Procedure 7, Fmoc-removal via General Procedure 8, reaction with MT-NHS according to general procedure 9 and deprotection according to General Procedure 10, followed by prep HPLC purification m/z calcd. for $C_{69}H_{94}N_{10}O_{14}S$=1332.7. found $[M+H+]^+$=1334.3 and $[(M+2H+)/2]^{2+}$=668.2.

Example 30

Compound DD: (S,E)-N-(2-((14S,17S)-1-(2,5-dioxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonyl)-2,5-dimethyl-4-((S)—N,3,3-trimethyl-2-((S)-3-methyl-2-(methylamino)-3-phenylbutanamido)butanamido)hex-2-enamide

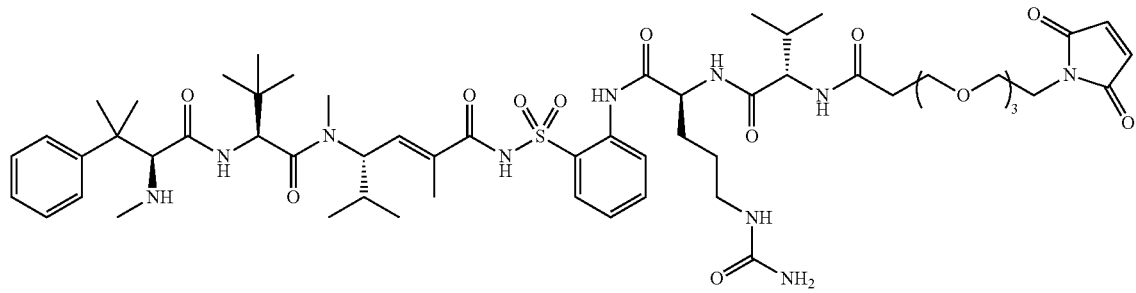

Compound DD-1: 2,2,2-trifluoro-N-(2-sulfamoylphenyl)acetamide

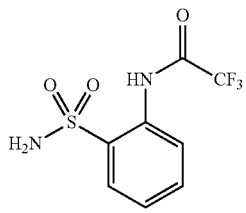 [SMILES: NS(=O)(=O)c1ccccc1NC(=O)C(F)(F)F]

The title compound was made from 2-aminobenzenesulfonamide according to General Procedure 2.

Compound DD-2: (S,E)-N-(2-aminophenylsulfonyl)-2,5-dimethyl-4-((S)—N,3,3-trimethyl-2-((S)-3-methyl-2-(methylamino)-3-phenylbutanamido)butanamido)hex-2-enamide

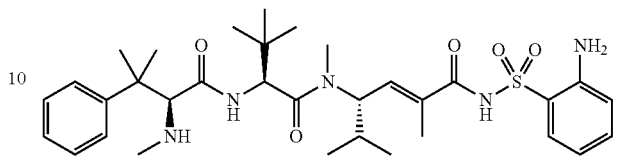

The title compound was made from Compound D-1 and Boc-HTI-286-OH according to General Procedures 3 and 5. $^1$H NMR (400 MHz, Methanol-$d_4$) δ 7.75 (dd, J=8.2, 1.5 Hz, 1H), 7.55 (d, J=7.8 Hz, 2H), 7.48 (t, J=7.7 Hz, 2H), 7.38 (t, J=7.4 Hz, 1H), 7.33-7.27 (m, 1H), 6.81 (d, J=8.2 Hz, 1H), 6.69 (t, J=7.5 Hz, 1H), 6.49 (dd, J=9.1, 1.5 Hz, 1H), 4.97 (t, J=10.1 Hz, 1H), 4.92 (s, 1H), 4.35 (s, 1H), 3.17 (s, 3H), 2.51 (s, 3H), 2.07 (m, 1H), 1.88 (d, J=1.4 Hz, 3H), 1.46 (s, 3H), 1.36 (s, 3H), 1.06 (s, 9H), 0.92 (t, J=6.8 Hz, 6H).

$C_{33}H_{49}N_5O_5S$ calcd m/z=627.35 amu. found $[M+H]^+$=628.36, $[M+Na]^+$=650.37, $[(M+2H)/2]^{2+}$=314.76.

Compound DD-3

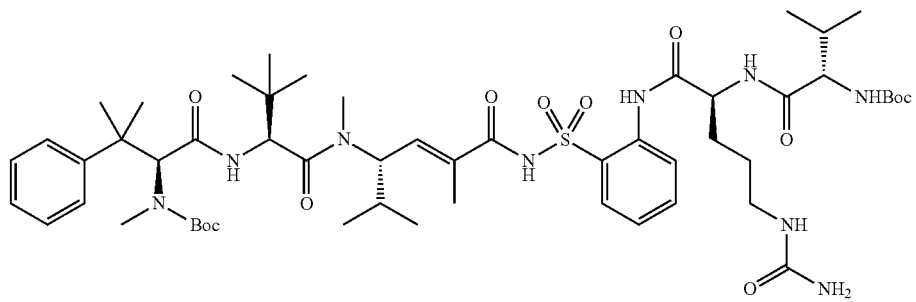 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)NS(=O)(=O)c1ccccc1NC(=O)[C@H](CCCNC(N)=O)NC(=O)[C@@H](NC(=O)OC(C)(C)C)C(C)C]

The title compound was generated from Compound DD-2 and Boc-Val-Cit-OH according to General Procedure 7. $C_{54}H_{85}N_9O_{12}S$ calcd m/z=1083.60 amu. found $[M+H]^+$=1084.8, [M+Na]=1106.7.

Compound DD-4: (S,E)-N-(2-((S)-2-((S)-2-amino-3-methylbutanamido)-5-ureidopentanamido)phenylsulfonyl)-2,5-dimethyl-4-((S)—N,3,3-trimethyl-2-((S)-3-methyl-2-(methylamino)-3-phenylbutanamido)butanamido)hex-2-enamide

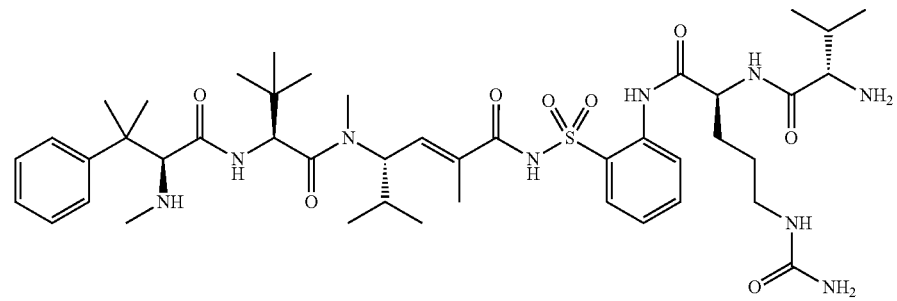 [SMILES: CN[C@H](C(=O)N[C@H](C(=O)N(C)[C@H](/C=C(\C)C(=O)NS(=O)(=O)c1ccccc1NC(=O)[C@H](CCCNC(N)=O)NC(=O)[C@@H](N)C(C)C)C(C)C)C(C)(C)C)C(C)(C)c1ccccc1]

The title compound was generated from Compound DD-3 according to General Procedure 10. $C_{44}H_{69}N_9O_8S$ calcd m/z=883.50 amu. found $[M+H]^+$=884.6, $[M+Na]^+$=906.6, $[(M+2H)/2]^{2+}$=442.8.

Compound DD: (S,E)-N-(2-((14S,17S)-1-(2,5-di-oxo-2,5-dihydro-1H-pyrrol-1-yl)-14-isopropyl-12,15-dioxo-17-(3-ureidopropyl)-3,6,9-trioxa-13,16-diazaoctadecanamido)phenylsulfonyl)-2,5-dimethyl-4-((S)—N,3,3-trimethyl-2-((S)-3-methyl-2-(methylamino)-3-phenylbutanamido)butanamido)hex-2-enamide

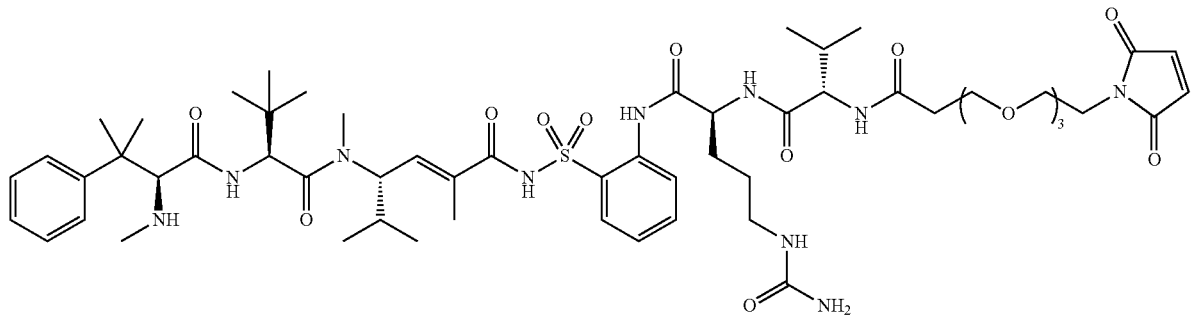

The title compound was generated from Compound DD-4 and MT-NHS according to General Procedure 9 before purification by preparative HPLC-MS. $^1$H NMR (400 MHz, Methanol-$d_4$) δ 8.16 (d, J=8.3 Hz, 1H), 7.95 (dd, J=8.0, 1.6 Hz, 1H), 7.50 (d, J=7.9 Hz, 2H), 7.42 (dt, J=15.5, 7.8 Hz, 3H), 7.29 (t, J=7.3 Hz, 1H), 7.19 (t, J=7.5 Hz, 1H), 6.85 (s, 2H), 6.62 (d, J=9.3 Hz, 1H), 4.66 (s, 1H), 4.61 (dd, J=9.1, 4.5 Hz, 1H), 4.37 (d, J=6.9 Hz, 1H), 3.76 (dd, J=7.5, 5.7 Hz, 2H), 3.73-3.67 (m, 2H), 3.67-3.56 (m, 10H), 3.29-3.13 (m, 4H), 3.11 (s, 3H), 2.70 (s, 6H), 2.65-2.49 (m, 2H), 2.22 (s, 3H), 2.11 (d, J=7.5 Hz, 2H), 2.00 (dt, J=17.2, 6.2 Hz, 2H), 1.86 (d, J=1.4 Hz, 3H), 1.66 (dt, J=14.5, 7.8 Hz, 2H), 1.01 (d, J=13.3 Hz, 15H), 0.87 (dd, J=21.4, 6.6 Hz, 6H).

$C_{57}H_{86}N_{10}O_{14}S$ calcd m/z=1166.60 amu. found $[M+H]^+$=1167.8, $[M+Na]^+$=1189.9, $[(M+2H)/2]^{2+}$=584.4.

BIOLOGICAL ASSAYS

Biological Example 1

Assay of Selective In Vitro Cytotoxic Killing of HER2-Positive Cells by Trastuzumab-Based ADCs Selective killing of HER2-positive cell lines such as NCI-N87 or HCC1954 over HER2-negative Jurkat cells was demonstrated for each conjugate prepared. For Table 1 summarizes the cytotoxic activity of the ADCs formed by the conjugation of Trastuzumab to Compounds A-DD when tested against the Human gastric carcinoma cell line NCI-N87 and/or the Human mammary carcinoma cell line HCC1954, and the Human T-cell leukemia cell line Jurkat.

Briefly, cells were obtained from the ATCC and cultured as described in the provided product sheet. Cells were seeded at 25000 cells/mL (2500 cells/well) in Costar 3904 black walled, flat bottomed 96-well plates. Adherent cell lines cells were incubated for one night at 37° C. in a 5% $CO_2$ atmosphere to allow the cells to attach to the microtitre plate surface, while suspension (Jurkat) cells were plated immediately before use. ADCs were diluted directly in the appropriate cell growth medium at five-times the desired final concentration. These ADCs were then titrated 1:3 over eight steps. A control with no test article present (growth medium alone) was included on each microtiter plate in sextuplicate. The prepared compound/ADC titrations were added (25 uL/well) in triplicate to both the HCC1954 and/or NCI-N87 cells and Jurkat cells. The cells and titrations were incubated at 37° C./5% $CO_2$ for three nights (Jurkat) and 3 or 5 nights (HCC1954/NCI-N87). After the incubation, cell viability was measured using CellTiter-Glo® reagent by adding thirty uL of prepared CellTiter-Glo® to each assay well. The mixtures were incubated for at least twenty minutes in the dark prior to measuring emitted luminescence using a microplate luminometer (500 ms integration time). The collected relative luminescence units (RLU) were converted to % cytotoxicity using the growth medium alone control mentioned above (% Cytotoxicity=1−[Well RLU/average medium alone control RLU]). Data (% Cytotoxicity vs. Concentration of ADC (log 10 [nM])) were plotted and were analyzed by non-linear regression methods using GraphPad Prism software v. 5.02 to obtain $EC_{50}$ estimates.

TABLE 1

| Trastuzumab ADC | EC50, nM Cell Line | | |
|---|---|---|---|
| | N87 | HCC1954 | Jurkat* |
| mAb-compound A | 0.017 | 0.079 | |
| mAb-compound B | 0.059 | 0.083 | |
| mAb-compound C | 0.039 | 0.084 | |
| mAb-compound D | 0.041 | 0.123 | |
| mAb-compound E | 0.033 | 0.018 | |
| mAb-compound F | 0.125 | 0.131 | |
| mAb-compound G | 0.056 | 0.128 | |
| mAb-compound H | 0.03 | 0.068 | |
| mAb-compound I | 0.047 | 0.065 | |
| mAb-compound J | 0.131 | 0.136 | |
| mAb-compound K | 0.055 | 0.103 | |
| mAb-compound KK | 0.091 | nd | |
| mAb-compound L | 0.099 | nd | |
| mAb-compound M | 0.031 | nd | |
| mAb-compound N | 0.44 | nd | |
| mAb-compound O | 0.010 | nd | |
| mAb-compound P | 0.010 | nd | |
| mAb-compound Q | 0.005 | nd | |
| mAb-compound R | 0.042 | nd | |
| mAb-compound S | 0.112 | nd | |
| mAb-compound T | 0.210 | nd | >10 nM |
| mAb-compound U | 0.333 | nd | |
| mAb-compound V | 0.247 | nd | >10 nM |
| mAb-compound W | 0.184 | nd | |
| mAb-compound X | 0.424 | nd | |
| mAb-compound Z | 0.007 | nd | |
| mAb-compound AA | 0.013 | nd | |

TABLE 1-continued

| Trastuzumab ADC | EC50, nM Cell Line | | |
|---|---|---|---|
| | N87 | HCC1954 | Jurkat* |
| mAb-compound BB | 0.020 | nd | |
| mAb-compound CC | 0.022 | nd | |
| mAb-compound-DD | 0.051 | nd | | nd—not determined
*no cytotoxicity observed on Jurkat cell line unless noted

Cathepsin B Linker Cleavage Assay

ADCs prepared by conjugation of Trastuzumab were assayed for sensitivity to cleavage and release of toxin by Cathepsin B (Sigma C8286). ADCs were buffer exchanged into 25 mM NaOAc, 1 mM EDTA, pH 5.0 using Zeba 40 KDa MWCO spin columns. ADC at concentrations between 1 and 3 mg/mL (estimated by BCA assay using a standard curve generated from Trastuzumab). In a typical experiment aliquots (50 uL; 100 ug) of each ADC were treated with Cathepsin B (~5 ug in 10 uL 20 mM DTT, 10 mM EDTA, 8 mM NaOAc) or buffer without enzyme and reactions were incubated at 37° C. After two hours the solutions were filtered through Pall NanoSep 30 KDa MWCO centrifugal spin filters and the filtrate was analyzed by liquid chromatography-mass spectrometry (after appropriate dilution) to identify small molecules released from the ADC by the action of Cathepsin B. RP-LCMS for free drug analysis was performed on a Waters Acquity H Class UPLC utilizing an Acquity UPLC BEH C18 column (1.7 µM, 2.1×50 mm). High resolution mass spectrometry detection was achieved using a MicroMass Q-TOF Premier with a scan range from 100 to 3000 m/z. Chromatography was performed with a linear gradient of 98% to 40% A over 5.5 minutes at 0.3 ml/min (A: 0.1% formic acid in H2O, B: 0.1% formic acid in ACN), followed by a washout and re-equilibration to initial conditions. Data collection and analysis was done with MassLynx 4.1. The qualitative results of the cleavage assay are shown in Table 1.

Of those conjugates tested, the following were released by cathepsin B in vitro: mAb-compound A; mAb-compound C; mAb-compound D; mAb-compound I; mAb-compound N; mAb-compound O; mAb-compound P; mAb-compound Q; mAb-compound R; mAb-compound S; mAb-compound T; mAb-compound U; mAb-compound V; mAb-compound W; mAb-compound Z; mAb-compound BB.

Biological Example 2

Efficacy Study of Toxins in NCI-N87 Tumor-Bearing Mice

Female NOD/SCID gamma (NSG) mice (Jackson Laboratories) were implanted subcutaneously in the back with the NCI-N87 tumour cell line. NCI-N87 human gastric carcinoma cells were derived from a liver metastasis of a well differentiated carcinoma of the stomach taken prior to cytotoxic therapy. The tumour was passaged as a xenograft in athymic nude mice for three passages before the cell line was established.

Tumours established over a period of 25 days, and test subjects were grouped (Table 2) according to tumour volume such that each group (n=10) had an equal distribution of tumour volumes (mean volume >170 mm$^3$).

Figure 12:
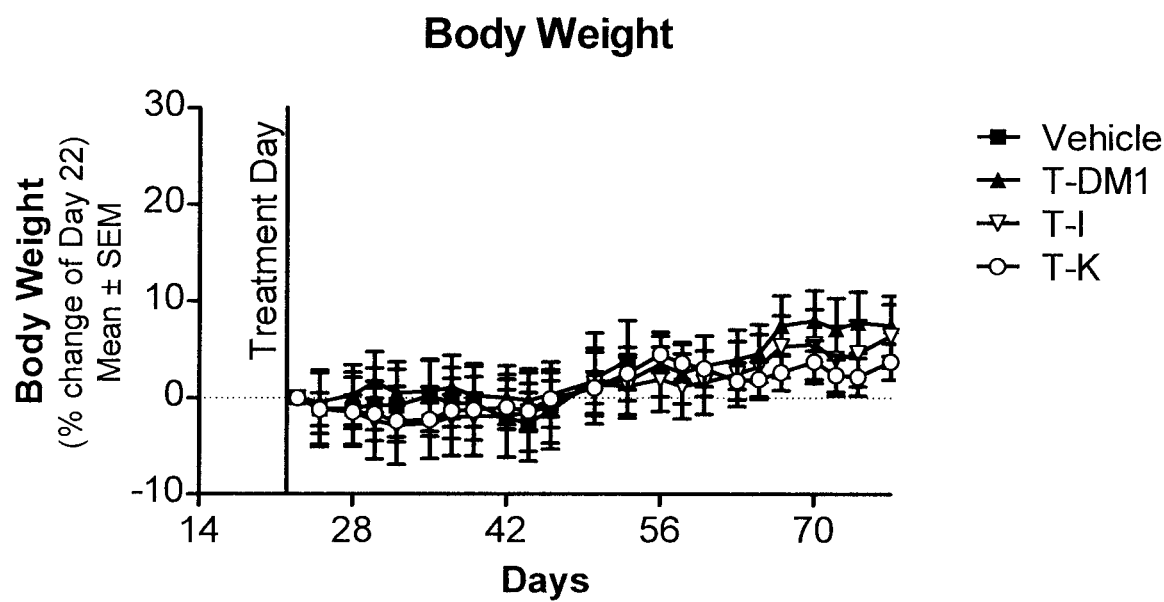
FIG. 12 shows the body weights of NSG mice inoculated with NCI-N87 tumor cells and treated on Day 22 with a single IV injection of either vehicle, T-DM1, T-Compound I, or T-Compound K at 12 mg/kg, n=10.
Figure 13:
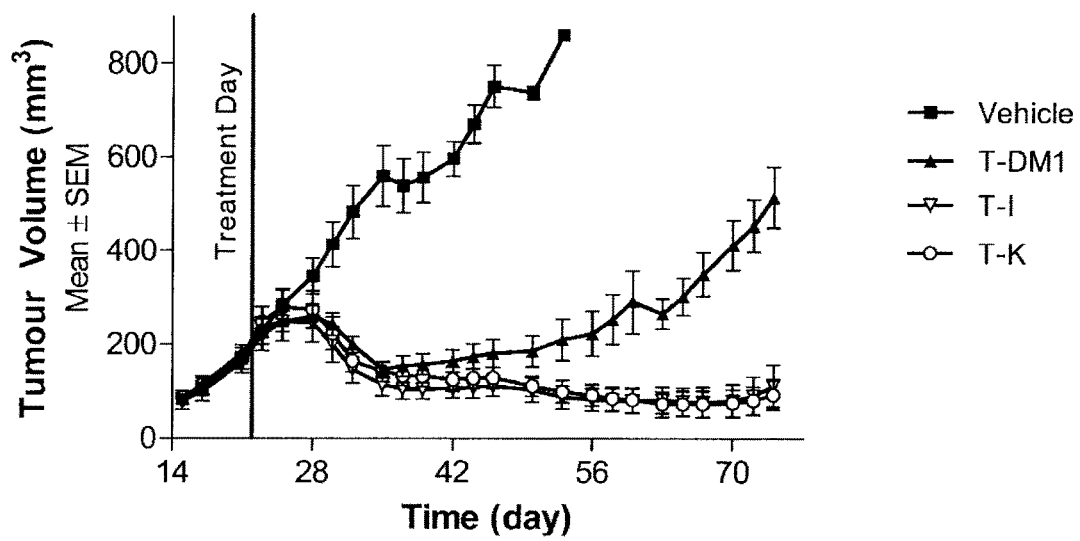
FIG. 13 shows the tumor volumes of NSG mice inoculated with NCI-N87 tumor cells and treated on Day 22 with a single IV injection of either vehicle, T-DM1, T-Compound I, or T-Compound K at 12 mg/kg, n=10.

Test articles were administered once (on Day 22) intravenously at the doses indicated in the study grouping table. Animal health was assessed acutely using Post Injection Clinical Observation Record (PICOR) forms. Body weights (FIG. 12) and tumour volumes (FIG. 13) were measured every Monday, Wednesday, and Friday. Animals remained on study until their tumours reached 800 mm$^3$ in size or they otherwise required euthanasia due to achieving a humane endpoint.

TABLE 2

BIOLOGICAL EXAMPLE 2 STUDY GROUPING.

| Group # | Test Article | n | Admin. Route | Dose (mg/kg) | Dose Volume (mL/kg) | Schedule |
|---|---|---|---|---|---|---|
| 1 | Vehicle | 10 | IV | N/A | 10 | qdx1 |
| 2 | T-DM1 | 10 | IV | 12 | 10 | qdx1 |
| 4 | T-Compound I | 10 | IV | 12 | 10 | qdx1 |
| 5 | T-Compound K | 10 | IV | 12 | 10 | qdx1 |

Figure 14:
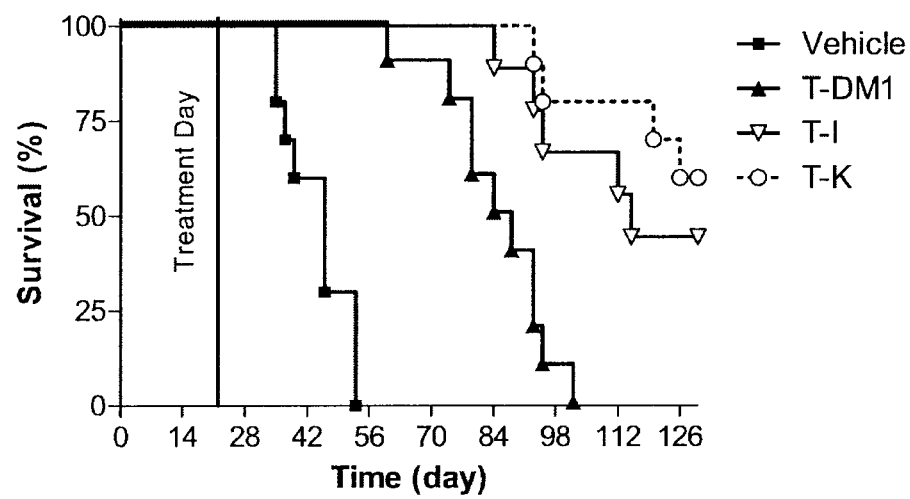
FIG. 14 shows the survival of NSG mice inoculated with NCI-N87 tumor cells and treated on Day 22 with a single IV injection of either vehicle, T-DM1, T-I, or T-K at 12 mg/kg, n=10.

The assessed ADCs are efficacious at reducing tumour volume and delaying tumour regrowth. All ADC tested significantly increased days to tumour recurrence when compared to vehicle (FIG. 14). T-Compound I had a significantly increased survival rate compared to T-DM1 but showed no significant difference when compared to T-Compound K. T-Compound K had a significantly increased survival rate compared to T-DM1 but showed no significant difference when compared T-Compound I.

Biological Example 3

Efficacy Study of Toxins in NCI-N87 Tumor-Bearing Mice

Female NOD/SCID gamma (NSG) mice (Jackson Laboratories) were implanted subcutaneously in the back with the NCI-N87 tumour cell line. NCI-N87 human gastric carcinoma cells were derived from a liver metastasis of a well differentiated carcinoma of the stomach taken prior to cytotoxic therapy. The tumour was passaged as a xenograft in athymic nude mice for three passages before the cell line was established.

Tumours established over a period of 25 days, and test subjects were grouped (Table 3) according to tumour volume such that each group (n=6-8) had an equal distribution of tumour volumes (mean volume >150 mm$^3$).

Figure 15:
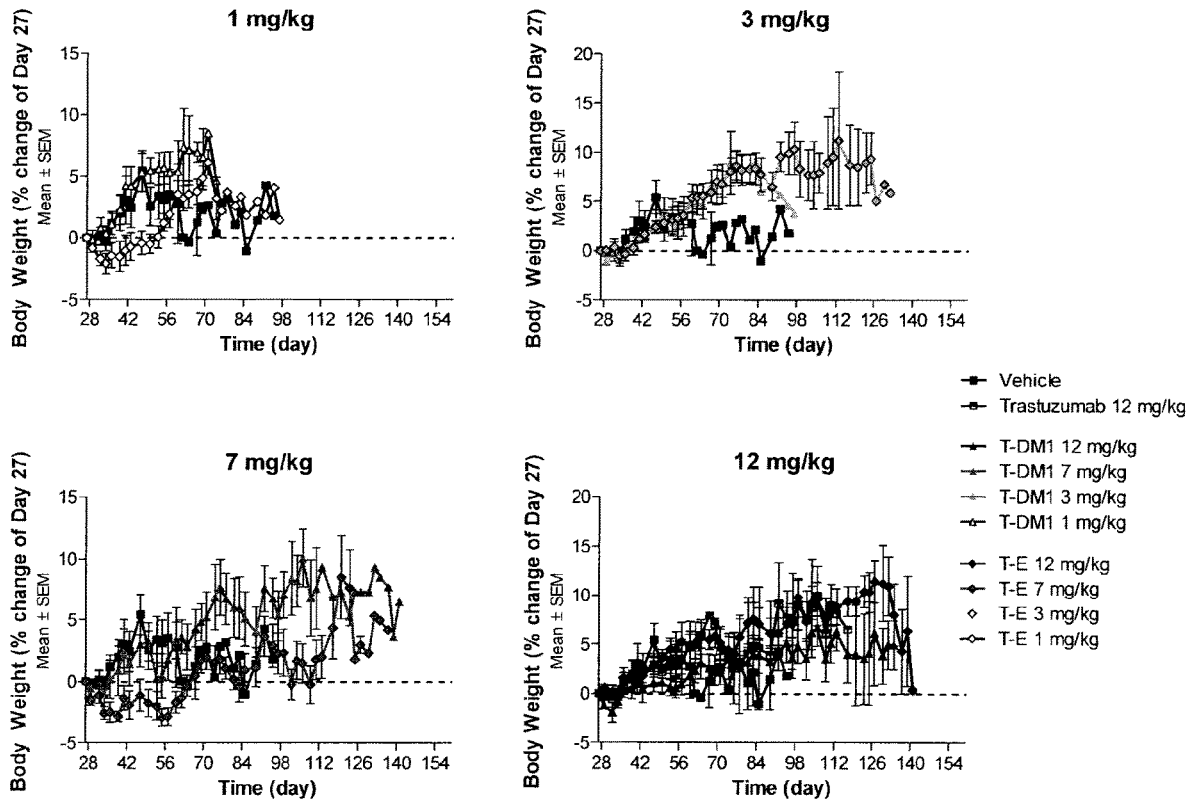
FIG. 15 shows the body weights of study mice, represented as percent change of baseline (Day 27), for NSG mice inoculated with NCI-N87 cells (with matrigel) and treated on Day 27 with a single IV injection of vehicle, Trastuzumab (T), T-DM1, T-Compound E at 1, 3, 7 or 12 mg/kg. Data is shown as averages (+/−SEM) n=6 (Veh and T), n=7 (T-DM1 3 mg/kg), and n=8 for all other groups.
Figure 16:
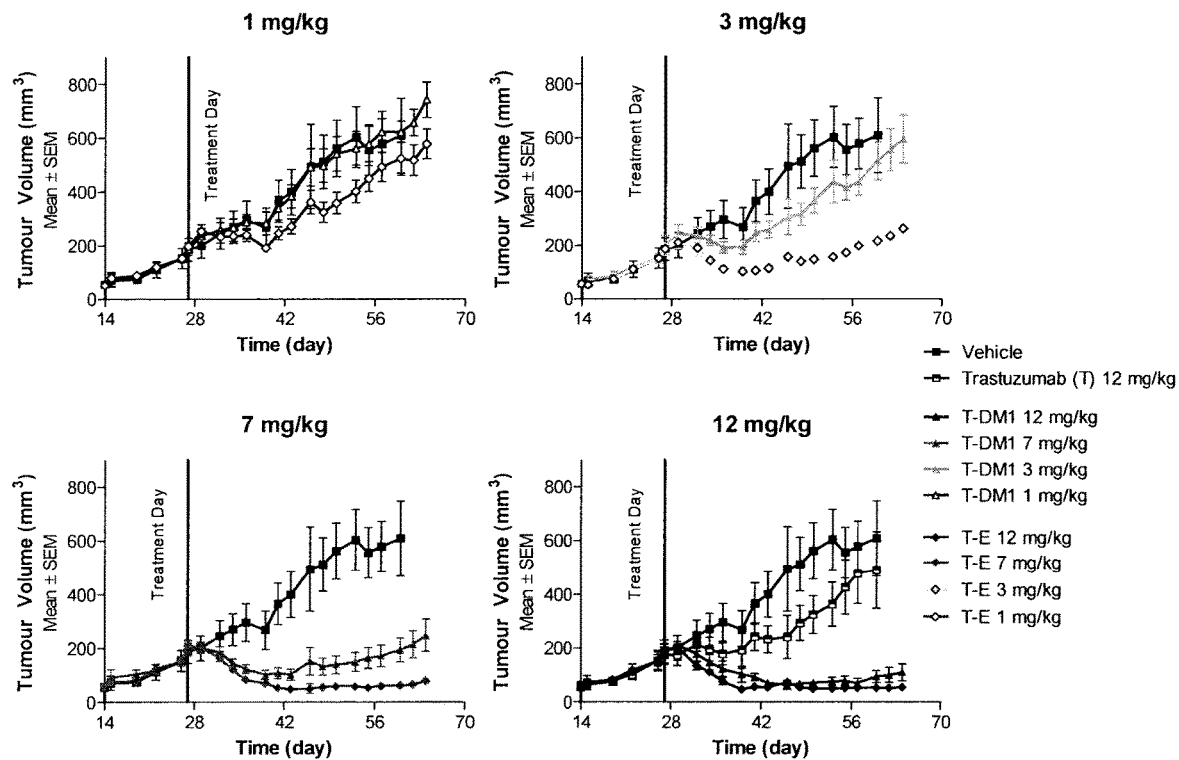
FIG. 16 shows the tumor volumes of study mice following a single dose of ADC, Trastuzumab, or vehicle.
Figure 17:
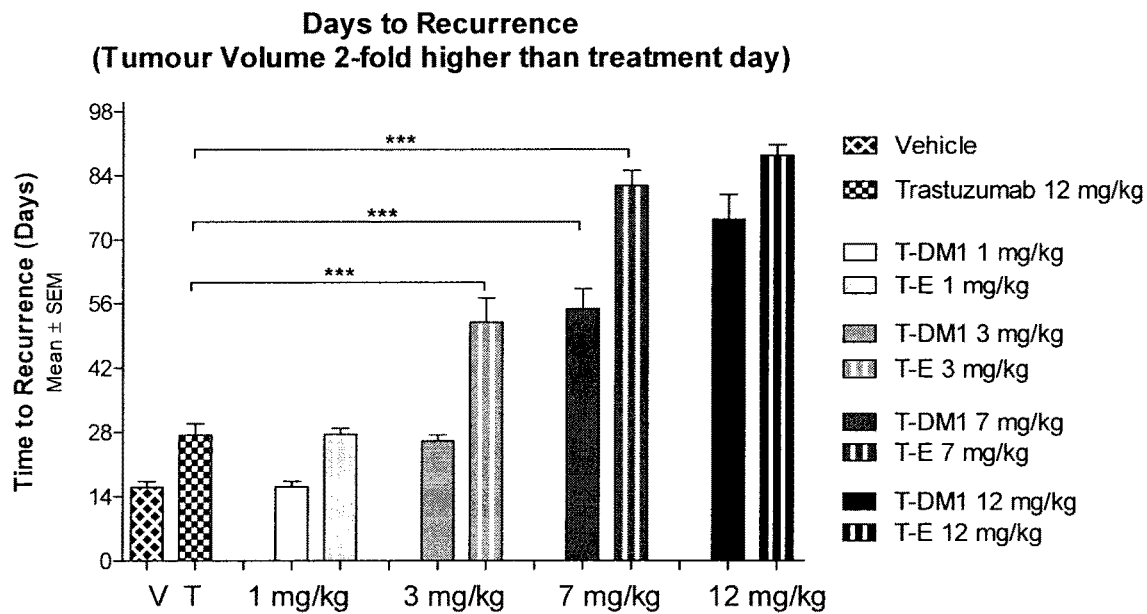
FIG. 17 shows the time to tumor recurrence (2-fold increase in volume compared to treatment day) of NCI N87 tumor volumes (with matrigel) in NSG mice treated on Day 27 with a single IV injection of vehicle, Trastuzumab (T), T-DM1, or T-Compound E at 1, 3, 7 or 12 mg/kg. Data are shown as averages (+/SEM) n=6 (Veh and T), n=7 (T-DM1 3 mg/kg), and n=8. *** P<0.001

Test articles were administered once (on Day 27) intravenously at the doses indicated in the study grouping in Table 3. Animal health was assessed acutely using Post Injection Clinical Observation Record (PICOR) forms. Body weights (FIG. 15) and tumour volumes (FIG. 16) were measured every Monday, Wednesday, and Friday. Animals remained on study until their tumours reached 800 mm$^3$ in size or they otherwise required euthanasia due to achieving a humane endpoint.

TABLE 3

BIOLOGICAL EXAMPLE 3 STUDY GROUPING

| Group # | Test Article | n | Admin. Route | Dose (mg/kg) | Dose Volume (mL/kg) | Schedule |
|---|---|---|---|---|---|---|
| 1 | Vehicle | 6 | IV | N/A | 10 | qdx1 |
| 2 | Trastuzumab | 6 | IV | 12 | 10 | qdx1 |

TABLE 3-continued

BIOLOGICAL EXAMPLE 3 STUDY GROUPING

| Group # | Test Article | n | Admin. Route | Dose (mg/kg) | Dose Volume (mL/kg) | Schedule |
|---|---|---|---|---|---|---|
| 3 | T-DM1 | 7 | IV | 12 | 10 | qdx1 |
| 4 | T-DM1 | 7 | IV | 7 | 10 | qdx1 |
| 5 | T-DM1 | 7 | IV | 3 | 10 | qdx1 |
| 6 | T-DM1 | 7 | IV | 1 | 10 | qdx1 |
| 11 | T-Compound E | 8 | IV | 12 | 10 | qdx1 |
| 12 | T-Compound E | 8 | IV | 7 | 10 | qdx1 |
| 13 | T-Compound E | 8 | IV | 3 | 10 | qdx1 |
| 14 | T-Compound E | 8 | IV | 1 | 10 | qdx1 |

T = Trastuzumab

The assessed ADCs are efficacious at reducing tumour volume and delaying tumour regrowth. T-Compound E had a significant effect on duration until recurrence at the 3 mg/kg dose, and survival rate at the 7 mg/kg dose (not shown) in NCI-N87 tumour bearing NSG mice following a single IV dose. There was a direct relationship between ADC dose and effect. Increasing doses of ADC resulted in the most significant effects on duration until recurrence and survival rate in NCI-N87 tumour bearing NSG mice. The highest dose, 12 mg/kg, resulted in the greatest reduction in tumour volumes, duration until tumour recurrence, and survival rate for all ADC. All treatments were well tolerated by the study mice.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

It is contemplated that the different parts of the present description may be combined in any suitable manner. For instance, the present examples, methods, aspects, embodiments or the like may be suitably implemented or combined with any other embodiment, method, example or aspect of the invention.

What is claimed is:

1. A conjugate having the following structure (Ia):

$$[(P)_o\text{-}(L)]_m\text{-}(T) \quad (Ia)$$

wherein:
(P) is a microtubule disrupting peptide toxin,
(L) is a linker,
(T) is a targeting moiety that specifically binds to a target antigen, the targeting moiety selected from an antibody and an antigen-binding antibody fragment,
m is an integer from 1 to 10, and
o is an integer from 1 to 20;
wherein:
(P) has structure (XX):

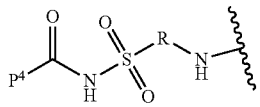

(XX)

and (L)-(T) has structure (III):

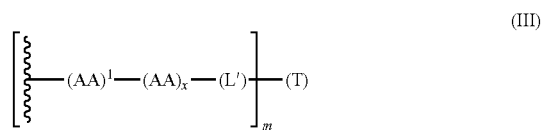

(III)

wherein:
$P^4$ is the remaining portion of (P);
R is selected from the group consisting of optionally substituted alkyl, optionally substituted alkylamino, optionally substituted cycloalkyl, optionally substituted aryl, optionally substituted heterocyclyl, and optionally substituted heteroaryl;
each AA is independently an amino acid;
$(AA)^1\text{-}(AA)_x$ is a dipeptide, a tripeptide, a tetrapeptide or a pentapeptide;
(L') is the remaining portion of linker (L) or is absent;
the —NH- group bonded to R in structure (XX) forms a junction peptide bond (JPB) with $(AA)^1$ in structure (III), and
wherein $(AA)^1\text{-}(AA)_x$ taken together forms a protease recognition sequence that facilitates cleavage of the JPB.

2. A conjugate having the following structure (Ia):

$$[(P)_o\text{-}(L)]_m\text{-}(T) \quad (Ia)$$

wherein:
(P) is a microtubule disrupting peptide toxin,
(L) is a linker,
(T) is a targeting moiety that specifically binds to a target antigen, the targeting moiety selected from an antibody and an antigen-binding antibody fragment,
m is an integer from 1 to 10, and
o is an integer from 1 to 20;
wherein:
(P) has structure (XX):

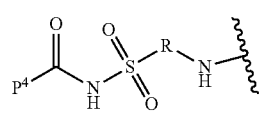

(XX)

wherein:
$P^4$ is the remaining portion of (P);
—R-NH- is selected from the group consisting of:

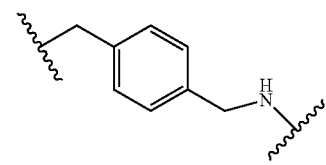

,

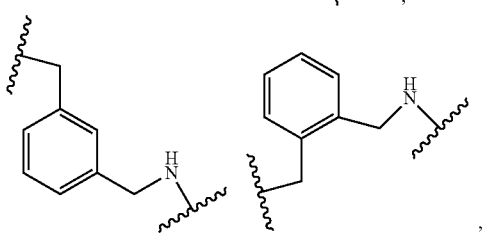

,

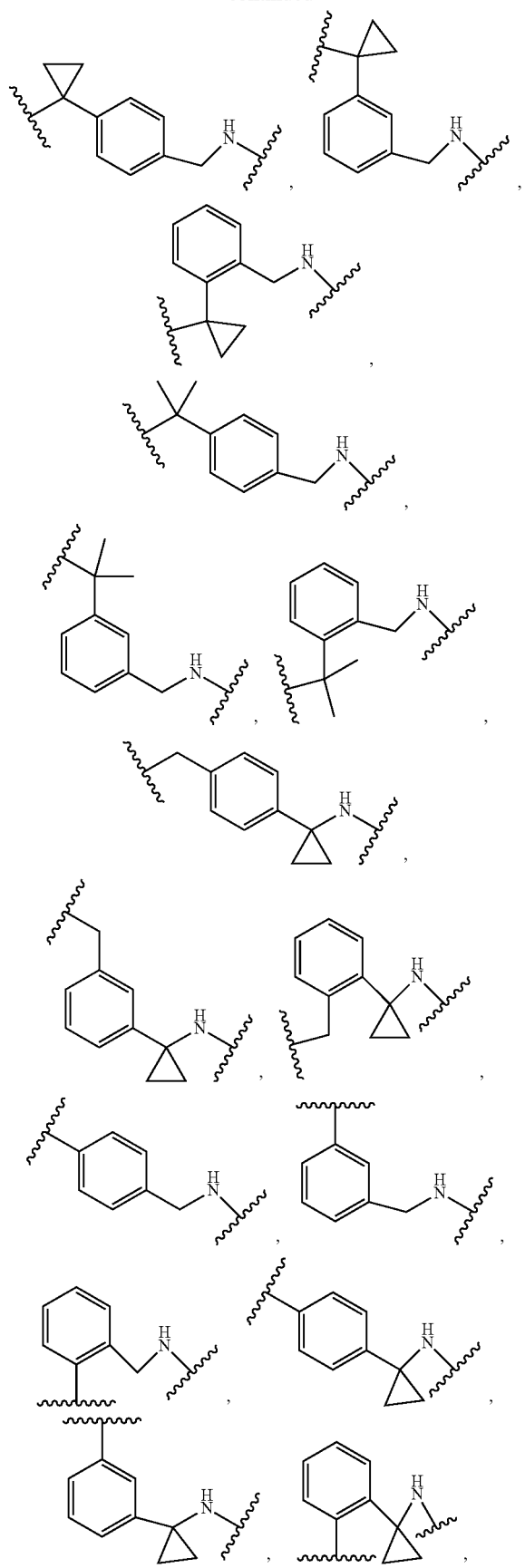
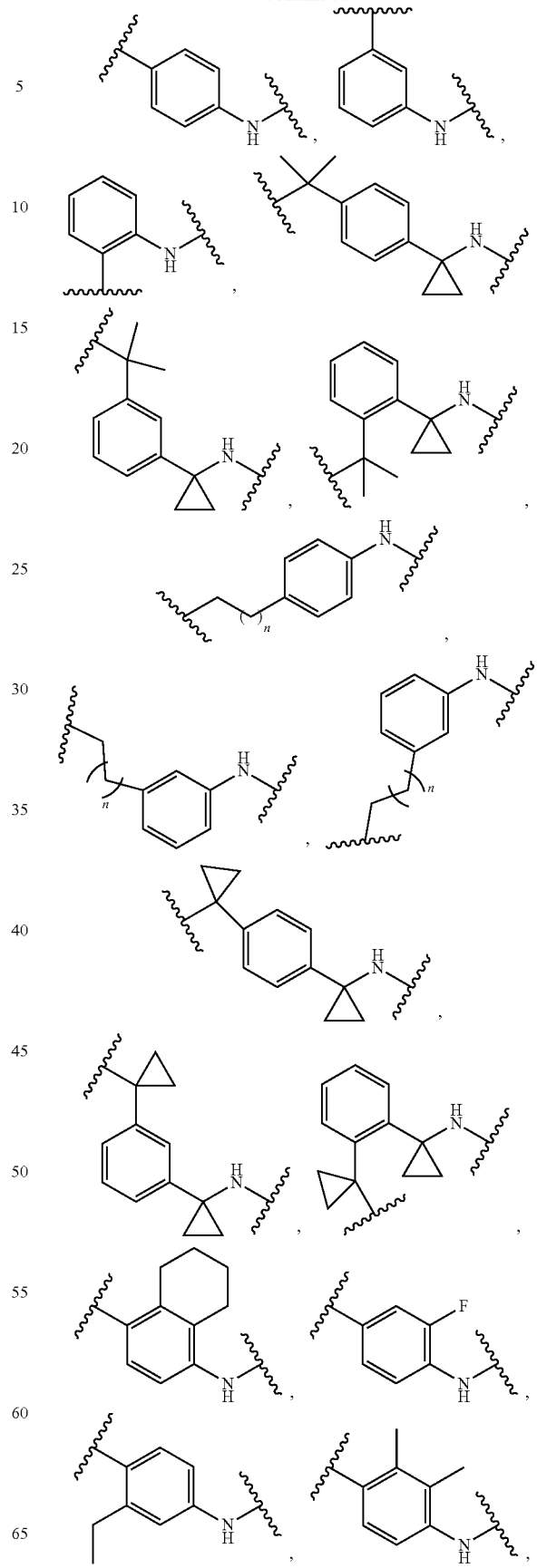

-continued

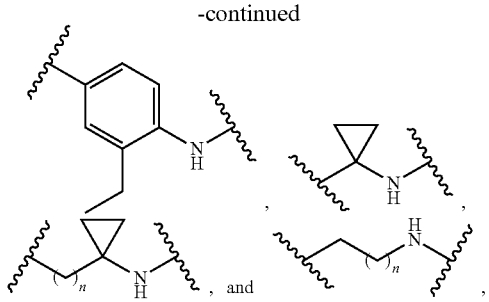

wherein each n is independently an integer from 0-10; and (L)-(T) has structure (III):

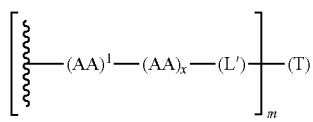

wherein:
each AA is independently an amino acid;
$(AA)^1$-$(AA)_x$ is a dipeptide, a tripeptide, a tetrapeptide or a pentapeptide;
(L') is the remaining portion of linker (L) or is absent;
the —NH- group bonded to R in structure (XX) forms a junction peptide bond (JPB) with $(AA)^1$ in structure (III), and
$(AA)^1$-$(AA)_x$ taken together forms a protease recognition sequence that facilitates cleavage of the JPB.

3. The conjugate of claim 2, wherein —R-NH- is selected from the group consisting of:

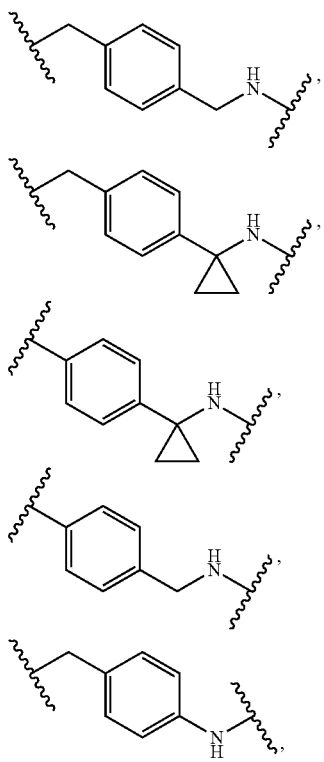

-continued

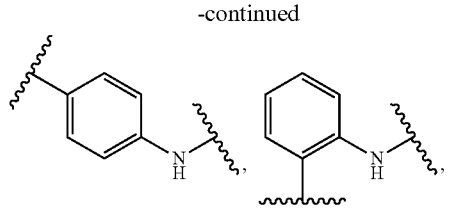

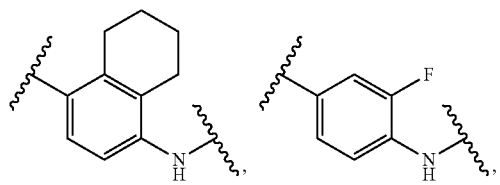

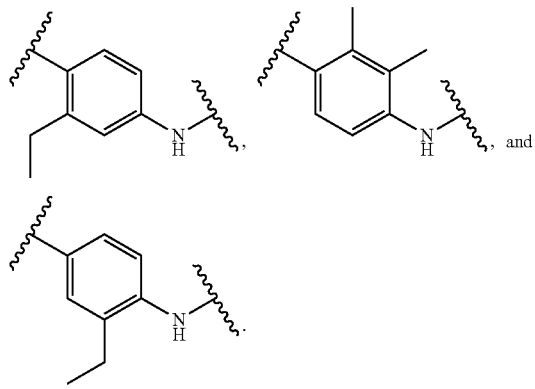

4. The conjugate of claim 3, wherein —R-NH- is selected from the group consisting of:

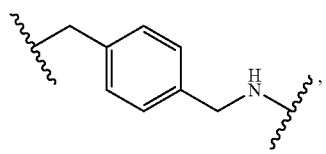

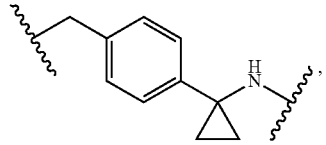

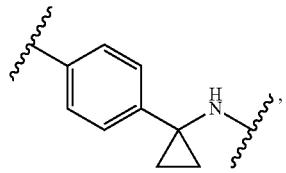

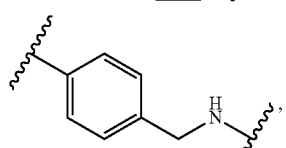

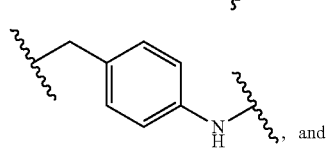

-continued

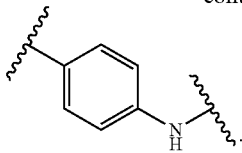

5. A pharmaceutical composition comprising a conjugate of claim 1, or a stereoisomer or pharmaceutically acceptable salt thereof, and a pharmaceutically acceptable carrier, diluent or excipient.

6. A method of treating cancer in a mammal comprising administering to a mammal in need thereof an effective amount of a conjugate of claim 1.

7. A method of inhibiting tumor growth in a mammal comprising administering to a mammal in need thereof an effective amount of a conjugate of claim 1.

8. The conjugate of claim 1, wherein the antibody or antigen-binding antibody fragment specifically binds to an antigen present on a tumor cell.

9. The conjugate of claim 1, wherein o is 1.

10. The conjugate of claim 1, wherein (P) has the following structure (XIV):

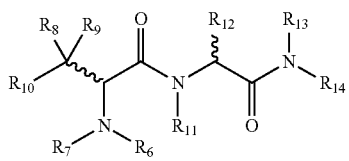

wherein:

$R_6$ and $R_7$ are independently selected from the group consisting of: H and a saturated or unsaturated moiety having a linear, branched, or non-aromatic cyclic skeleton containing one to ten carbon atoms, and the carbon atoms are optionally substituted with: —OH, —I, —Br, —Cl, —F, —CN, —CO$_2$H, —CHO, —COSH, or —NO$_2$; or $R_7$ and $R_{10}$ are fused and form a ring;

$R_8$ and $R_9$ are independently selected from the group consisting of: H, R', and ArR'—, or $R_8$ and $R_9$ are joined to form a ring, wherein the ring is a three to seven-member non-aromatic cyclic skeleton within the definition of R';

$R_{10}$ is selected from the group consisting of: H, R', ArR'—, and Ar;

$R_{11}$ is selected from the group consisting of: H, R', and ArR'—;

$R_{12}$ and $R_{13}$ are independently selected from the group consisting of: H, R', and ArR'—;

$R_{14}$ is:

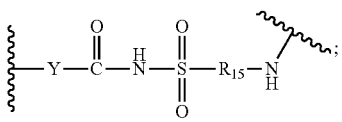

$R_{15}$ is selected from the group consisting of optionally substituted alkyl, optionally substituted alkylamino, optionally substituted cycloalkyl, optionally substituted aryl, optionally substituted heterocyclyl, and optionally substituted heteroaryl;

R' is a saturated or unsaturated moiety having a linear, branched, or non-aromatic cyclic skeleton containing one to ten carbon atoms, zero to four nitrogen atoms, zero to four oxygen atoms, and zero to four sulfur atoms, and the carbon atoms are optionally substituted with: =O, =S, OH, —OR$_{16}$, —O$_2$CR$_{16}$, —SH, —SR$_{16}$, —SOCR$_{16}$, —NH$_2$, —NHR$_{16}$, —N(R$_{16}$)$_2$, —NHCOR$_{16}$, —NR$_{16}$COR$_{16}$, —I, —Br, —Cl, —F, —CN, —CO$_2$H, —CO$_2$R$_{16}$, —CHO, —COR$_{16}$, —CONH$_2$, —CONHR$_{16}$, —CON(R$_{16}$)$_2$, —COSH, —COSR$_{16}$, —NO$_2$, —SO$_3$H, —SOR$_{16}$, or —SO$_2$R$_{16}$, wherein $R_{16}$ is a linear, branched or cyclic, one to ten carbon saturated or unsaturated alkyl group;

Y is a linear, saturated or unsaturated, one to six carbon alkyl group, optionally substituted with R', ArR'—, or X; and X is selected from the group consisting of: —OH, —OR', =O, =S, —O$_2$CR', —SH, —SR', —SOCR', —NH$_2$, —NHR', —N(R')$_2$, —NHCOR', —NRCOR', —I, —Br, —Cl, —F, —CN, —CO$_2$H, —CO$_2$R', —CHO, —COR', —CONH$_2$, —CONHR', —CON(R')$_2$, —COSH, —COSR', —NO$_2$, —SO$_3$H, —SOR', and —SO$_2$R'; and wherein the —NH— group bonded to $R_{15}$ in structure (XIV) forms the junction peptide bond (JPB) with (AA)$^1$.

11. The conjugate of claim 1, wherein (AA)$^1$-(AA)$_x$, is Val-Cit, Ala-Phe, Phe-Lys, Val-Ala, Val-Lys, Ala-Lys, Phe-Cit, Leu-Cit, Ile-Cit, Trp-Cit, Phe-Arg, Val-Lys(Ac), Phe-Lys(Ac), Me-Val-Cit, Gly-Val-Cit, Pro-Pro-Pro, D-Ala-Phe-Lys, (D)-Val-Leu-Lys, Gly-Gly-Arg, Ala-Ala-Asn, Lys-Ser-Gly-Arg, Gly-Phe-Leu-Gly, Leu-Ser-Gly-Arg, Ala-Leu-Ala-Leu, Gly-Gly-Gly-Arg-Arg, Gly-Lys-Ala-Phe-Arg-Arg or HomoGly-Arg-Ser-Arg-Gly.

12. The conjugate of claim 1, wherein (AA)$^1$-(AA)$_x$, is Val-Cit, Phe-Lys, Val-Lys, Ala-Pro, D-Ala-Phe-Lys or D-Phe-Phe-Lys.

13. The conjugate of claim 1, wherein (L') comprises a stretcher moiety and —(AA)$^1$-(AA)$_x$-(L')-(T) has one of the structures (VII) or (VIII):

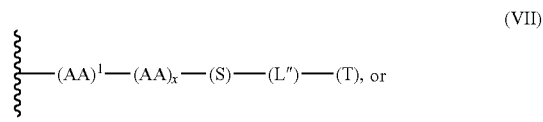

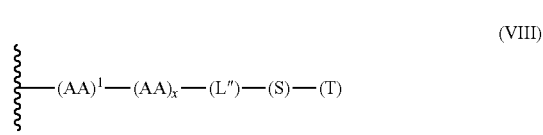

wherein:

L" is a remaining portion of linker (L) or is absent, and (S) is the stretcher moiety.

14. The conjugate of claim 1, wherein L' comprises one or more alkyloxy units.

15. The conjugate of claim 2, wherein (P) is a monovalent radical of a compound selected from:
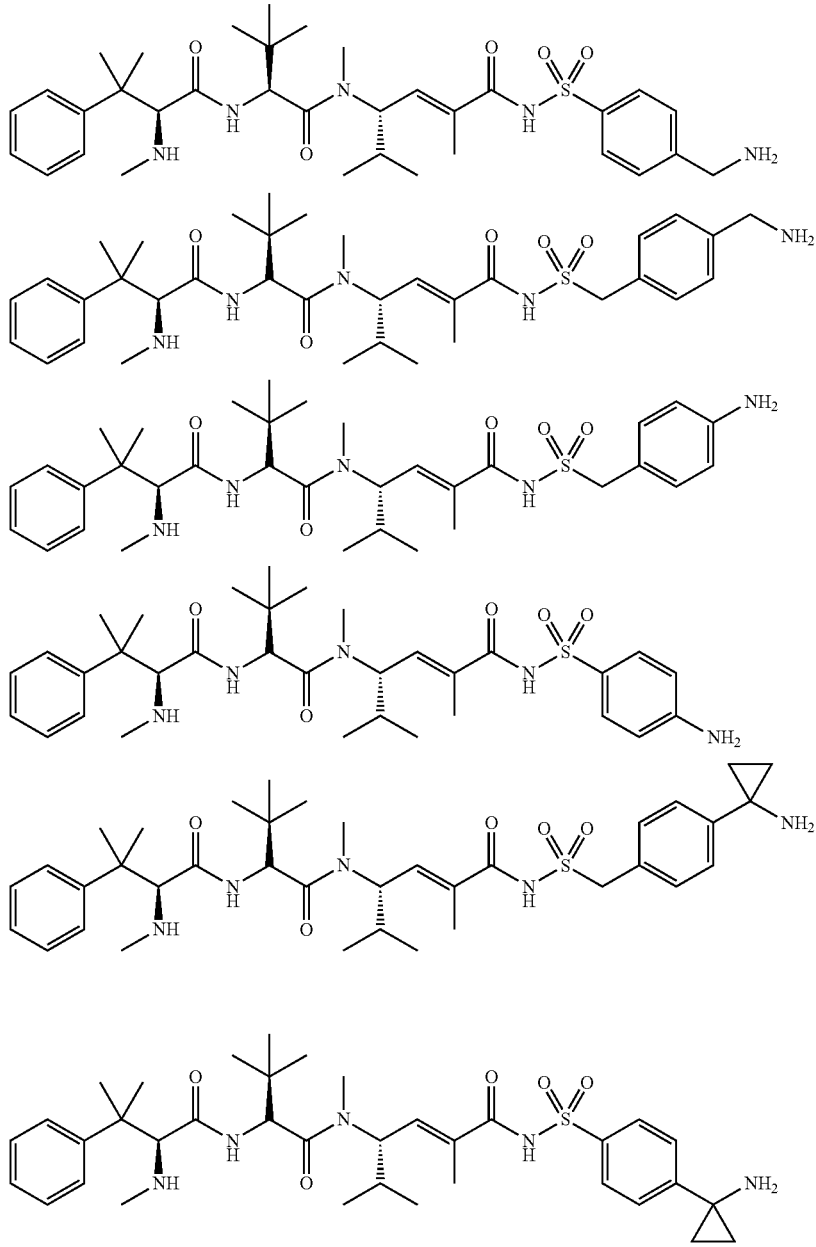
Compound A-5
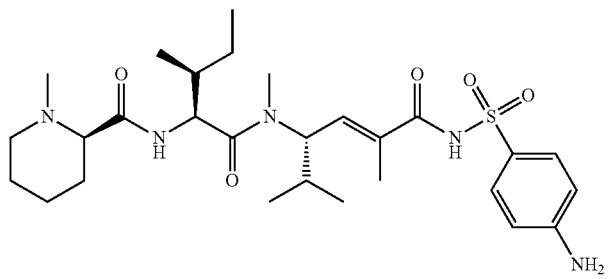
Compound L-6

Compound M-3
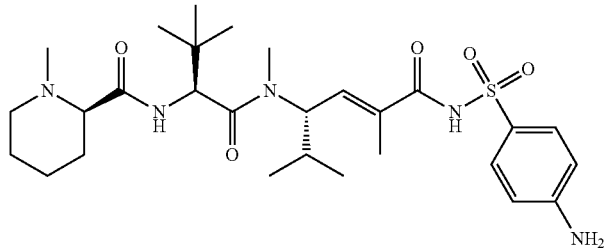
Compound N-2
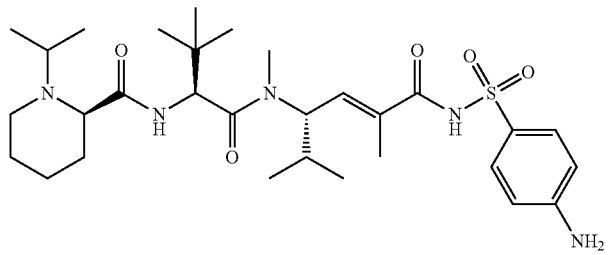
Compound S-2
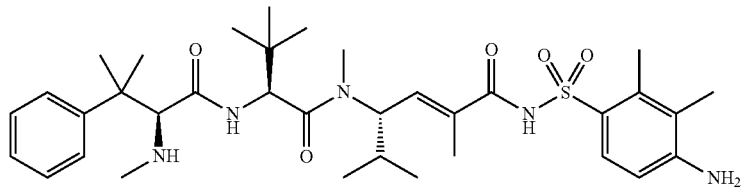
Compound T-2
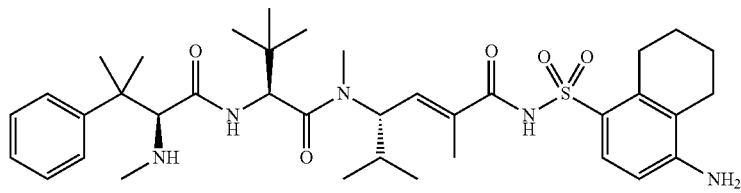
Compound U-2
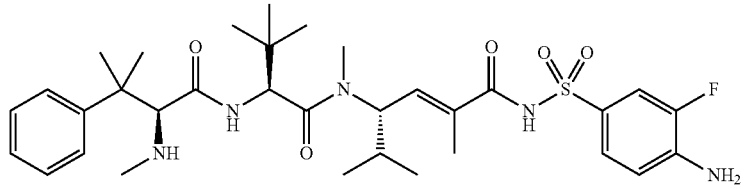
Compound V-2
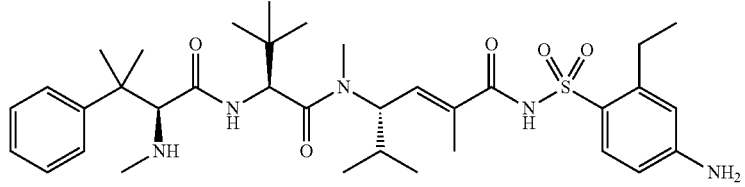

Compound W-2
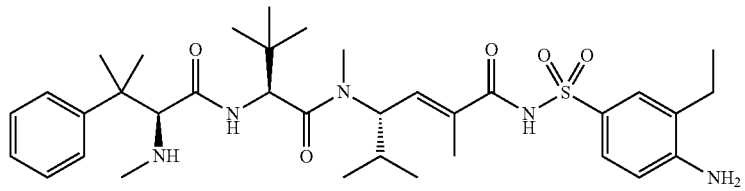
and
Compound DD-2
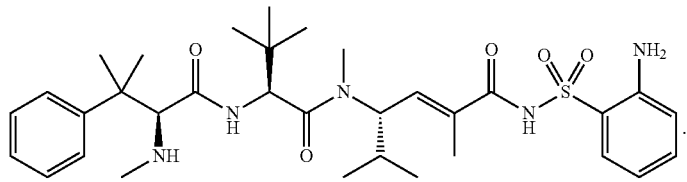
16. The conjugate of claim 2, wherein (P)-(L)- is a monovalent radical of a compound selected from:
Compound A
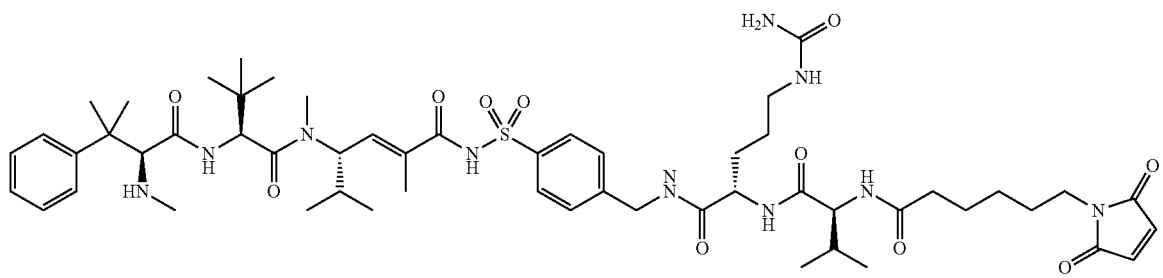
Compound B
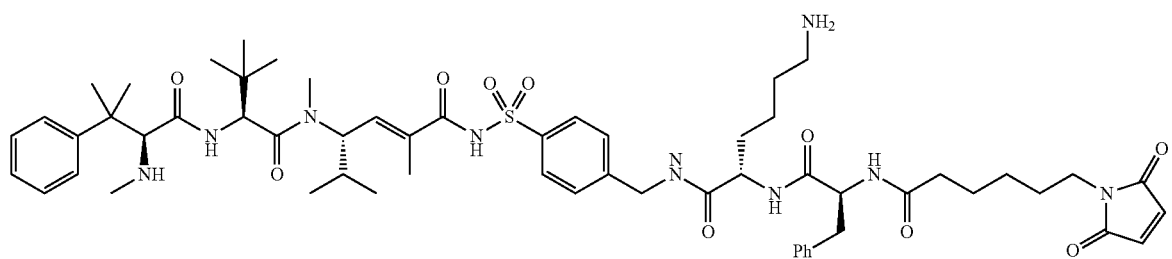
Compound C
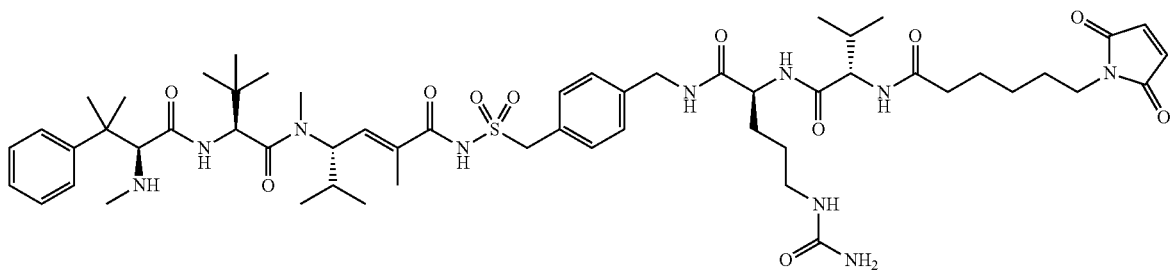

Compound D
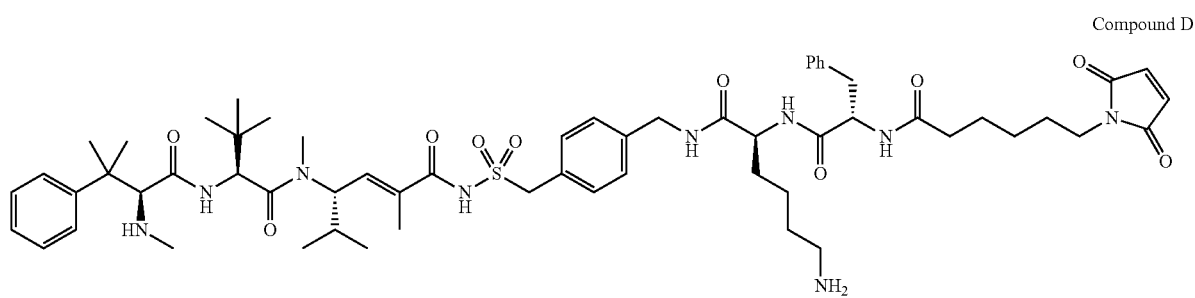
Compound E
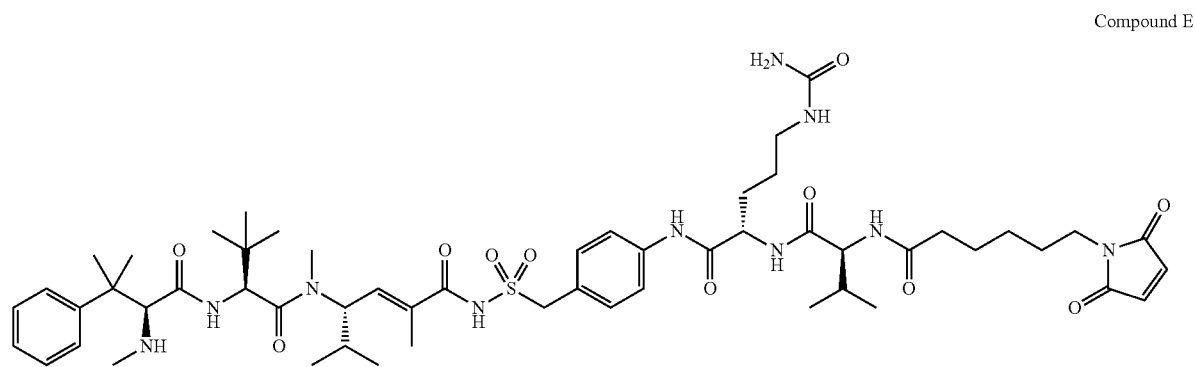
Compound F
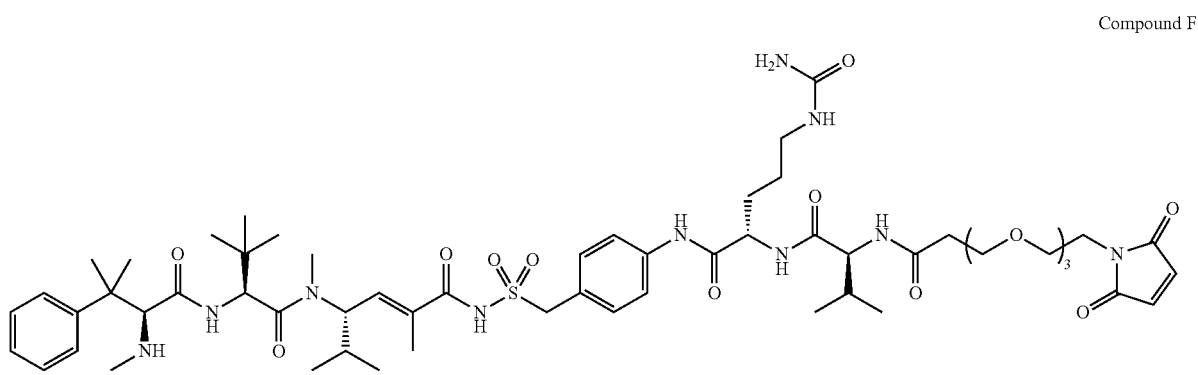
Compound G
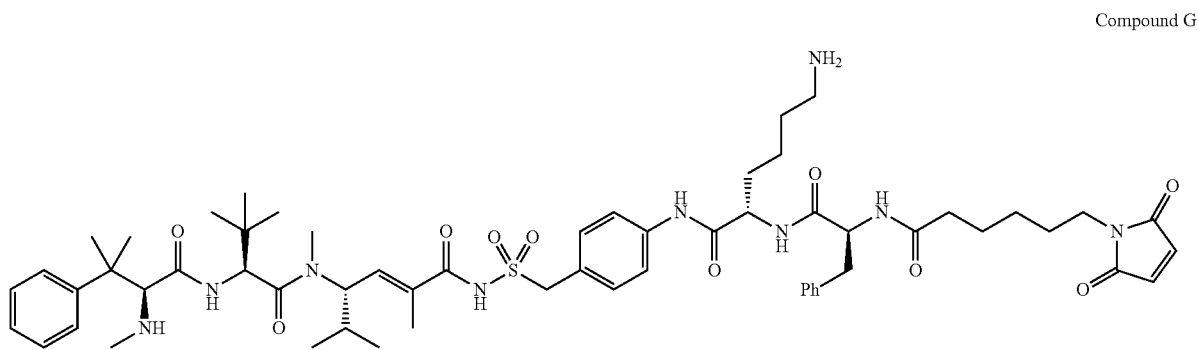

Compound H
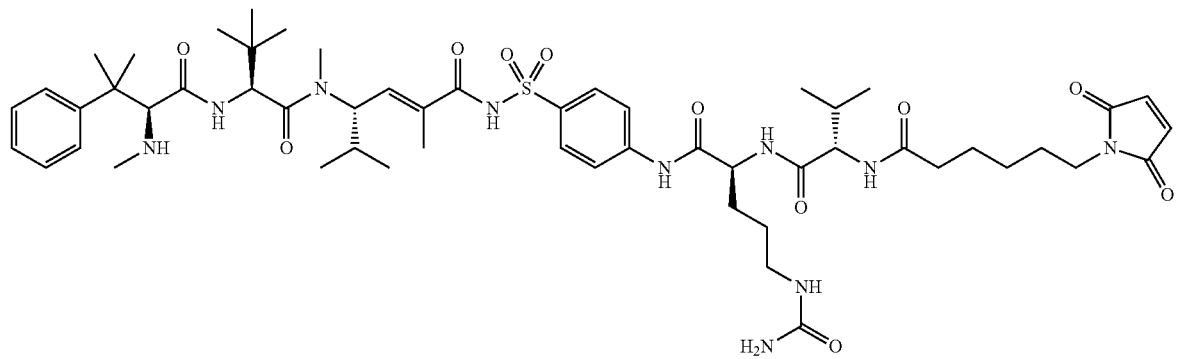
Compound I
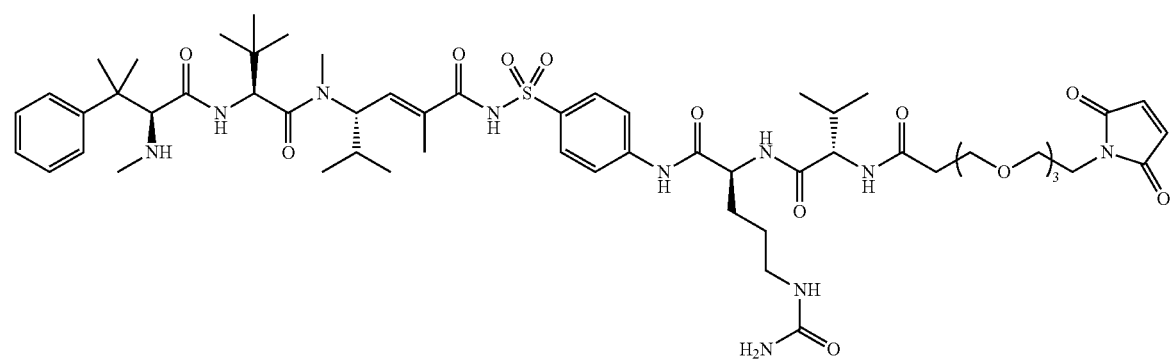
Compound J
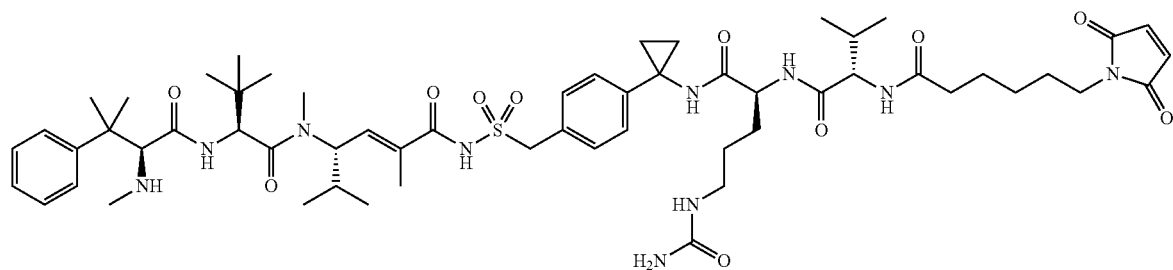
Compound K
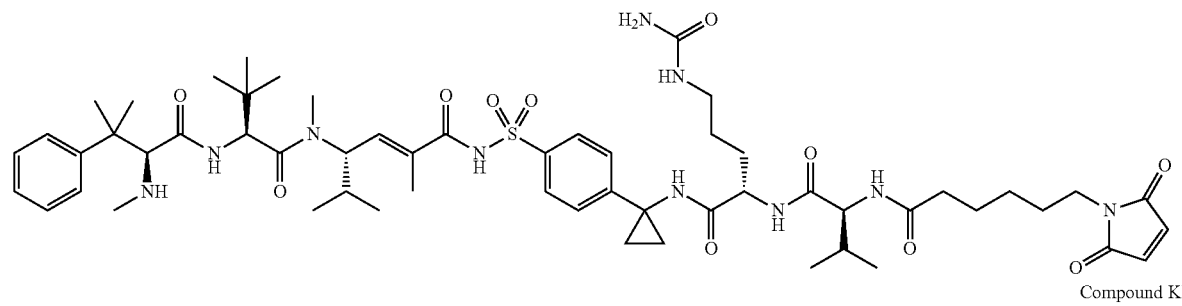
Compound KK
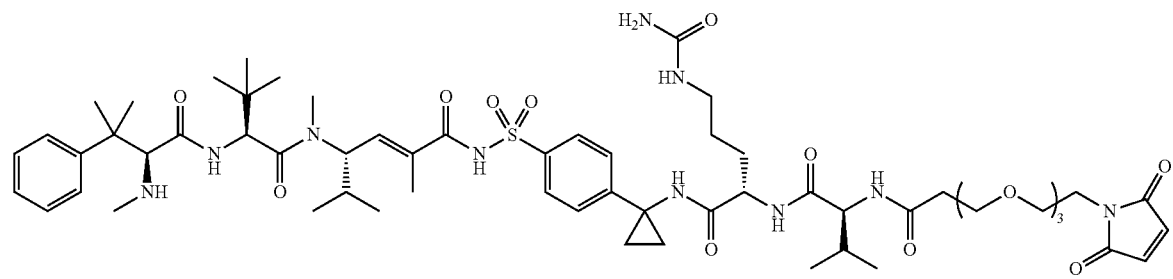

-continued
Compound L
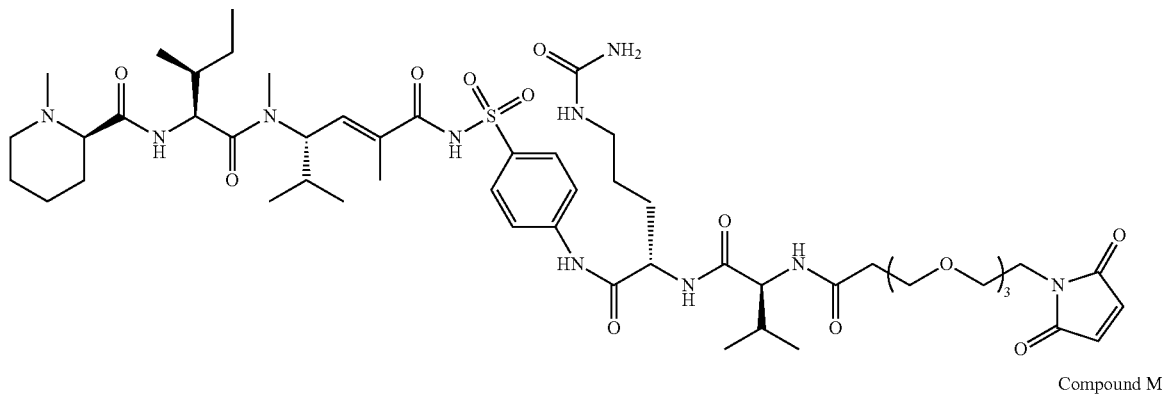
Compound M
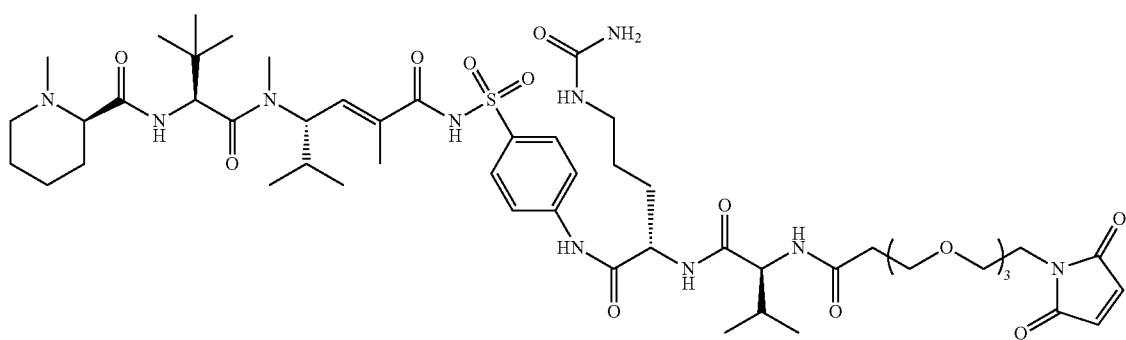
Compound N
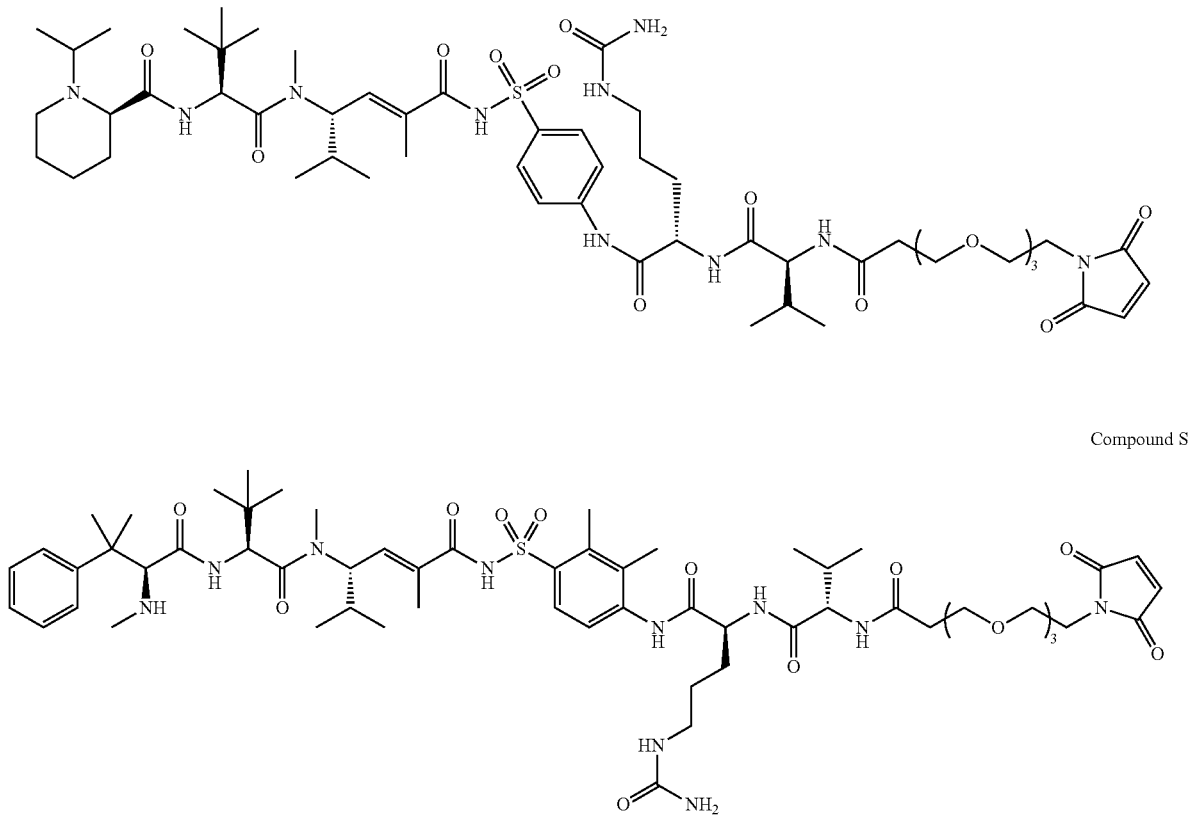
Compound S Compound T
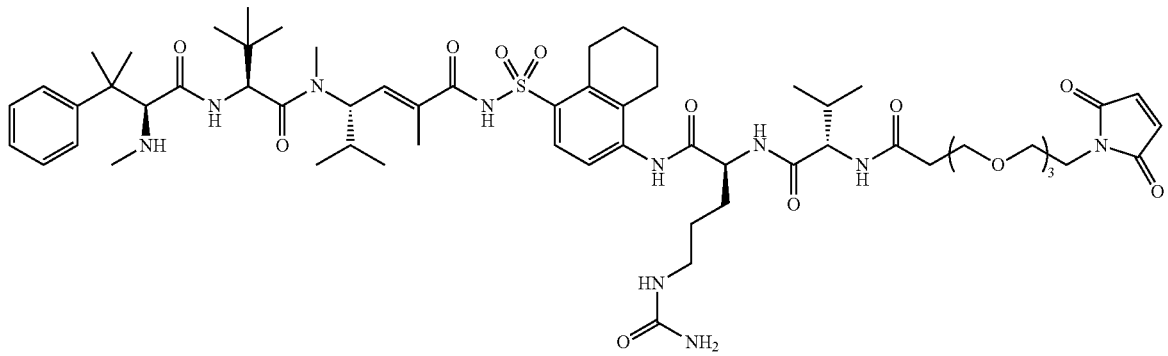
Compound U
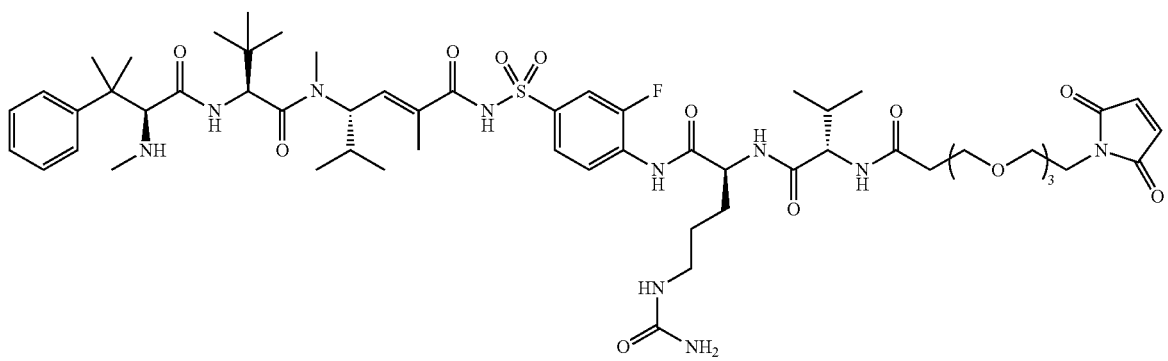
Compound V
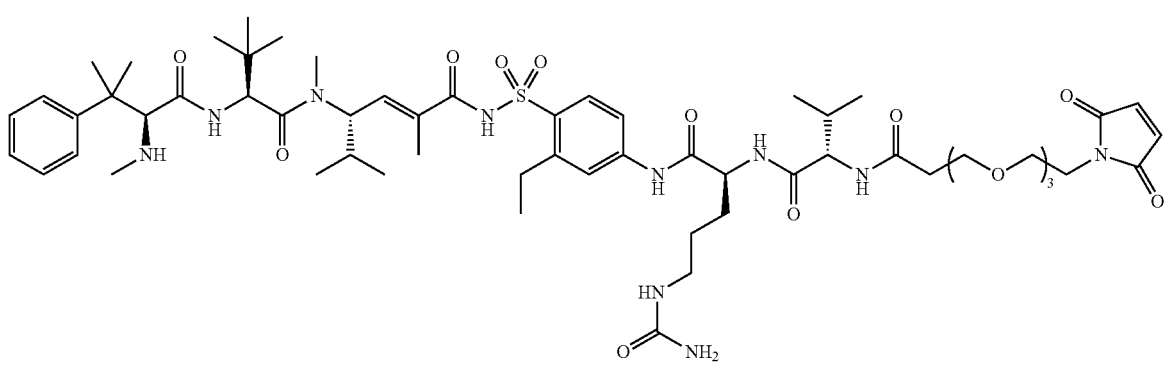
Compound W
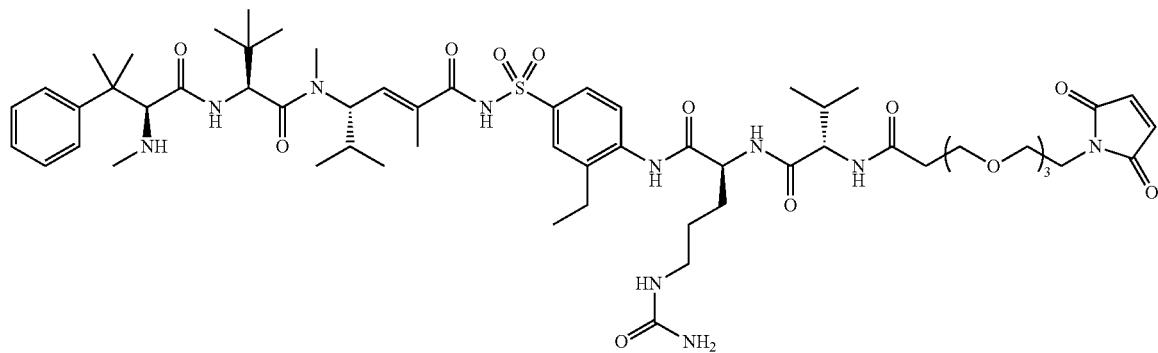

Compound X
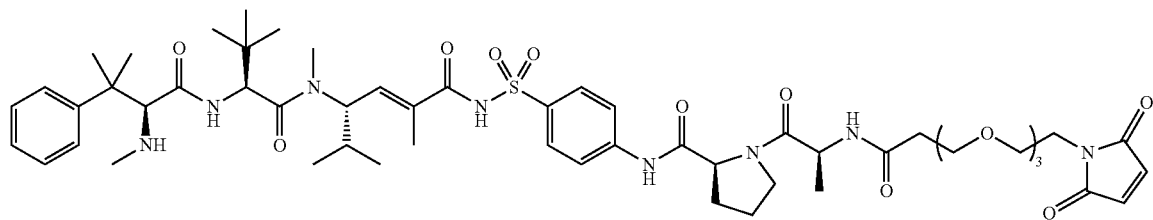
Compound Z
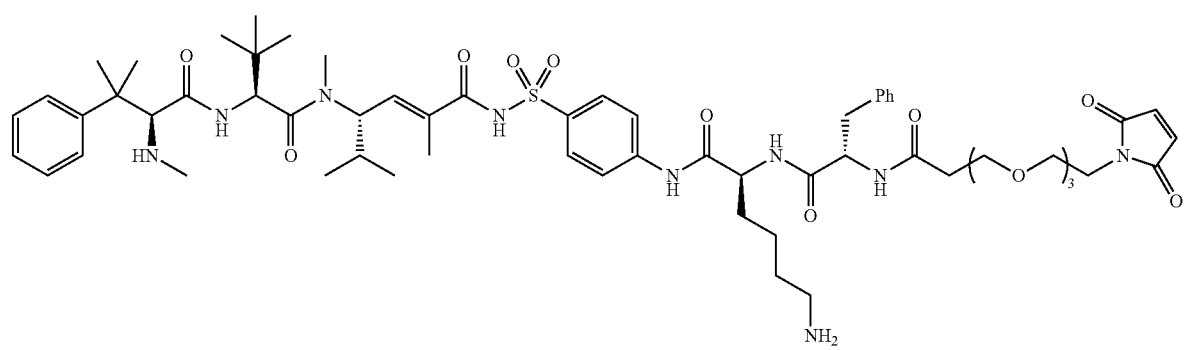
Compound AA
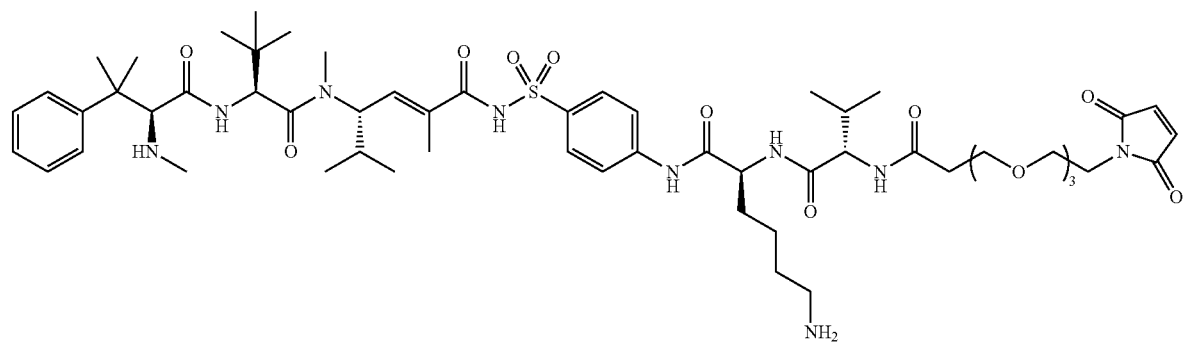
Compound BB
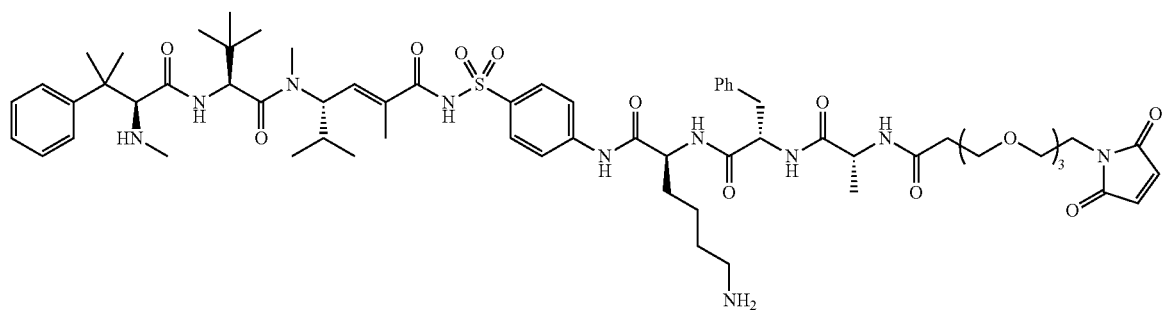

-continued

Compound CC

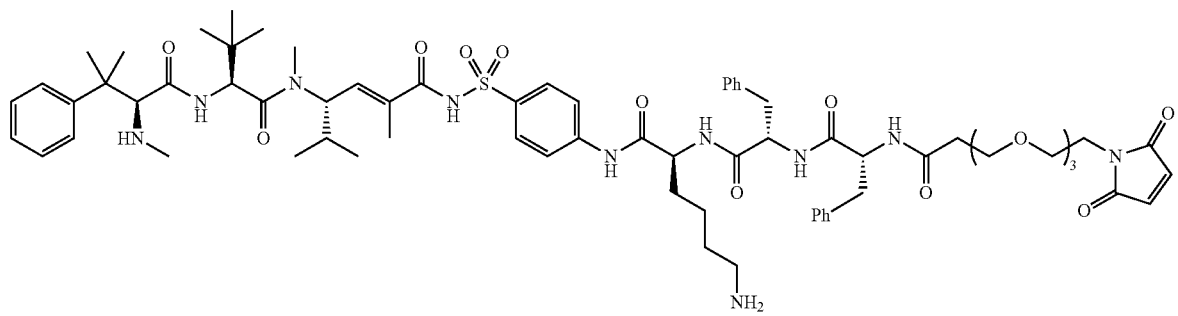

and

Compound DD

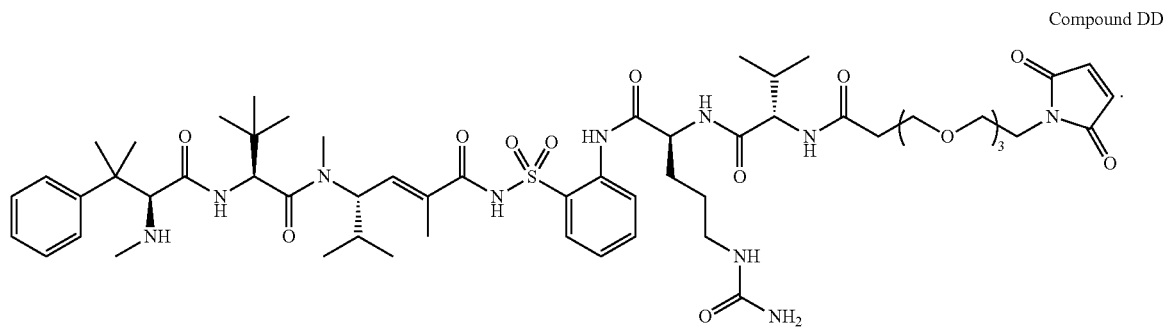

17. The conjugate of claim 1, wherein (P) has the structure (VI):

(VI)

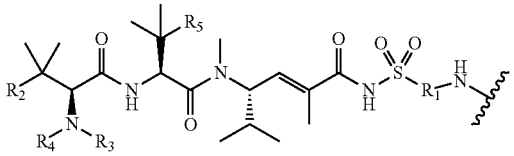

wherein:
R₁ is selected from the group consisting of: optionally substituted alkyl, optionally substituted alkylamino, optionally substituted cycloalkyl, optionally substituted aryl, optionally substituted heterocyclyl, and optionally substituted heteroaryl;
R₂ is selected from the group consisting of: optionally substituted alkyl, optionally substituted alkylamino, optionally substituted cycloalkyl, optionally substituted aryl, optionally substituted heterocyclyl and optionally substituted heteroaryl;
R₃ and R₄ are each independently H or C₁₋₆ alkyl; and
R₅ is C₁₋₆ alkyl or —SH, and wherein the —NH— group bonded to R₁ in structure (VI) forms the junction peptide bond (JPB) with (AA)¹.

18. The conjugate of claim 17, wherein R₁ is optionally substituted aryl.

19. The conjugate of claim 2, wherein (P) has the structure (VI):

(VI)

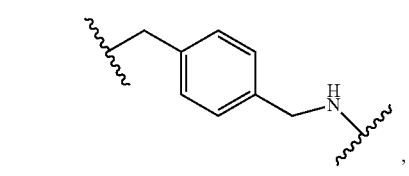

wherein:
—R₁—NH— is selected from the group consisting of:

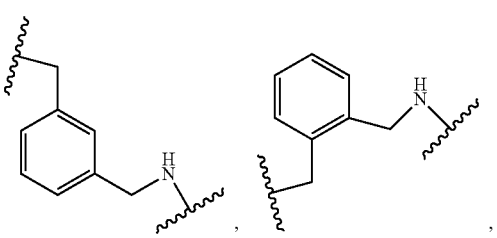

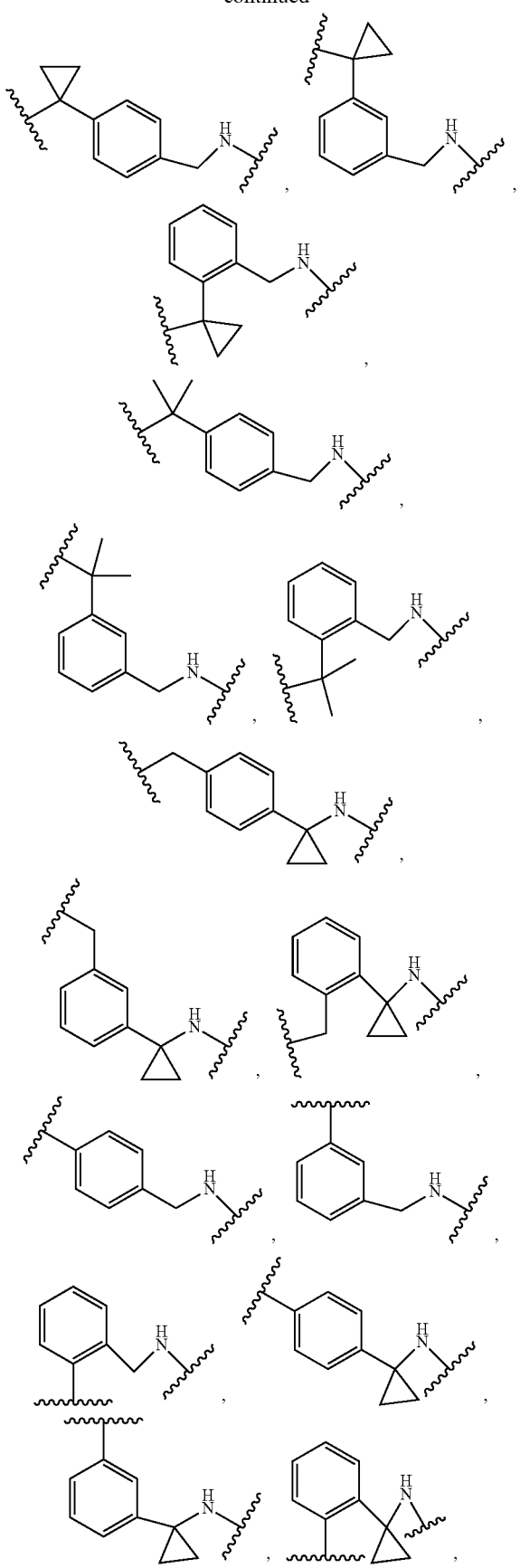
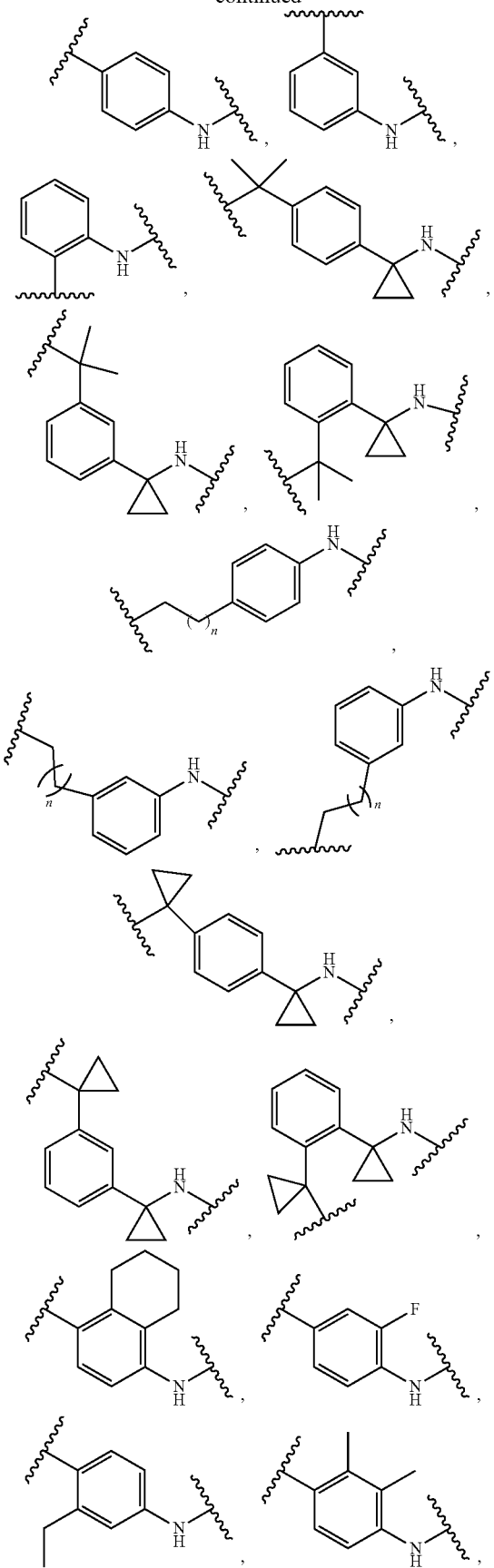

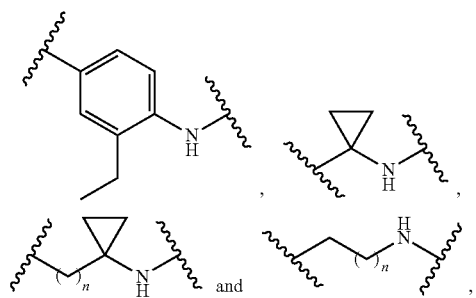

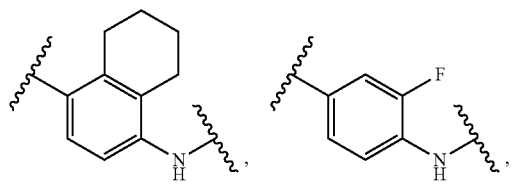

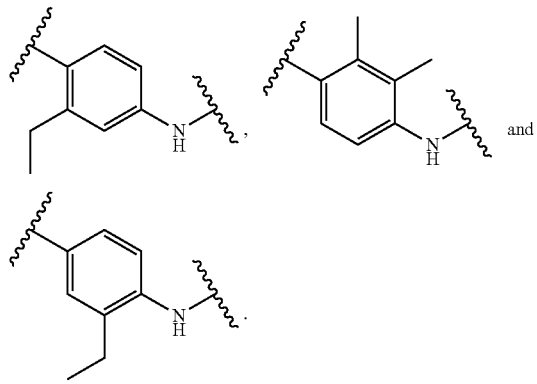

wherein each n is independently an integer from 0 to 10;

$R_2$ is selected from the group consisting of: optionally substituted alkyl, optionally substituted alkylamino, optionally substituted cycloalkyl, optionally substituted aryl, optionally substituted heterocyclyl and optionally substituted heteroaryl;

$R_3$ and $R_4$ are each independently H or $C_{1-6}$ alkyl; and $R_5$ is $C_{1-6}$ alkyl or —SH, and wherein the —NH— group bonded to $R_1$ in structure (VI) forms the junction peptide bond (JPB) with $(AA)^1$.

20. The conjugate of claim 19, wherein —$R^1$—NH— is selected from the group consisting of:

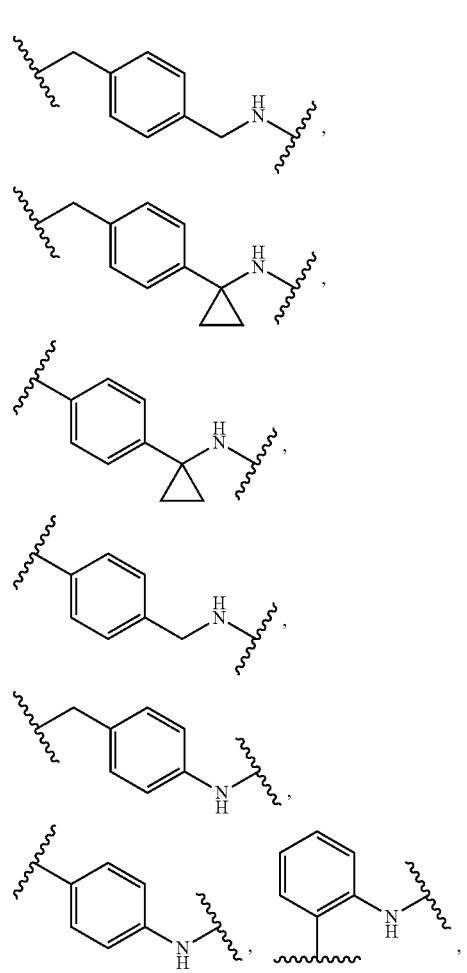

21. The conjugate of claim 19, wherein —$R^1$—NH— is selected from the group consisting of:

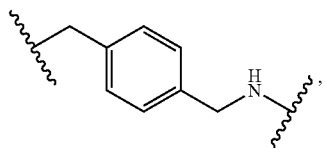

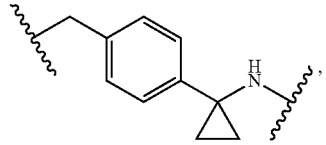

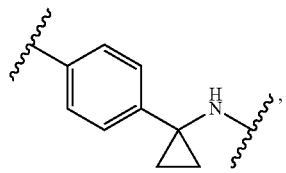

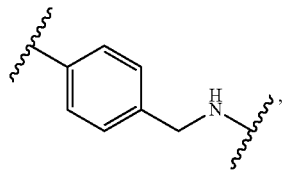

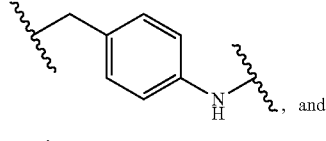

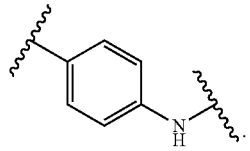

22. The conjugate of claim 17, wherein $R_2$ is selected from the group consisting of:

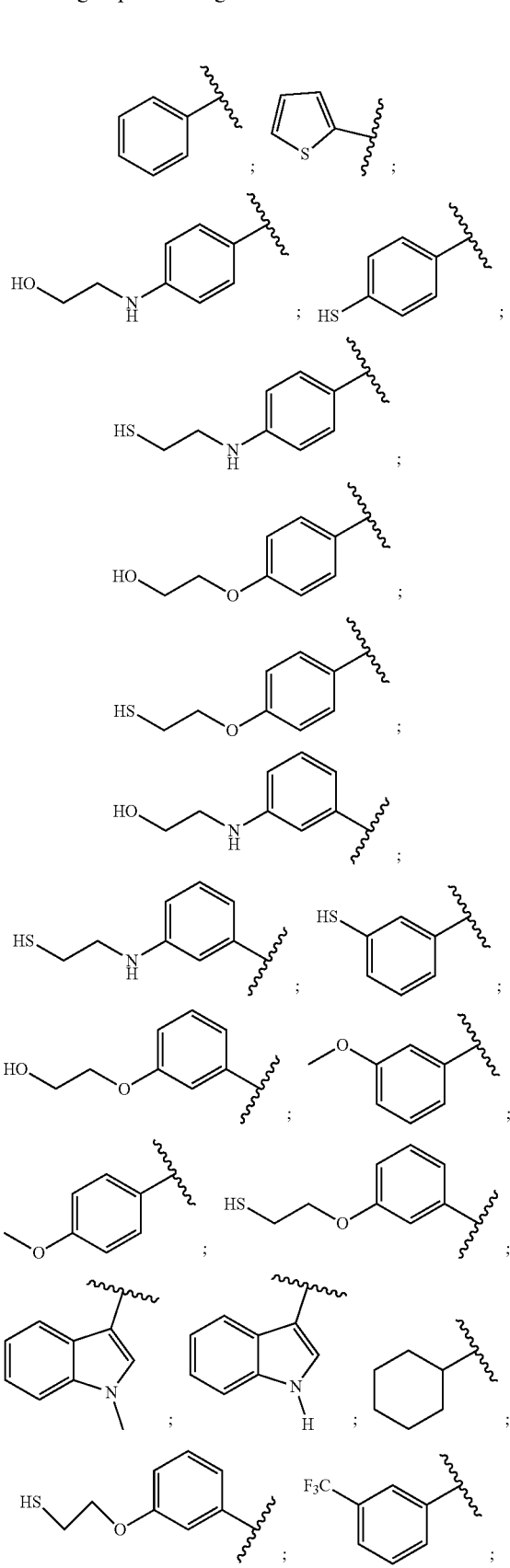

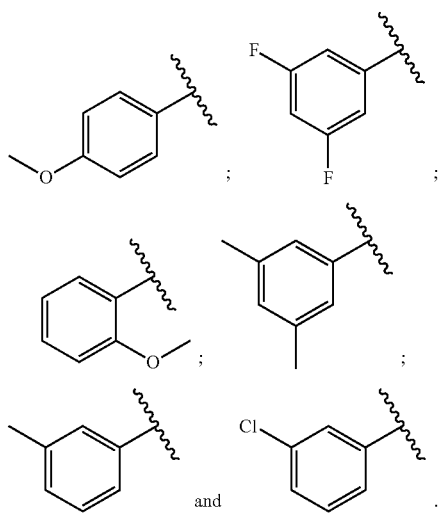

and

23. The conjugate of claim 1, wherein R is optionally substituted aryl.

24. The conjugate of claim 2, wherein R is optionally substituted aryl.

25. The conjugate of claim 2, wherein o is 1.

26. The conjugate of claim 2, wherein the antibody or antigen-binding antibody fragment specifically binds to an antigen present on a tumor cell.

27. The conjugate of claim 2, wherein $(AA)^1\text{-}(AA)_x$ is Val-Cit, Ala-Phe, Phe-Lys, Val-Ala, Val-Lys, Ala-Lys, Phe-Cit, Leu-Cit, Ile-Cit, Trp-Cit, Phe-Arg, Val-Lys(Ac), Phe-Lys(Ac), Me-Val-Cit, Gly-Val-Cit, Pro-Pro-Pro, D-Ala-Phe-Lys, (D)-Val-Leu-Lys, Gly-Gly-Arg, Ala-Ala-Asn, Lys-Ser-Gly-Arg, Gly-Phe-Leu-Gly, Leu-Ser-Gly-Arg, Ala-Leu-Ala-Leu, Gly-Gly-Gly-Arg-Arg, Gly-Lys-Ala-Phe-Arg-Arg or HomoGly-Arg-Ser-Arg-Gly.

28. The conjugate of claim 2, wherein $(AA)^1\text{-}(AA)_x$ is Val-Cit, Phe-Lys, Val-Lys, Ala-Pro, D-Ala-Phe-Lys or D-Phe-Phe-Lys.

29. The conjugate of claim 2, wherein (L') comprises a stretcher moiety and $\text{-}(AA)^1\text{-}(AA)_x\text{-}(L')\text{-}(T)$ has one of the structures (VII) or (VIII):

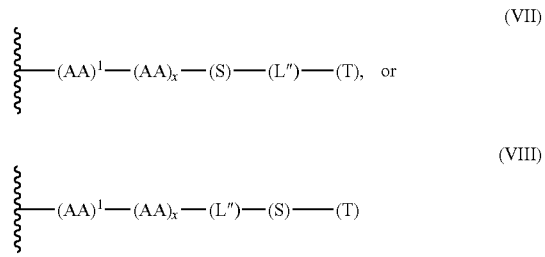

wherein:

L" is a remaining portion of linker (L) or is absent, and (S) is the stretcher moiety.

30. The conjugate of claim 2, wherein L' comprises one or more alkyloxy units.

31. The conjugate of claim 19, wherein $R_2$ is selected from the group consisting of:

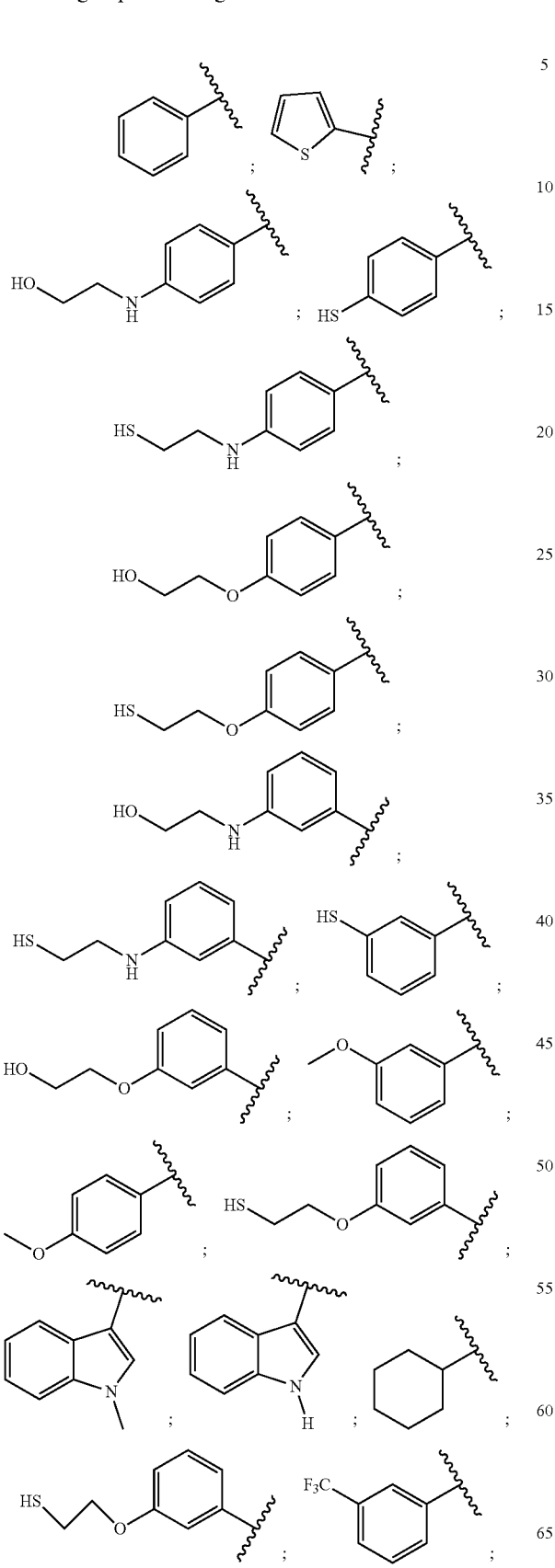

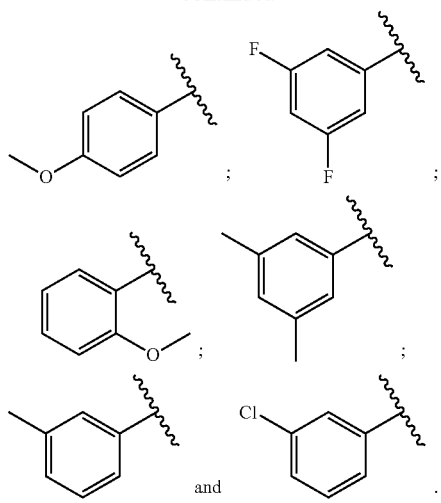

and

32. The conjugate of claim 31, wherein —$R^1$—NH- is selected from the group consisting of:

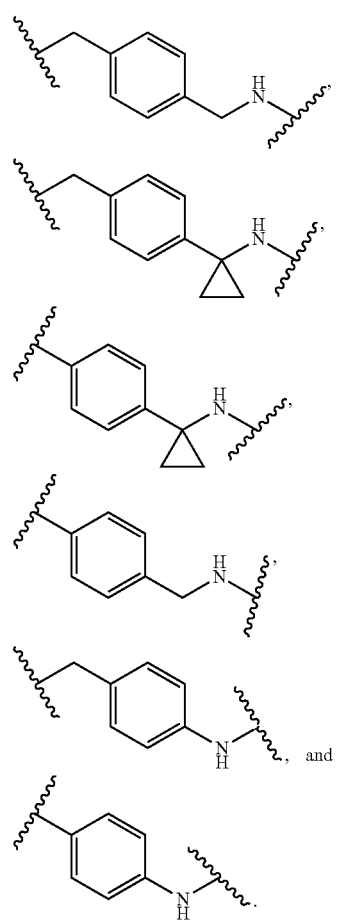

33. The conjugate of claim 19, wherein $(AA)^1$-$(AA)_X$ is Val-Cit, Ala-Phe, Phe-Lys, Val-Ala, Val-Lys, Ala-Lys, Phe-Cit, Leu-Cit, Ile-Cit, Trp-Cit, Phe-Arg, Val-Lys(Ac), Phe-Lys(Ac), Me-Val-Cit, Gly-Val-Cit, Pro-Pro-Pro, D-Ala-Phe-Lys, (D)-Val-Leu-Lys, Gly-Gly-Arg, Ala-Ala-Asn, Lys-Ser- Gly-Arg, Gly-Phe-Leu-Gly, Leu-Ser-Gly-Arg, Ala-Leu-Ala-Leu, Gly-Gly-Gly-Arg-Arg, Gly-Lys-Ala-Phe-Arg-Arg or HomoGly-Arg-Ser-Arg-Gly.

34. The conjugate of claim 19, wherein $(AA)^1\text{-}(AA)_X$ is Val-Cit, Phe-Lys, Val-Lys, Ala-Pro, D-Ala-Phe-Lys or D-Phe-Phe-Lys.

35. The conjugate of claim 19, wherein (L') comprises a stretcher moiety and —$(AA)^1\text{-}(AA)_X\text{-}(L')\text{-}(T)$ has one of the structures (VII) or (VIII):

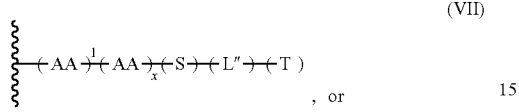

, or

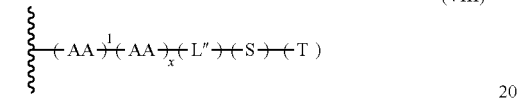

wherein:
L" is a remaining portion of linker (L) or is absent, and
(S) is the stretcher moiety.

36. The conjugate of claim 19, wherein L' comprises one or more alkyloxy units.

37. The conjugate of claim 19, wherein the antibody or antigen-binding antibody fragment specifically binds to an antigen present on a tumor cell.

38. A pharmaceutical composition comprising the conjugate of claim 2 and a pharmaceutically acceptable carrier, diluent or excipient.

* * * * *